United States Patent
Yoon et al.

(10) Patent No.: US 11,767,324 B2
(45) Date of Patent: Sep. 26, 2023

(54) COMPOUND AND ORGANIC LIGHT-EMITTING DEVICE COMPRISING SAME

(71) Applicants: LG CHEM, LTD., Seoul (KR); RESEARCH BUSINESS FOUNDATION SUNGKYUNKWAN UNIVERSITY, Gyeonggi-do (KR)

(72) Inventors: Hongsik Yoon, Daejeon (KR); Jun Yeob Lee, Gyeonggi-do (KR); Ho Jung Lee, Daejeon (KR); Minseung Chun, Daejeon (KR); Wanpyo Hong, Daejeon (KR); Sang Duk Suh, Daejeon (KR); Yujin Kang, Daejeon (KR)

(73) Assignees: LG Chem, Ltd., Seoul (KR); Research Business Foundation Sungkyunkwan University, Gyeonggi-do (KR)

( * ) Notice: Subject to any disclaimer, the term of this patent is extended or adjusted under 35 U.S.C. 154(b) by 729 days.

(21) Appl. No.: 16/761,348

(22) PCT Filed: Jan. 4, 2019

(86) PCT No.: PCT/KR2019/000146
§ 371 (c)(1),
(2) Date: May 4, 2020

(87) PCT Pub. No.: WO2019/135633
PCT Pub. Date: Jul. 11, 2019

(65) Prior Publication Data
US 2021/0179622 A1    Jun. 17, 2021

(30) Foreign Application Priority Data
Jan. 4, 2018    (KR) .......... 10-2018-0001244

(51) Int. Cl.
*C07D 407/12* (2006.01)
*C07D 409/12* (2006.01)
(Continued)

(52) U.S. Cl.
CPC ......... *C07D 487/04* (2013.01); *H10K 85/615* (2023.02); *H10K 85/654* (2023.02);
(Continued)

(58) Field of Classification Search
CPC .. C07D 251/24; C07D 487/04; H01L 51/0072
See application file for complete search history.

(56) References Cited

U.S. PATENT DOCUMENTS

| 10,510,966 B2 | 12/2019 | Jeon et al. |
| 2004/0251816 A1 | 12/2004 | Leo et al. |

(Continued)

FOREIGN PATENT DOCUMENTS

| CN | 106661001 A | 5/2017 |
| CN | 109942551 | 6/2019 |

(Continued)

OTHER PUBLICATIONS

Office Action of Chinese Patent Office in Appl'n No. 201980005328.3, dated Jan. 12, 2022.

*Primary Examiner* — Vu A Nguyen
(74) *Attorney, Agent, or Firm* — Bryan Cave Leighton Paisner LLP

(57) ABSTRACT

Provided is a compound of Chemical Formula 1:

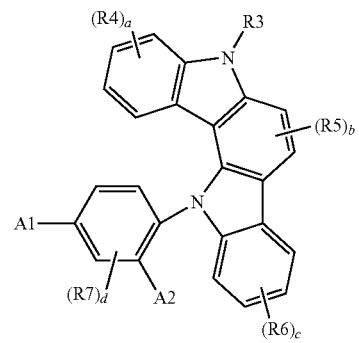

wherein:
one of A1 and A2 is a substituent of Chemical Formula 2:

(Continued)

| 4 |
|---|
| 3 |
| 2 |
| 1 |

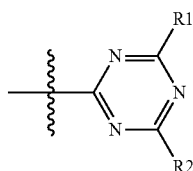

and the other one is a cyano group;

R3 is a substituted or unsubstituted aryl or heteroaryl group;

R4 to R7 are each independently a hydrogen, deuterium, halogen, or a substituted or unsubstituted: silyl, alkyl, amine, arylamine, alkylamine, aryl, or heteroaryl group;

R1 and R2 are each independently a substituted or unsubstituted aryl or heteroaryl group; and (1) at least one of R1 to R3 is a substituted phenyl group, or a substituted or unsubstituted heteroaryl group or $C_{10}$ or higher aryl group; or (2) R7 is deuterium and d is 1 or greater, and an organic light-emitting device comprising the same.

15 Claims, 1 Drawing Sheet

(51) Int. Cl.
| | | |
|---|---|---|
| *H01L 51/00* | (2006.01) | |
| *H01L 51/50* | (2006.01) | |
| *C07D 487/04* | (2006.01) | |
| *H10K 85/60* | (2023.01) | |
| *H10K 50/11* | (2023.01) | |
| *H10K 50/15* | (2023.01) | |
| *H10K 50/16* | (2023.01) | |
| *H10K 50/18* | (2023.01) | |
| *H10K 50/17* | (2023.01) | |
| *H10K 101/30* | (2023.01) | |

(52) U.S. Cl.
CPC ..... *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/171* (2023.02); *H10K 50/18* (2023.02); *H10K 2101/30* (2023.02)

(56) References Cited

U.S. PATENT DOCUMENTS

| | | |
|---|---|---|
| 2017/0062718 A1 | 3/2017 | Numata et al. |
| 2017/0069848 A1 | 3/2017 | Zeng et al. |
| 2017/0141323 A1 | 5/2017 | Miyazaki et al. |
| 2017/0244049 A1 | 8/2017 | Aspuru-Guzik et al. |
| 2017/0352816 A1* | 12/2017 | Jeon ................ H05B 33/14 |
| 2019/0177303 A1* | 6/2019 | Danz ................ H01L 51/0067 |
| 2020/0127214 A1 | 4/2020 | Choi et al. |

FOREIGN PATENT DOCUMENTS

| | | |
|---|---|---|
| CN | 111081888 | 4/2020 |
| CN | 112533900 | 3/2021 |
| KR | 10-20100131939 | 12/2010 |
| KR | 10-20160087331 | 7/2016 |
| KR | 10-20170005853 | 1/2017 |
| KR | 10-20170025990 | 3/2017 |
| KR | 10-20170056951 | 5/2017 |
| KR | 10-20170136256 | 12/2017 |
| WO | 2003012890 | 2/2003 |

\* cited by examiner

【FIG. 1】

| |
|:-:|
| 4 |
| 3 |
| 2 |
| 1 |

【FIG. 2】

| |
|:-:|
| 4 |
| 7 |
| 3 |
| 6 |
| 5 |
| 2 |
| 1 |

【FIG. 3】

| |
|:-:|
| 4 |
| 10 |
| 9 |
| 3 |
| 8 |
| 6 |
| 5 |
| 2 |
| 1 |

COMPOUND AND ORGANIC LIGHT-EMITTING DEVICE COMPRISING SAME

This application is a National Stage Application of International Application No. PCT/KR2019/000146 filed on Jan. 4, 2019, which claims priority to and the benefits of Korean Patent Application No. 10-2018-0001244, filed with the Korean Intellectual Property Office on Jan. 4, 2018, the entire contents of which are incorporated herein by reference.

TECHNICAL FIELD

The present specification relates to a novel compound and an organic light emitting device comprising same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often foamed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification describes a novel compound and an organic light emitting device comprising same.

Technical Solution

One embodiment of the present specification provides a compound of Chemical Formula 1:

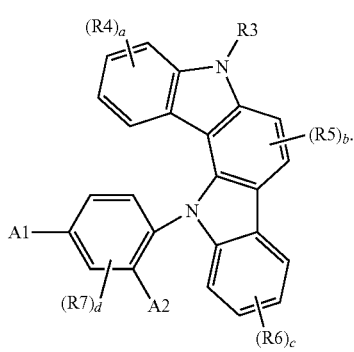

Chemical Formula 1

In Chemical Formula 1,
one of A1 and A2 is a substituent of the following Chemical Formula 2, and the other one is a cyano group;
R3 is a substituted or unsubstituted aryl group or a substituted or unsubstituted heteroaryl group;
R4 to R7 are each independently hydrogen, deuterium, a halogen group, a substituted or unsubstituted silyl group, a substituted or unsubstituted alkyl group, a substituted or unsubstituted amine group, a substituted or unsubstituted arylamine group, a substituted or unsubstituted alkylamine group, a substituted or unsubstituted aryl group, or a substituted or unsubstituted heteroaryl group;
a is an integer of 0 to 4, and when a is 2 or greater, the R4s are the same as or different from each other;
b is an integer of 0 to 2, and when b is 2, the R5s are the same as or different from each other;
c is an integer of 0 to 4, and when c is 2 or greater, the R6s are the same as or different from each other; and
d is an integer of 0 to 3, and when d is 2 or greater, the R7s are the same as or different from each other,

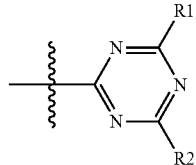

Chemical Formula 2 wherein in Chemical Formula 2:
R1 and R2 are each independently a substituted or unsubstituted aryl group or a substituted or unsubstituted heteroaryl group; and
(1) at least one of R1 to R3 is a substituted phenyl group, a substituted or unsubstituted $C_{10}$ or higher aryl group, or a substituted or unsubstituted heteroaryl group, or (2) R7 is deuterium and d is 1 or greater.

Another embodiment of the present specification provides an organic light emitting device comprising a first electrode, a second electrode, and one or more organic material layers disposed between the first electrode and the second electrode, wherein the organic material layer comprises the compound according to some embodiments of the present specification.

Advantageous Effects

A compound described in the present specification can be used as a material of an organic material layer of an organic light emitting device. The compound according to at least one embodiment is capable of enhancing efficiency, lowering a driving voltage, enhancing color purity and/or enhancing lifetime properties in an organic light emitting device. Particularly, the compound can be used as a light emitting material described in the present specification.

The compound according to one embodiment of the present disclosure has a small difference between singlet energy and triplet energy, and can be used as a delayed fluorescent material.

In addition, the compound according to one embodiment of the present disclosure has a structure exhibiting a high electron accepting ability and has excellent heat resistance, and therefore, is capable of maintaining a proper deposition temperature when manufacturing an organic light emitting device. In addition, the compound has a high sublimation temperature, and therefore, high purification can be obtained using a sublimation purification method, and, when manufacturing an organic light emitting device, does not cause contamination on a film-forming apparatus for deposition or the organic light emitting device.

DESCRIPTION OF DRAWINGS

FIG. 1 illustrates an example of an organic light emitting device formed with a substrate (1), an anode (2), a light emitting layer (3) and a cathode (4).

FIG. 2 illustrates an example of an organic light emitting device formed with a substrate (1), an anode (2), a hole injection layer (5), a hole transfer layer (6), a light emitting layer (3), an electron transfer layer (7) and a cathode (4).

FIG. 3 illustrates an example of an organic light emitting device formed with a substrate (1), an anode (2), a hole injection layer (5), a hole transfer layer (6), an electron blocking layer (8), a light emitting layer (3), a hole blocking layer (9), an electron injection and transfer layer (10) and a cathode (4).

DETAILED DESCRIPTION

Hereinafter, the present specification will be described in more detail.

Examples of substituents are described below, however, the substituents are not limited thereto.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one or more substituents selected from the group consisting of deuterium, a halogen group, a nitrile group, a nitro group, —C(=O)R, —C(=O)OR, —NR$_2$, —P(=O)R$_2$, —OR, —SR, —S(=O)R, —SiR$_3$, —BR$_2$, an alkyl group, a cycloalkyl group, an alkenyl group, an aryl group, and a heteroaryl group or being unsubstituted, or substituted with a substituent linking two or more substituents selected from the group or being unsubstituted. R is hydrogen, deuterium, an alkyl group, an aryl group, or a heteroaryl group, and when there are two or more Rs, the Rs are the same as or different from each other.

In some embodiments of the present specification, the term "substituted or unsubstituted" more preferably means being substituted with one or more substituents selected from the group consisting of deuterium, a halogen group, a nitro group, an alkyl group, a cycloalkyl group, an alkenyl group, an aryl group, and a heteroaryl group or being unsubstituted, or substituted with a substituent linking two or more substituents selected from the group or being unsubstituted.

In the present specification, examples of the halogen group can include fluorine, chlorine, bromine or iodine.

In the present specification, the alkyl group can be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group can include methyl, ethyl, n-propyl, isopropyl, n-butyl, isobutyl, tert-butyl, sec-butyl, 1-methylbutyl, 1-ethylbutyl, n-pentyl, isopentyl, neopentyl, tert-pentyl, n-hexyl, 1-methylpentyl, 2-methylpentyl, 3,3-dimethylbutyl, 2-ethylbutyl, n-heptyl, 1-methylhexyl, cyclopentylmethyl, cyclohexylmethyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the alkoxy group can be linear, branched or cyclic. The number of carbon atoms of the alkoxy group is not particularly limited, but is preferably from 1 to 40. Specific examples thereof can include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyl-oxy, n-nonyloxy, n-decyloxy, benzyloxy, p-methylbenzyloxy and the like, but are not limited thereto.

In the present specification, the alkenyl group can be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to another embodiment, the number of carbon atoms of the alkenyl group is from 2 to 6. Specific examples thereof can include vinyl, propenyl, 1-butenyl, 2-butenyl, 1-pentenyl, 2-pentenyl, 3-pentenyl, 3-methyl-1-butenyl, 1,3-butadienyl, allyl, 1-phenyl-vinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of carbon atoms of the cycloalkyl group is from 3 to 20. According to another embodiment, the number of carbon atoms of the cycloalkyl group is from 3 to 6. Specific examples thereof can include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the silyl group can be a chemical formula of —SiR$_a$R$_b$R$_c$, and R$_a$, R$_b$ and R$_c$ each independently can be hydrogen, a substituted or unsubstituted alkyl group, or a substituted or unsubstituted aryl group. Specific examples of the silyl group can include a trimethylsilyl group, a triethylsilyl group, a t-butyl-dimethylsilyl group, a vinyldimethylsilyl group, a propyl-dimethylsilyl group, a triphenylsilyl group, a diphenylsilyl group, a phenylsilyl group and the like, but are not limited thereto.

In the present specification, the number of carbon atoms of the alkylamine group is not particularly limited, but is preferably from 1 to 40. Specific examples of the alkylamine group can include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, a phenylnaphthylamine group, a ditolylamine group, a phenyltolylamine group, a triphenylamine group and the like, but are not limited thereto.

In the present specification, specific examples of the arylamine group include a substituted or unsubstituted monoarylamine group or a substituted or unsubstituted diarylamine group. The aryl group in the arylamine group can be a monocyclic aryl group or a polycyclic aryl group. The arylamine group including two or more aryl groups can include monocyclic aryl groups, polycyclic aryl groups, or both monocyclic aryl groups and polycyclic aryl groups.

In the present specification, the aryl group means a hydrocarbon ring having totally or partially unsaturated aromaticity. The number of carbon atoms of the aryl group is not particularly limited, but is preferably from 6 to 60, and the aryl group can be a monocyclic aryl group or a polycyclic aryl group. According to one embodiment, the number of carbon atoms of the aryl group is from 6 to 45. According to one embodiment, the number of carbon atoms of the aryl group is from 6 to 35. Examples of the monocyclic aryl group can include a phenyl group, a biphenyl group, a terphenyl group and the like, but are not limited thereto. Examples of the polycyclic aryl group can include a naphthyl group, an anthracenyl group, a phenanthrenyl group, a pyrenyl group, a perylenyl group, a chrysenyl group, a fluorenyl group, a triphenylenyl group and the like, but are not limited thereto.

In the present specification, when mentioning that the fluorenyl group can be substituted, the substituted fluorenyl group even includes compounds in which substituents of the fluorene pentagonal ring spiro bond to each other to form an aromatic hydrocarbon ring. Examples of the substituted fluorenyl group can include 9,9'-spirobifluorene, spiro[cyclopentane-1,9'-fluorene], spiro[benzo[c]fluorene-7,9-fluorene] and the like, but are not limited thereto.

In the present specification, the heteroaryl group means an aromatic ring including one or more of N, O and S as a heteroatom. The number of carbon atoms of the heteroaryl group is not particularly limited, but is preferably from 2 to 60. According to one embodiment, the number of carbon atoms of the heteroaryl group is from 2 to 45. According to another embodiment, the number of carbon atoms of the heteroaryl group is from 2 to 35. Examples of the heteroaryl group can include a thiophenyl group, a furanyl group, a pyrrolyl group, an imidazolyl group, a triazolyl group, an oxazolyl group, an oxadiazolyl group, a triazolyl group, a pyridinyl group, a bipyridinyl group, a pyrimidinyl group, a diazinyl group, a triazinyl group, a triazolyl group, an acridinyl group, a carbolinyl group, an acenaphthoquinoxalinyl group, an indenopyrimidinyl group, an indenoquinazolinyl group, an indenoisoquinolinyl group, an indenoquinolinyl group, a pyridoindolyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzoquinazolinyl group, a benzo-quinolinyl group, a benzimidazolyl group, a benzothiazolyl group, a benzocarbazolyl group, a benzothiophenyl group, a dibenzothiophenyl group, a benzofuranyl group, a dibenzofuranyl group, a phenanthrolinyl group, a thiazolyl group, an isoxazolyl group, an oxadiazolyl group, a thiadiazolyl group, a benzothiazolyl group, a phenoxazinyl group, a phenothiazinyl group, a naphthridinyl group, a pteridinyl group and the like, but are not limited thereto.

In the present specification, the number of atoms forming the ring of the heteroaryl group is from 3 to 25. In another embodiment, the number of atoms forming the ring of the heteroaryl group is from 5 to 17.

In the present specification, descriptions on the aryl group provided above can apply to the arylene group except for being divalent.

In the present specification, descriptions on the heteroaryl group provided above can apply to the heteroarylene group except for being divalent.

In the present specification, triplet energy (T1) is a value of a difference between an energy level of a ground state and an energy level of a triplet excited state.

In the present specification, singlet energy (S1) is a value of a difference between an energy level of a ground state and an energy level of a singlet excited state.

In the present specification, the triplet energy and the singlet energy can be measured using a spectrometer capable of measuring fluorescence and phosphorescence.

The triplet energy can be identified by preparing a solution in a $10^{-5}$ M concentration using toluene or tetrahydrofuran (THF) as a solvent at a cryogenic temperature using liquid nitrogen, excluding singlet emission from a spectrum emitting by irradiating a light source having an absorption wavelength band of the material on the solution, and analyzing a triplet emission spectrum. When electrons are excited from a light source, the time of the electrons staying at a triplet energy level is much longer than the time of staying at a singlet energy level, and therefore, the two components can be separated at a cryogenic temperature.

The singlet energy is measured using a fluorescence instrument, and, unlike the method of measuring triplet energy level described above, can be measured by irradiating a light source at room temperature. Methods of measuring the triplet energy and the singlet energy are described in more detail in the following examples.

In the present specification, a "HOMO" is the highest occupied molecular orbital, and a "LUMO" is the lowest unoccupied molecular orbital.

In the present specification, the "energy level" means energy magnitude. Therefore, even when the energy level is expressed in a negative (−) direction from the vacuum level, the energy level is interpreted to mean an absolute value of the corresponding energy value. For example, the energy level being 'large' means the absolute value increasing in a negative direction from the vacuum level. In addition, in the present specification, the expression such as energy level being 'deep' or 'high' has the same meaning as the expression of energy level being large.

The HOMO energy level can be measured using either UV photoelectron spectroscopy (UPS) irradiating UV on a thin film surface and measuring ionization potential of a material through detecting electrons that come out, or using cyclic voltammetry (CV) dissolving a material to measure in a solvent together with an electrolyte liquid and measuring oxidation potential through a voltage sweep.

The LUMO energy level can be obtained through inverse photoelectron spectroscopy (IPES) or measuring electrochemical reduction potential. In addition to the above-described methods, the LUMO energy level can be calculated using the HOMO energy level and the singlet energy level.

In one embodiment of the present specification, the HOMO energy level and the LUMO energy level can be a value measured using a cyclic voltammetry (CV) method identifying oxidation and reduction potential of a dimethylformamide (DMF) solution dissolving a compound to measure in a concentration of 5 mM and an electrolyte in a concentration of 0.1 M through comparison based on a ferrocene compound. Specifically, the HOMO energy level and the LUMO energy level of the present specification are measured using an energy level measuring method of examples to describe later.

One embodiment of the present specification provides a compound of Chemical Formula 1.

In order for a compound to develop a delayed fluorescence phenomenon, it is effective to reduce a difference between triplet energy and singlet energy ($\Delta E_{ST}$) of the organic compound, and in order to reduce the $\Delta E_{ST}$, localizing (clearly separating) the highest occupied molecular orbital (HOMO) and the lowest unoccupied molecular orbital (LUMO) in the molecule is important. In the compound of the present disclosure, a triazine group and indolocarbazole are linked through a benzene ring, and therefore, the HOMO is distributed in the indolocarbazole, and the LUMO is distributed in the triazine group. The compound of Chemical Formula 1 has localized HOMO and LUMO and exhibits delayed fluorescence properties.

In the compound of Chemical Formula 1, CN of A1 or A2 performs a role of adjusting a light emission wavelength by adjusting a molecular LUMO energy level.

A Hammett parameter is a constant affecting a reaction rate or equilibrium. By the compound of Chemical Formula 1 including CN having a Hammett parameter ($\sigma_{meta}$) of greater than 0.5, the synthesis time of the material is short, and the yield is high.

$\sigma_{meta}$ can be obtained by, based on benzoic acid, measuring a degree of ionization of the benzoic acid depending on the changes in the substituents. Specifically, the $\sigma_{meta}$ value can be obtained from the equation $\log(k/k_0)=\rho\times\sigma_{meta}$ or $\log(K/K_0)=\rho\times\sigma_{meta}$ established between the substituent of the meta-substituted benzene derivative and a reaction rate constant or an equilibrium constant. In the equation, k represents a rate constant of the benzene derivative that does not have a substituent, $k_0$ represents a rate constant of the benzene derivative substituted with a substituent, K represents an equilibrium constant of the benzene derivative that does not have a substituent, $K_0$ represents an equilibrium constant of the benzene derivative substituted with a substituent, and ρ represents a reaction constant determined by a type and a condition of the reaction.

The compound according to one embodiment of the present specification has triazine and CN positioned at a meta position of the benzene ring. By the CN having a Hammett parameter ($\sigma_{meta}$) of greater than 0.5 positioning at a meta position with respect to the triazine, an organic light emitting device having high efficiency and long lifetime is obtained.

In Chemical Formula 1, triazine and CN are an electron acceptor, and indolocarbazole is an electron donor. By the electron acceptor and the electron donor positioning at a para position of the benzene, light emission quantum efficiency (PLQY) of the delayed fluorescent compound and light emission efficiency of an organic light emitting device are enhanced.

In Chemical Formula 1, triazine and CN are introduced at a meta position of the benzene. When triazine and CN are introduced at an ortho position of the benzene, two electron acceptors are crowded on one side of the compound even when the electron acceptor and the electron donor are introduced at a para position of the benzene, and color purity to obtain in the present disclosure may not be obtained since the light emission wavelength becomes too long.

In one embodiment of the present specification, the compound of Chemical Formula 1 has a light emission wavelength of 480 nm to 570 nm, and preferably 500 nm to 550 nm.

According to one embodiment of the present specification, R3 is a substituted or unsubstituted $C_6$ to $C_{20}$ aryl group or a substituted or unsubstituted $C_2$ to $C_{20}$ heteroaryl group.

According to one embodiment of the present specification, R3 is a substituted or unsubstituted $C_6$ to $C_{15}$ aryl group or a substituted or unsubstituted $C_2$ to $C_{15}$ heteroaryl group.

According to one embodiment of the present specification, R3 is an aryl group that is unsubstituted or substituted with one or more substituents selected from the group consisting of deuterium, an alkyl group, an aryl group and a heteroaryl group, or unsubstituted or substituted with a substituent in which two or more substituents selected from the group consisting of deuterium, an alkyl group, an aryl group and a heteroaryl group are linked to each other; or a heteroaryl group that is unsubstituted or substituted with one or more substituents selected from the group consisting of deuterium, an alkyl group, an aryl group and a heteroaryl group, or unsubstituted or substituted with a substituent in which two or more substituents selected from the group consisting of deuterium, an alkyl group, an aryl group and a heteroaryl group are linked to each other.

According to one embodiment of the present specification, R3 is a $C_6$ to $C_{20}$ aryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; or a $C_2$ to $C_{20}$ heteroaryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other.

According to one embodiment of the present specification, R3 is a $C_6$ to $C_{15}$ aryl group that is unsubstituted or substituted with one or more substituents selected from the group consisting of deuterium, a $C_1$ to $C_6$ alkyl group, a $C_6$ to $C_{15}$ aryl group and a $C_2$ to $C_{15}$ heteroaryl group, or unsubstituted or substituted with a substituent in which two or more substituents selected from the group consisting of deuterium, a $C_1$ to $C_6$ alkyl group, a $C_6$ to $C_{15}$ aryl group and a $C_2$ to $C_{15}$ heteroaryl group are linked to each other; or a $C_2$ to $C_{15}$ heteroaryl group that is unsubstituted or substituted with one or more substituents selected from the group consisting of deuterium, a $C_1$ to $C_6$ alkyl group, a $C_6$ to $C_{15}$ aryl group and a $C_2$ to $C_{15}$ heteroaryl group, or unsubstituted or substituted with a substituent in which two or more substituents selected from the group consisting of deuterium, a $C_1$ to $C_6$ alkyl group, a $C_6$ to $C_{15}$ aryl group and a $C_2$ to $C_{15}$ heteroaryl group are linked to each other.

According to one embodiment of the present specification, R3 is a $C_6$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium, a $C_1$ to $C_{10}$ alkyl group or a $C_6$ to $C_{20}$ aryl group.

According to one embodiment of the present specification, R3 is a $C_6$ to $C_{15}$ aryl group that is unsubstituted or substituted with deuterium, a $C_1$ to $C_6$ alkyl group or a $C_6$ to $C_{15}$ aryl group; or a $C_2$ to $C_{15}$ heteroaryl group that is unsubstituted or substituted with deuterium, a $C_1$ to $C_6$ alkyl group or a $C_6$ to $C_{15}$ aryl group.

According to one embodiment of the present specification, R3 is a $C_6$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium.

According to one embodiment of the present specification, R3 is a $C_6$ to $C_{15}$ aryl group that is unsubstituted or substituted with deuterium, a $C_1$ to $C_6$ alkyl group or a $C_6$ to $C_{15}$ aryl group; or a $C_2$ to $C_{15}$ heteroaryl group that is unsubstituted or substituted with deuterium.

According to one embodiment of the present specification, R3 is a $C_6$ to $C_{15}$ aryl group that is unsubstituted or substituted with deuterium, a $C_1$ to $C_6$ alkyl group or a $C_6$ to $C_{12}$ aryl group; or a $C_2$ to $C_{15}$ heteroaryl group that is unsubstituted or substituted with deuterium.

According to one embodiment of the present specification, R3 is a substituted or unsubstituted phenyl group, a substituted or unsubstituted $C_{10}$ or higher aryl group, or a substituted or unsubstituted heteroaryl group.

According to one embodiment of the present specification, R3 is a phenyl group that is unsubstituted or substituted with deuterium or a $C_6$ to $C_{15}$ aryl group; a $C_{10}$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium.

According to one embodiment of the present specification, R3 is a phenyl group substituted with deuterium or a $C_6$ to $C_{15}$ aryl group; a $C_{10}$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium.

According to one embodiment of the present specification, R3 is a phenyl group substituted with deuterium or a $C_6$ to $C_{12}$ aryl group; a $C_6$ to $C_{15}$ aryl group that is unsubstituted or substituted with deuterium, a $C_1$ to $C_6$ alkyl group or a $C_6$ to $C_{15}$ aryl group; or a $C_2$ to $C_{15}$ heteroaryl group that is unsubstituted or substituted with deuterium.

According to one embodiment of the present specification, R3 is a substituted or unsubstituted phenyl group; a substituted or unsubstituted biphenyl group; a substituted or unsubstituted fluorenyl group; a substituted or unsubstituted naphthyl group; a substituted or unsubstituted dibenzofuranyl group; or a substituted or unsubstituted dibenzothiophenyl group.

According to one embodiment of the present specification, R3 is a phenyl group; a phenyl group substituted with deuterium; a biphenyl group; a fluorenyl group that is unsubstituted or substituted with a $C_2$ to $C_6$ alkyl group; a naphthyl group; a dibenzofuranyl group; or a dibenzothiophenyl group.

According to one embodiment of the present specification, R3 is a phenyl group substituted with deuterium; a biphenyl group; a fluorenyl group that is unsubstituted or substituted with a $C_1$ to $C_6$ alkyl group; a naphthyl group; a dibenzofuranyl group; or a dibenzothiophenyl group.

According to one embodiment of the present specification, R3 is a $C_{10}$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group.

According to one embodiment of the present specification, R3 is a $C_{10}$ to $C_{20}$ aryl group that is unsubstituted or substituted with deuterium, a $C_1$ to $C_{10}$ alkyl group or a $C_6$ to $C_{20}$ aryl group.

According to one embodiment of the present specification, R3 is a $C_2$ to $C_{20}$ heteroaryl group.

According to one embodiment of the present specification, R4 is hydrogen or deuterium.

According to one embodiment of the present specification, R4 is hydrogen.

According to one embodiment of the present specification, R6 is hydrogen or deuterium.

According to one embodiment of the present specification, R6 is hydrogen.

According to one embodiment of the present specification, R1 and R2 are each independently a substituted or unsubstituted $C_6$ to $C_{20}$ aryl group or a substituted or unsubstituted $C_2$ to $C_{20}$ heteroaryl group.

According to one embodiment of the present specification, R1 and R2 are each independently a substituted or unsubstituted $C_6$ to $C_{15}$ aryl group or a substituted or unsubstituted $C_2$ to $C_{15}$ heteroaryl group.

According to one embodiment of the present specification, R1 and R2 are each independently a $C_6$ to $C_{20}$ aryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; or a $C_2$ to $C_{20}$ heteroaryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other.

According to one embodiment of the present specification, R1 and R2 are each independently a $C_6$ to $C_{15}$ aryl group that is unsubstituted or substituted with one or more substituents selected from the group consisting of deuterium, a $C_1$ to $C_6$ alkyl group, a $C_6$ to $C_{15}$ aryl group and a $C_2$ to $C_{15}$ heteroaryl group, or unsubstituted or substituted with a substituent in which two or more substituents selected from the group consisting of deuterium, a $C_1$ to $C_6$ alkyl group, a $C_6$ to $C_{15}$ aryl group and a $C_2$ to $C_{15}$ heteroaryl group are linked to each other; or a $C_2$ to $C_{15}$ heteroaryl group that is unsubstituted or substituted with one or more substituents selected from the group consisting of deuterium, a $C_1$ to $C_6$ alkyl group, a $C_6$ to $C_{15}$ aryl group and a $C_2$ to $C_{15}$ heteroaryl group, or unsubstituted or substituted with a substituent in which two or more substituents selected from the group consisting of deuterium, a $C_1$ to $C_6$ alkyl group, a $C_6$ to $C_{15}$ aryl group and a $C_2$ to $C_{15}$ heteroaryl group are linked to each other.

According to one embodiment of the present specification, R1 and R2 are each independently a $C_6$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium or a $C_6$ to $C_{20}$ aryl group.

According to one embodiment of the present specification, R1 and R2 are each independently a $C_6$ to $C_{15}$ aryl group that is unsubstituted or substituted with deuterium, a $C_1$ to $C_6$ alkyl group or a $C_6$ to $C_{15}$ aryl group; or a $C_2$ to $C_{15}$ heteroaryl group that is unsubstituted or substituted with deuterium or a $C_6$ to $C_{15}$ aryl group.

According to one embodiment of the present specification, R1 and R2 are each independently a phenyl group that is unsubstituted or substituted with deuterium, a $C_1$ to $C_{10}$ alkyl group or a $C_6$ to $C_{20}$ aryl group; a $C_{10}$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium or a $C_6$ to $C_{20}$ aryl group.

According to one embodiment of the present specification, R1 and R2 are each independently a phenyl group that is unsubstituted or substituted with deuterium, a $C_1$ to $C_6$ alkyl group or a $C_6$ to $C_{15}$ aryl group; a $C_{10}$ to $C_{15}$ aryl group that is unsubstituted or substituted with deuterium, a $C_1$ to $C_6$ alkyl group or a $C_6$ to $C_{15}$ aryl group; or a $C_2$ to $C_{15}$ heteroaryl group that is unsubstituted or substituted with deuterium or a $C_6$ to $C_{15}$ aryl group.

According to one embodiment of the present specification, R1 and R2 are each independently a phenyl group; a phenyl group substituted with deuterium; a phenyl group substituted with a $C_6$ to $C_{20}$ aryl group; a $C_{10}$ to $C_{20}$ aryl group that is unsubstituted or substituted with a $C_1$ to $C_{10}$ alkyl group or a $C_6$ to $C_{20}$ aryl group; or a $C_2$ to $C_{20}$ heteroaryl group that is unsubstituted or substituted with a $C_6$ to $C_{20}$ aryl group.

According to one embodiment of the present specification, R1 and R2 are each independently a phenyl group; a phenyl group substituted with deuterium; a phenyl group substituted with a $C_6$ to $C_{15}$ aryl group; a $C_{10}$ to $C_{15}$ aryl group that is unsubstituted or substituted with a $C_1$ to $C_6$ alkyl group or a $C_6$ to $C_{15}$ aryl group; or a $C_2$ to $C_{15}$ heteroaryl group that is unsubstituted or substituted with a $C_6$ to $C_{15}$ aryl group.

According to one embodiment of the present specification, R1 and R2 are each independently an unsubstituted phenyl group, a substituted phenyl group, a substituted or unsubstituted biphenyl group, a substituted or unsubstituted carbazolyl group, a substituted or unsubstituted dibenzofuranyl group, or a substituted or unsubstituted dibenzothiophenyl group.

According to one embodiment of the present specification, R1 and R2 are each independently a phenyl group, a (phenyl-$D_5$) group, a biphenyl group, an N-phenylcarbazolyl group, a dibenzofuranyl group, or a dibenzothiophenyl group.

According to one embodiment of the present specification, R1 and R2 are each independently a (phenyl-$D_5$) group, a biphenyl group, an N-phenylcarbazolyl group, a dibenzofuranyl group, or a dibenzothiophenyl group.

According to one embodiment of the present specification, (1) at least one of R1 to R3 is a phenyl group substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; a substituted or unsubstituted $C_{10}$ to $C_{20}$ aryl group; or a substituted or unsubstituted $C_2$ to $C_{20}$ heteroaryl group, or (2) R7 is deuterium and d is 1 or greater.

According to one embodiment of the present specification, (1) at least one of R1 to R3 is a phenyl group substituted with one or more substituents selected from the group consisting of deuterium, a $C_1$ to $C_6$ alkyl group, a $C_6$ to $C_{20}$ aryl group and a $C_2$ to $C_{20}$ heteroaryl group, or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; a $C_A$ to $C_{20}$ aryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; or a $C_2$ to $C_{20}$ heteroaryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent linking two or more substituents selected from the group, or (2) R7 is deuterium and d is 1 or greater.

According to one embodiment of the present specification, (1) at least one of R1 to R3 is a phenyl group substituted with deuterium, a $C_6$ to $C_{20}$ aryl group or a $C_2$ to $C_{20}$ heteroaryl group; a substituted or unsubstituted $C_{10}$ to $C_{20}$ aryl group; or a substituted or unsubstituted $C_2$ to $C_{20}$ heteroaryl group, or (2) R7 is deuterium and d is 1 or greater.

According to one embodiment of the present specification, (1) at least one of R1 to R3 is a phenyl group substituted with deuterium, a $C_1$ to $C_{10}$ alkyl group, a $C_6$ to $C_{20}$ aryl group or a $C_2$ to $C_{20}$ heteroaryl group; a $C_{10}$ to $C_{20}$ aryl group that is unsubstituted or substituted with deuterium, a $C_1$ to $C_{10}$ alkyl group, a $C_6$ to $C_{20}$ aryl group or a $C_2$ to $C_{20}$ heteroaryl group; or a $C_2$ to $C_{20}$ heteroaryl group that is unsubstituted or substituted with deuterium, a $C_1$ to $C_{10}$ alkyl group, a $C_6$ to $C_{20}$ aryl group or a $C_2$ to $C_{20}$ heteroaryl group or (2) R7 is deuterium and d is 1 or greater.

According to one embodiment of the present specification, (1) at least one of R1 to R3 is a phenyl group substituted with deuterium or a $C_6$ to $C_{20}$ aryl group; a substituted or unsubstituted $C_{10}$ to $C_{20}$ aryl group; or a substituted or unsubstituted $C_2$ to $C_{20}$ heteroaryl group, or (2) R7 is deuterium and d is 1 or greater.

According to one embodiment of the present specification, (1) at least one of R1 to R3 is a phenyl group substituted with deuterium or a $C_6$ to $C_{20}$ aryl group; a $C_{10}$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium or a $C_6$ to $C_{20}$ aryl group, or (2) R7 is deuterium and d is 1 or greater.

According to one embodiment of the present specification, (1) at least one of R1 to R3 is a substituted or unsubstituted phenyl group substituted with deuterium; a substituted or unsubstituted aryl group substituted with deuterium; or a substituted or unsubstituted heteroaryl group substituted with deuterium, or (2) R7 is deuterium and d is 1 or greater.

According to one embodiment of the present specification, at least one of R1 to R3 is a phenyl group substituted with deuterium; a phenyl group substituted with a $C_2$ to $C_{20}$ aryl group; a substituted or unsubstituted $C_{10}$ to $C_{20}$ aryl group; or a substituted or unsubstituted $C_2$ to $C_{20}$ heteroaryl group.

According to one embodiment of the present specification, at least one of R1 to R3 is a phenyl group substituted with a $C_2$ to $C_{20}$ aryl group; a substituted or unsubstituted $C_{10}$ to $C_{20}$ aryl group; or a substituted or unsubstituted $C_2$ to $C_{20}$ heteroaryl group, or (2) R7 is deuterium and d is 1 or greater.

According to one embodiment of the present specification, at least one of R1 to R3 is a substituted or unsubstituted $C_{10}$ to $C_{20}$ aryl group; or a substituted or unsubstituted $C_2$ to $C_{20}$ heteroaryl group.

According to one embodiment of the present specification, at least one of R1 and R2 is a phenyl group substituted with deuterium, a $C_6$ to $C_{20}$ aryl group or a $C_2$ to $C_{20}$ heteroaryl group; a substituted or unsubstituted $C_{10}$ to $C_{20}$ aryl group; or a substituted or unsubstituted $C_2$ to $C_{20}$ heteroaryl group.

According to one embodiment of the present specification, at least one of R1 and R2 is a phenyl group substituted with deuterium or a $C_6$ to $C_{20}$ aryl group; a substituted or unsubstituted $C_{10}$ to $C_{20}$ aryl group; or a substituted or unsubstituted $C_2$ to $C_{20}$ heteroaryl group.

According to one embodiment of the present specification, at least one of R1 and R2 is a phenyl group substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; a $C_{10}$ to $C_{20}$ aryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; or a $C_2$ to $C_{20}$ heteroaryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked of each other.

According to one embodiment of the present specification, at least one of R1 and R2 is a phenyl group substituted with deuterium, a $C_1$ to $C_{10}$ alkyl group, a $C_6$ to $C_{20}$ aryl group or a $C_2$ to $C_{20}$ heteroaryl group; a $C_{10}$ to $C_{20}$ aryl group that is unsubstituted or substituted with deuterium, a $C_1$ to $C_{10}$ alkyl group, a $C_6$ to $C_{20}$ aryl group or a $C_2$ to $C_{20}$ heteroaryl group; or a $C_2$ to $C_{20}$ heteroaryl group that is unsubstituted or substituted with deuterium, a $C_1$ to $C_{10}$ alkyl group, a $C_6$ to $C_{20}$ aryl group or a $C_2$ to $C_{20}$ heteroaryl group.

According to one embodiment of the present specification, at least one of R1 and R2 is a phenyl group substituted with a $C_6$ to $C_{20}$ aryl group; a substituted or unsubstituted $C_{10}$ to $C_{20}$ aryl group; or a substituted or unsubstituted $C_2$ to $C_{20}$ heteroaryl group.

According to one embodiment of the present specification, at least one of R1 and R2 is a $C_{10}$ to $C_{20}$ aryl group that is unsubstituted or substituted with deuterium, a $C_1$ to $C_{10}$ alkyl group or a $C_6$ to $C_{20}$ aryl group.

According to one embodiment of the present specification, at least one of R1 and R2 is a $C_2$ to $C_{20}$ heteroaryl group that is unsubstituted or substituted with a $C_6$ to $C_{20}$ aryl group.

According to one embodiment of the present specification, R1 is a $C_{10}$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium or a $C_6$ to $C_{20}$ aryl group, and R2 is a $C_6$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium or a $C_6$ to $C_{15}$ aryl group.

According to one embodiment of the present specification, R1 is a $C_{10}$ to $C_{20}$ aryl group that is unsubstituted or substituted with deuterium, a $C_1$ to $C_{10}$ alkyl group or a $C_6$ to $C_{20}$ aryl group, and R2 is a $C_6$ to $C_{20}$ aryl group that is unsubstituted or substituted with deuterium, a $C_1$ to $C_{10}$ alkyl group or a $C_6$ to $C_{20}$ aryl group; or a $C_2$ to $C_{20}$ heteroaryl group that is unsubstituted or substituted with deuterium or a $C_6$ to $C_{15}$ aryl group.

According to one embodiment of the present specification, at least one of R1 and R2 is a phenyl group substituted with deuterium, a $C_6$ to $C_{20}$ aryl group or a $C_2$ to $C_{20}$ heteroaryl group; a substituted or unsubstituted $C_{10}$ to $C_{20}$ aryl group; or a substituted or unsubstituted $C_2$ to $C_{20}$ heteroaryl group.

According to one embodiment of the present specification, R3 is a phenyl group substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; a $C_{10}$ to $C_{20}$ aryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other; or a $C_2$ to $C_{20}$ heteroaryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of deuterium, a $C_1$ to $C_{10}$ alkyl group, a $C_6$ to $C_{20}$ aryl group and a $C_2$ to $C_{20}$ heteroaryl group are linked to each other.

According to one embodiment of the present specification, R7 is hydrogen or deuterium.

According to one embodiment of the present specification, d is 3.

In one embodiment of the present disclosure, the compound of Chemical Formula 1 comprises at least one deuterium. When the compound of Chemical Formula 1 comprises deuterium, lifetime properties of a device are particularly enhanced. In one embodiment, lifetime properties of a device can be enhanced by 15% or greater when the compound of Chemical Formula 1 includes deuterium compared to compounds that do not include deuterium.

In one embodiment of the present disclosure, the compound of Chemical Formula 1 is any one selected from among the following compounds:

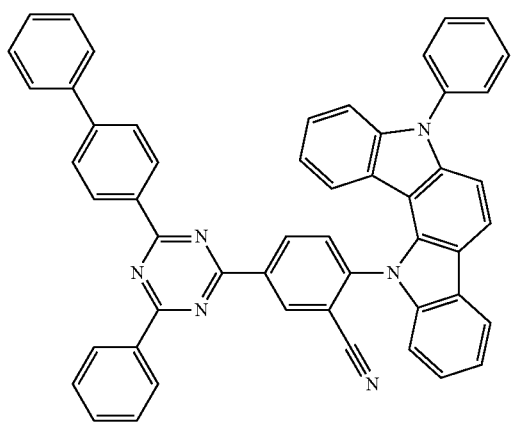
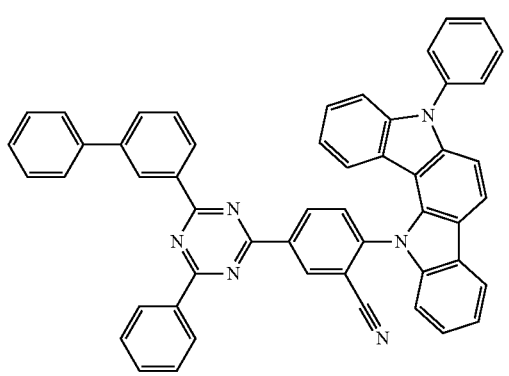
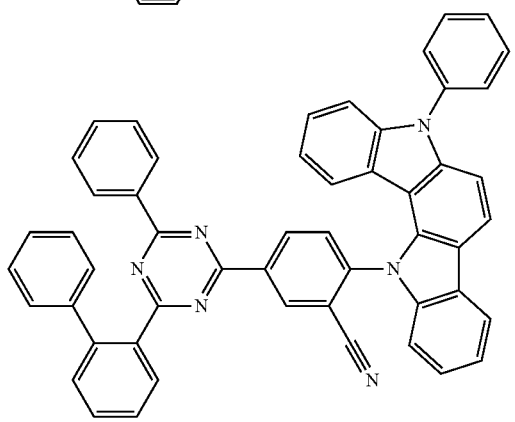
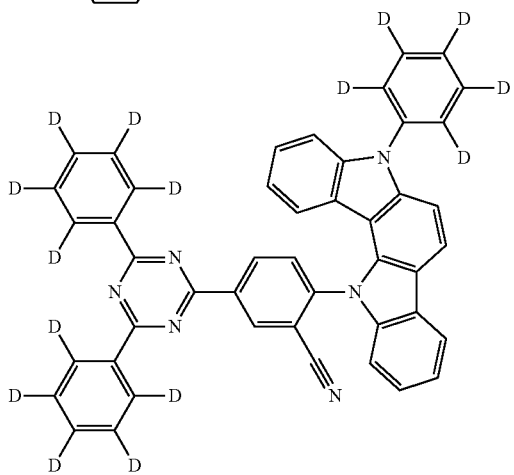
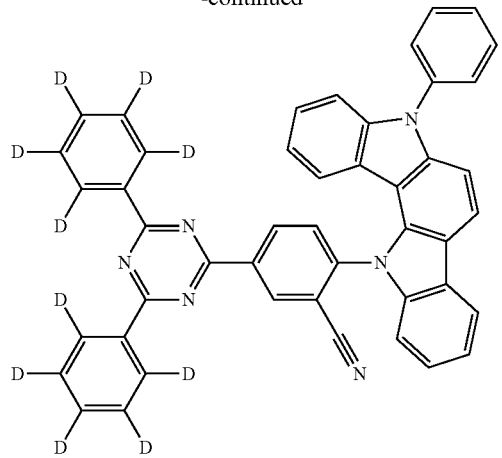
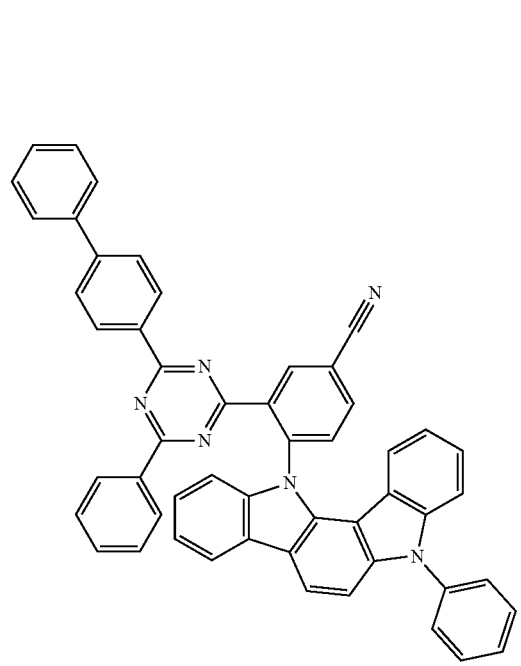
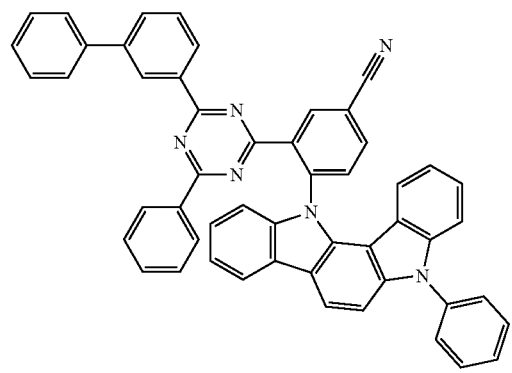

17
-continued
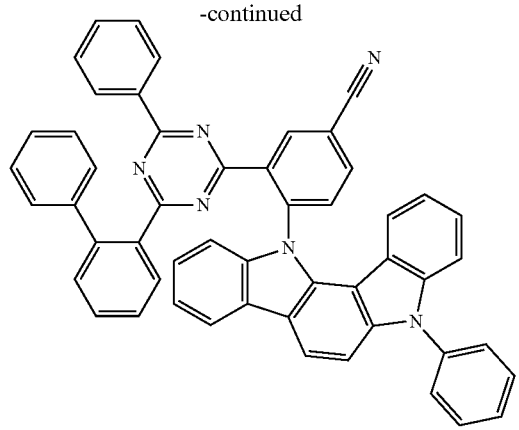
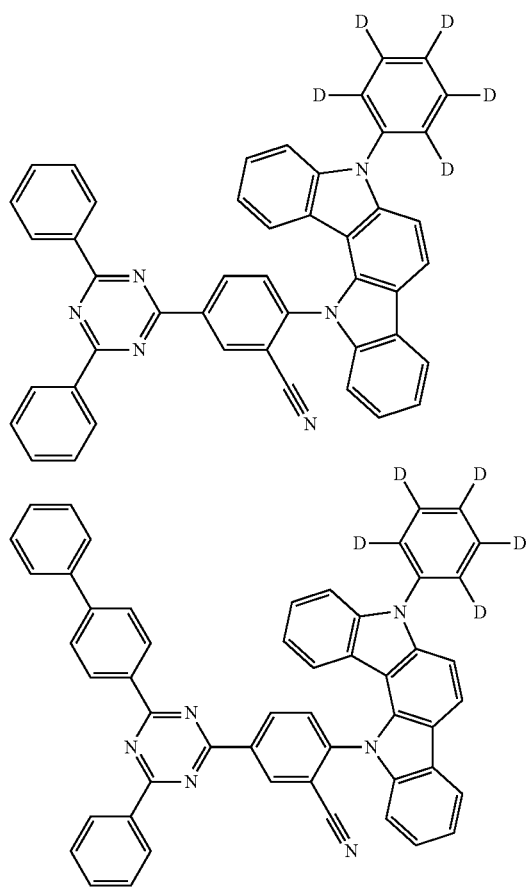
18
-continued
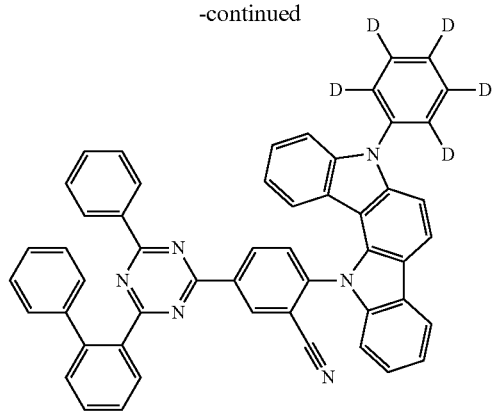
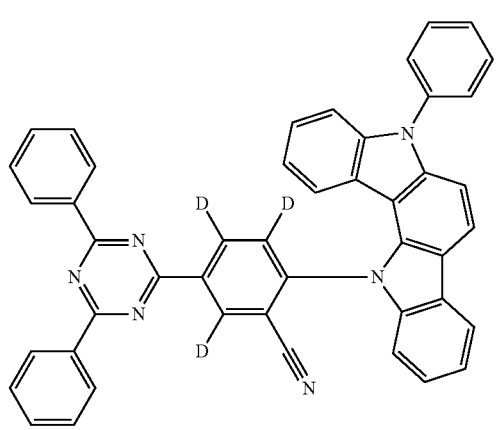
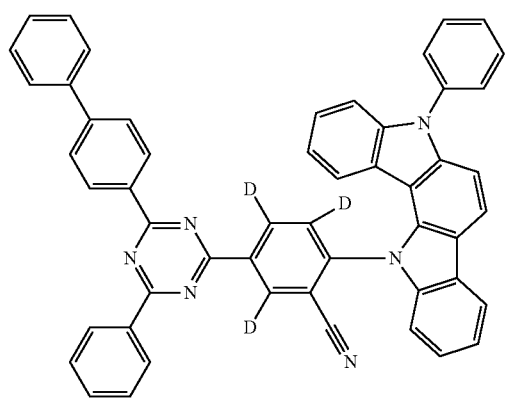
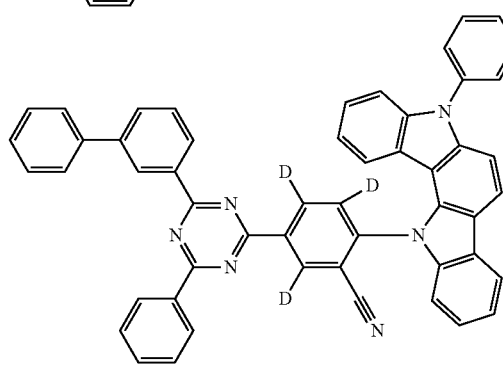

19
-continued
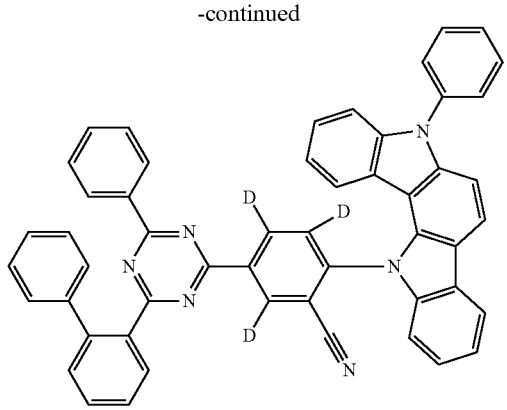
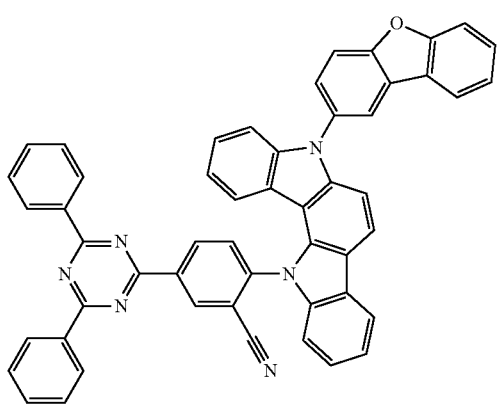
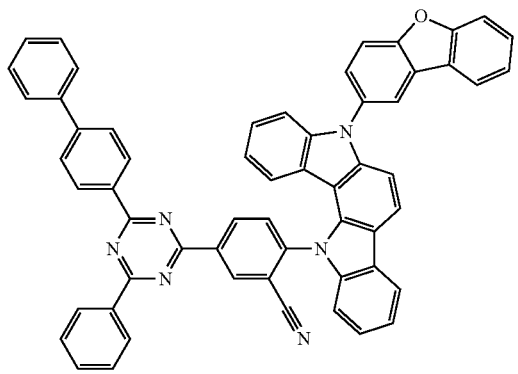
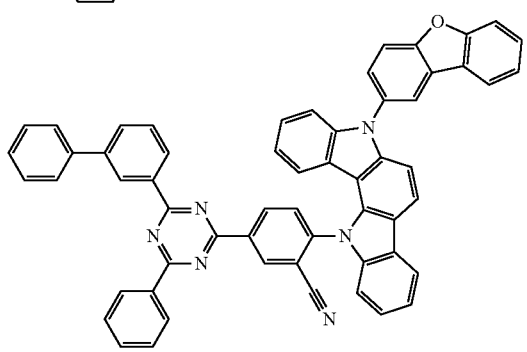
20
-continued
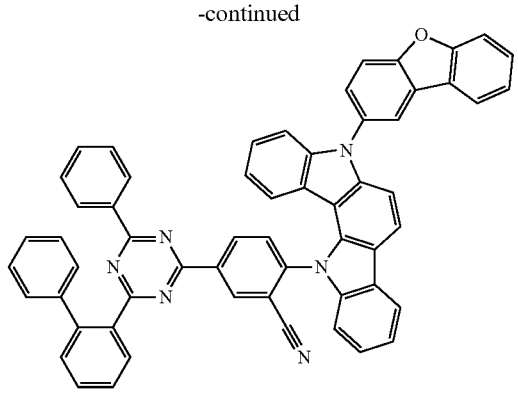
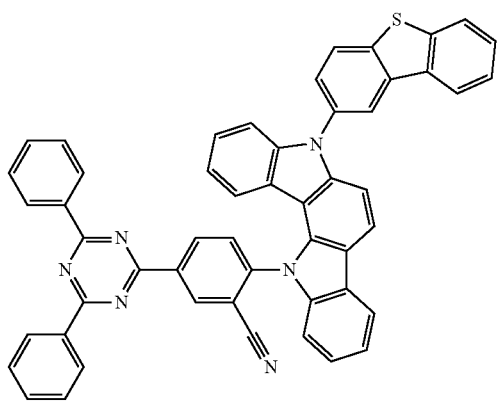
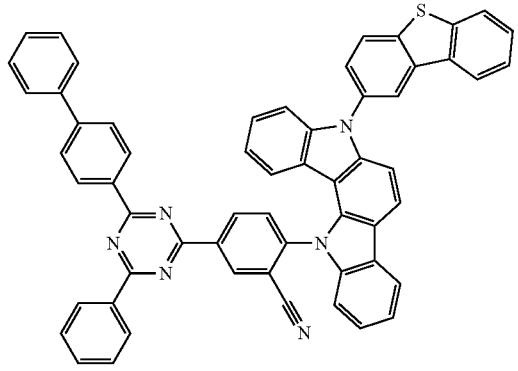
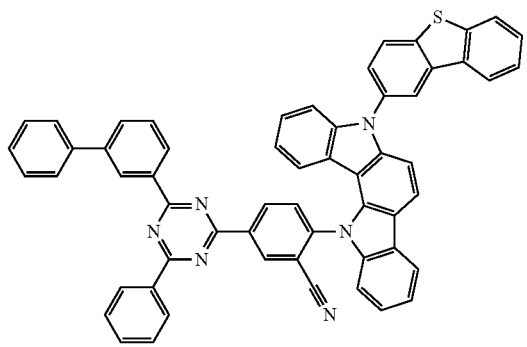

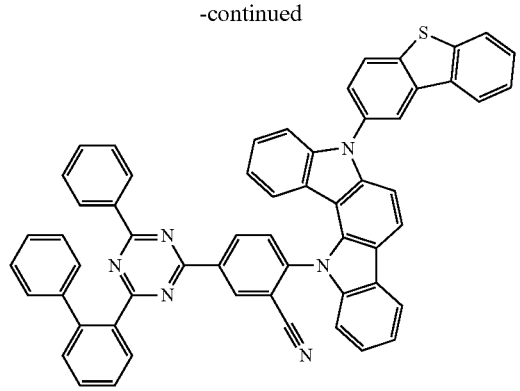
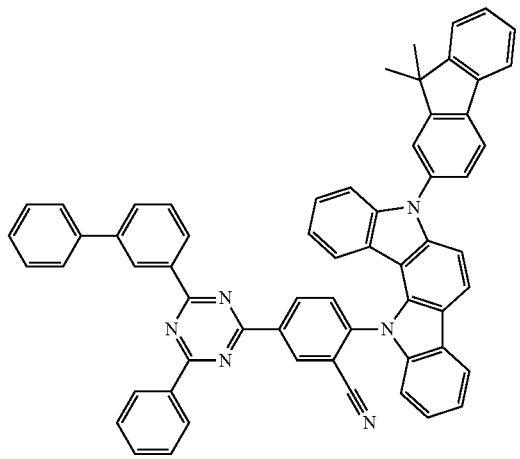
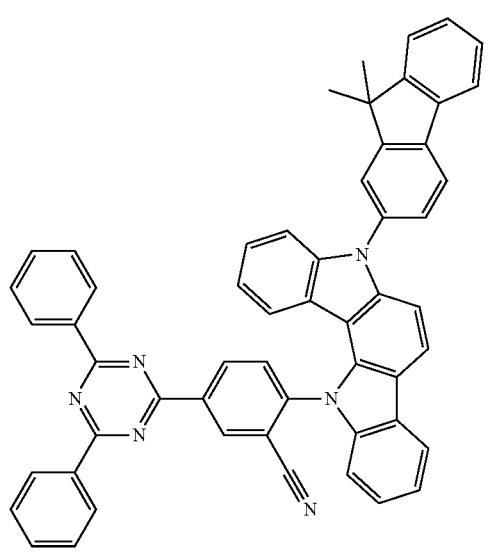
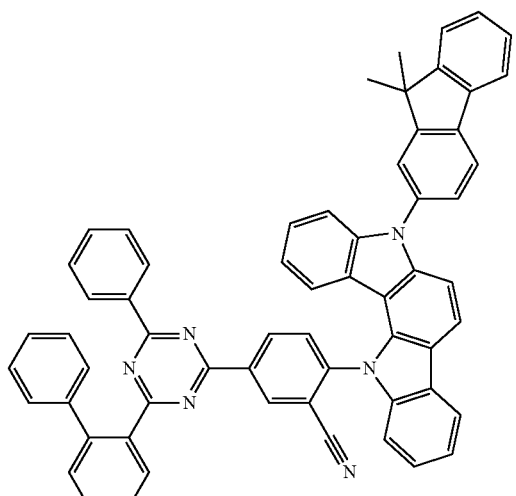
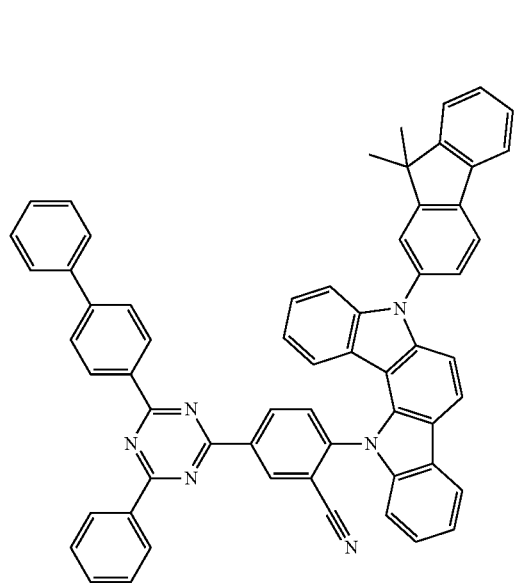
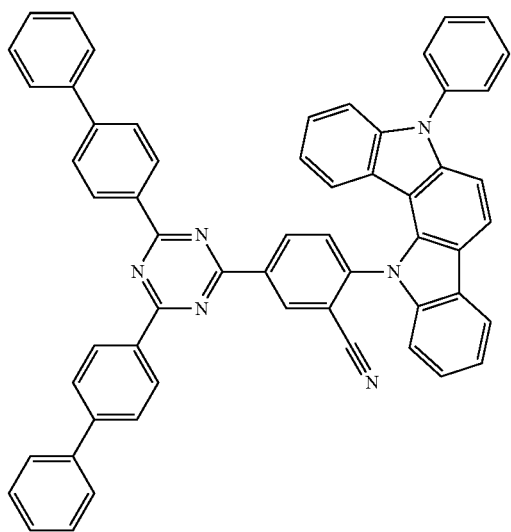

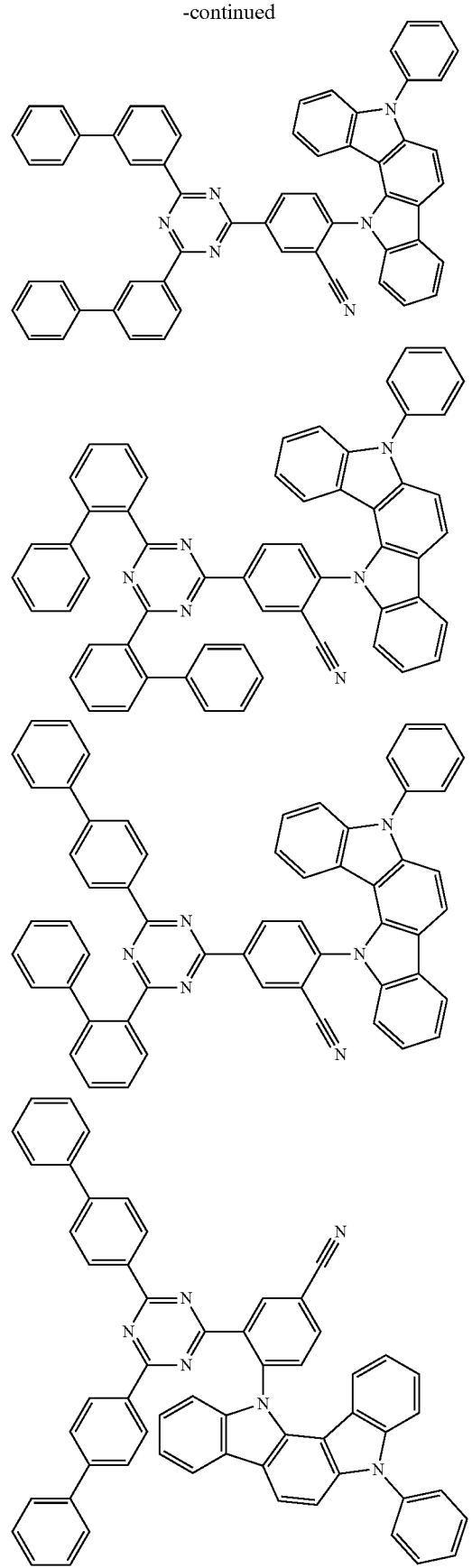
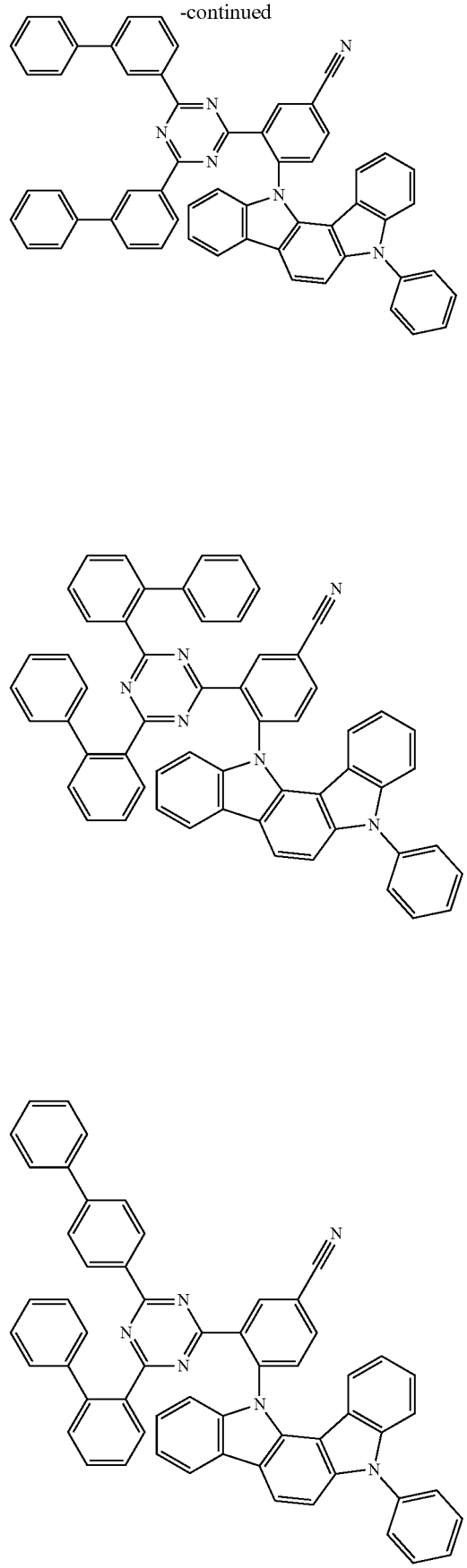

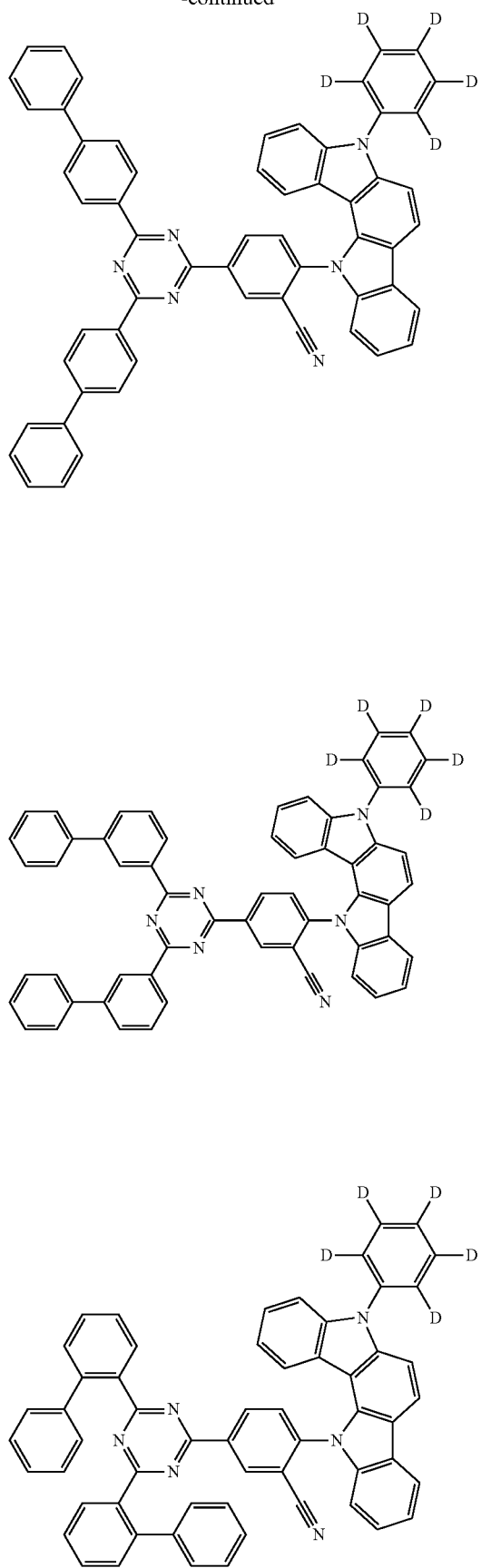
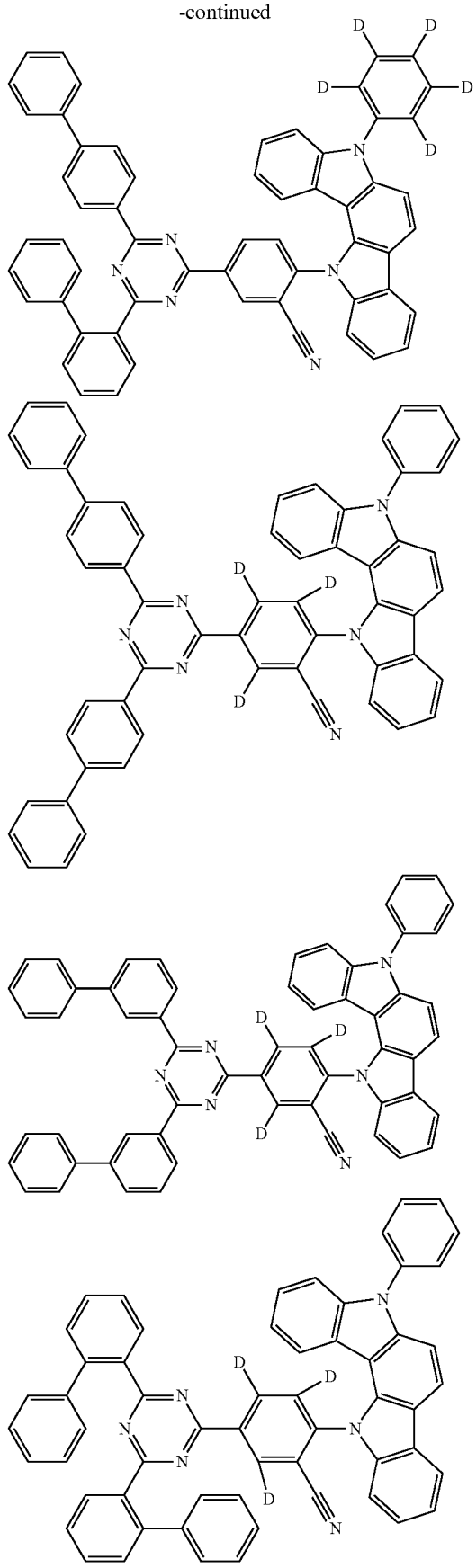

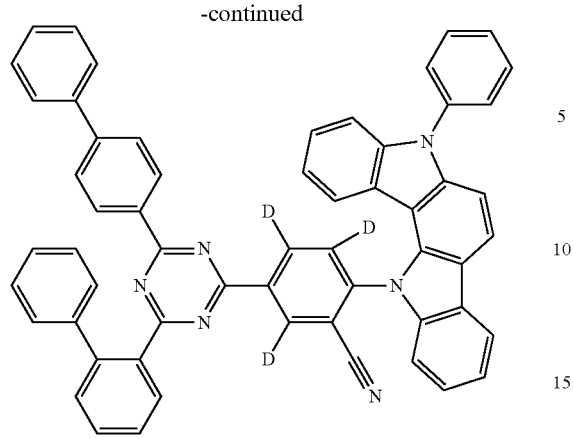
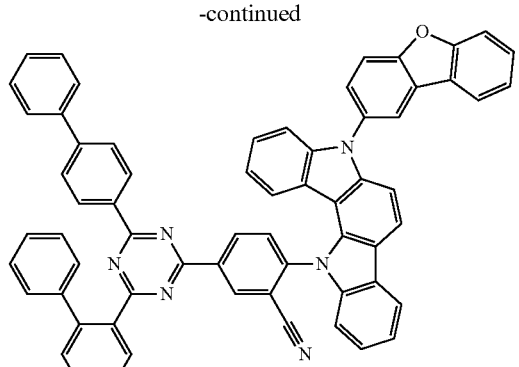
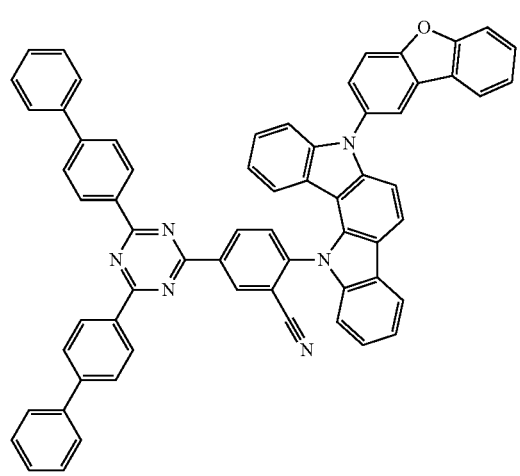
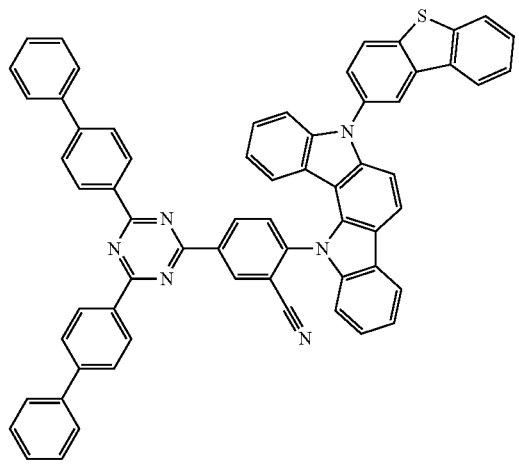
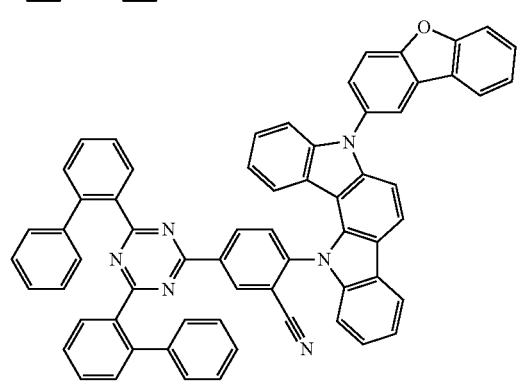
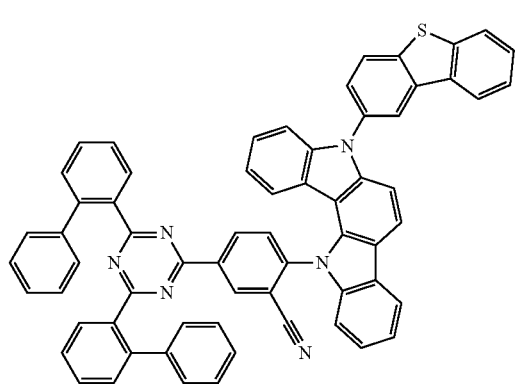

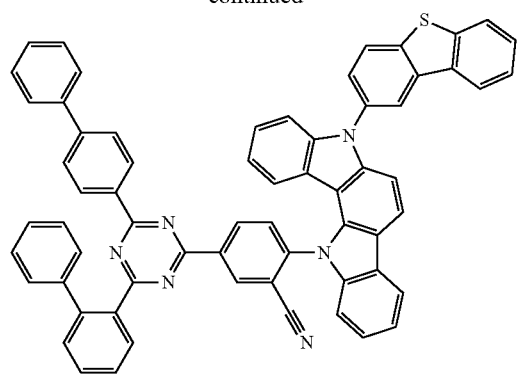
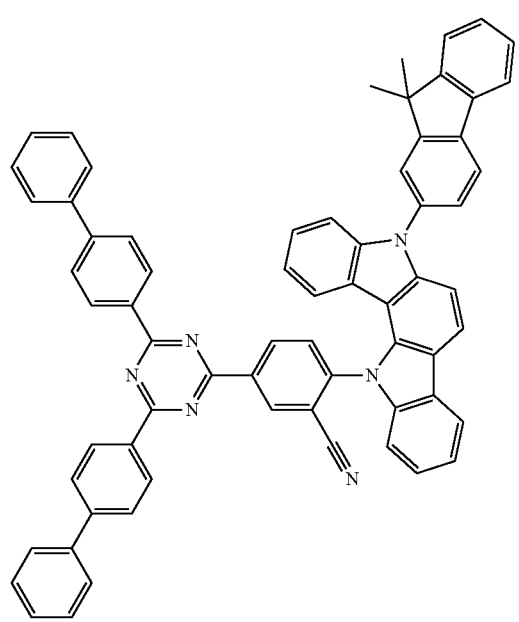

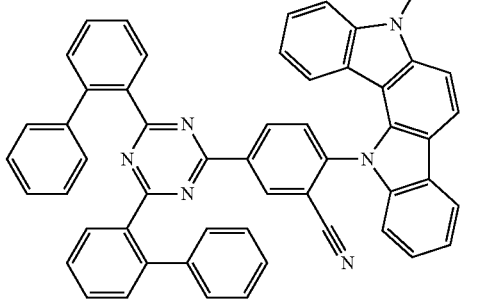
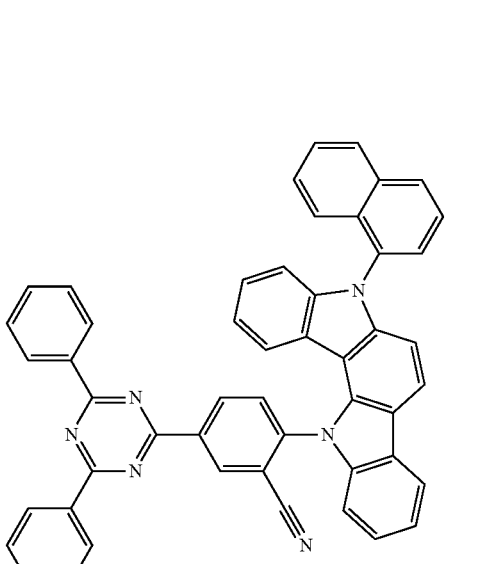
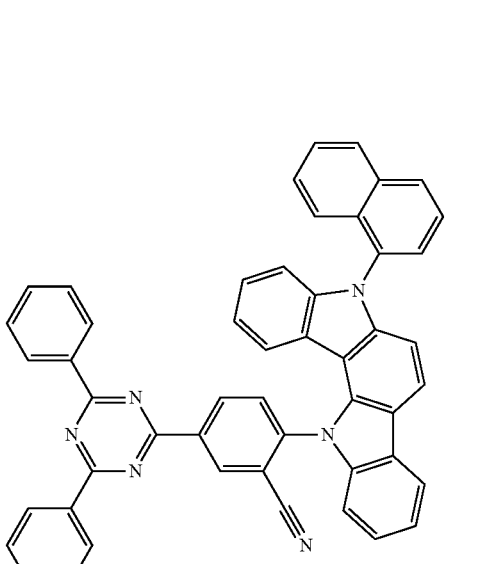

31
-continued
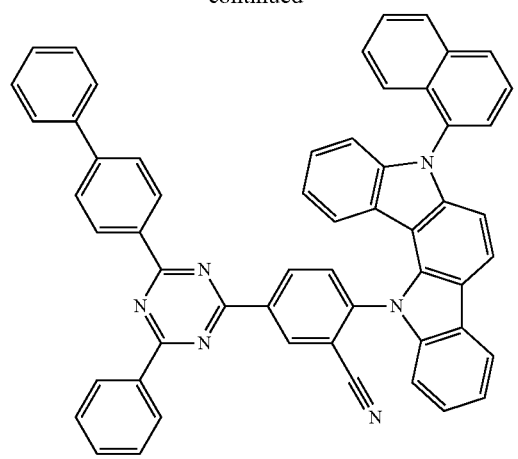
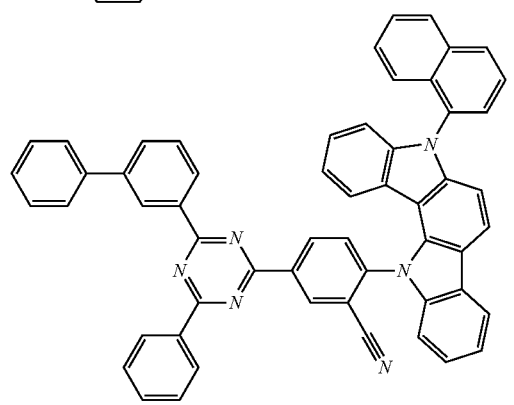
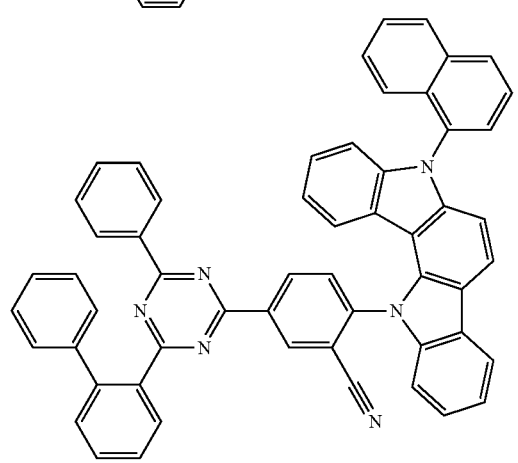
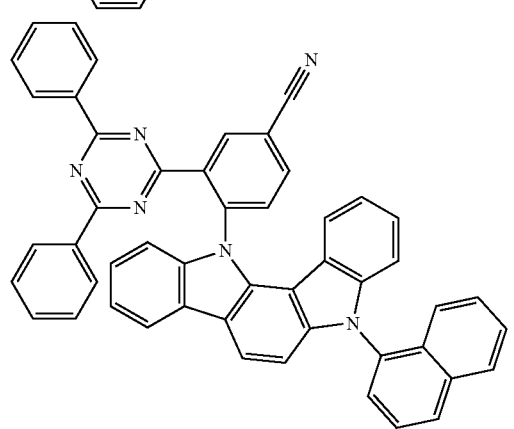
32
-continued
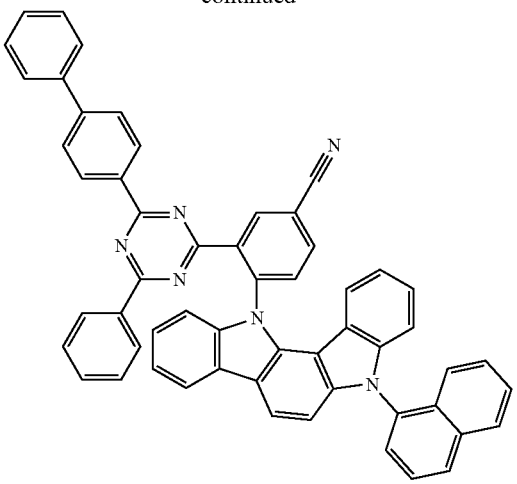
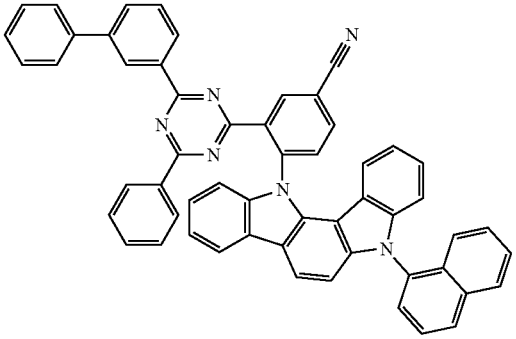
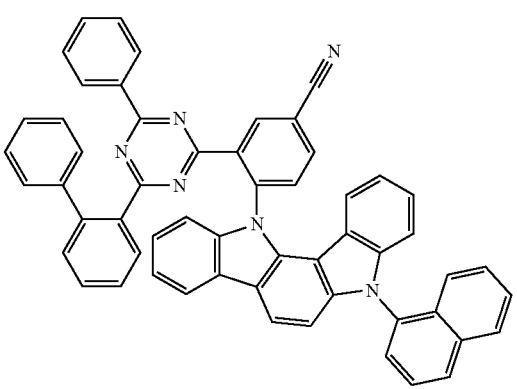

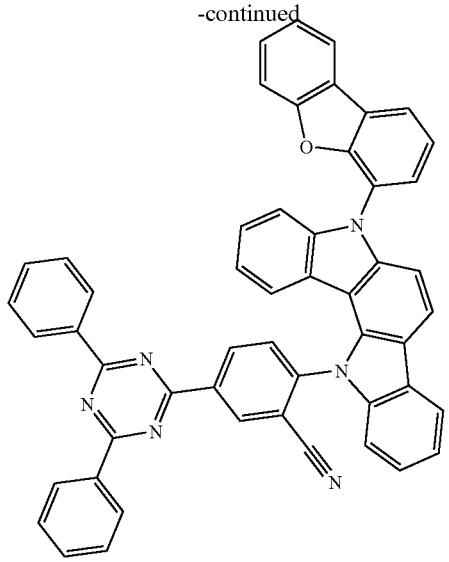
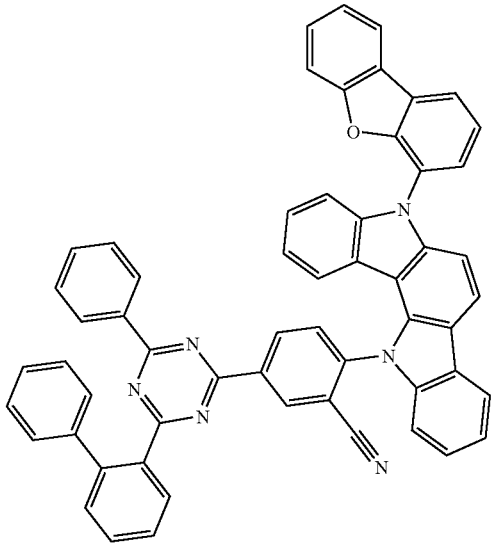
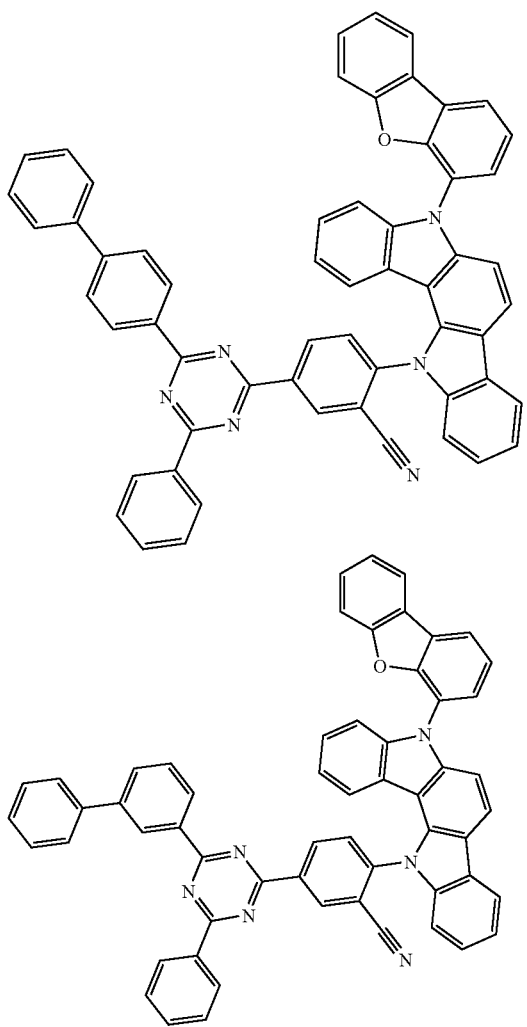
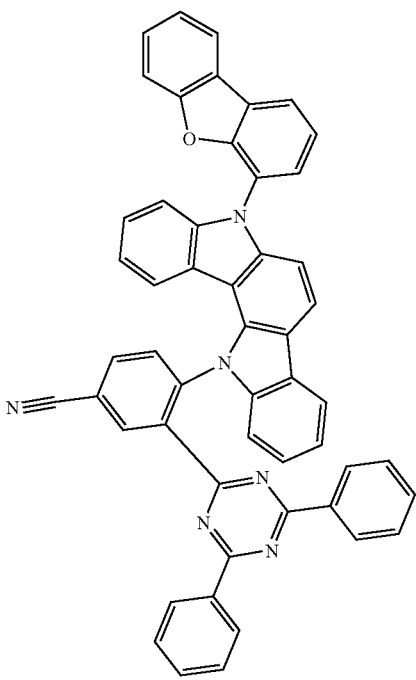

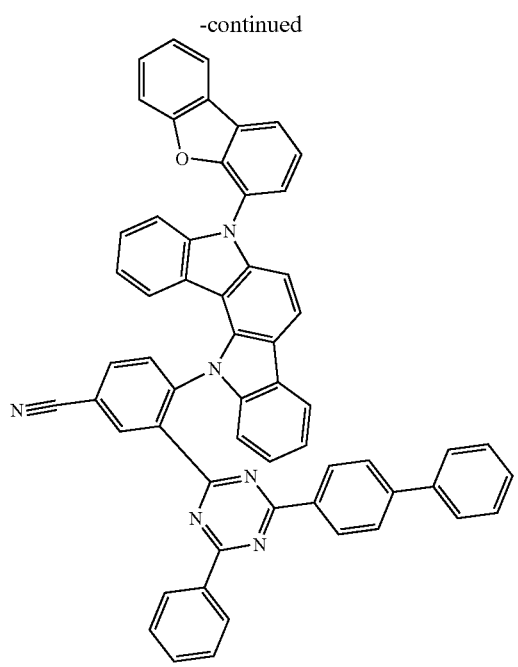
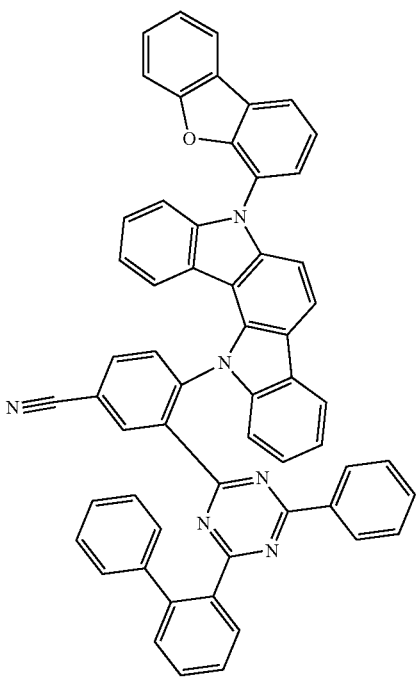

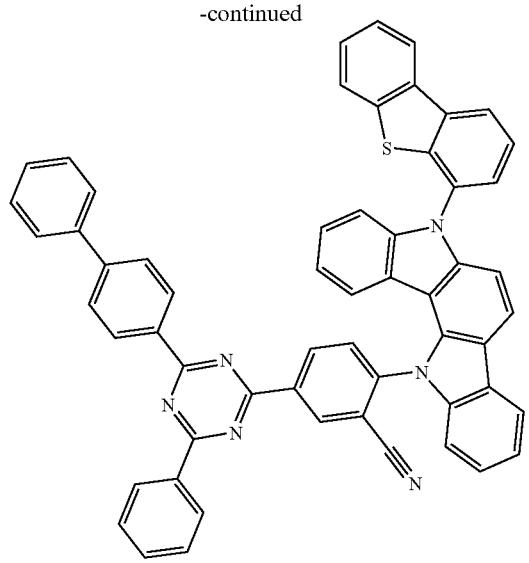
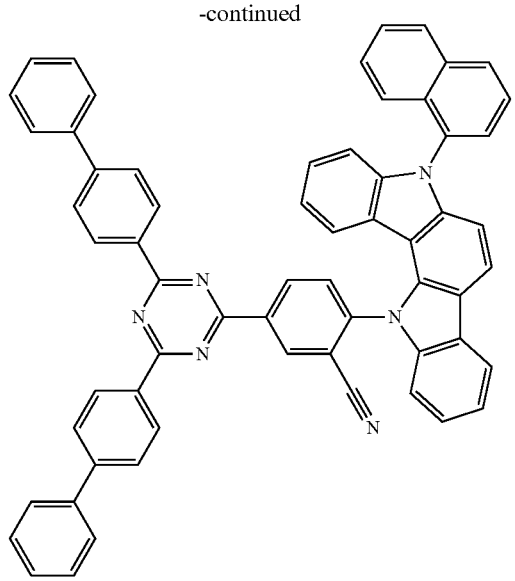
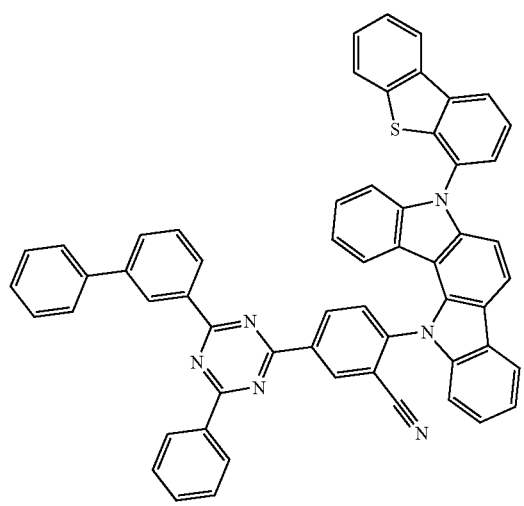
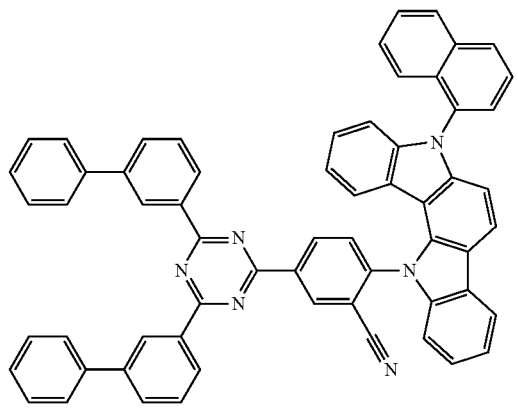
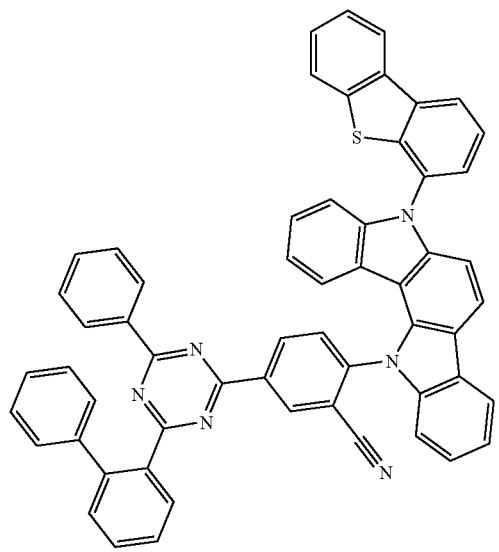
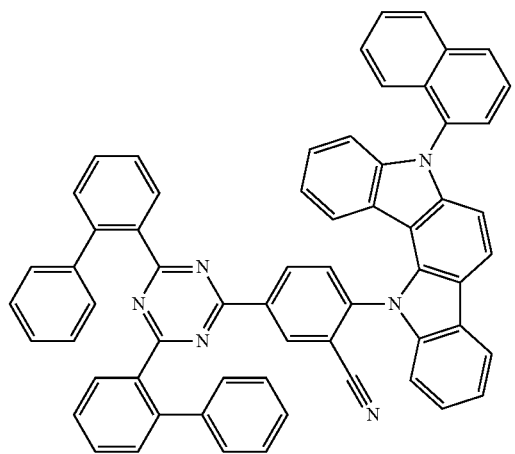

-continued
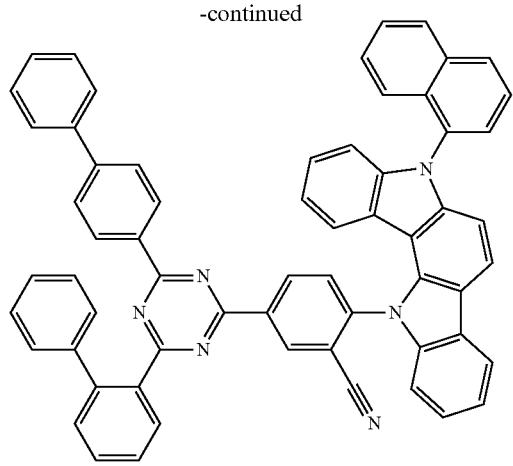
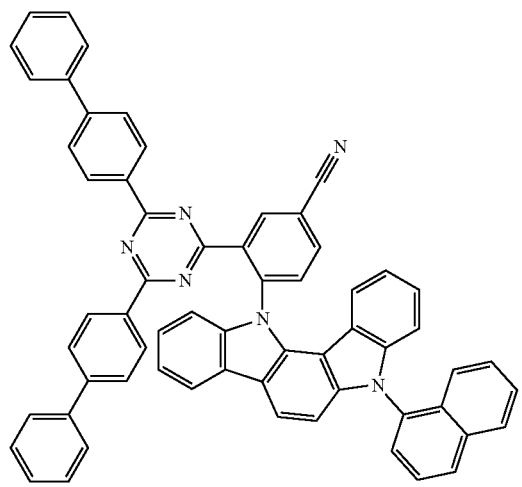
-continued
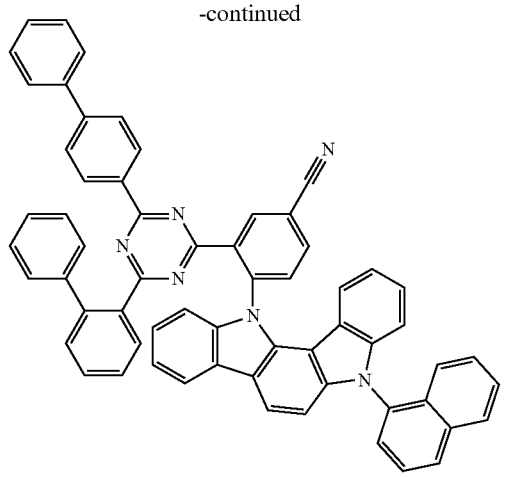
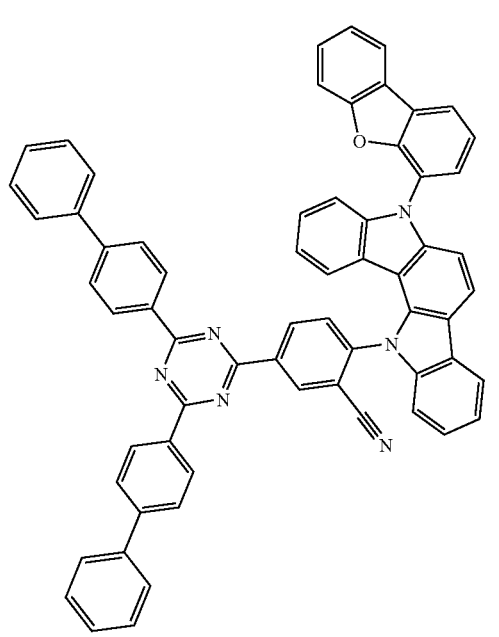
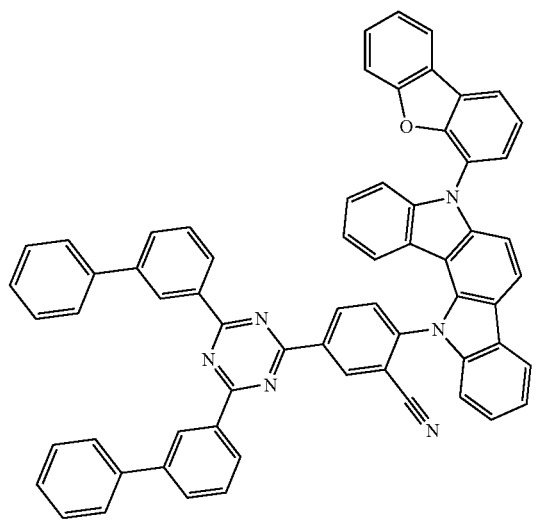

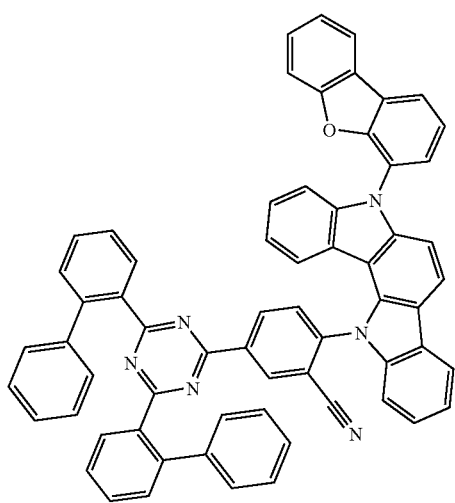
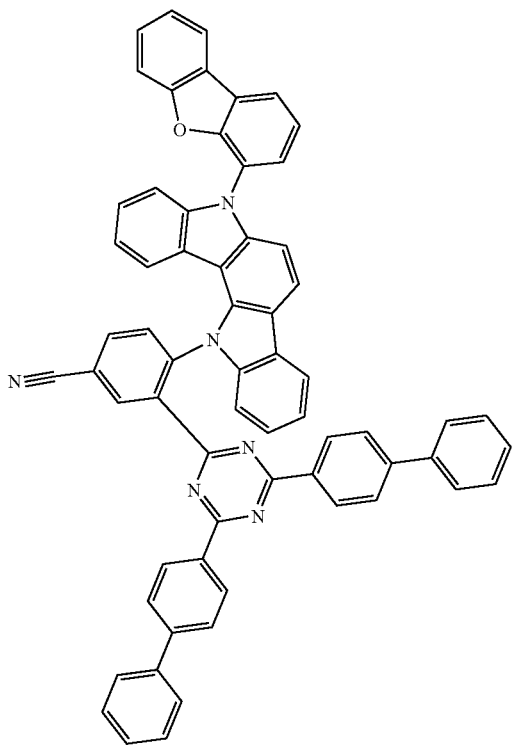
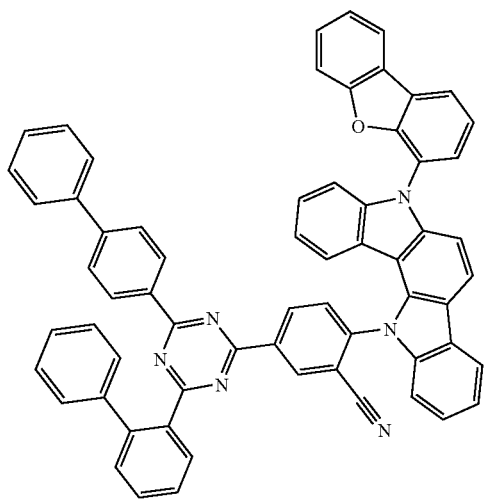
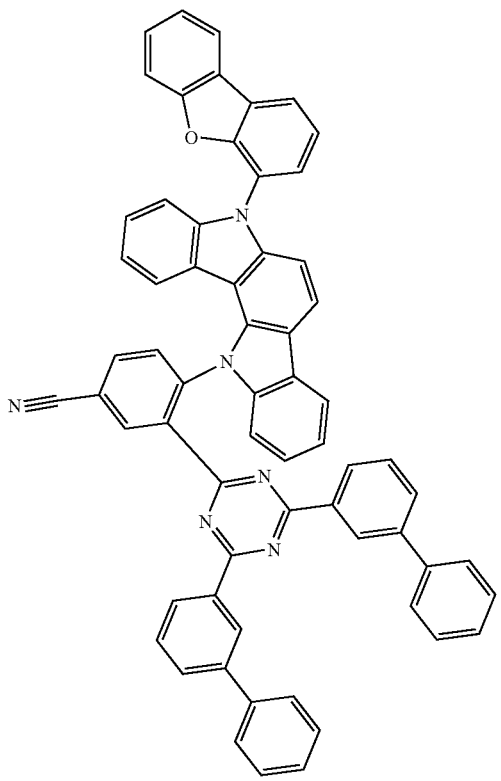

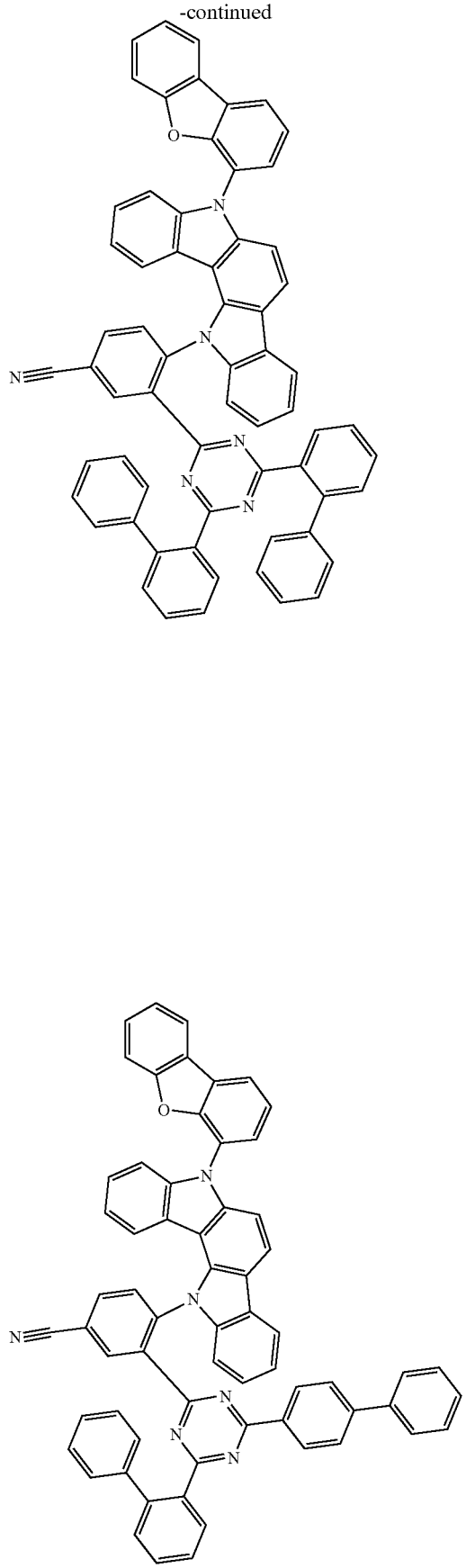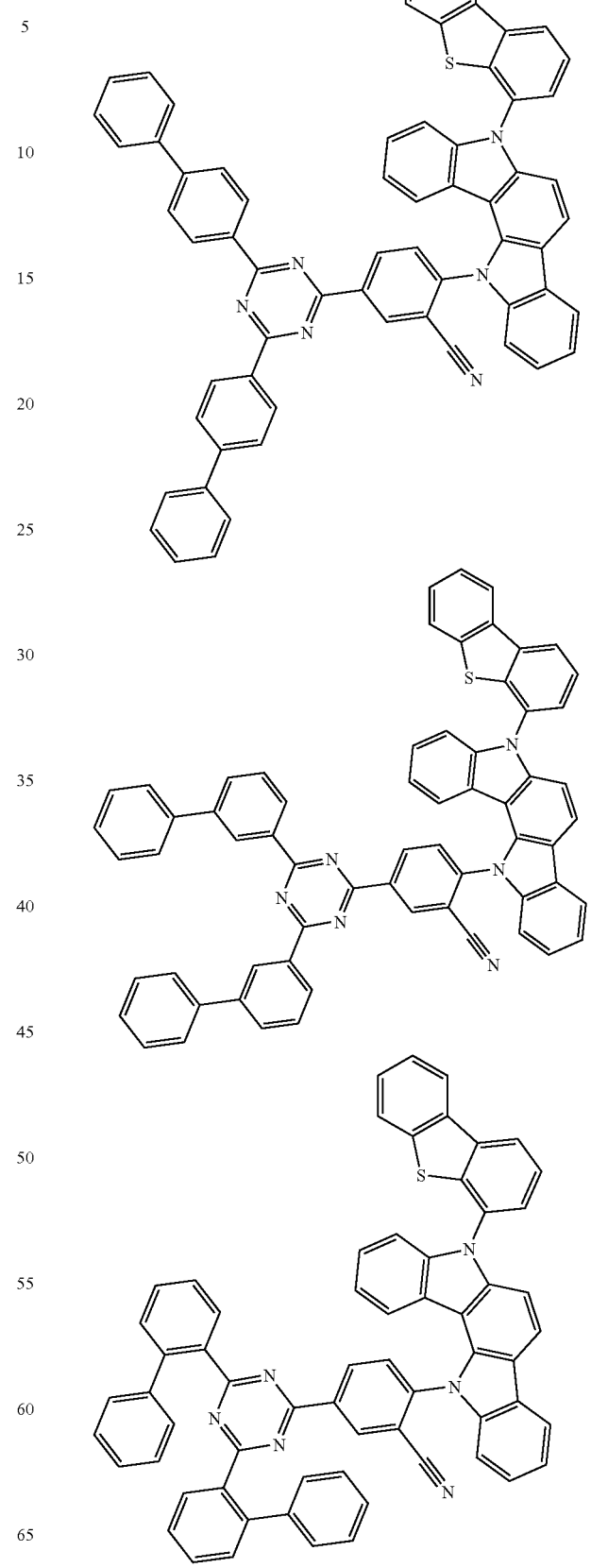

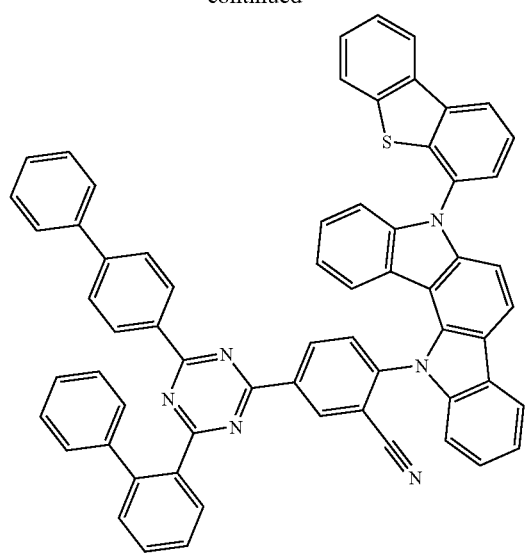
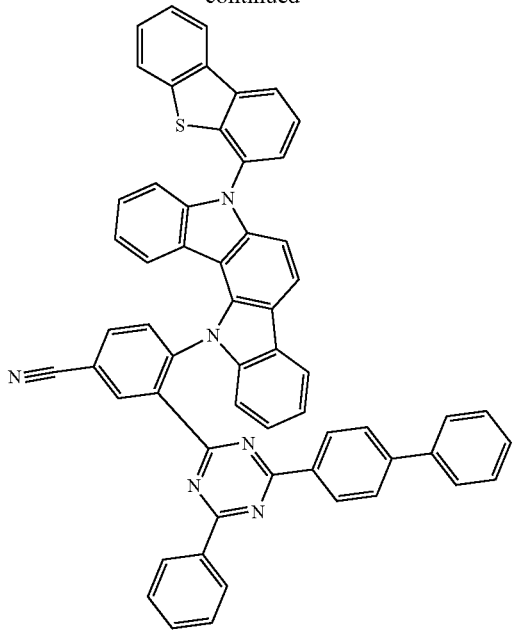
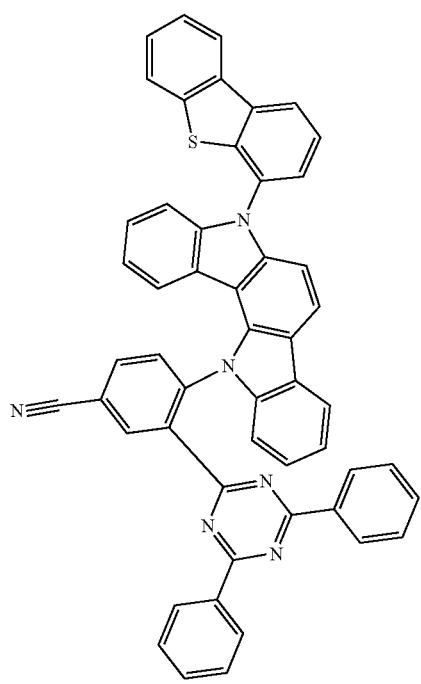
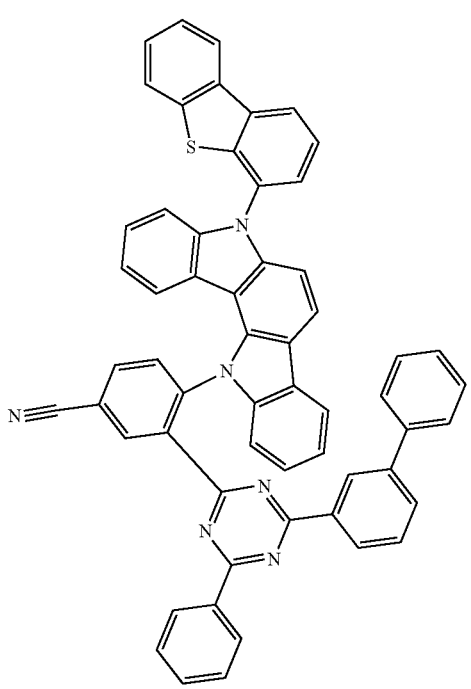

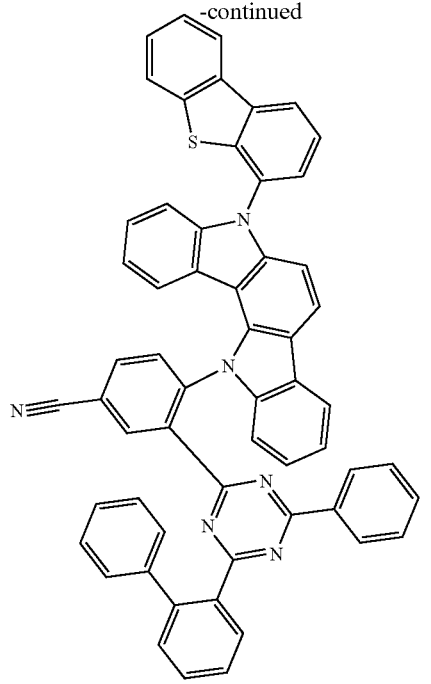
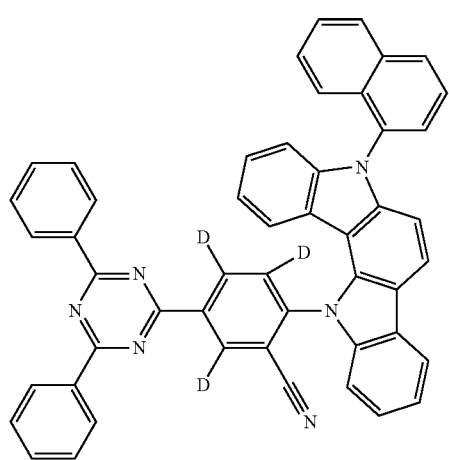
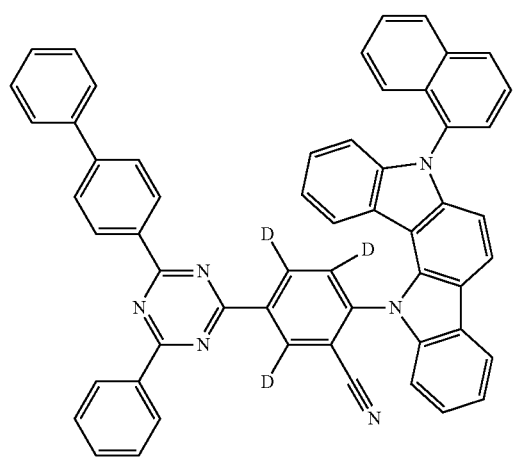
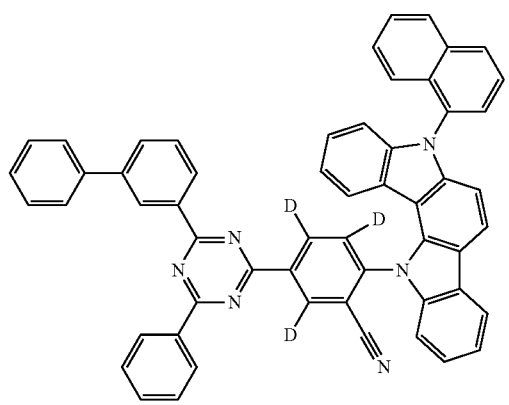
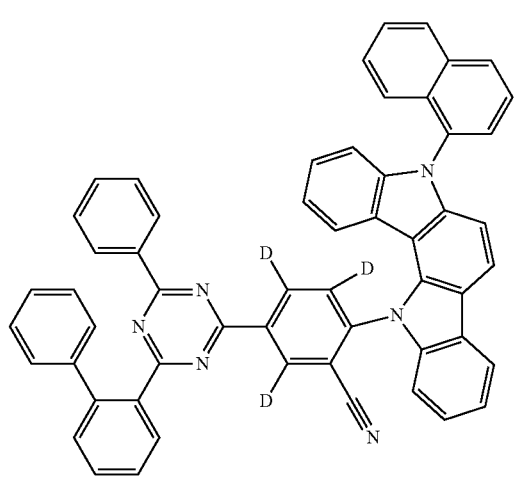
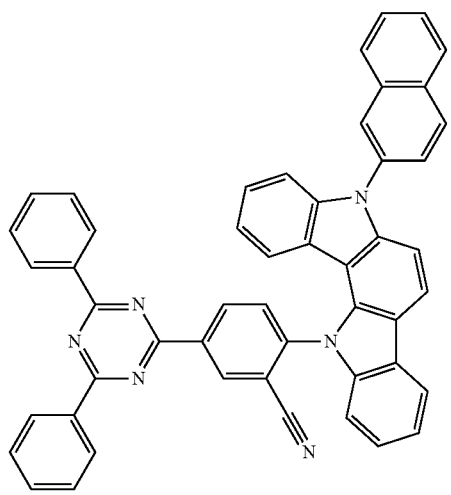

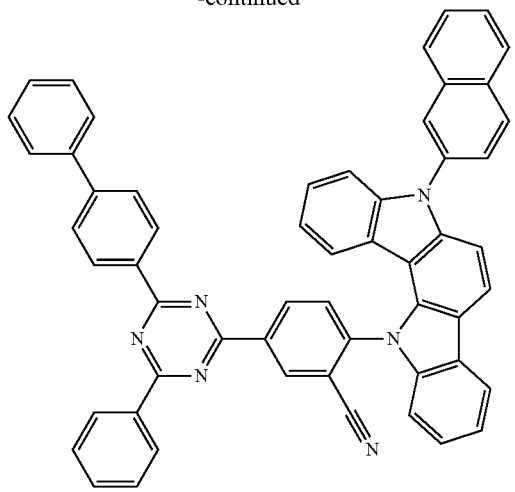
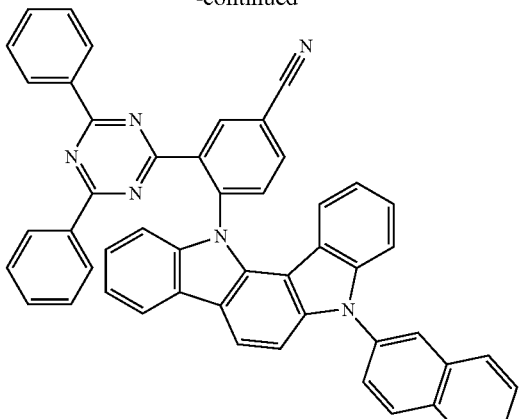

51
-continued
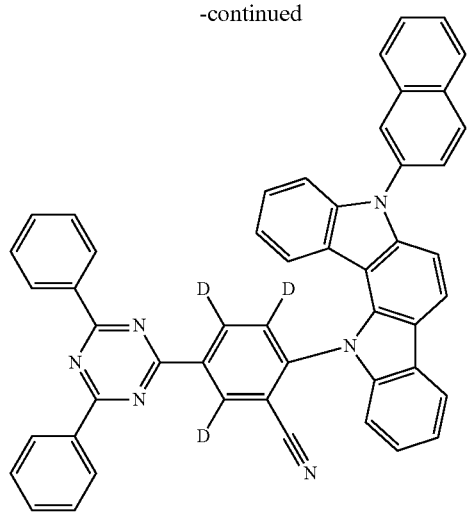
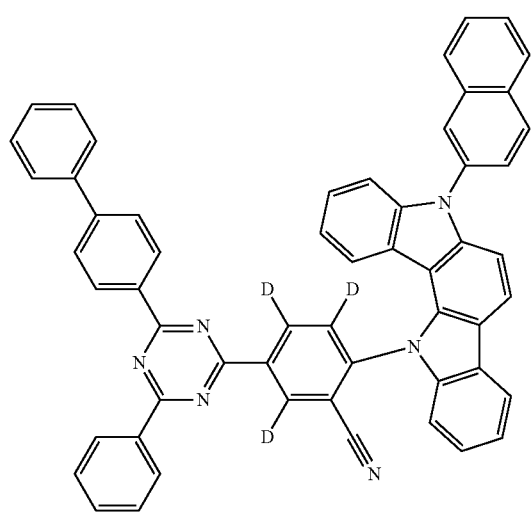
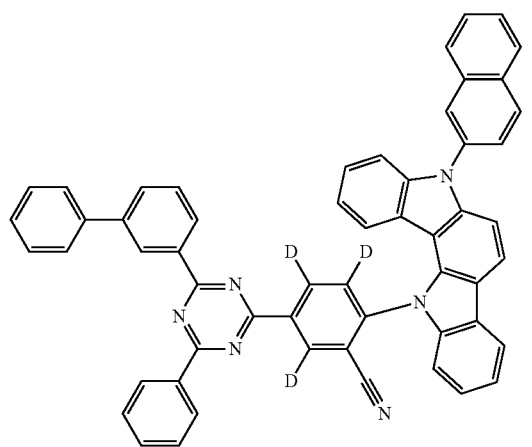
52
-continued
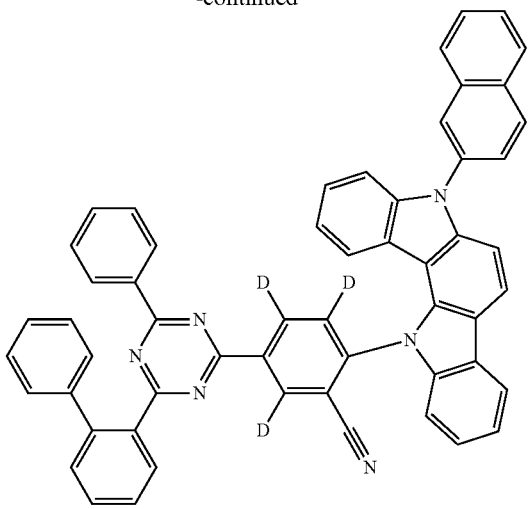
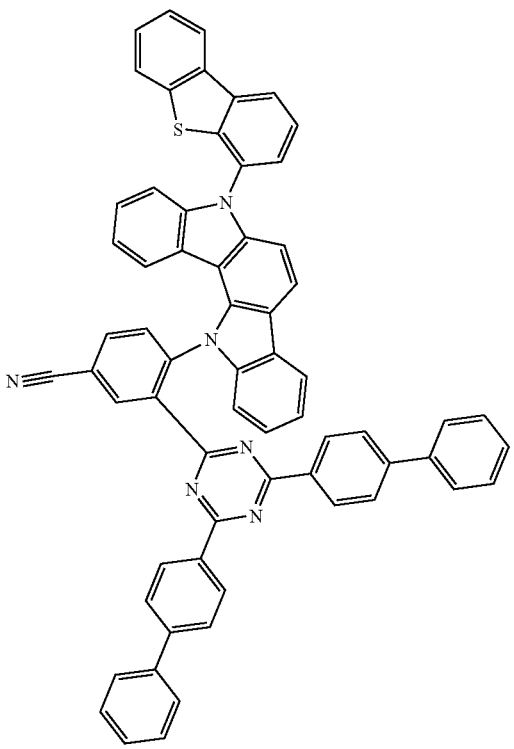

53
-continued
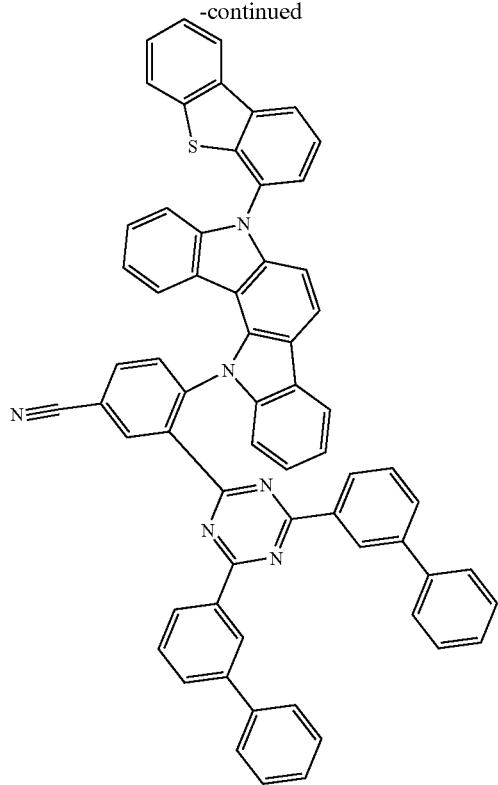
54
-continued
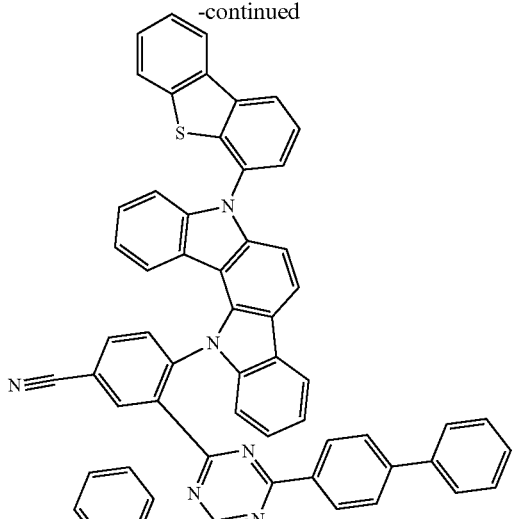
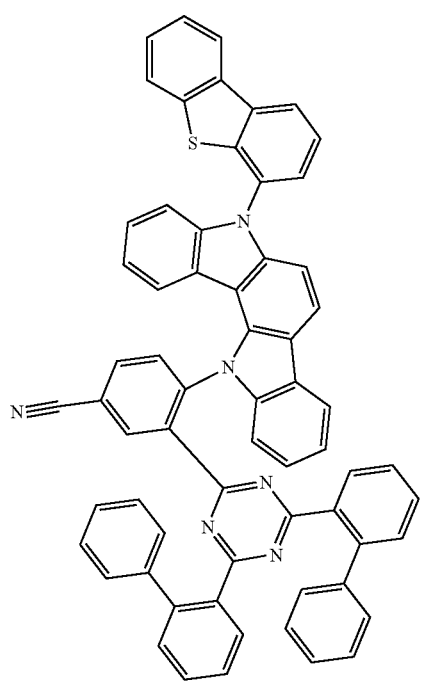
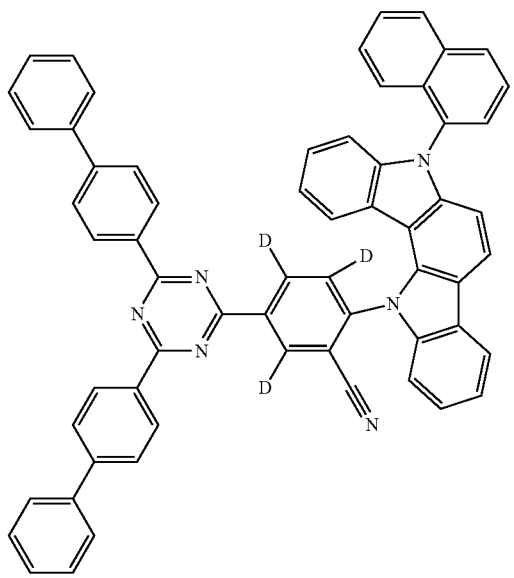
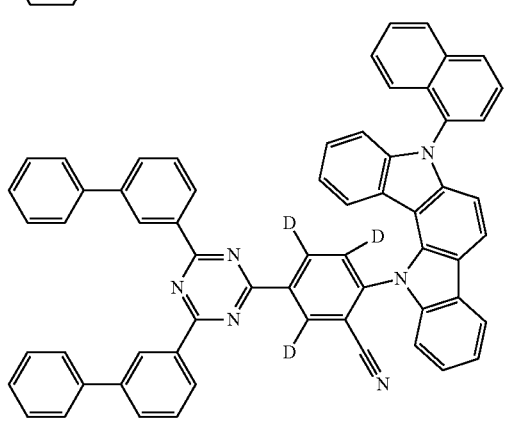

55
-continued
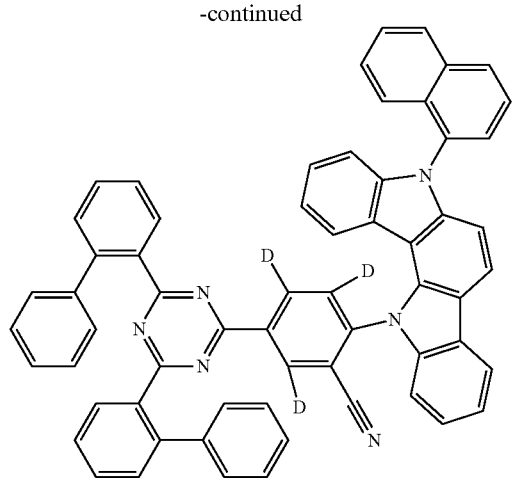
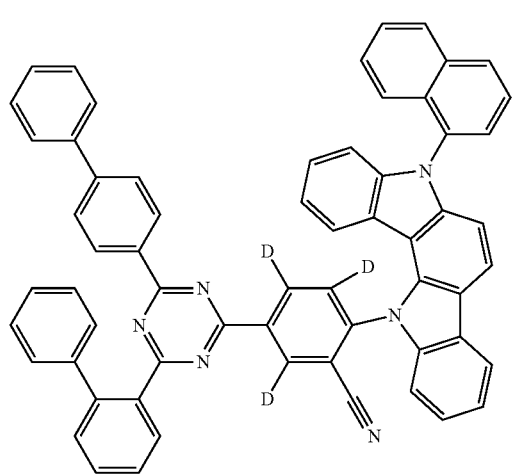
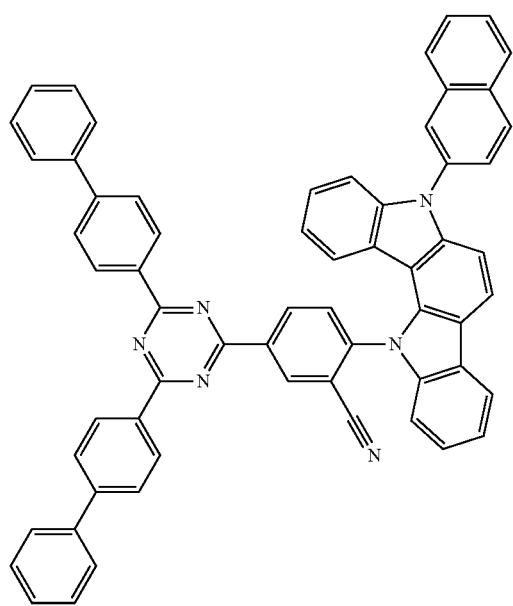
56
-continued
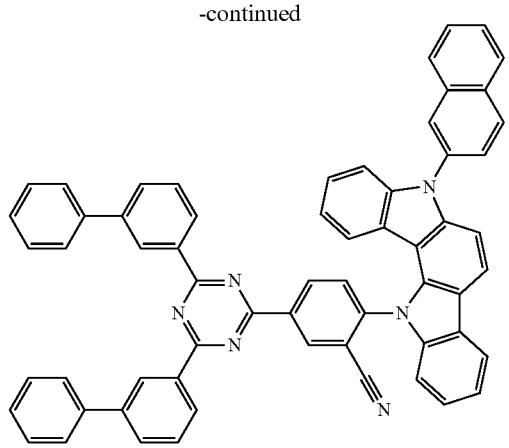
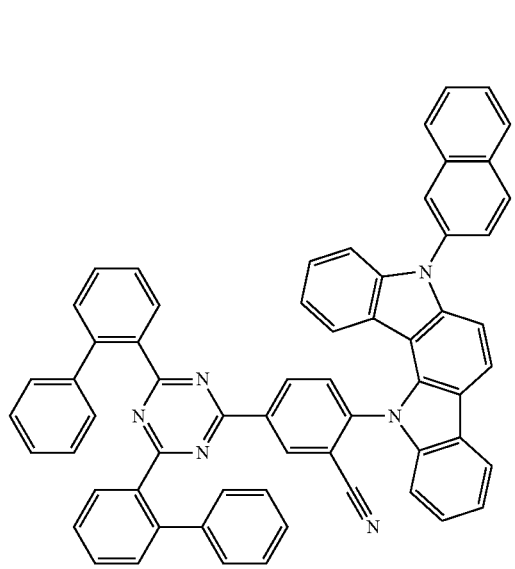
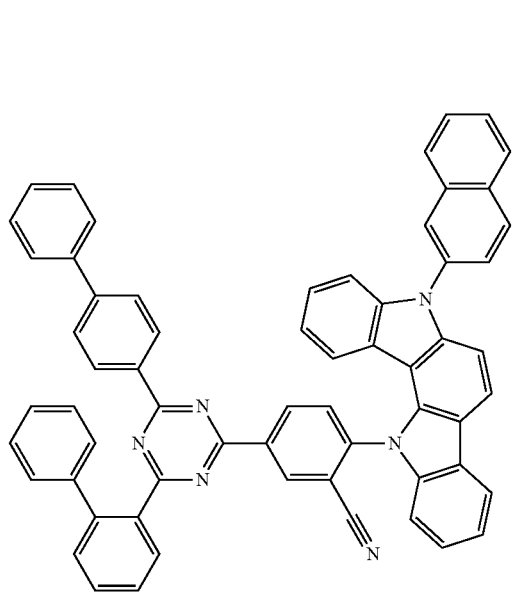

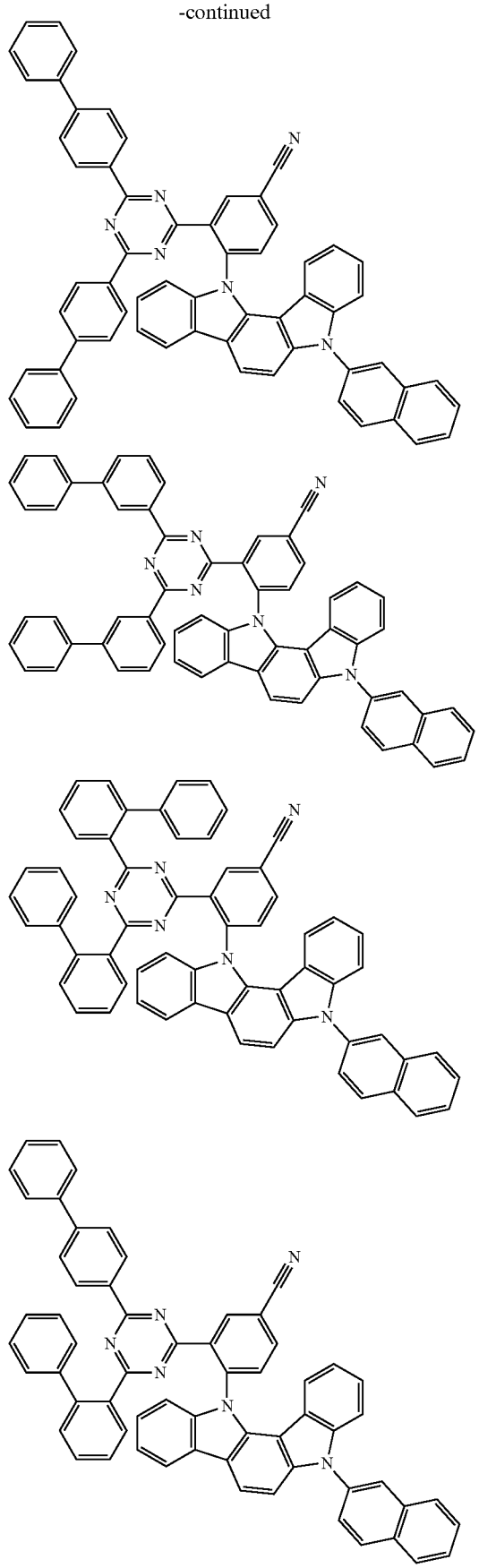
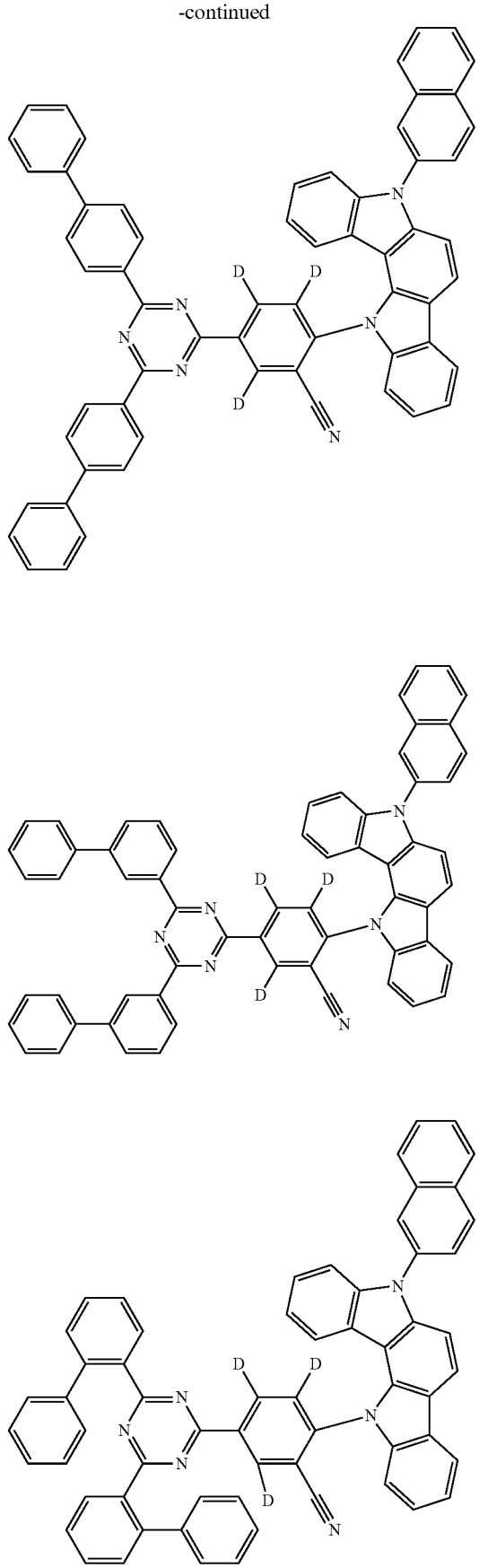

59
-continued
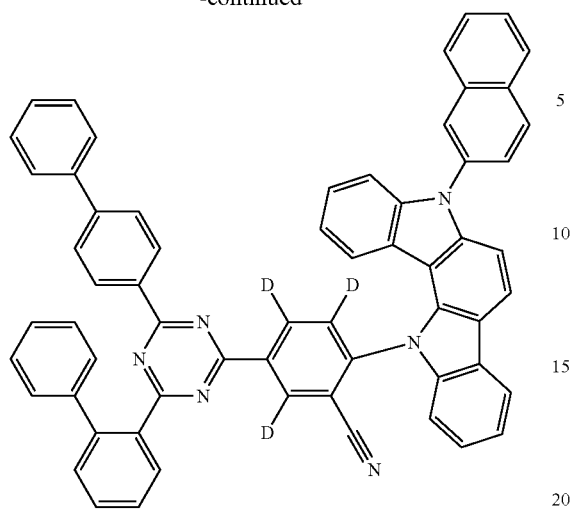
60
-continued
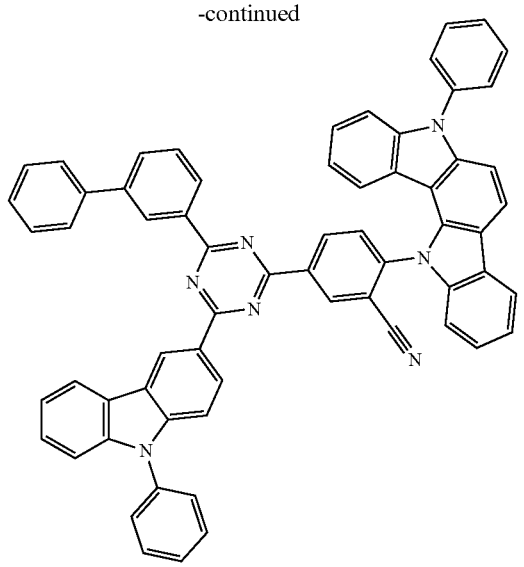
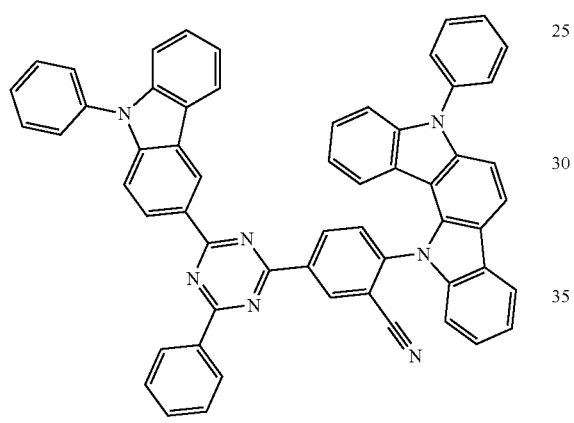
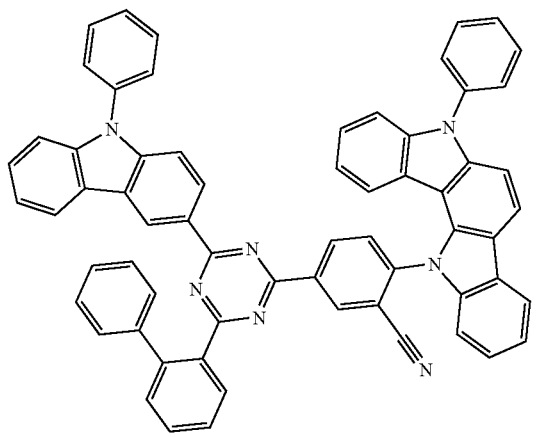
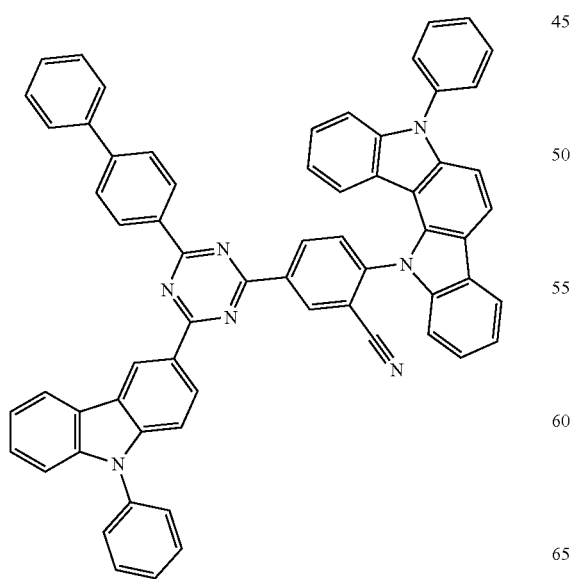
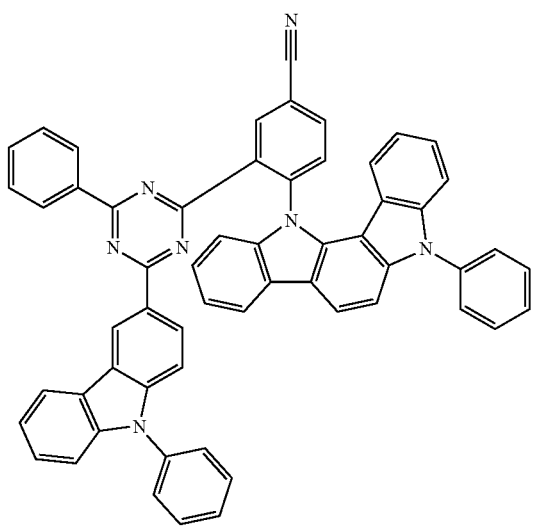

61
-continued
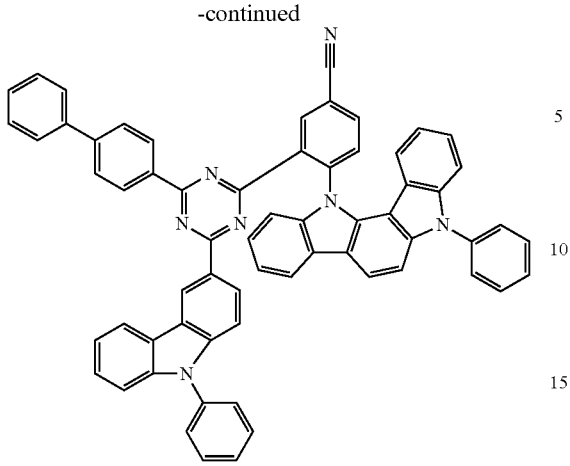
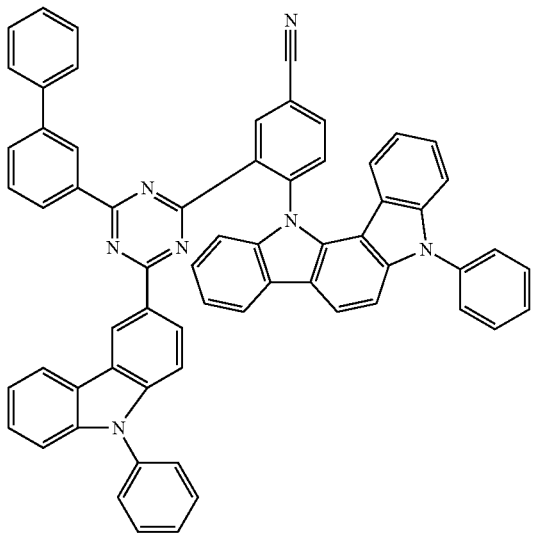
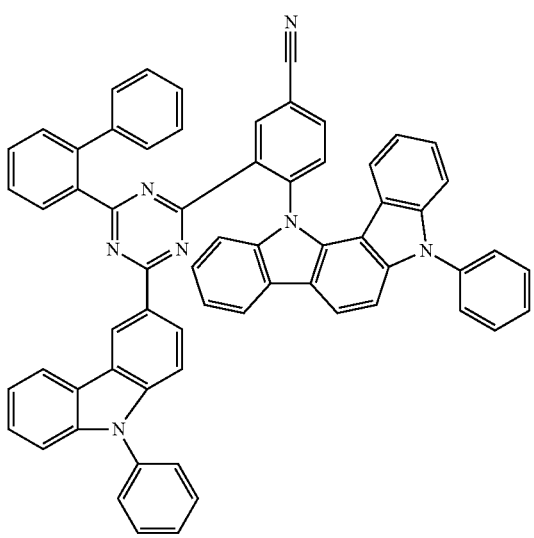
62
-continued
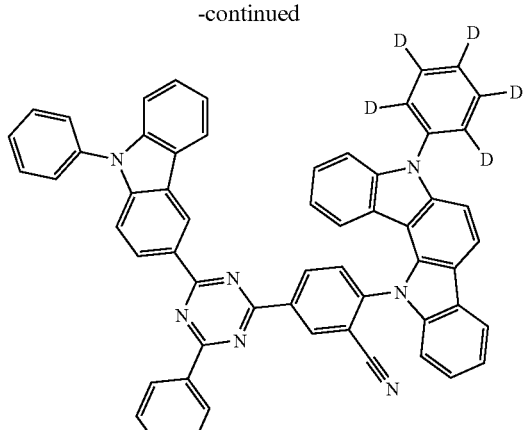
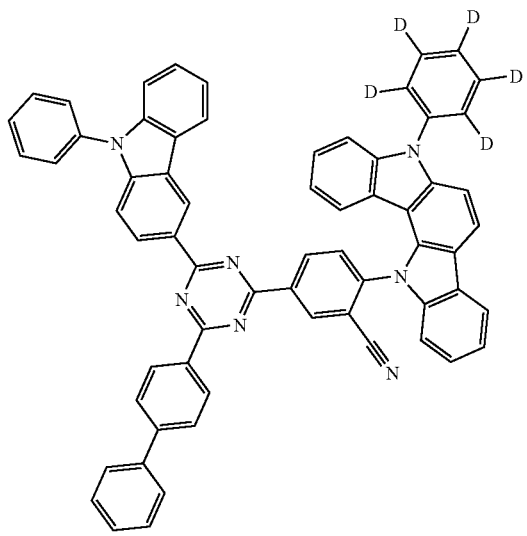
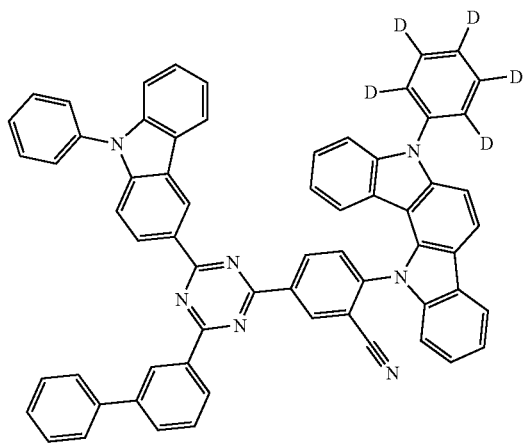

-continued
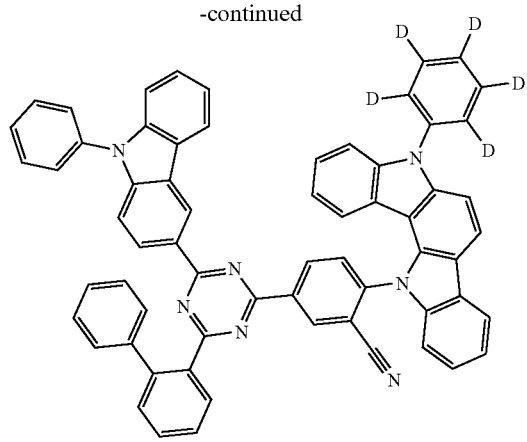
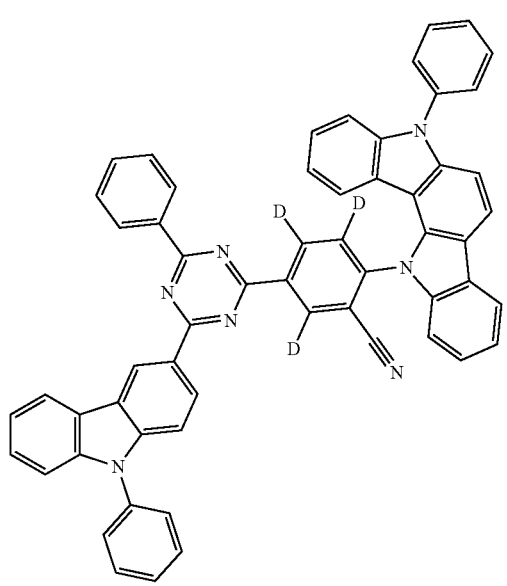
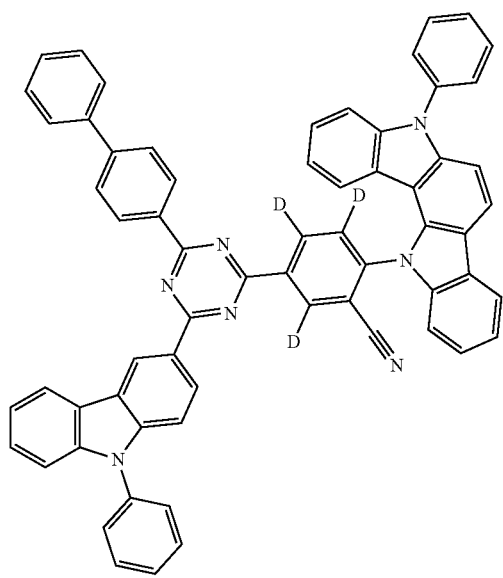
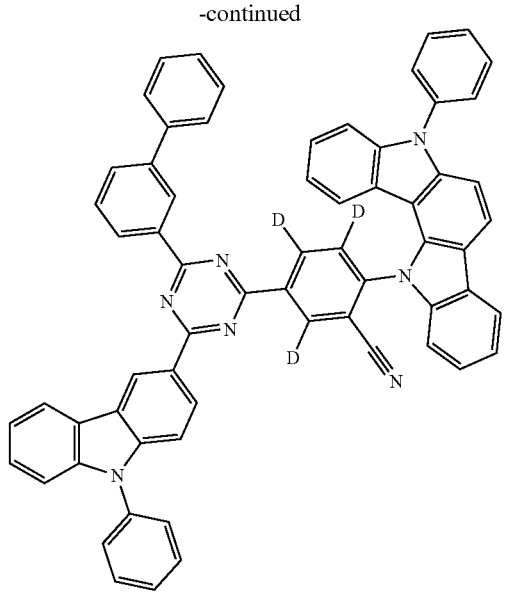
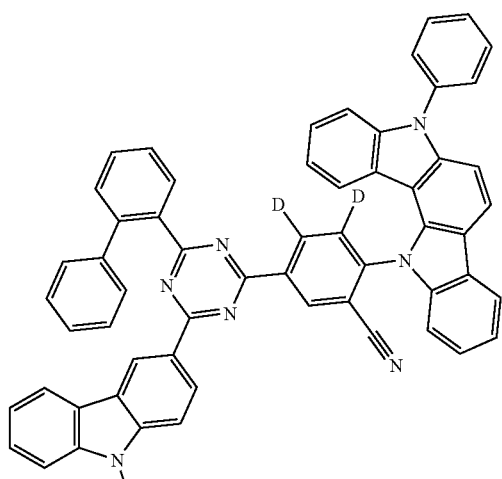
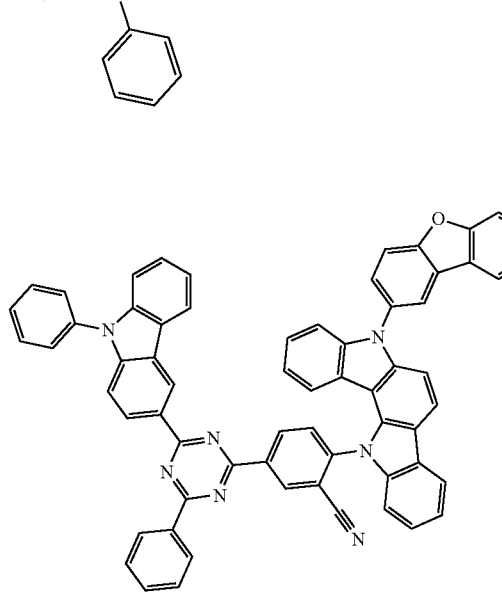

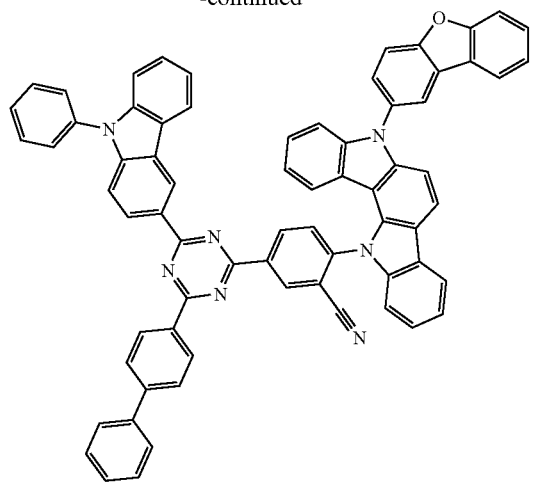
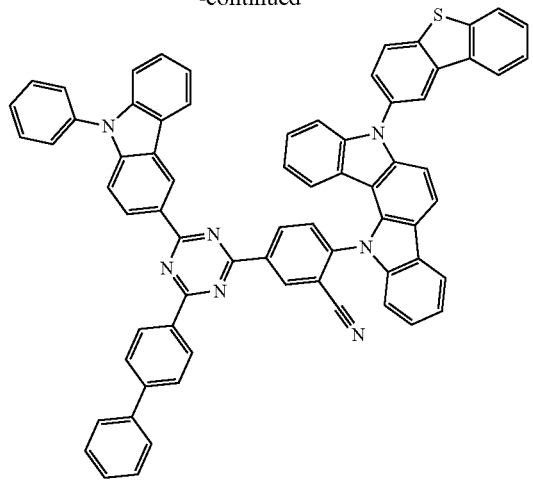
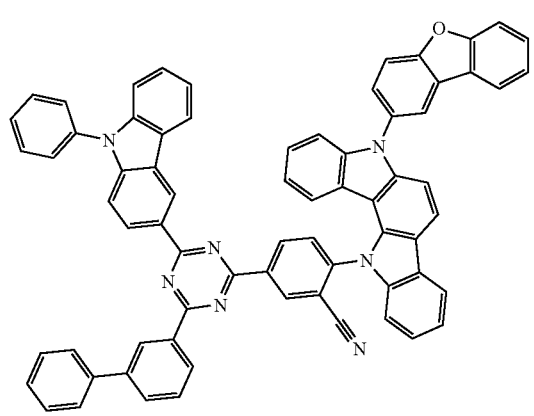
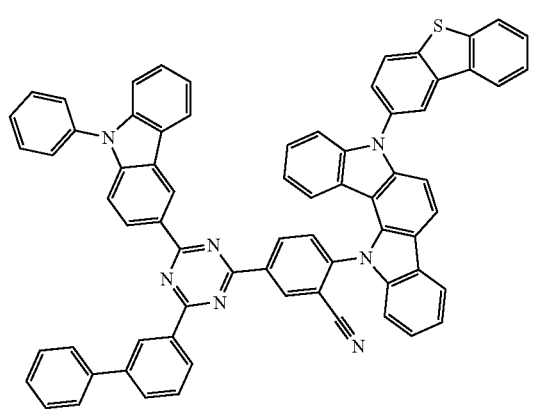
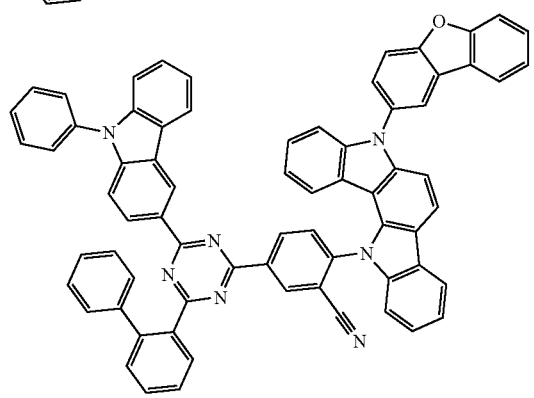
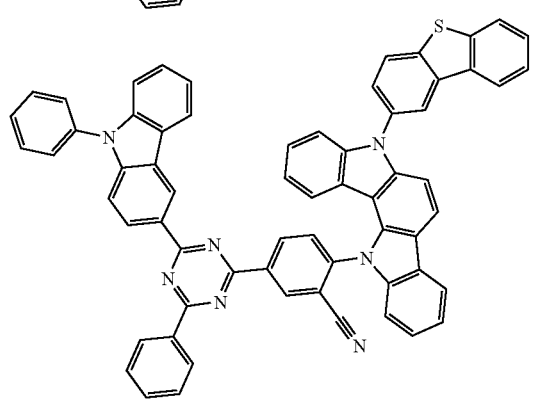
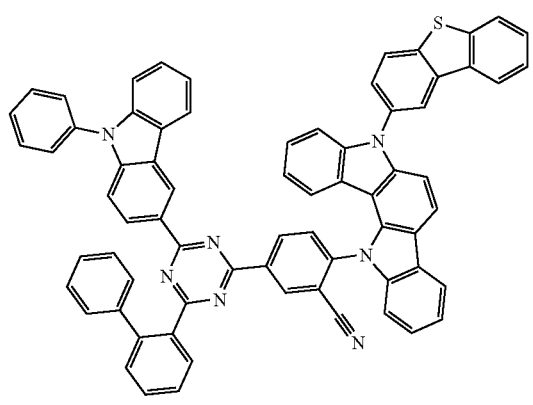

67
-continued
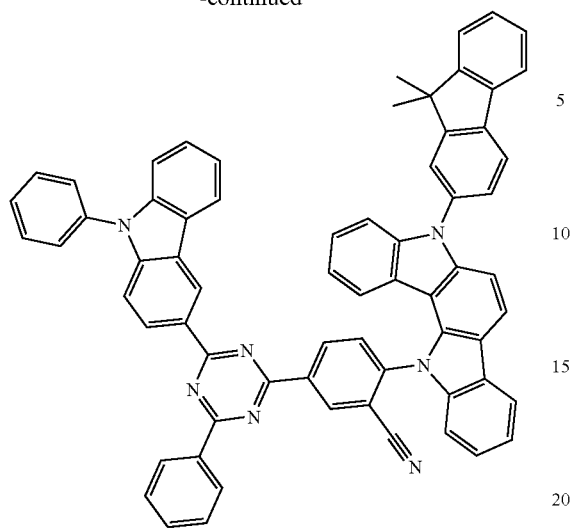
68
-continued
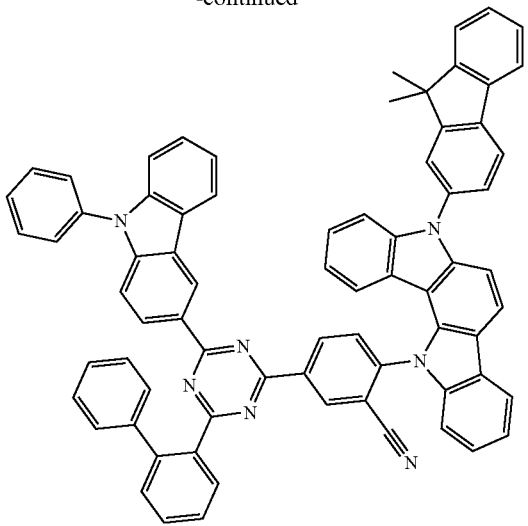
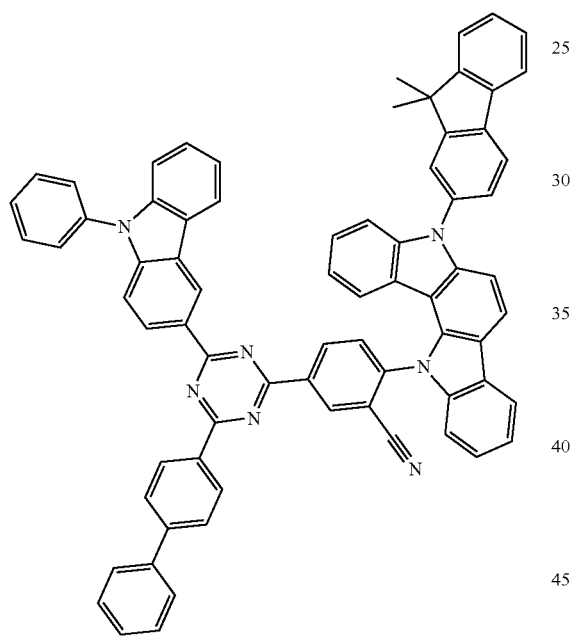
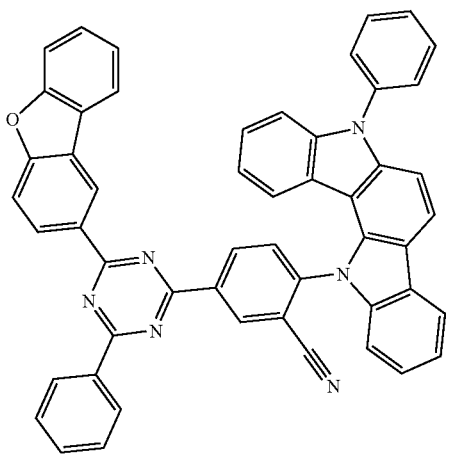
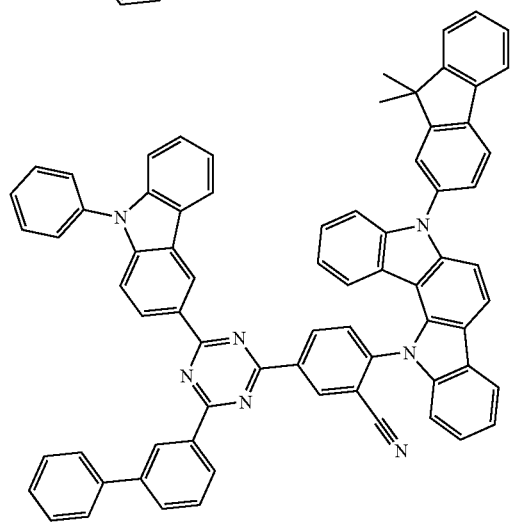
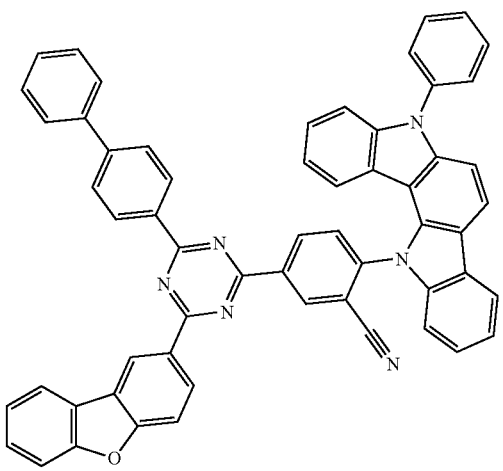

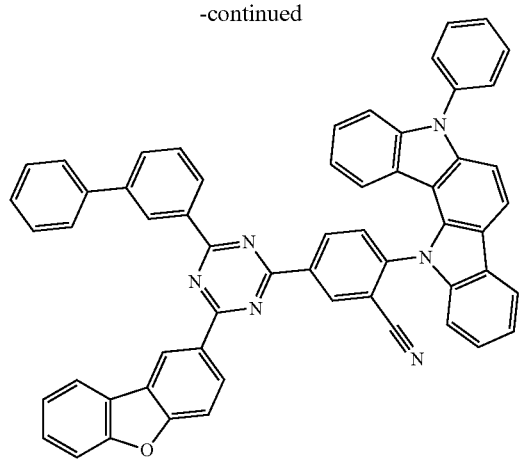
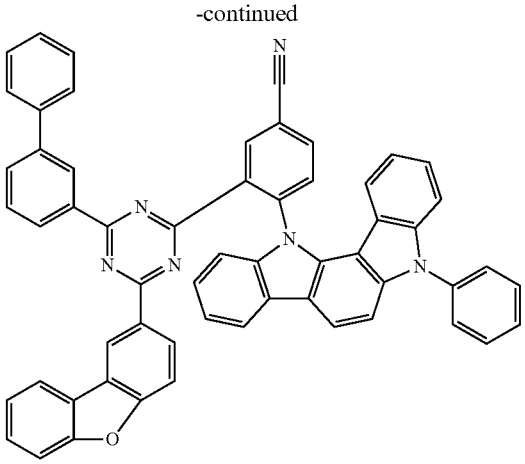
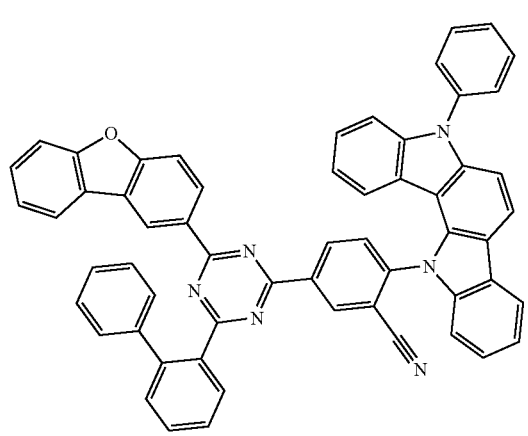
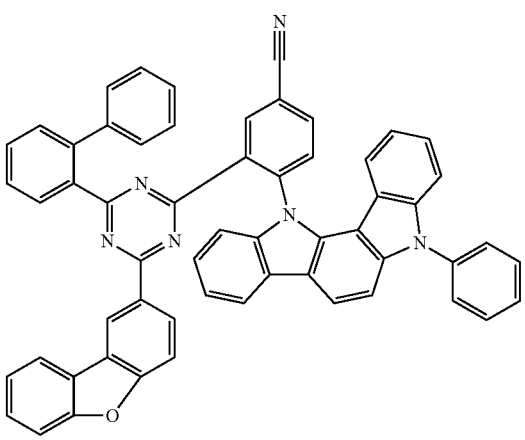
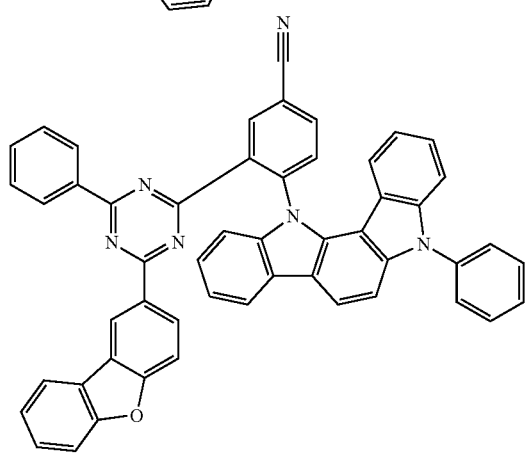
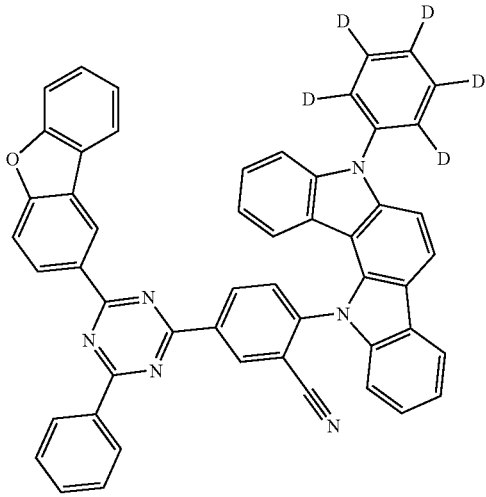

71
-continued
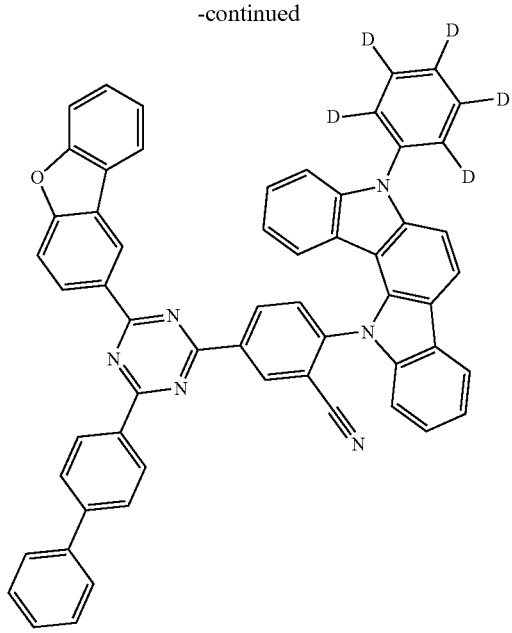
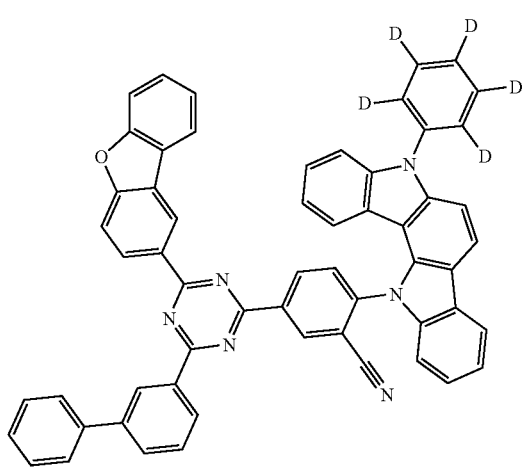
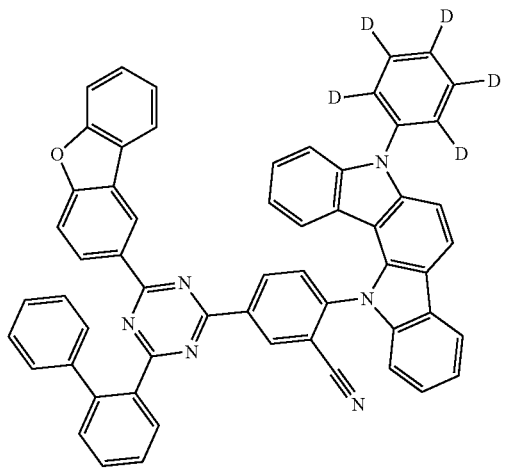
72
-continued
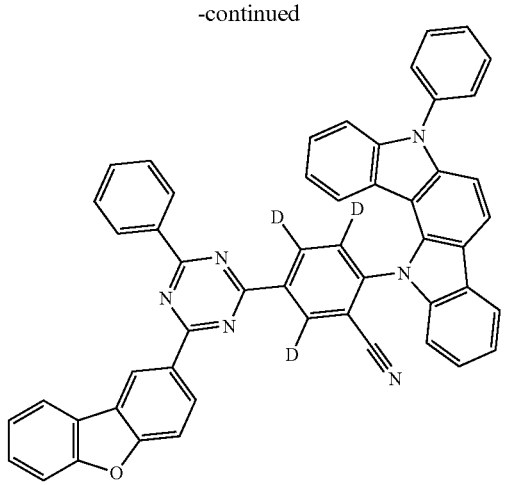
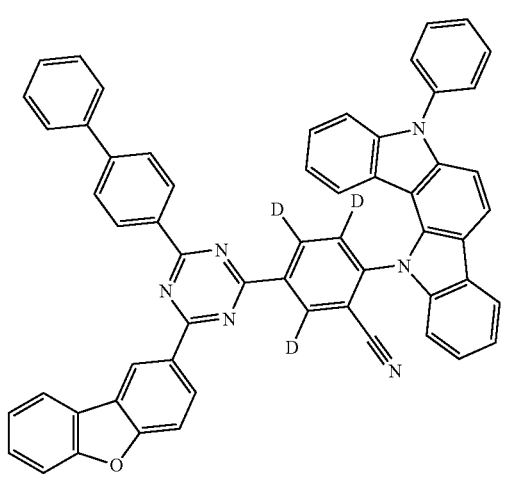
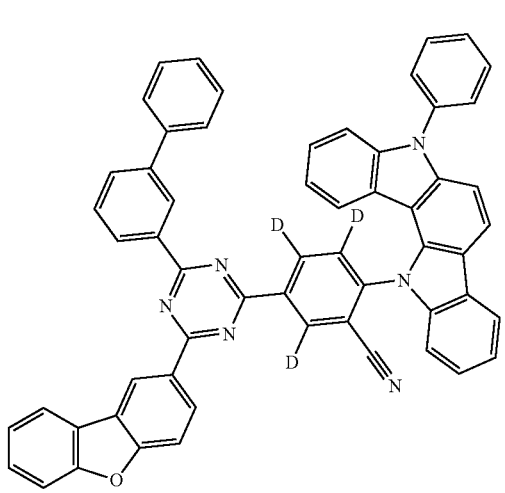

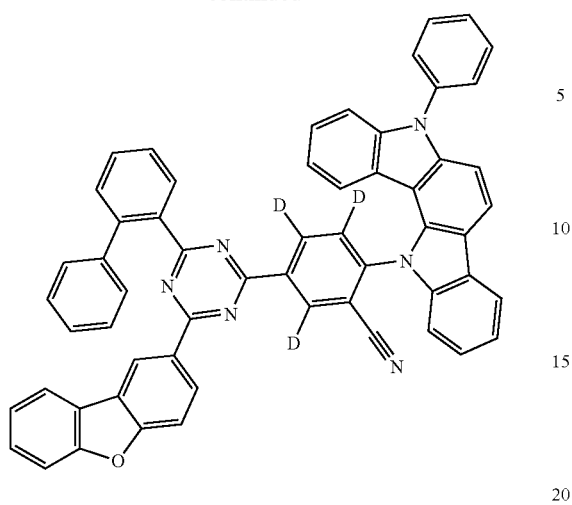
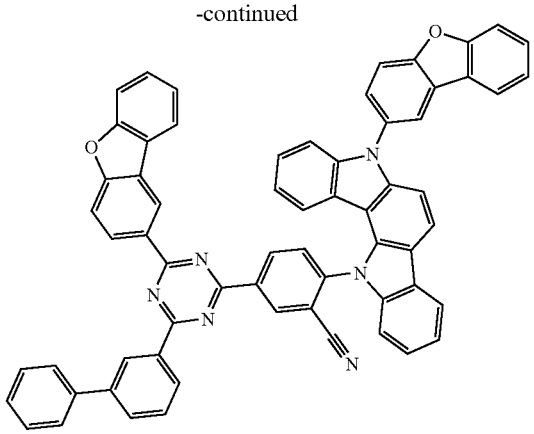
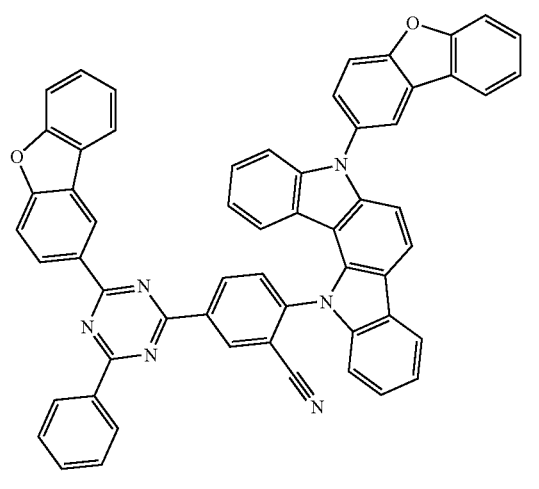
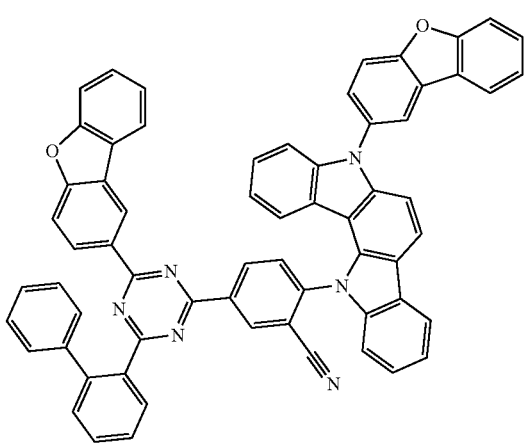
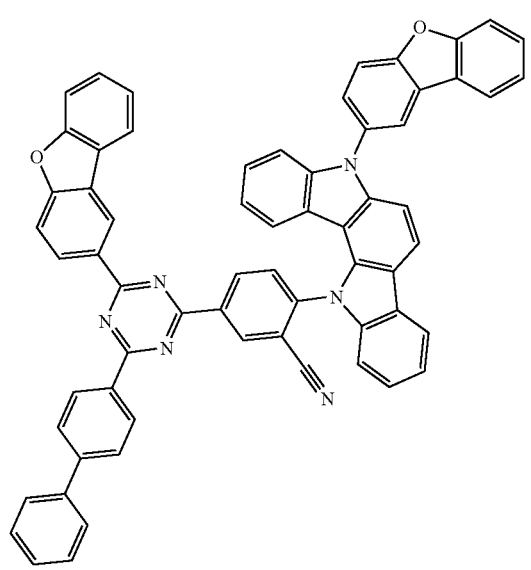
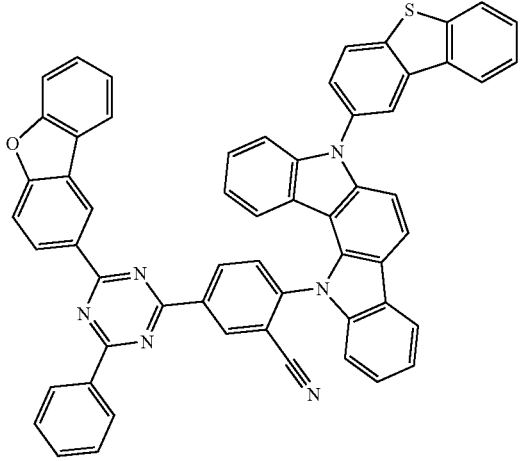

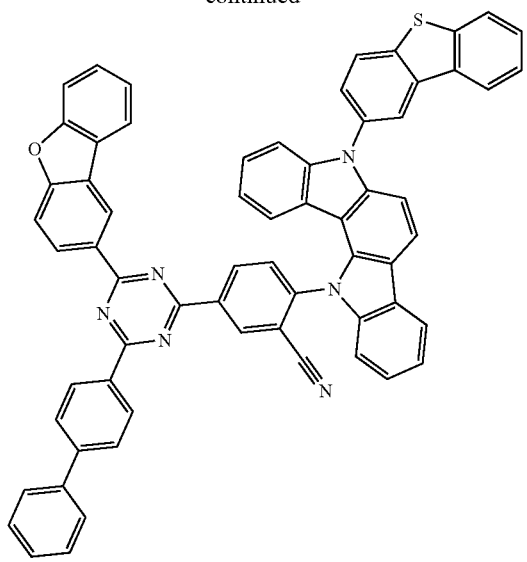
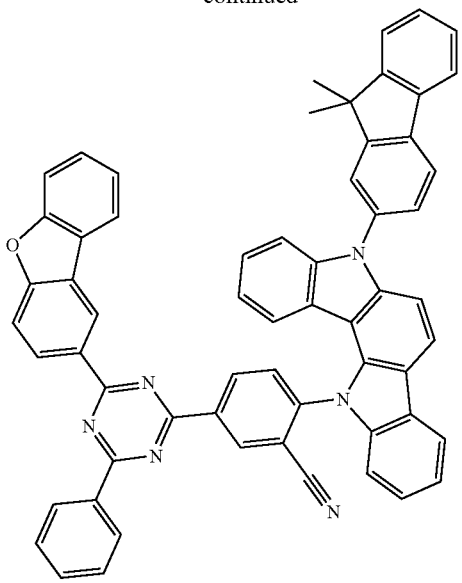
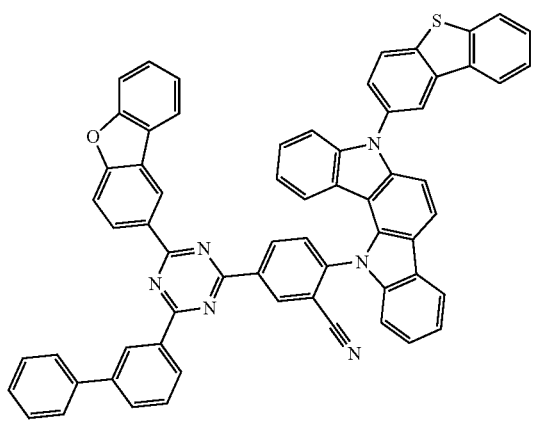
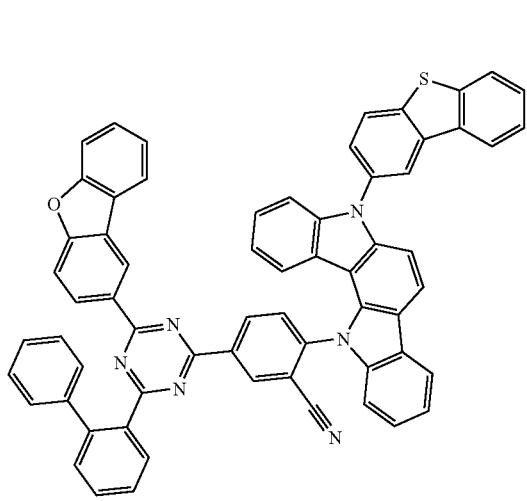
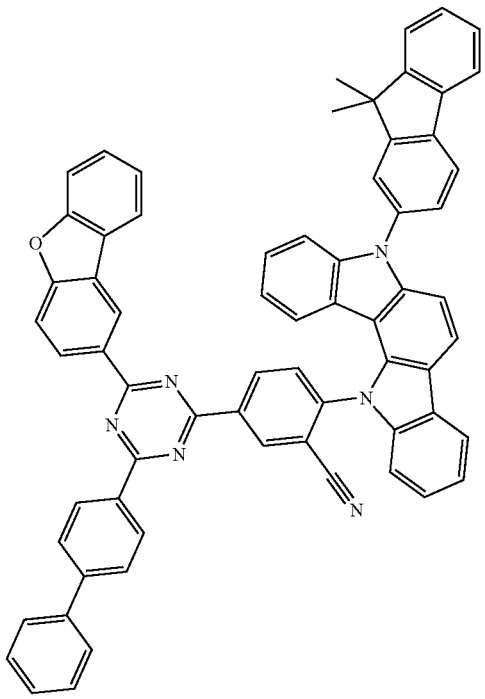

77
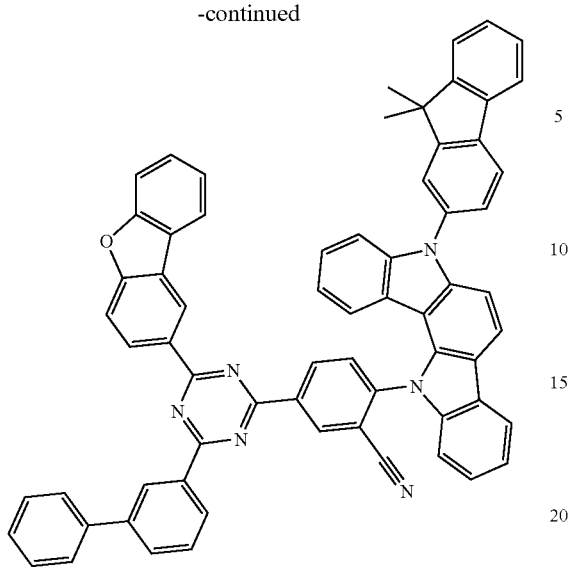
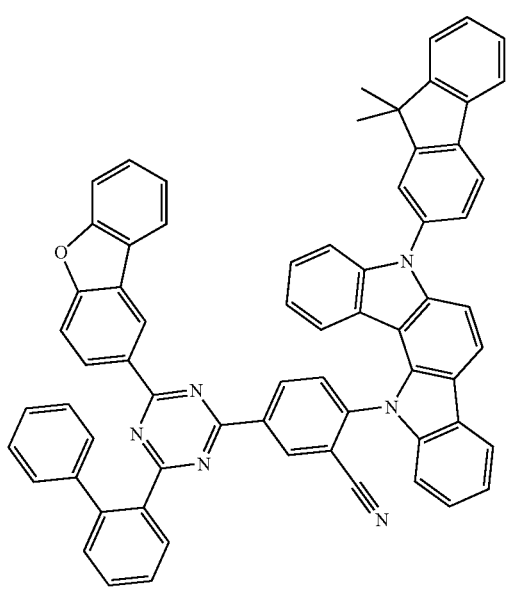
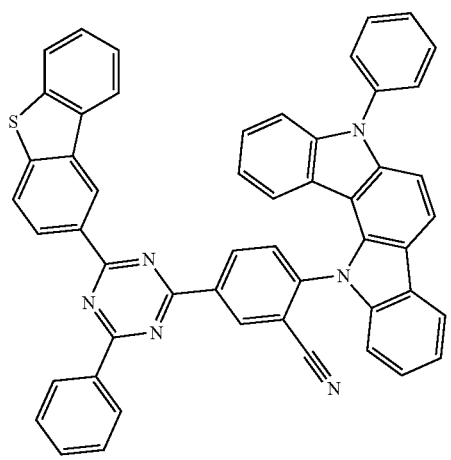
78
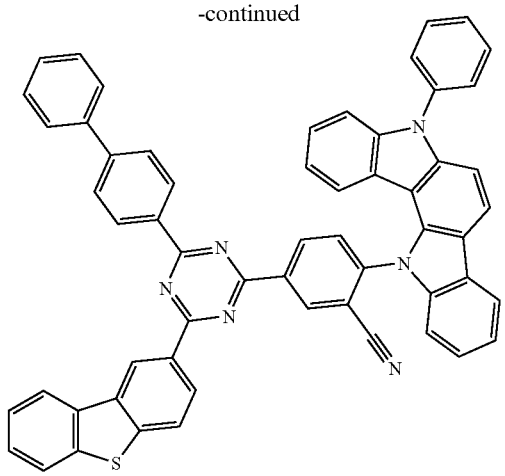
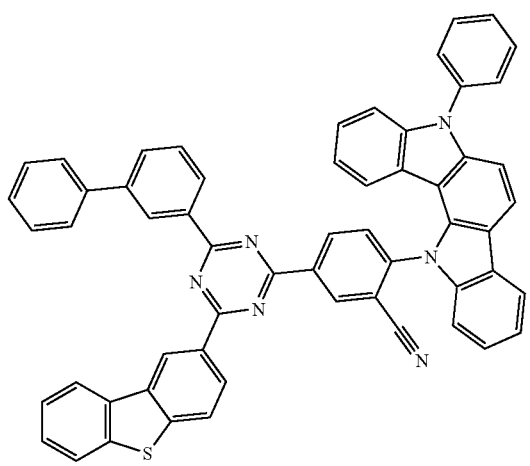
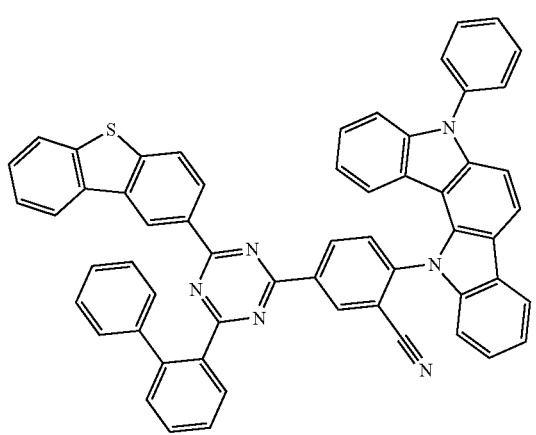

-continued
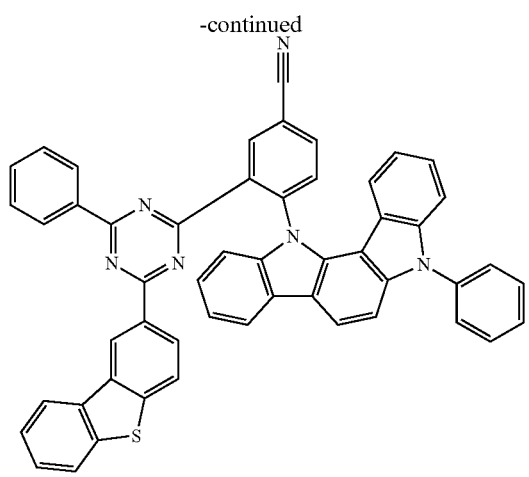
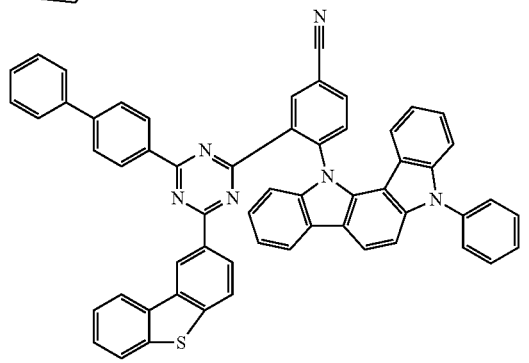
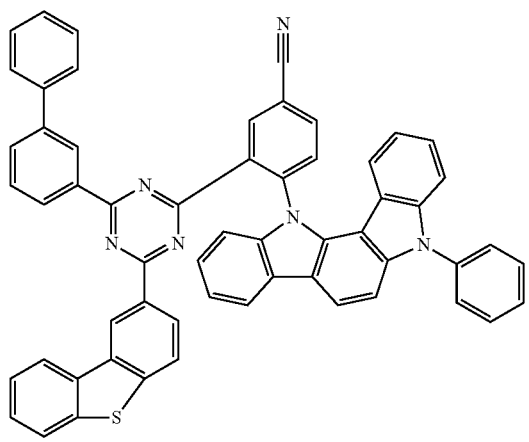
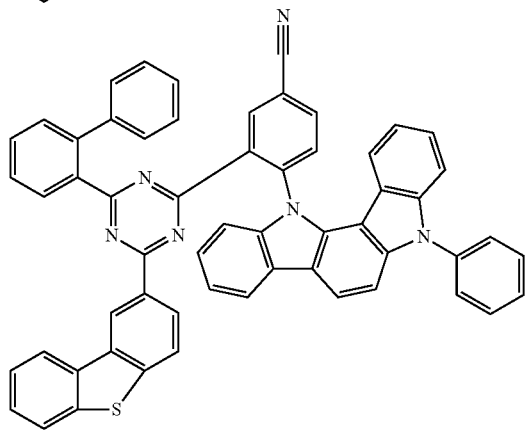
-continued
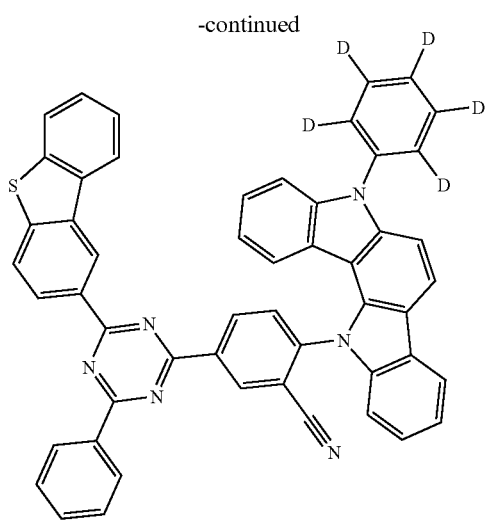
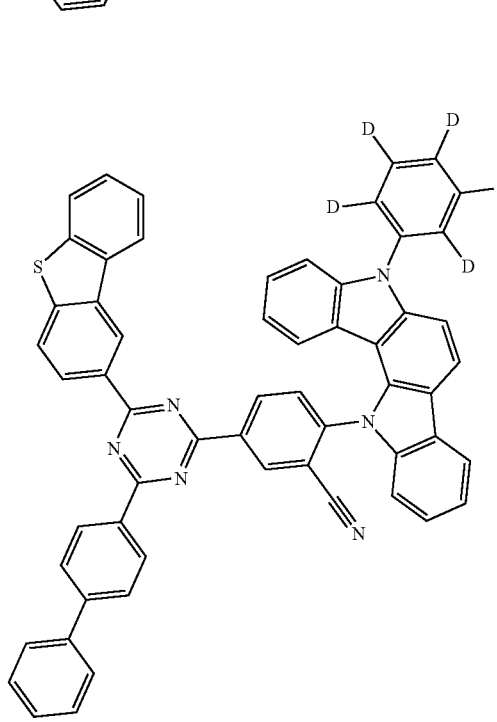
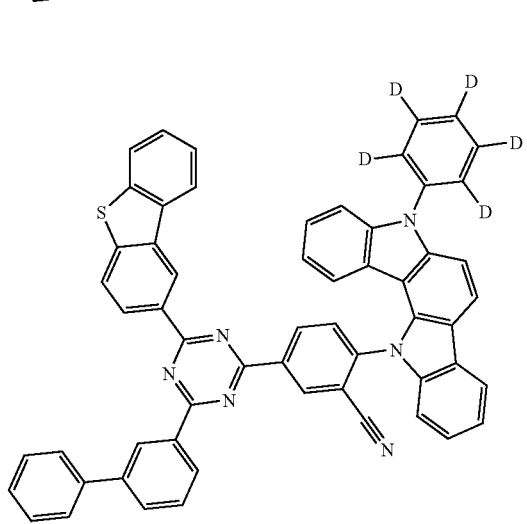

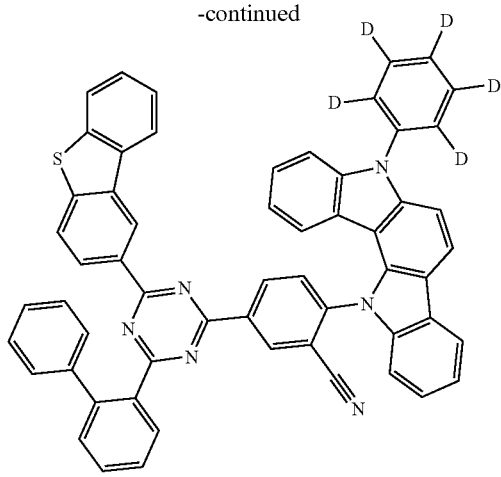
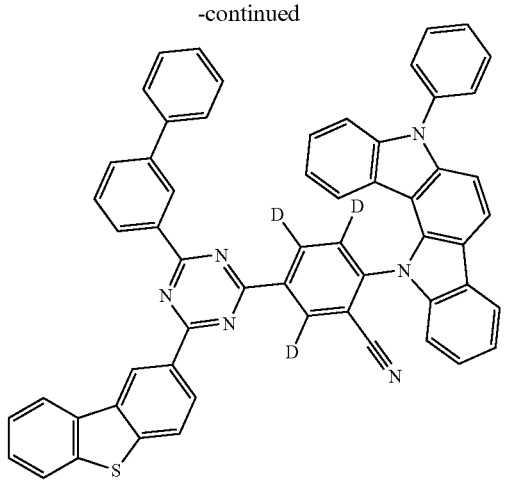
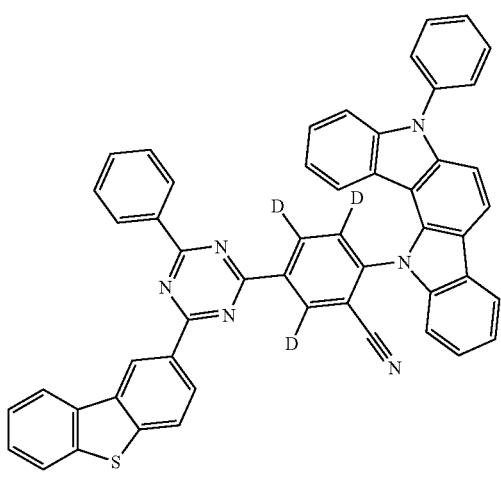
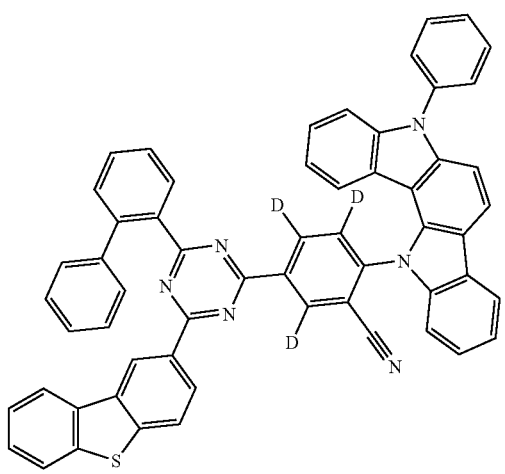
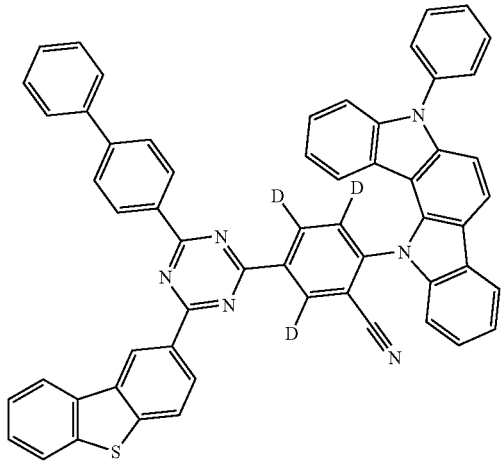
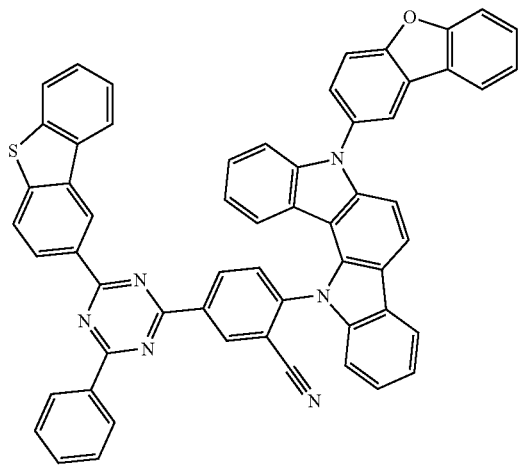

83
-continued
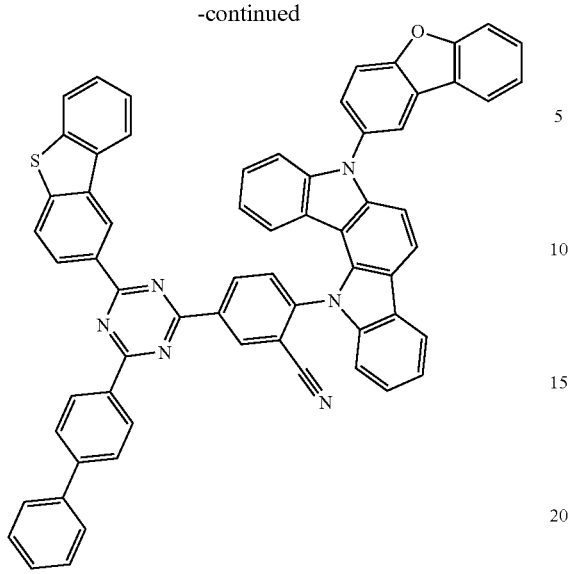
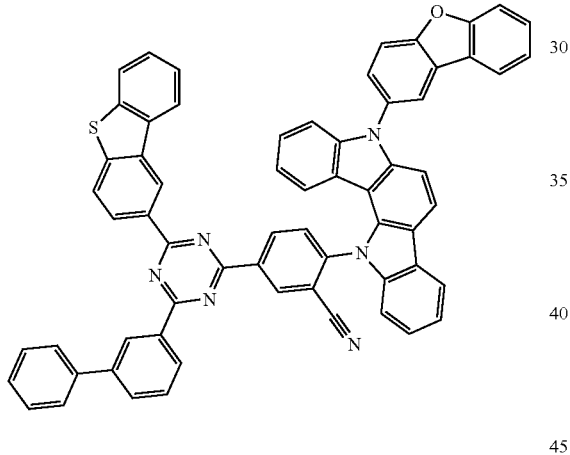
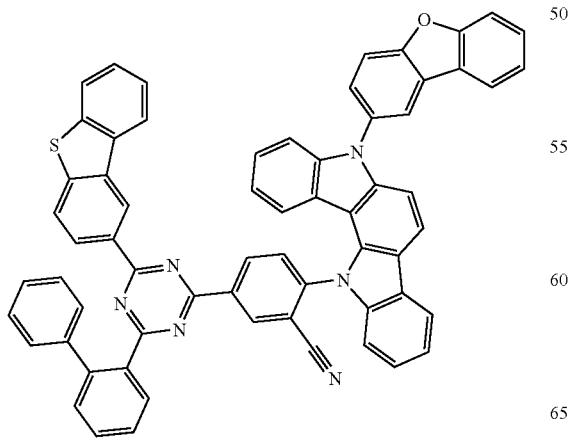
84
-continued
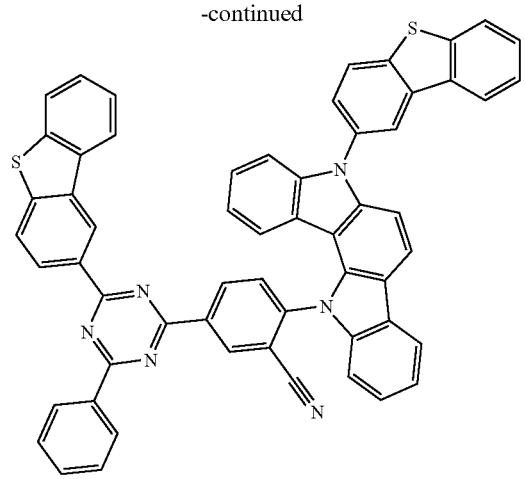
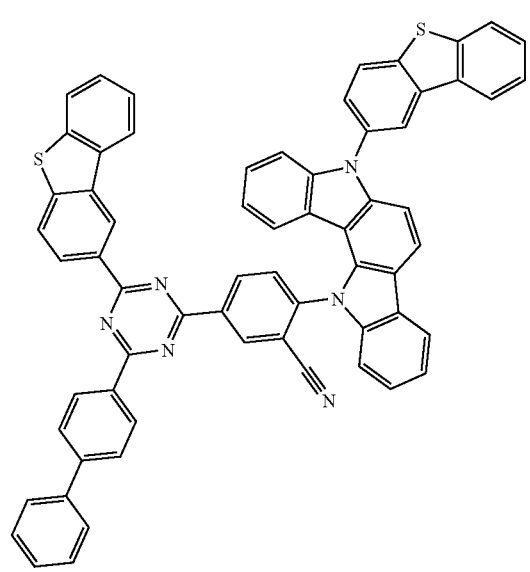
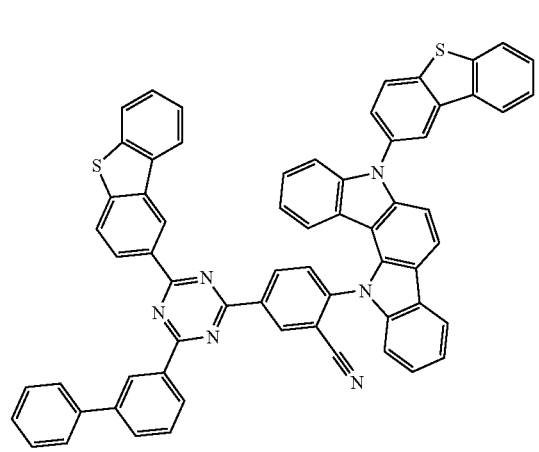

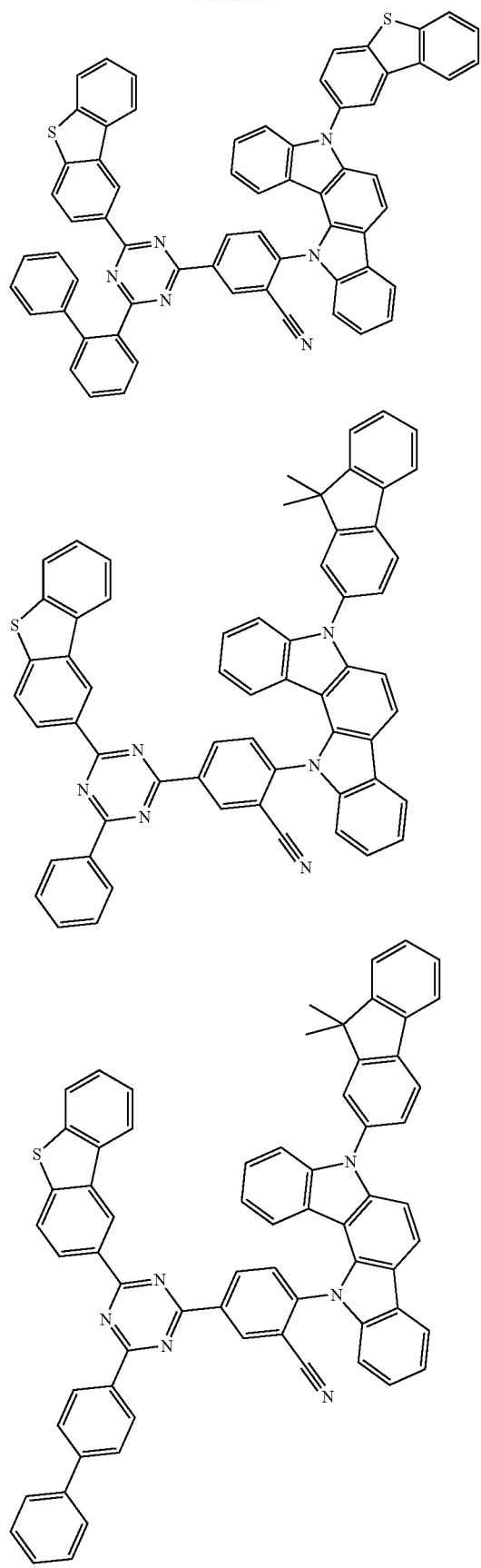
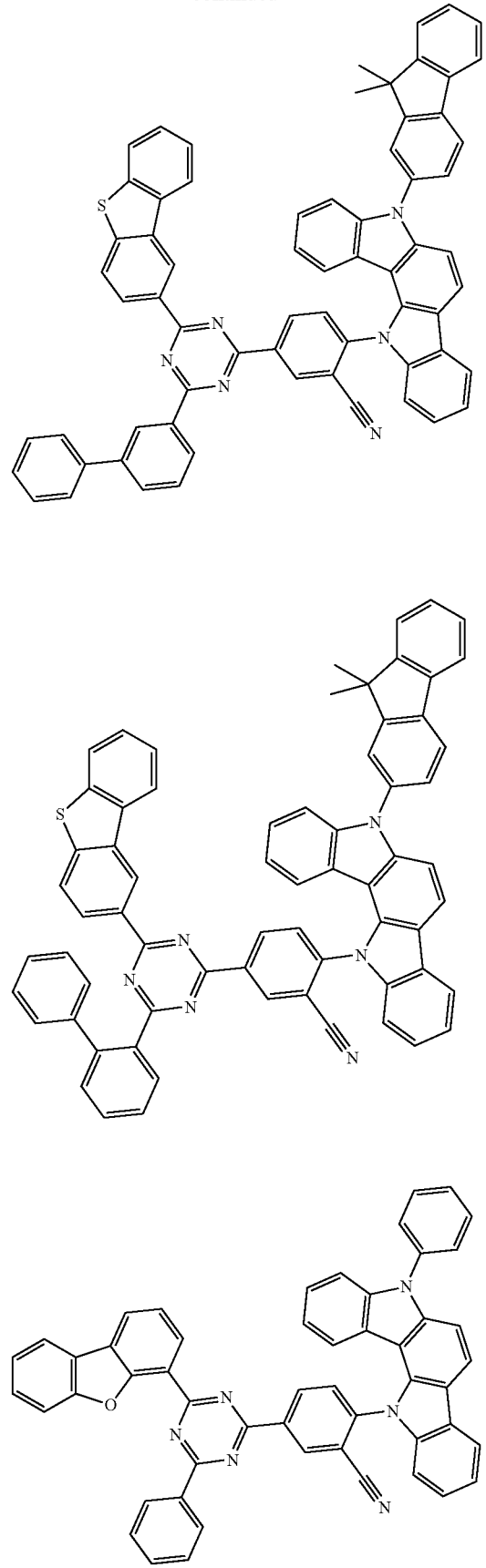

87
-continued
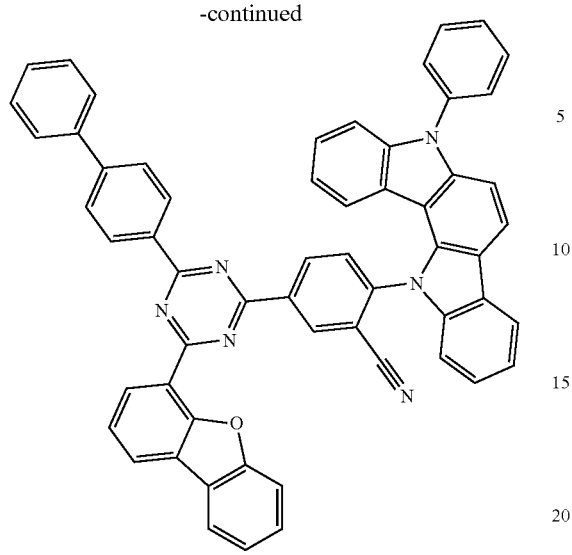
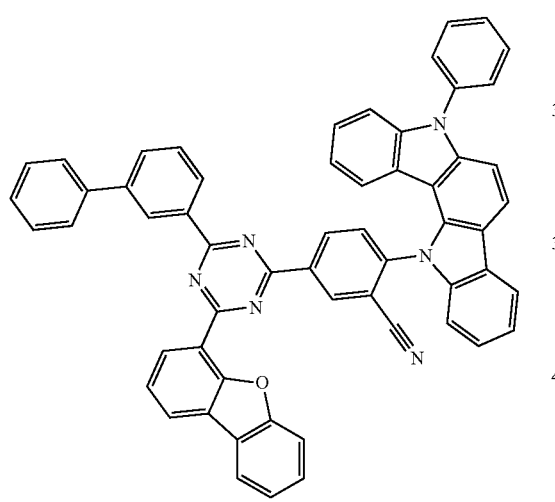
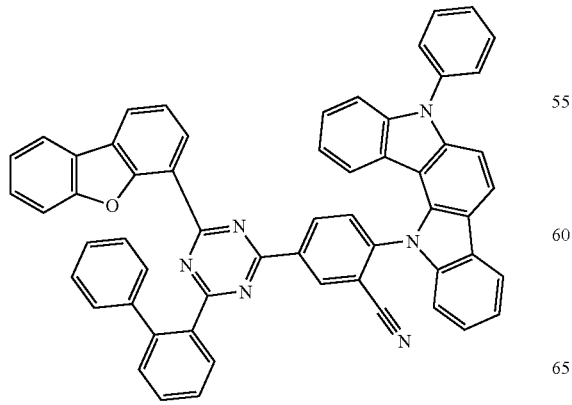
88
-continued
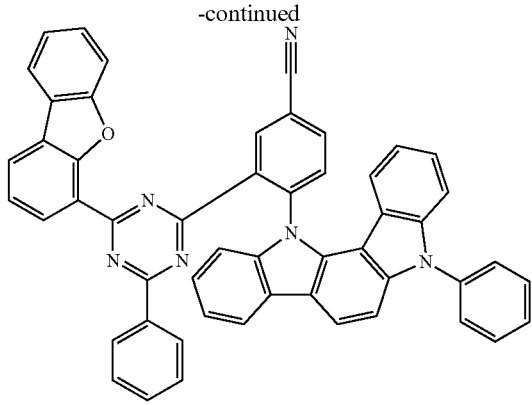
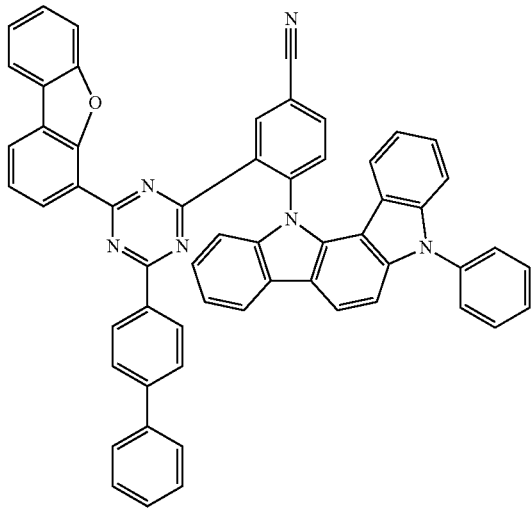
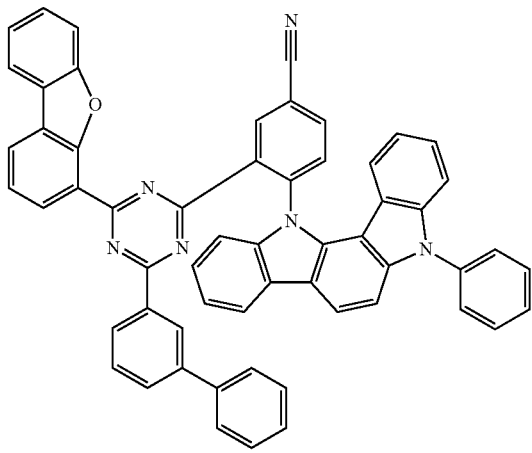

89
-continued
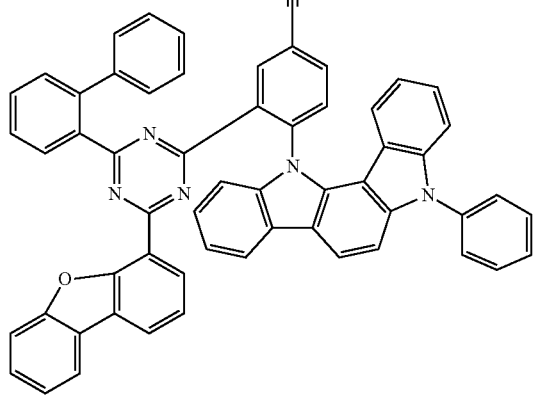
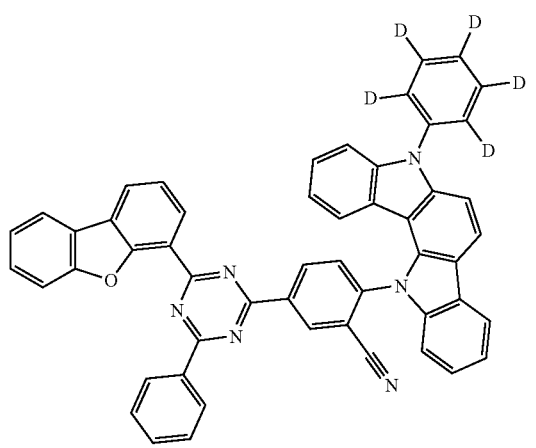
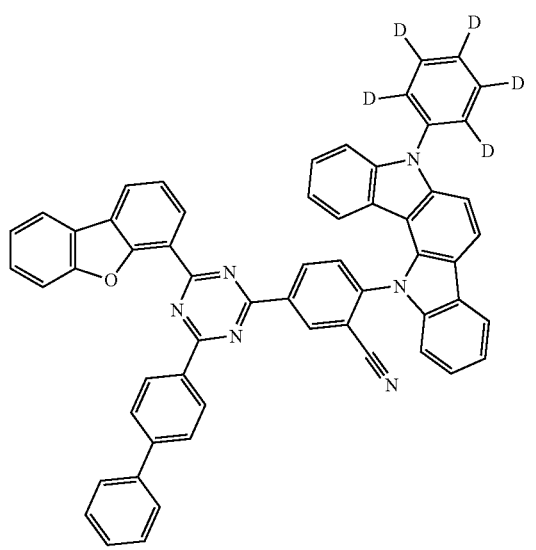
90
-continued
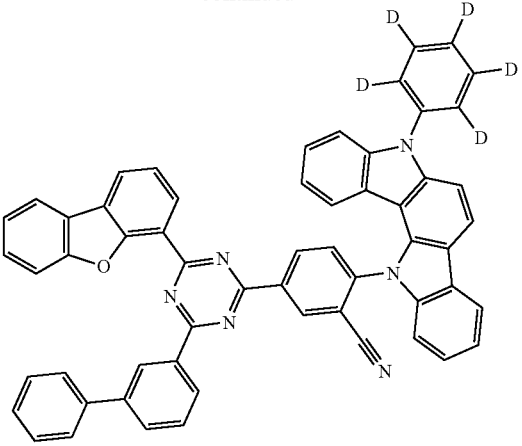
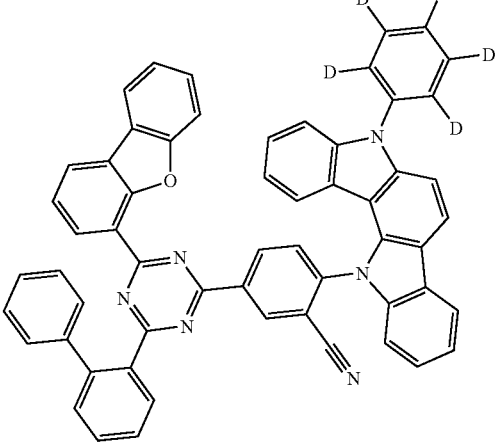
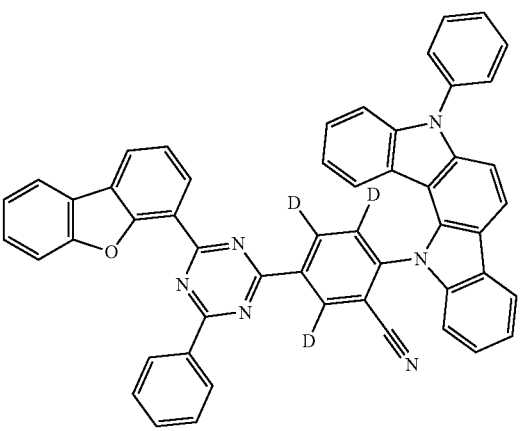

91
-continued
92
-continued
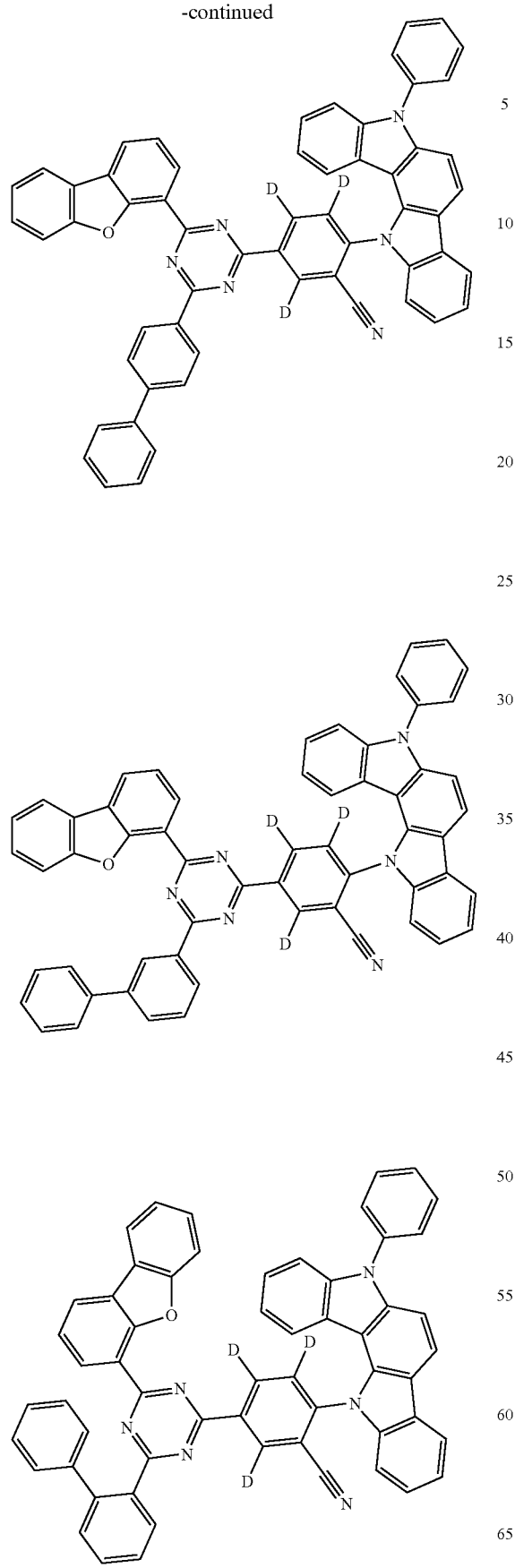
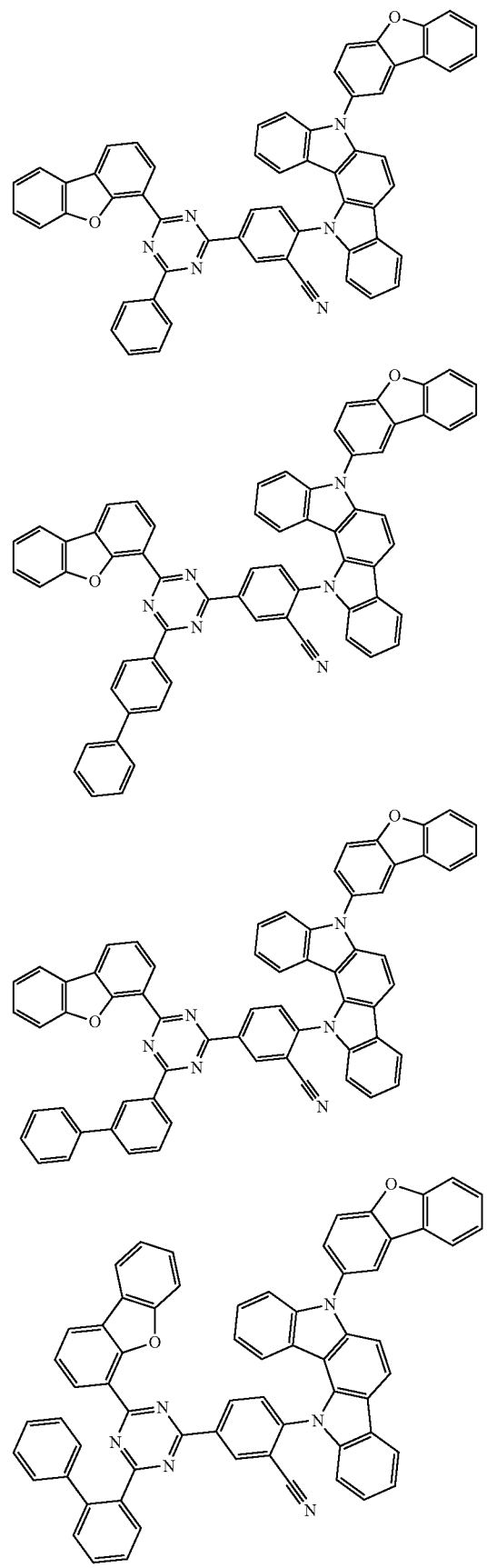

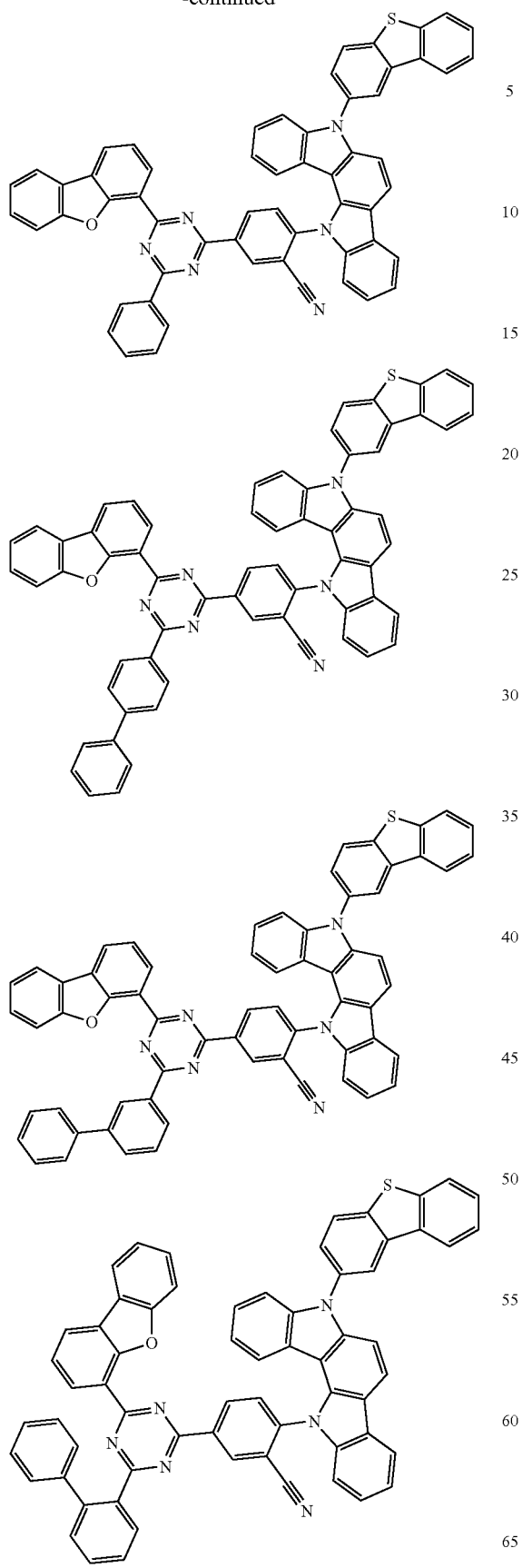
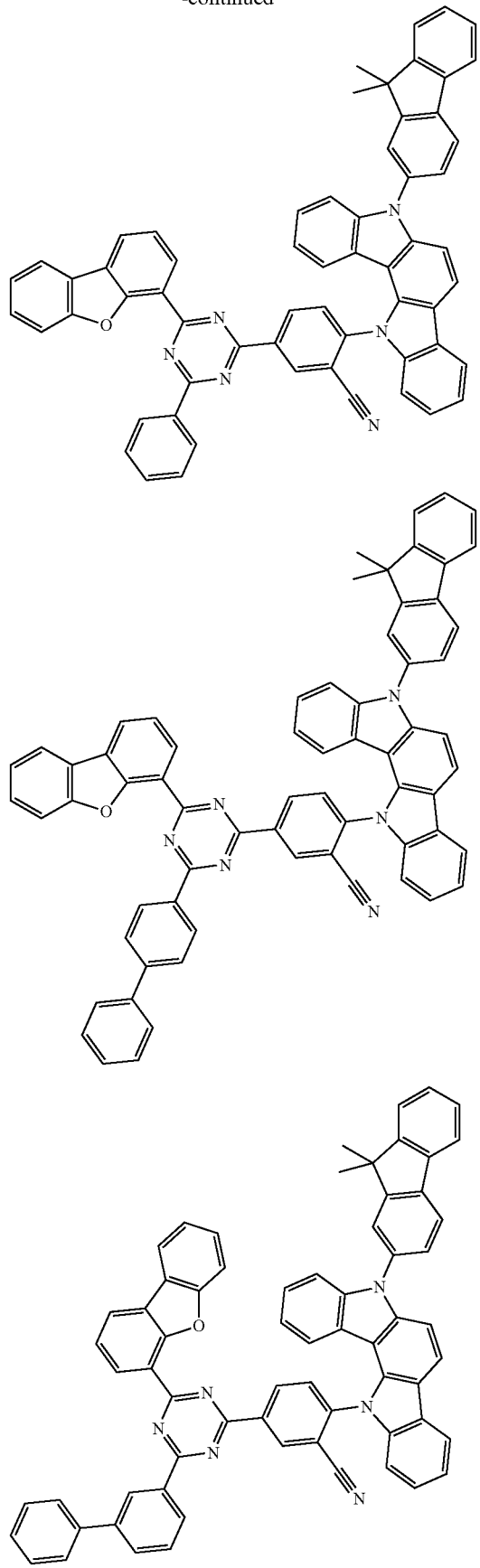

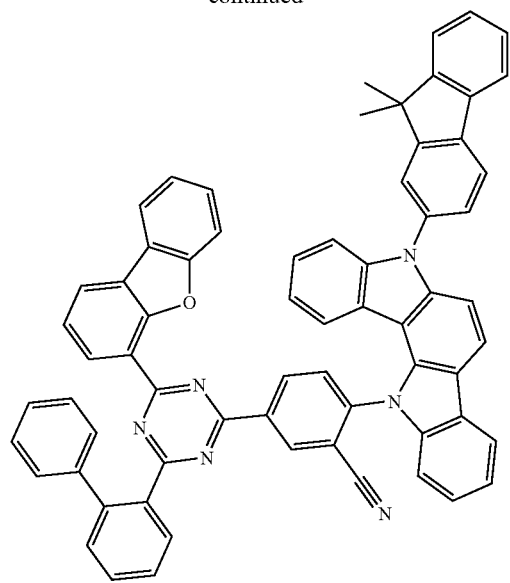
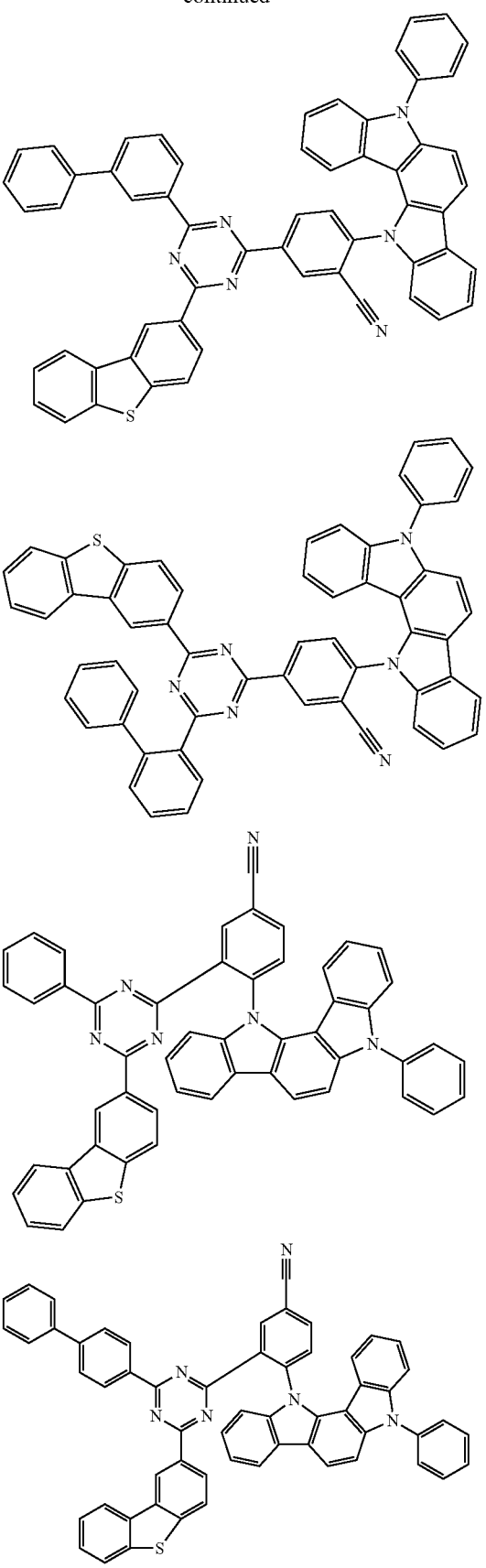

97
-continued
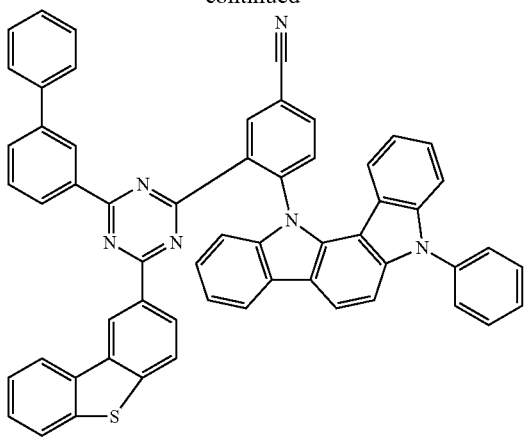
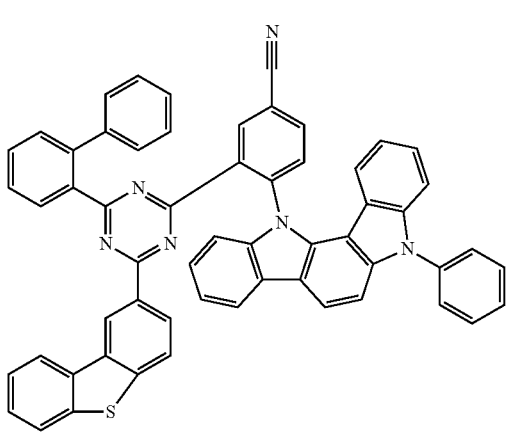
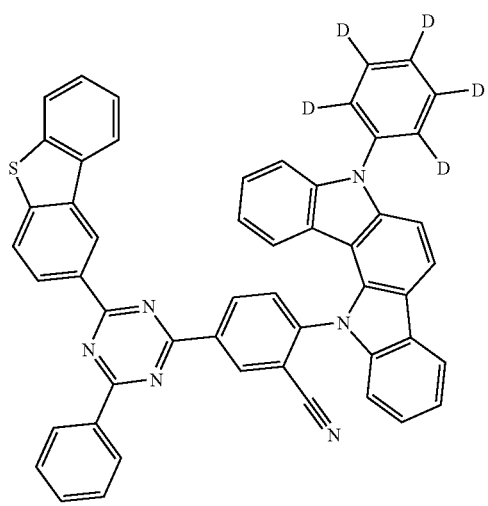
98
-continued
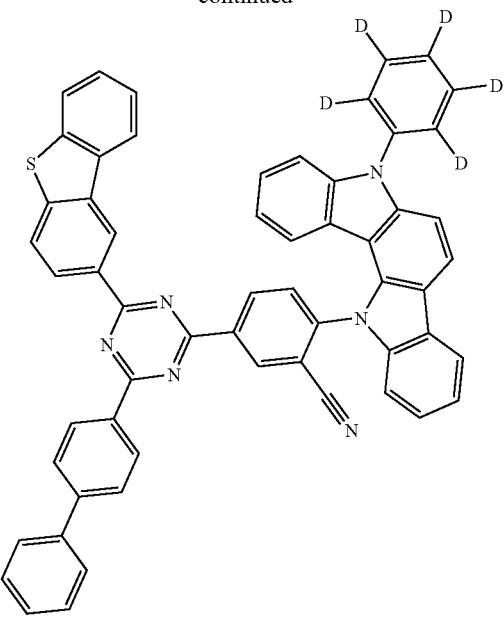
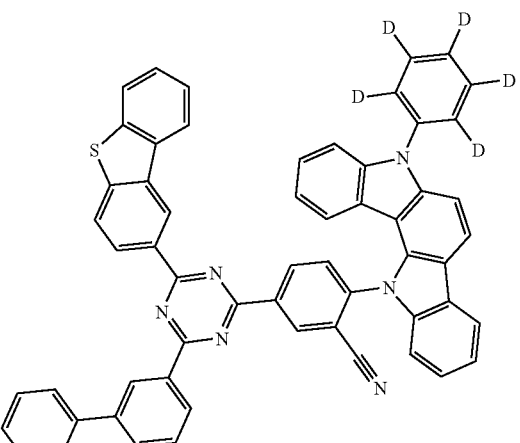
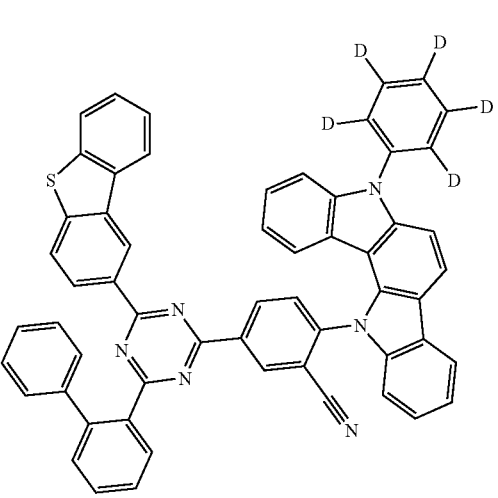

99
-continued
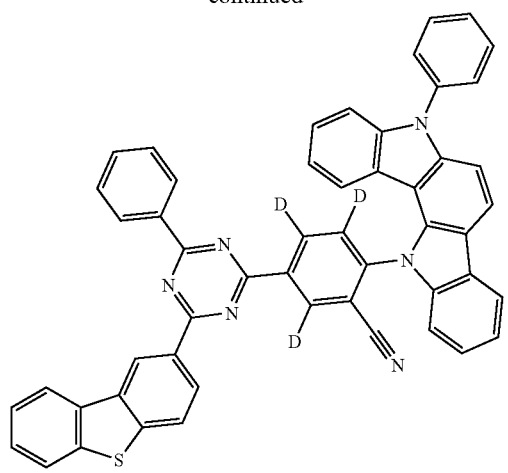
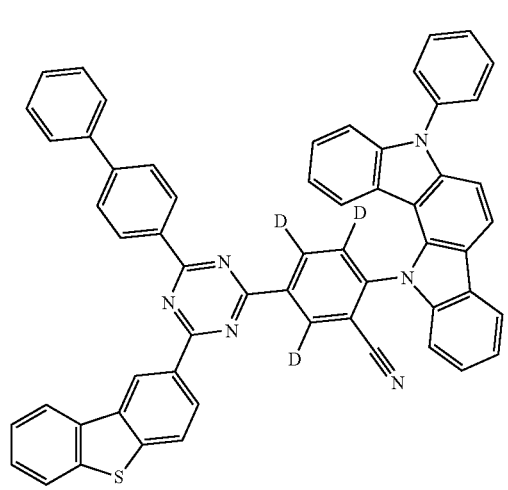
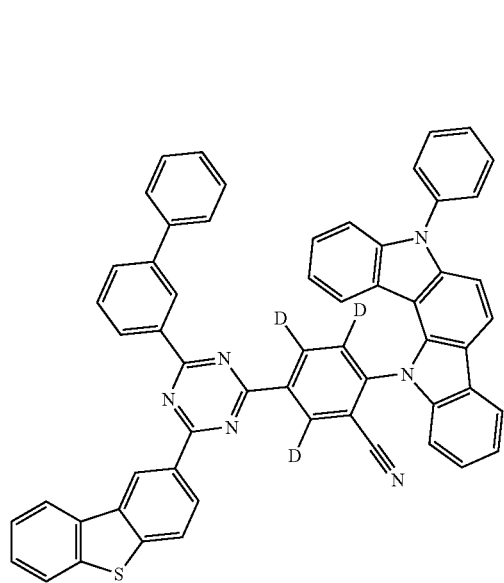
100
-continued
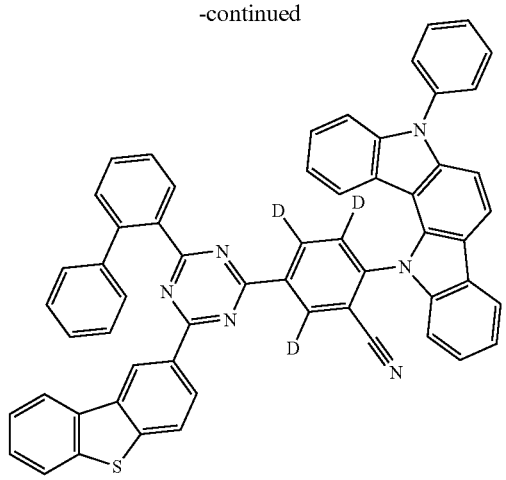
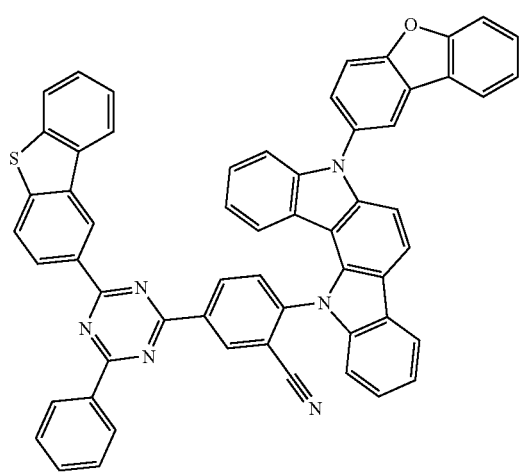
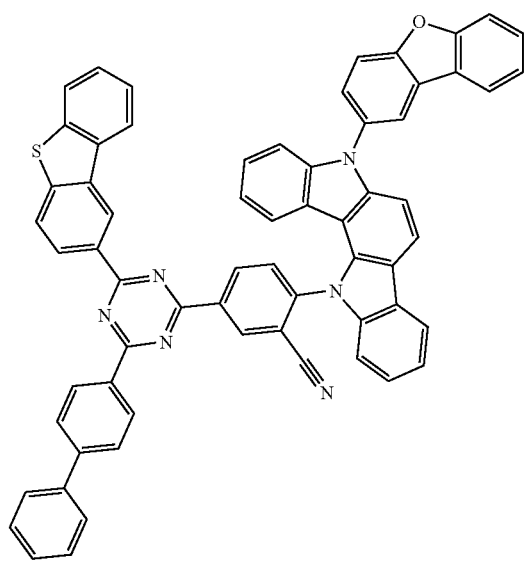

101
-continued
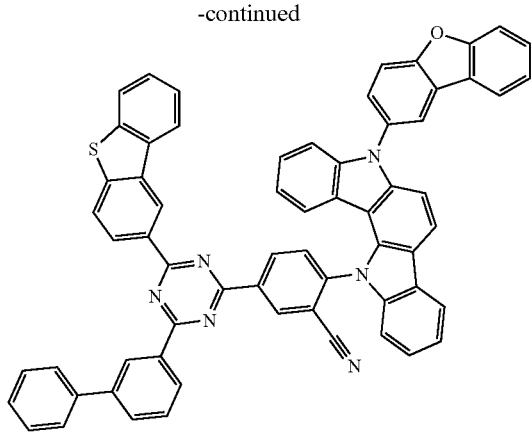
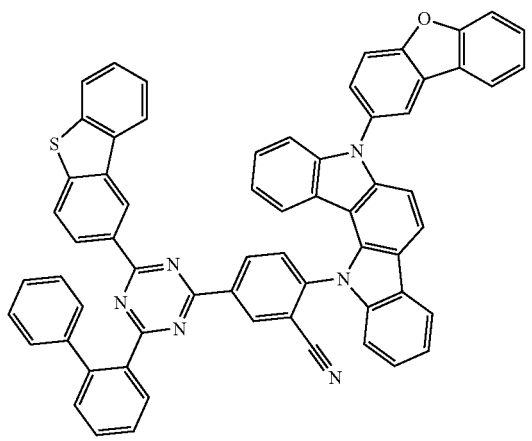
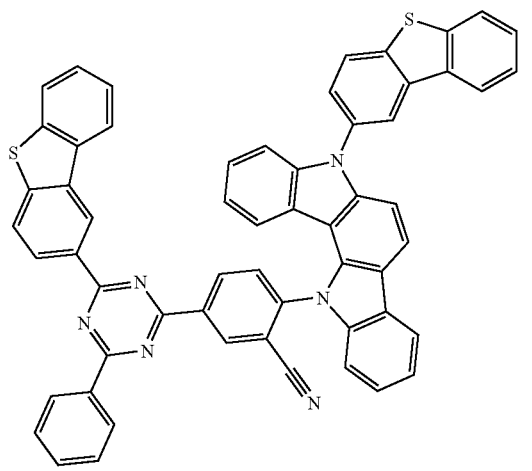
102
-continued
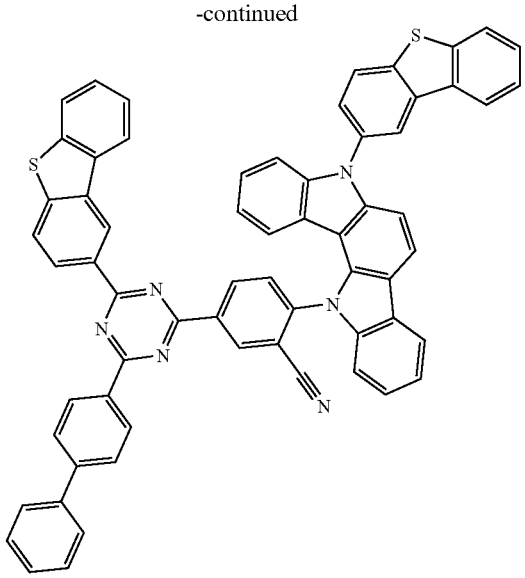
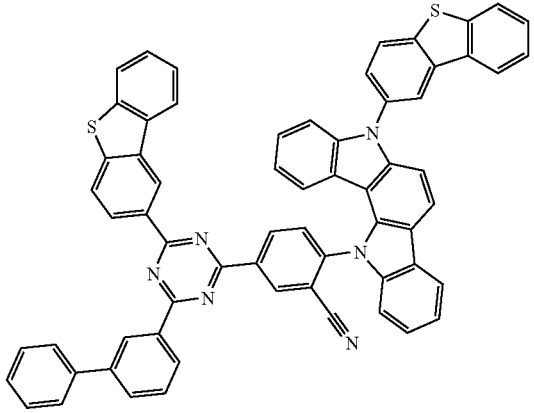
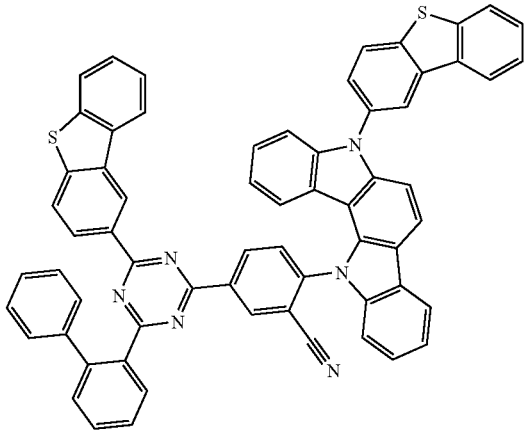

103
-continued
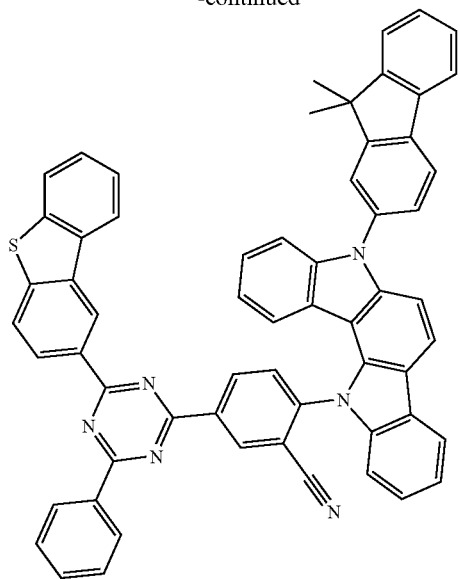
104
-continued
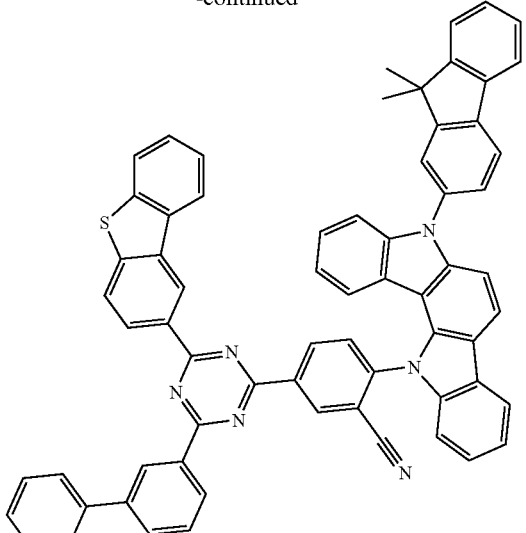
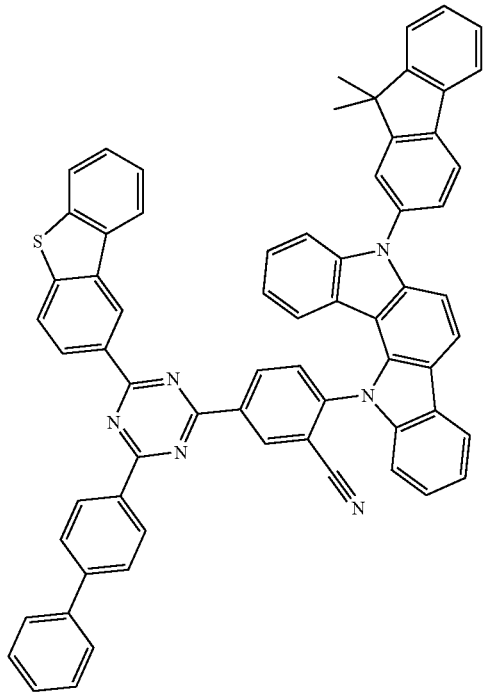
According to one embodiment of the present specification, the compound of Chemical Formula 1 described above can be formed by, as in the following Reaction Formula 1, introducing a triazine group using (cyano-fluorophenyl) boronic acid, and then reacting the result with indolocarbazole using a base under a DMF solution.
[Reaction Formula 1]
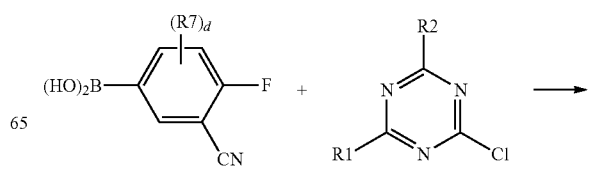

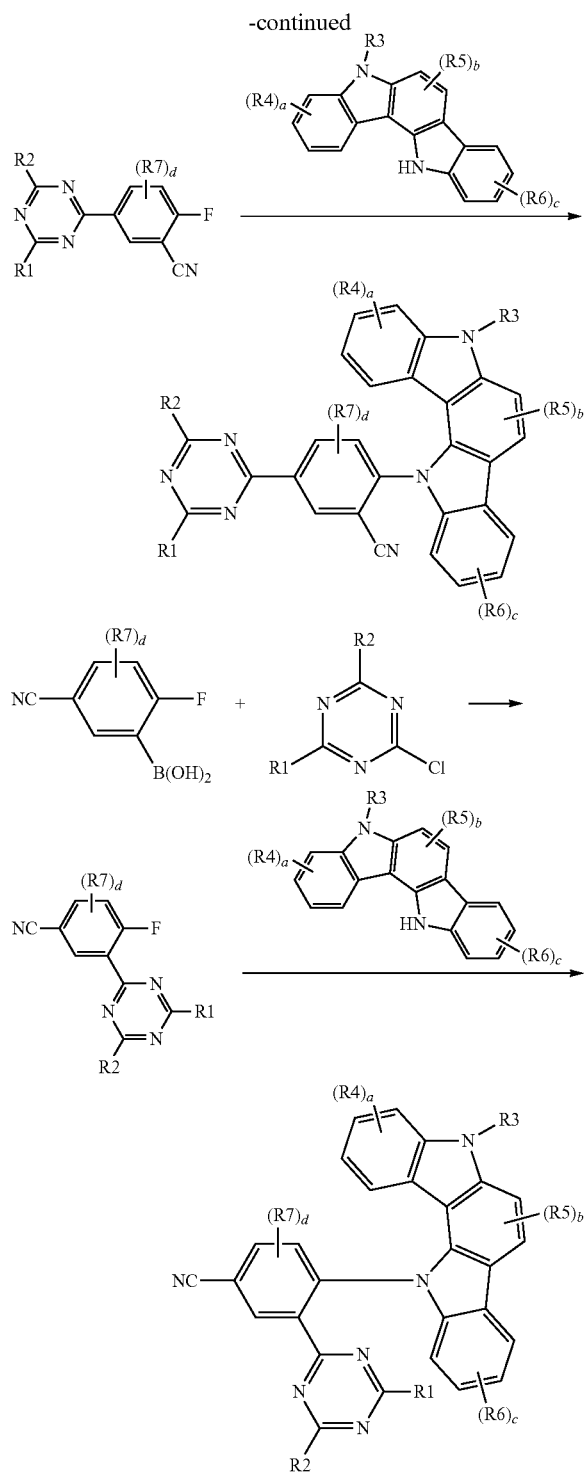

In Reaction Formula 1, R1 to R7, A1, A2 and a to d have the same definitions as in Chemical Formula 1.

In one embodiment, the compound of Chemical Formula 1 is a delayed fluorescent material. Unlike a phosphorescent material changing a singlet exciton to a triplet exciton to convert to light, a delayed fluorescent material is a material changing a triplet exciton to a singlet exciton to convert to light, and exhibits delayed fluorescence characteristics due to this process. Theoretically, a delayed fluorescent material can convert both a singlet exciton and a triplet exciton to light, and therefore, 100% internal quantum efficiency can be obtained, and limits in the lifetime and the efficiency that a phosphorescent material has can be overcome.

A delayed fluorescence (also referred to as thermally activated delayed fluorescence: hereinafter, properly abbreviated as 'TADF') phenomenon is a phenomenon in which 75% of triplet excitons generated by electric field excitation at room temperature or a temperature of a light emitting layer in a light emitting device go through reverse intersystem crossing (hereinafter, properly abbreviated as 'RISC') to singlet excitons. The singlet excitons generated by the reverse intersystem crossing emit fluorescence like 25% of singlet excitons generated by direct excitation enabling 100% internal quantum efficiency.

In order to develop the TADF phenomenon, it is important to reduce a difference between triplet energy and singlet energy ($\Delta E_{ST}$) of an organic compound. In order to reduce the $\Delta E_{ST}$, localizing (clearly separating) the highest occupied molecular orbital (HOMO) and the lowest unoccupied molecular orbital (LUMO) in the molecule is important.

One embodiment of the present specification provides an organic light emitting device comprising the compound of Chemical Formula 1.

One embodiment of the present specification provides an organic light emitting device comprising a first electrode, a second electrode, and one or more organic material layers disposed between the first electrode and the second electrode, wherein the organic material layer comprises the compound of Chemical Formula 1 described above.

In one embodiment, the organic material layer comprises a light emitting layer, and the light emitting layer comprises the compound of Chemical Formula 1 described above.

In one embodiment, the light emitting layer can be formed only with the compound of Chemical Formula 1 described above, or can further include other different materials in addition to the compound of Chemical Formula 1. In one embodiment, the compound of Chemical Formula 1 can be used as a host, or can be used together with other host materials to perform a role of a dopant.

In one embodiment, the organic material layer comprises a light emitting layer, and the light emitting layer comprises the compound of Chemical Formula 1 described above in 1 parts by weight to 100 parts by weight; and preferably in 10 parts by weight to 70 parts by weight with respect to a total 100 parts by weight of the light emitting layer.

In one embodiment, the organic material layer comprises a light emitting layer, and the light emitting layer comprises the compound of Chemical Formula 1 described above as a dopant.

In one embodiment, the light emitting layer comprises the compound of Chemical Formula 1 and further comprises a host.

In one embodiment, the organic material layer comprises a light emitting layer, and the organic material layer comprises a host and the compound of Chemical Formula 1. The host can be a phosphorescent host or a fluorescent host.

In one embodiment, a mechanism that can produce light emission in the light emitting layer is not limited, and the mechanism can vary depending on the compound used in the light emitting layer.

In one embodiment, after holes and electrons migrate to the compound of Chemical Formula 1 (dopant) through a host and excitons are produced in triplet and singlet in a ratio of 3:1 in the dopant, the excitons produced in the triplet of the dopant emit light by transitioning to the singlet of the dopant, and the excitons produced in the singlet can emit light as it is in the singlet. In another embodiment, a host functioning only as a matrix material is included in the light emitting layer, and holes; electrons; or holes and electrons can be injected to a dopant without passing through the host to form excitons in triplet and singlet. However, this is just one example of a light emission mechanism, and light emission can occur by other different light emission mechanisms.

In one embodiment, a difference ($\Delta E_{ST\_D}$) between singlet energy ($S1_D$) and triplet energy ($T1_D$) of the compound of Chemical Formula 1 is greater than or equal to 0 eV and less than or equal to 0.3 eV; greater than or equal to 0 eV and less than or equal to 0.2 eV; or greater than or equal to 0 eV and less than or equal to 0.1 eV. When the different between singlet energy ($S1_D$) and triplet energy ($T1_D$) of the compound of Chemical Formula 1 satisfies the above-mentioned range, a ratio and a speed of the excitons at the triplet energy level moving to the singlet energy level by reverse intersystem crossing increase reducing the time of the excitons staying at the triplet energy, which is advantageous in increasing efficiency and lifetime of the organic light emitting device.

In one embodiment, the compound of Chemical Formula 1 has a triplet energy ($T1_D$) of 2.1 eV to 2.7 eV.

In one embodiment, the host has a triplet energy ($T1_H$) of 2.4 eV to 3.1 eV.

In one embodiment, the host has a singlet energy ($S1_H$) of 2.6 eV to 3.3 eV.

In one embodiment, a triplet energy ($T1_H$) of the host is larger than a triplet energy ($T1_D$) of the heterocyclic compound of Chemical Formula 1.

In one embodiment, a singlet energy ($S1_H$) of the host is larger than a singlet energy ($S1_D$) of the compound of Chemical Formula 1. Satisfying the above-mentioned energy relation can prevent excitons of the dopant from moving backward to the host.

In one embodiment, the host can be any one selected from among the following compounds, however, this is just one example, and the host can be used without limit as long as it is a compound suitable to obtain delayed fluorescence properties of the dopant of the present disclosure:

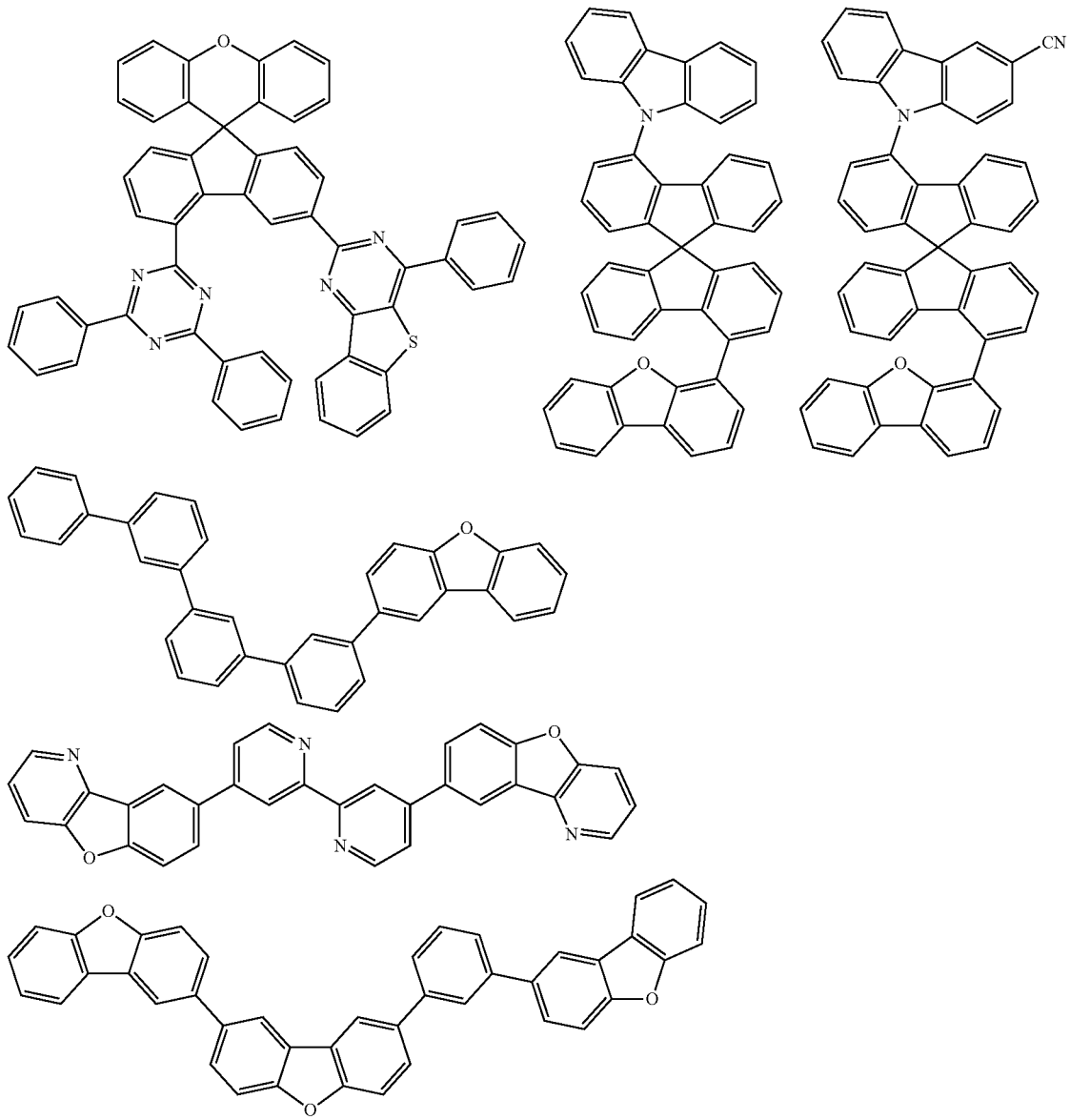

-continued
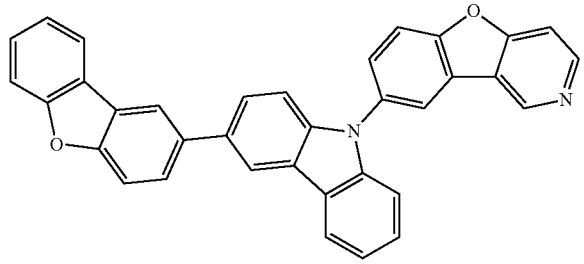
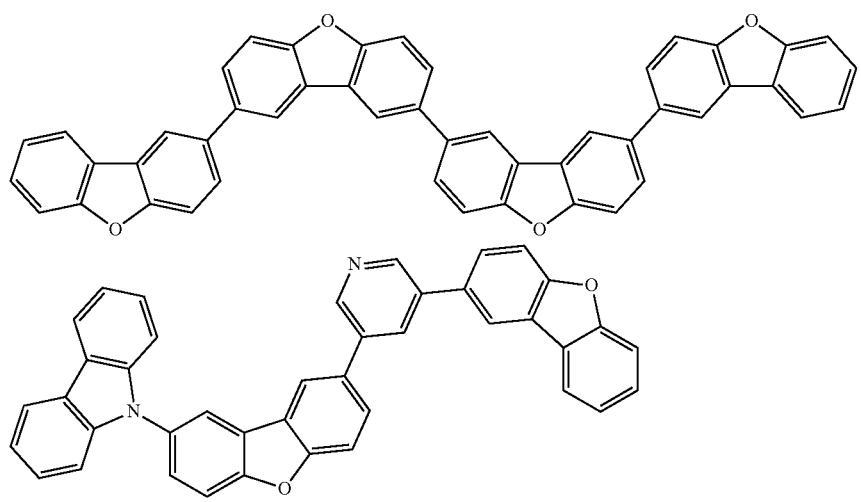
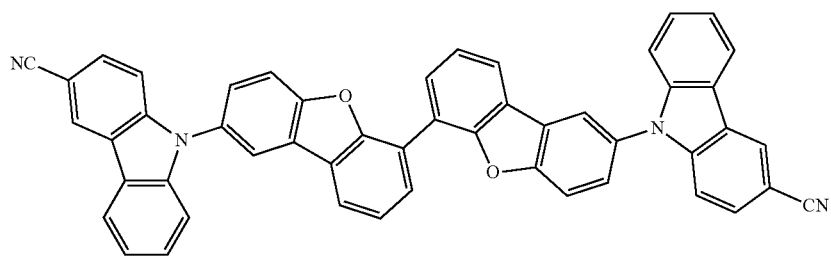
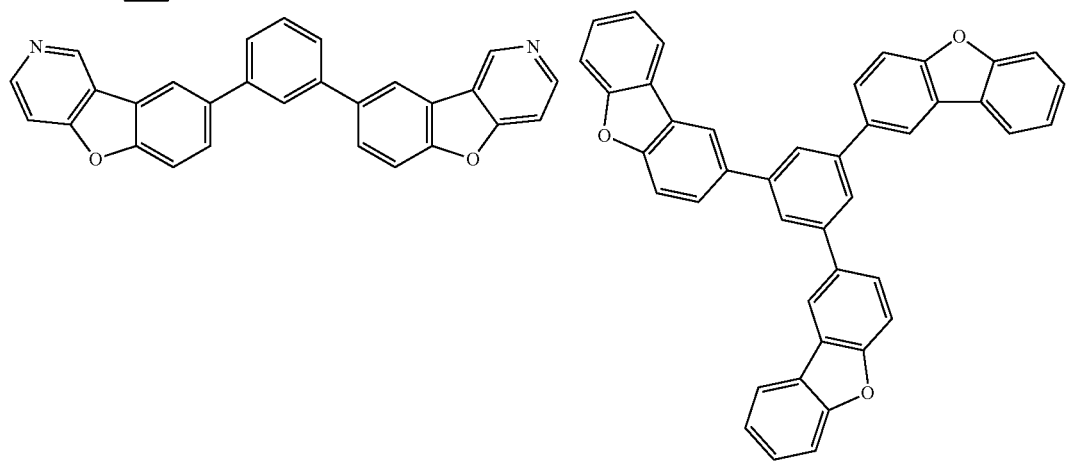

-continued
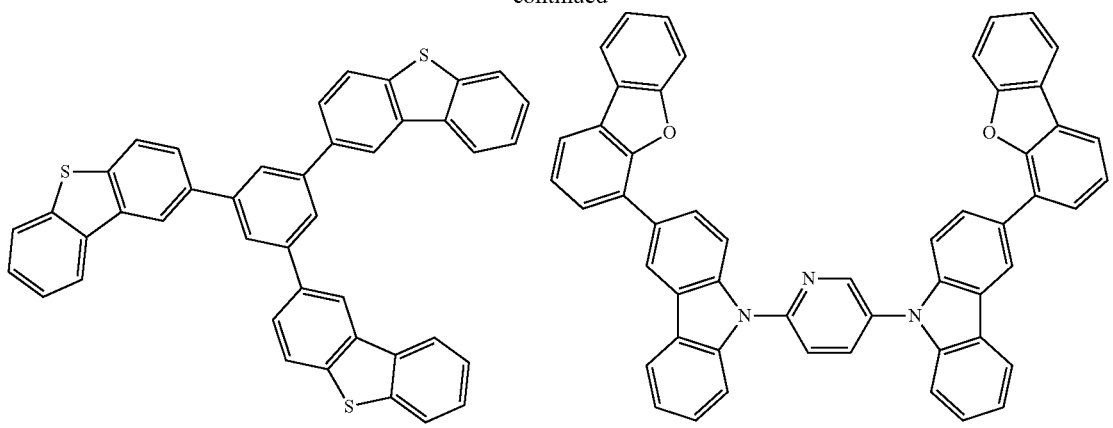
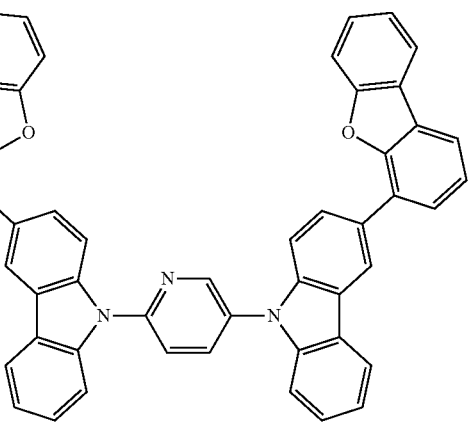
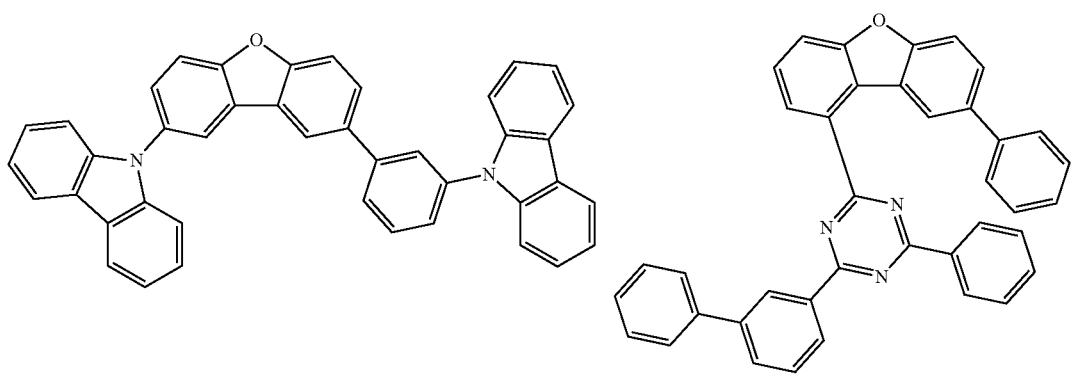
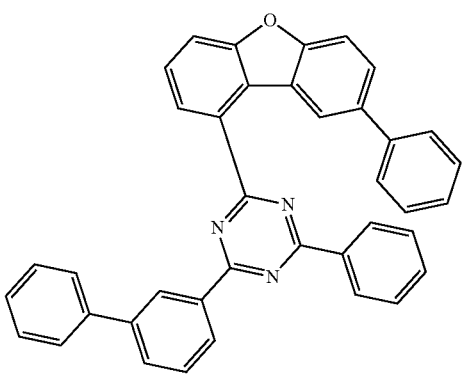
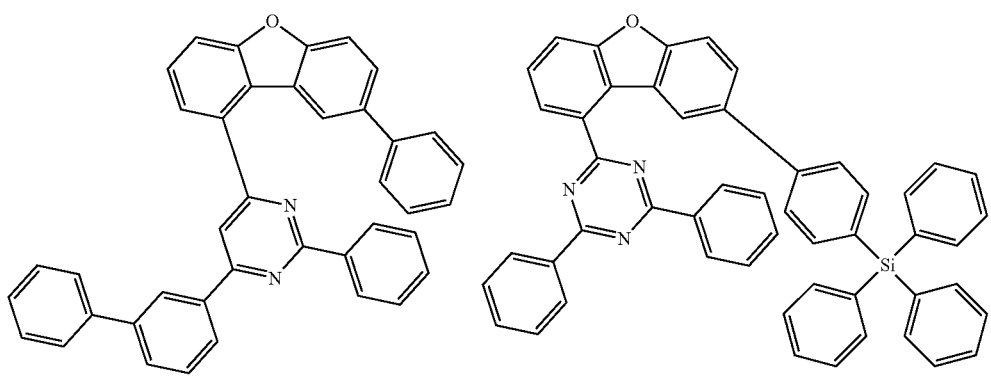
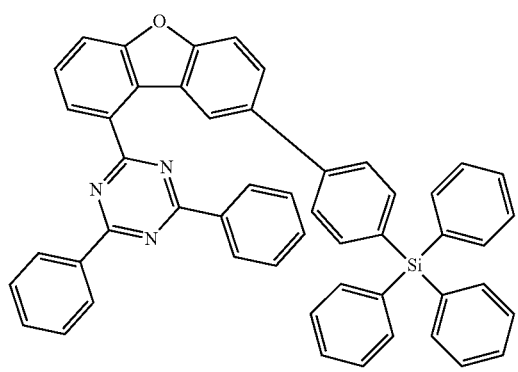
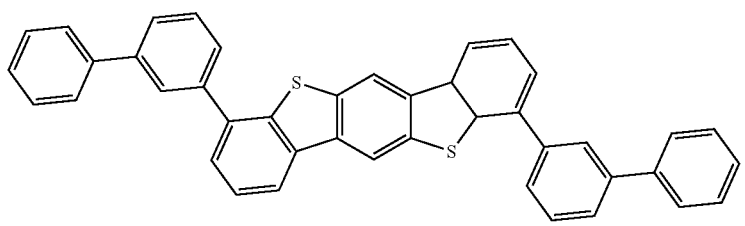

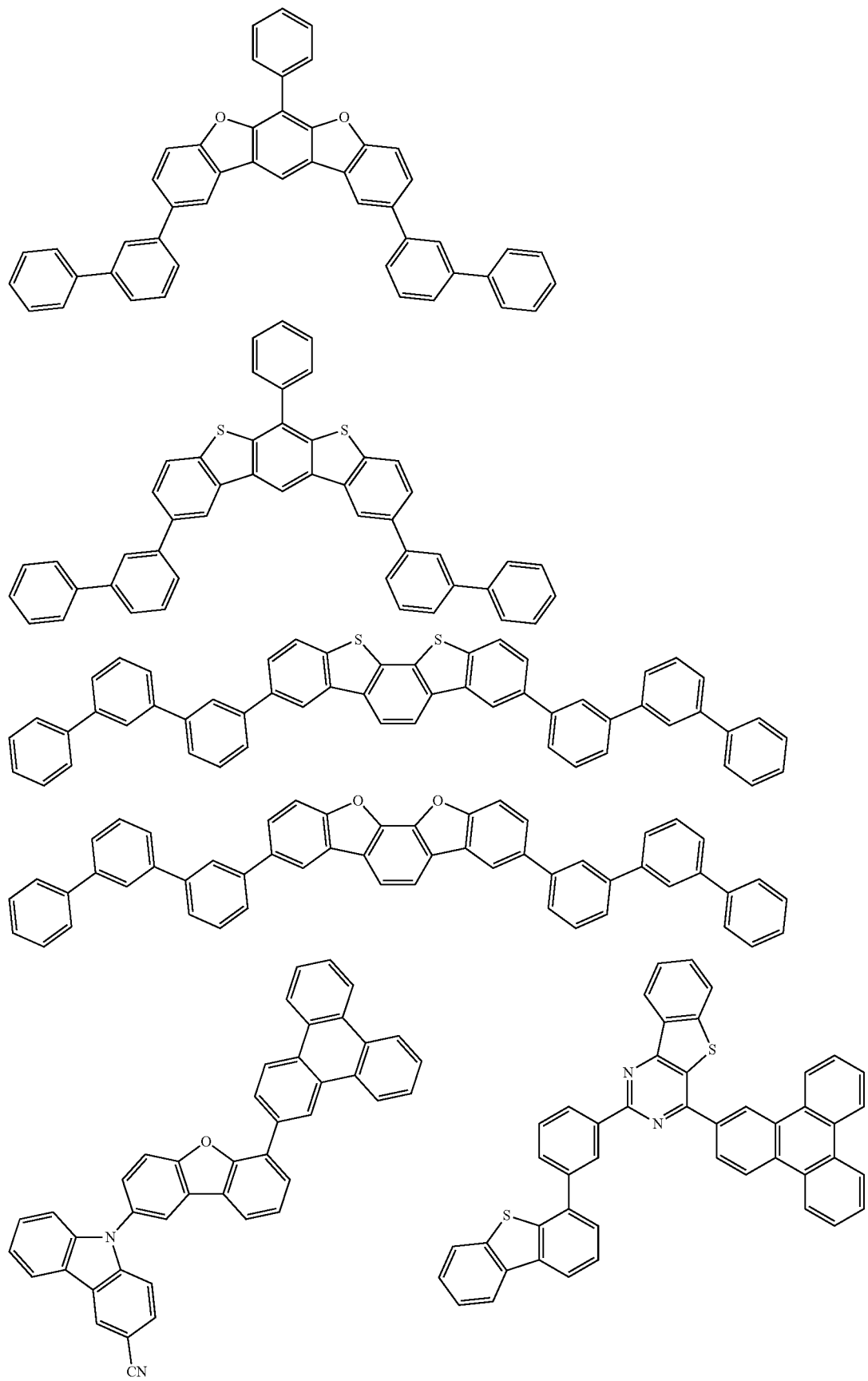

-continued
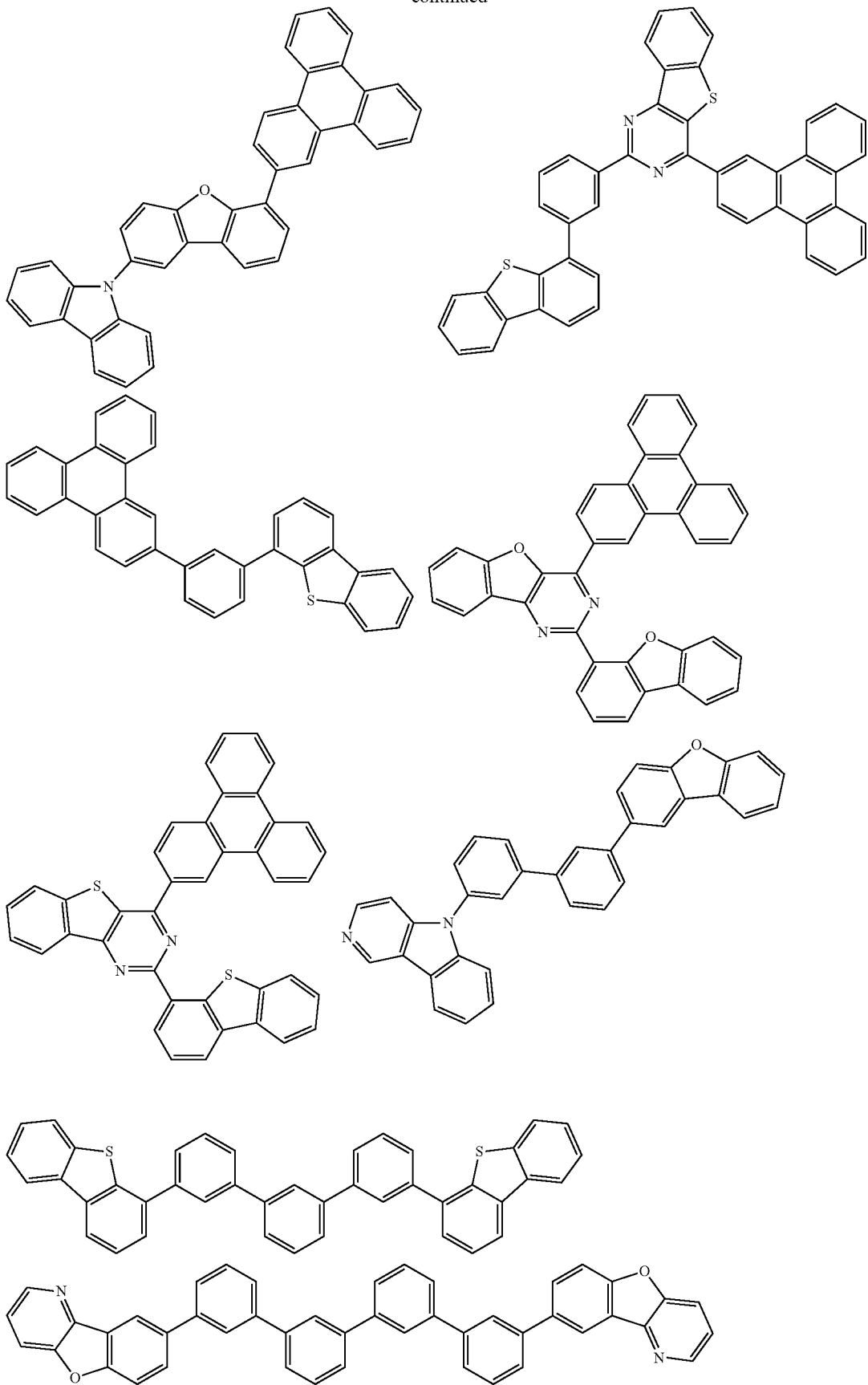

-continued
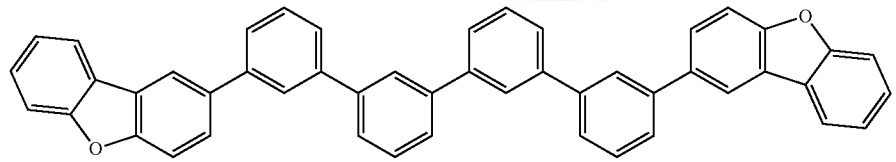
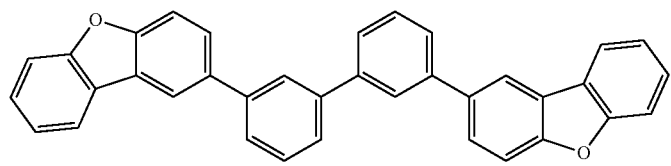
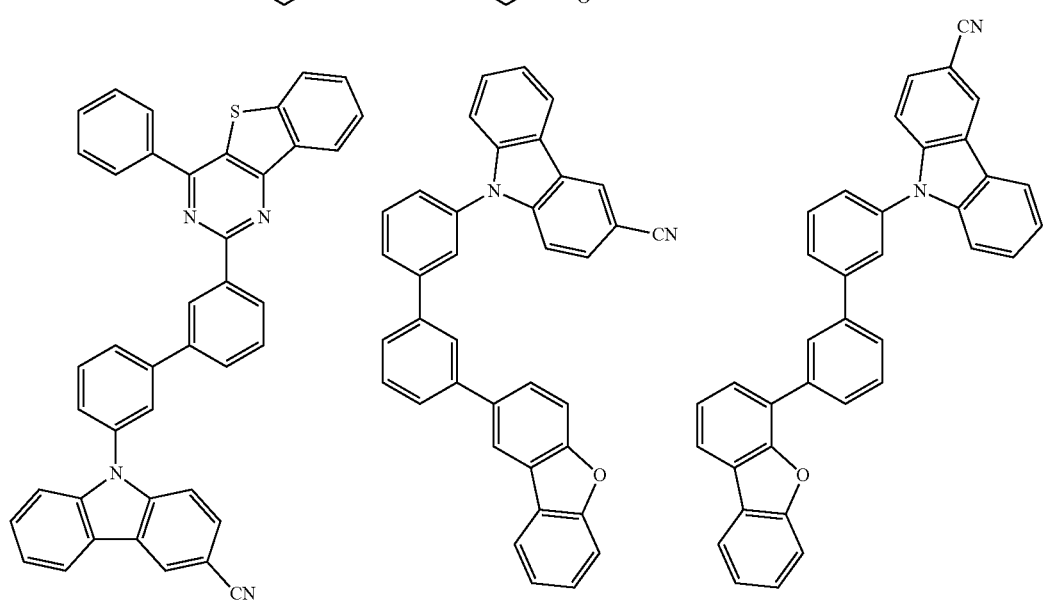
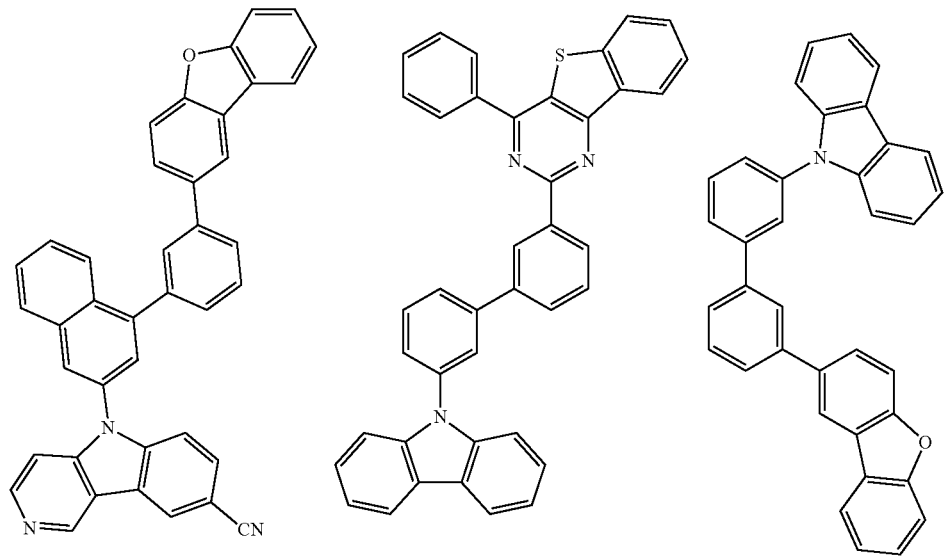

-continued
119
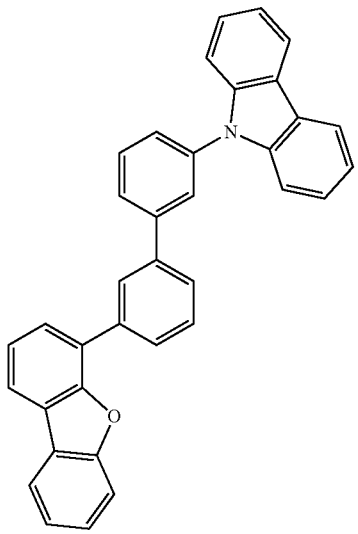
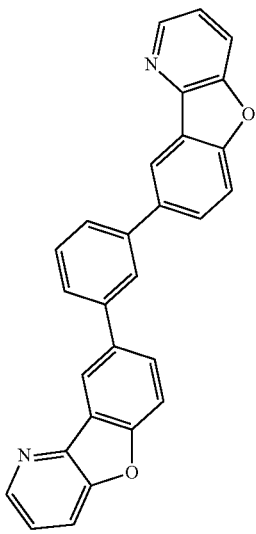
120
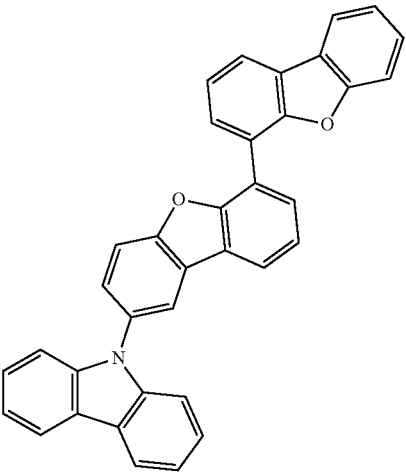
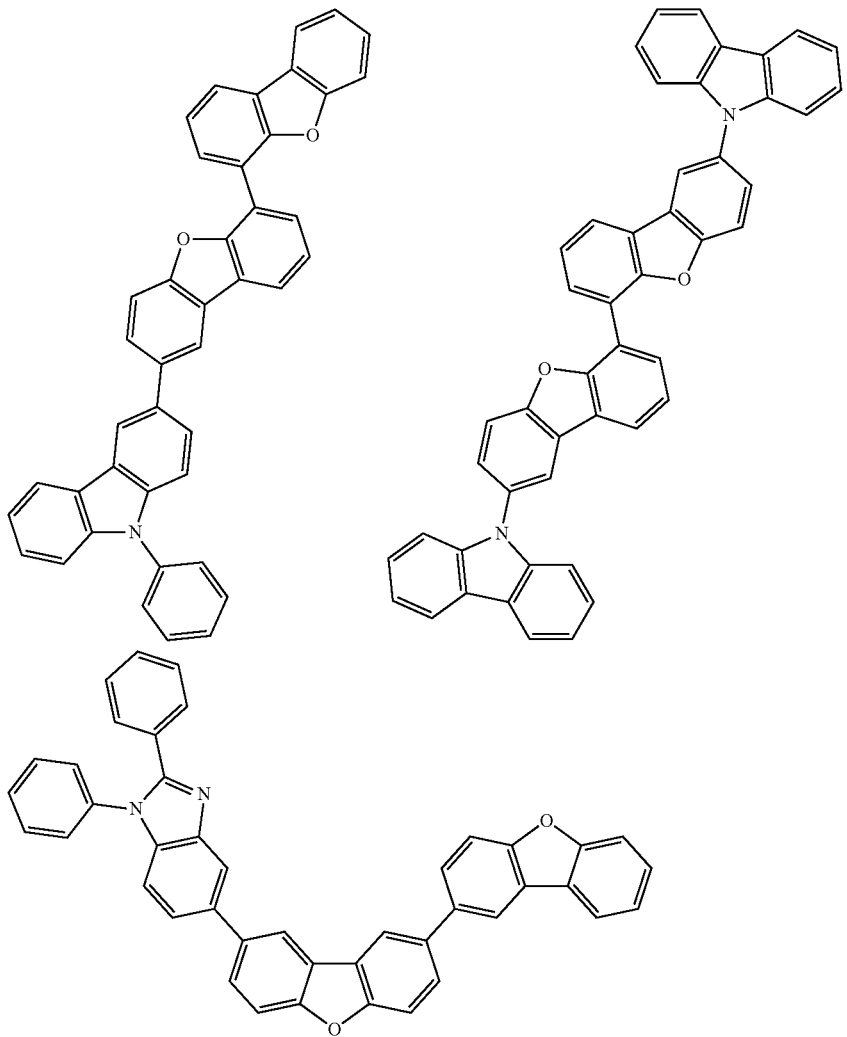

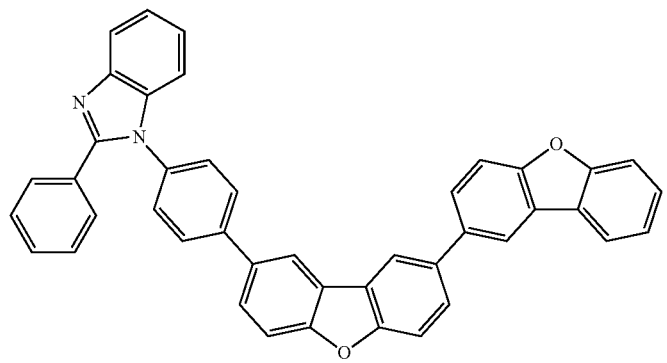
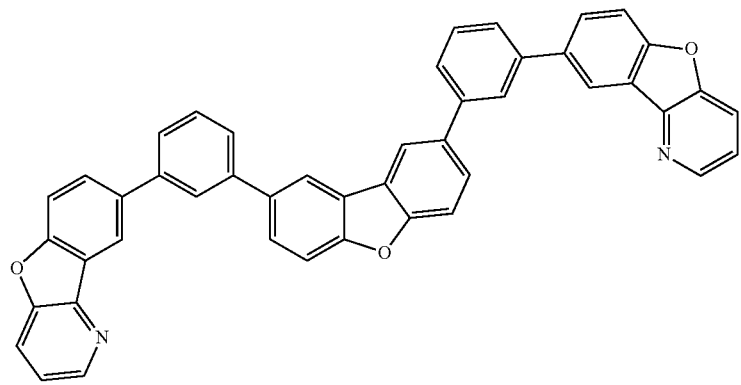
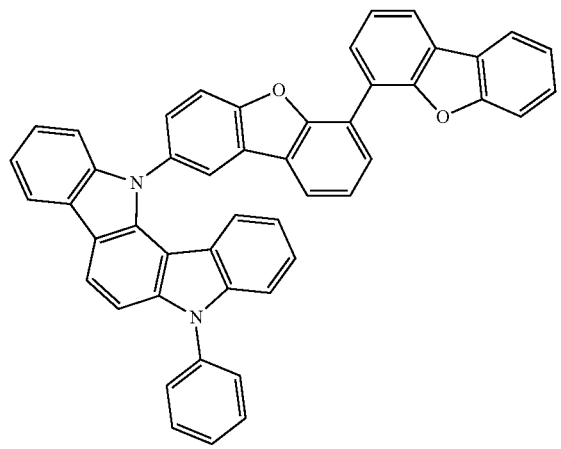
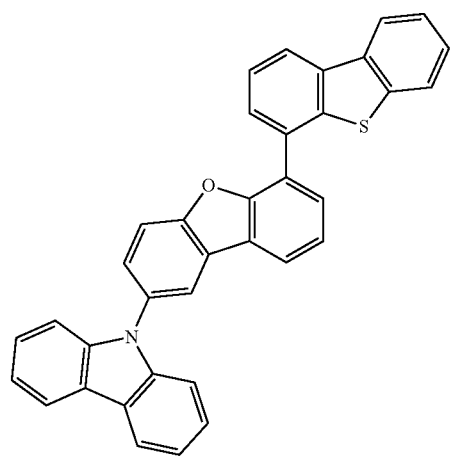
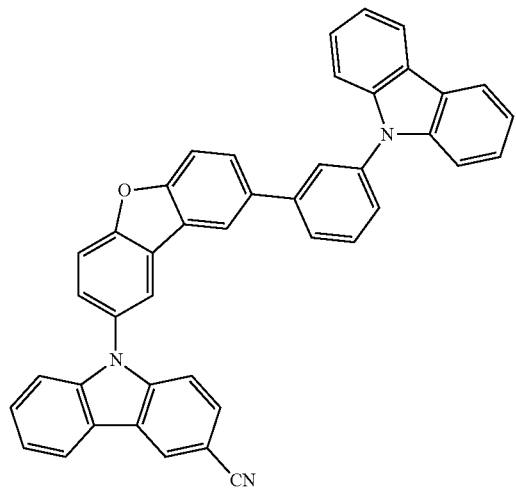
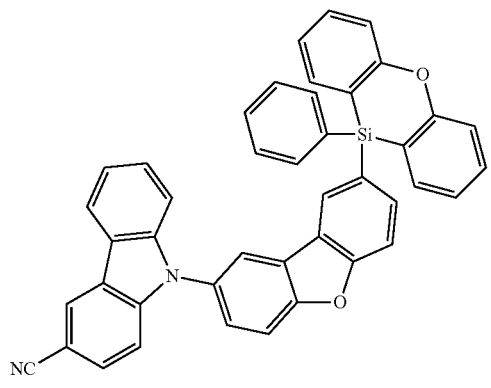

-continued
123
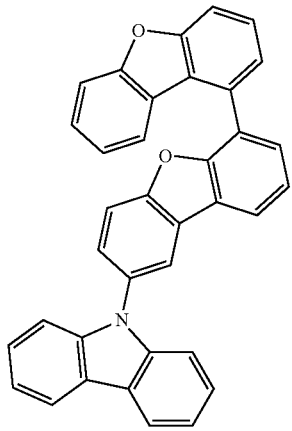
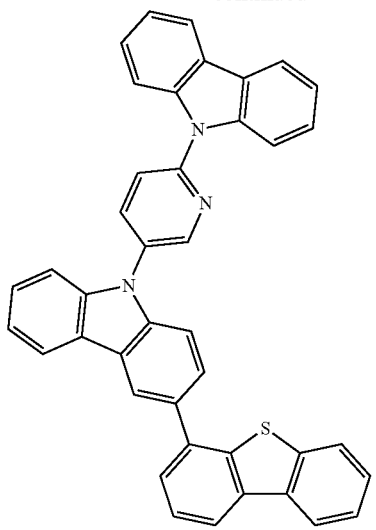
124
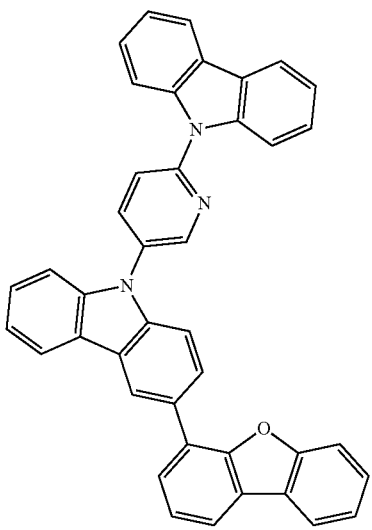
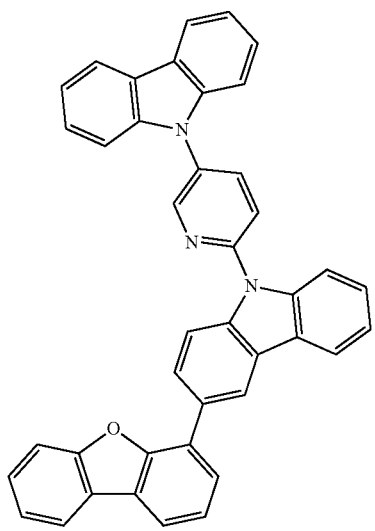
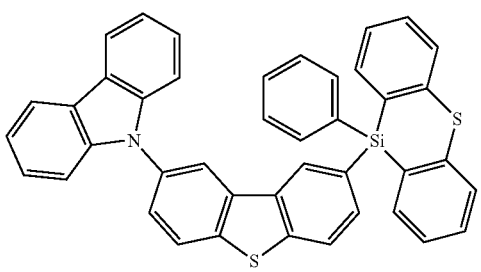
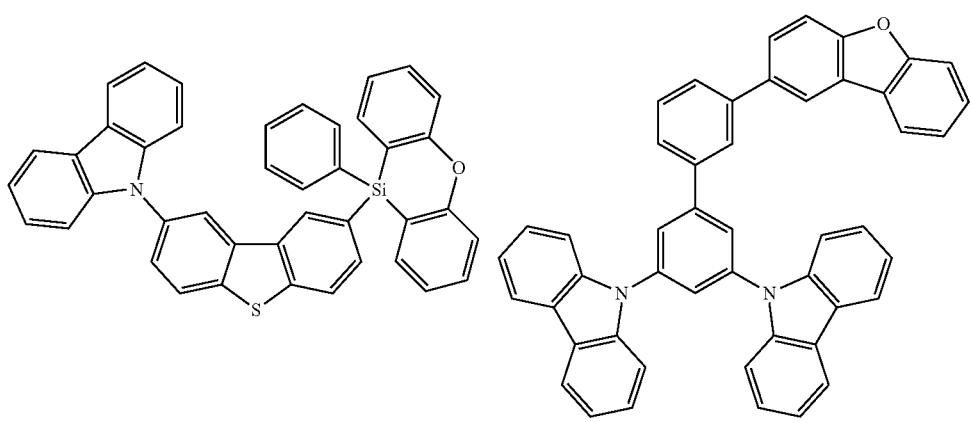

125 126
-continued
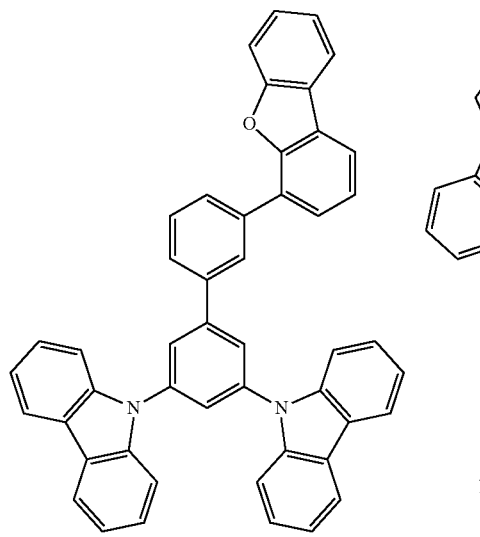 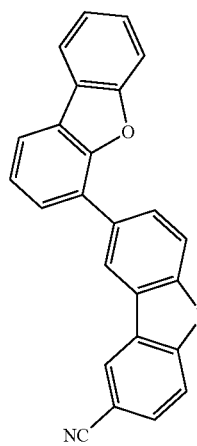 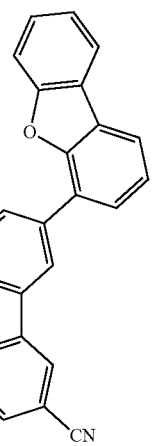
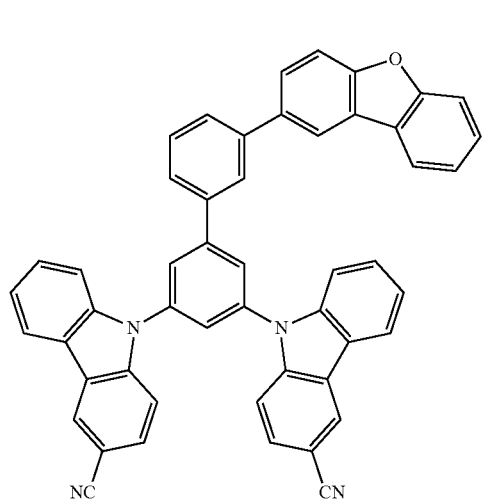 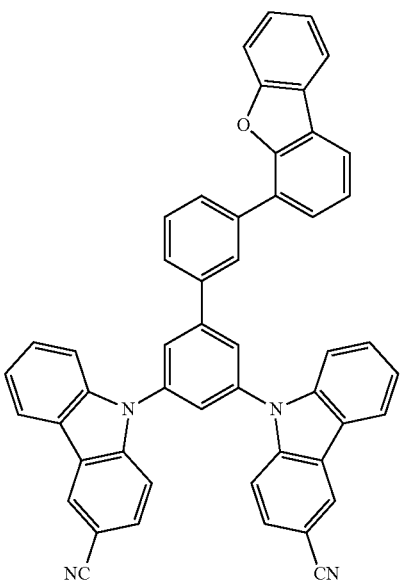
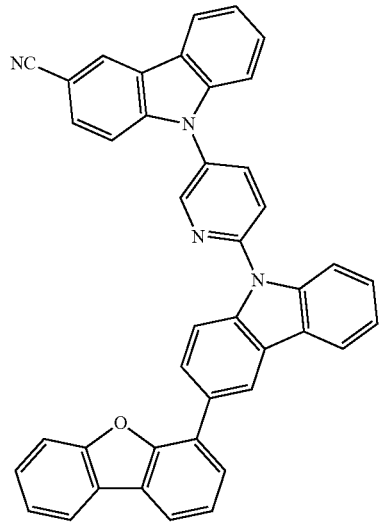 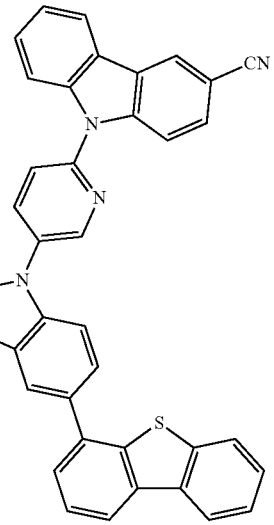 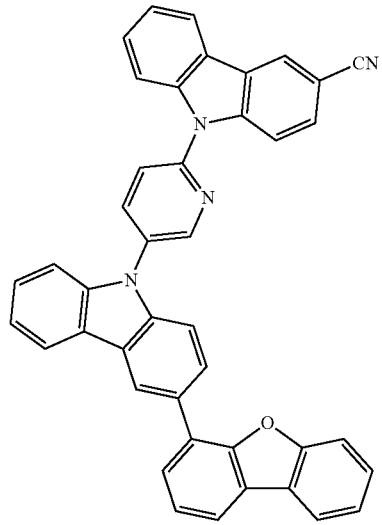

127
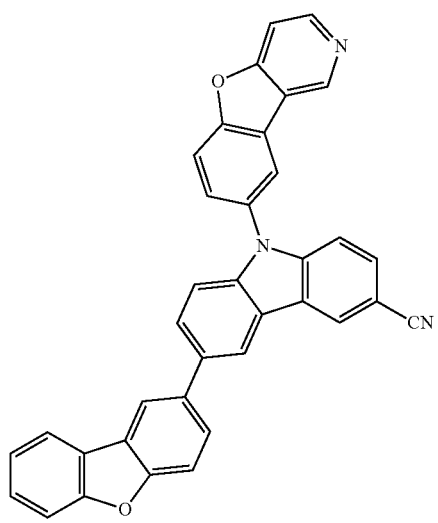
128
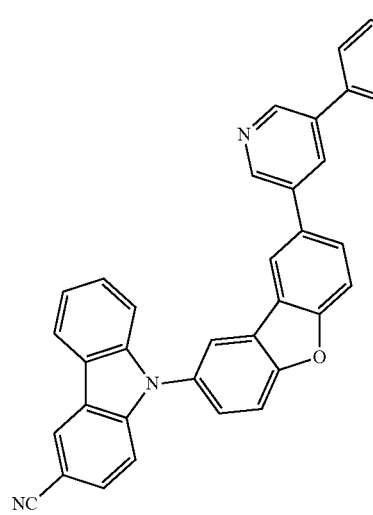
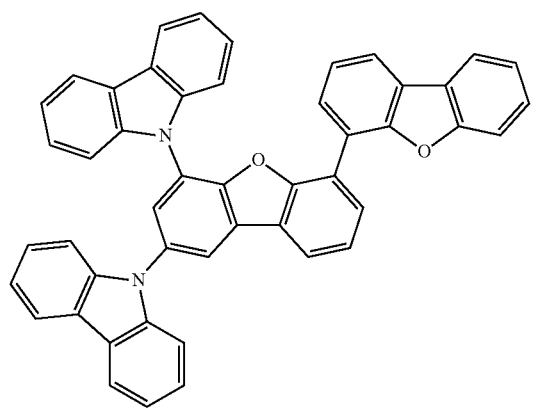
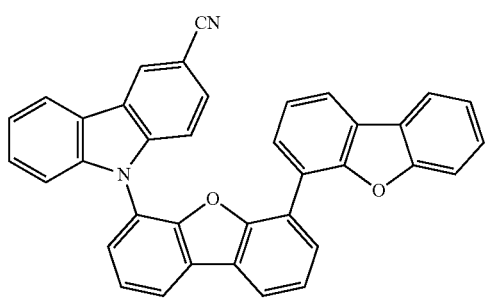
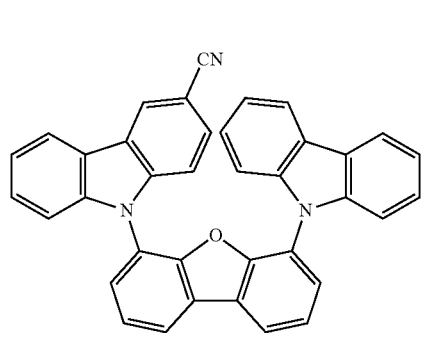
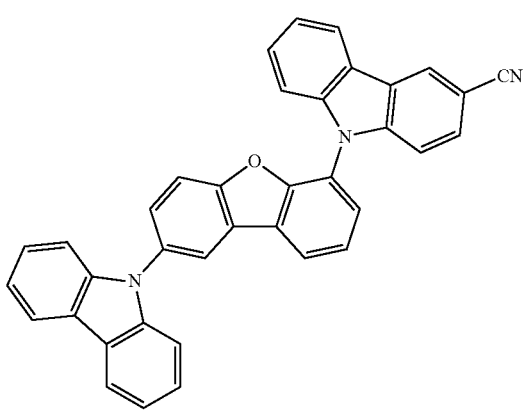

129 130
-continued
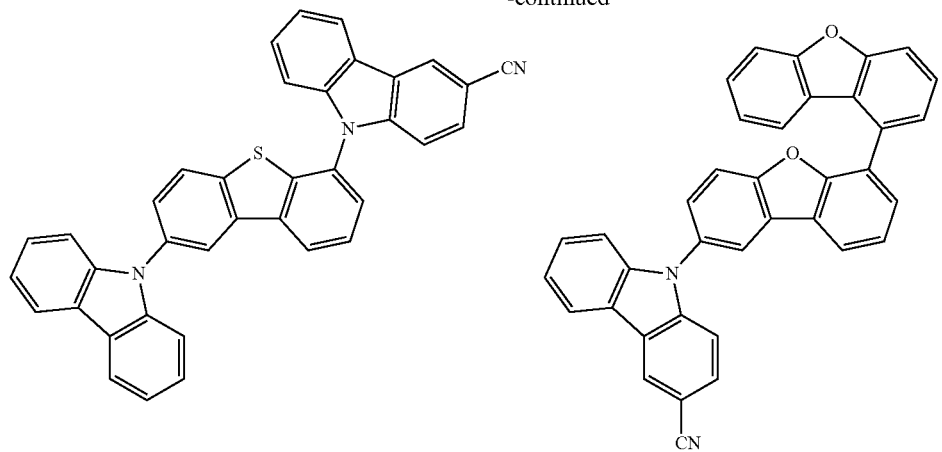
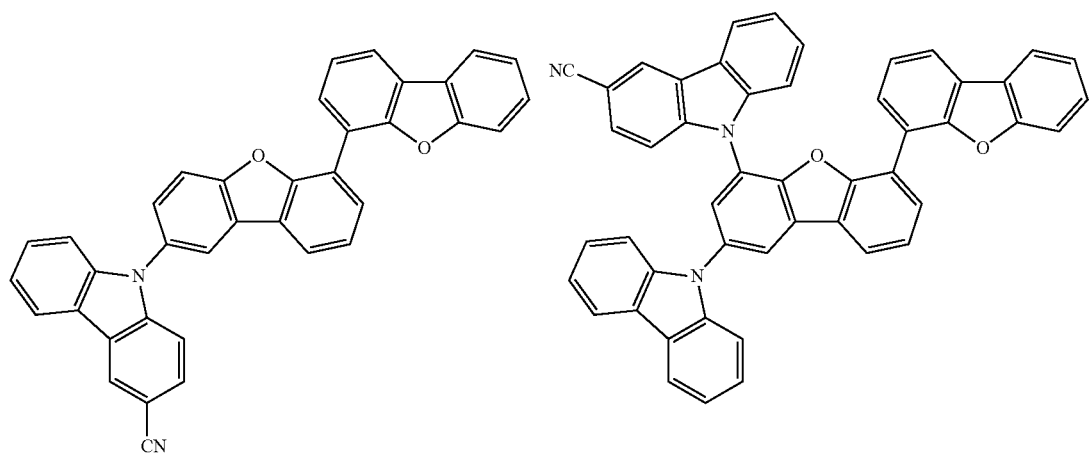
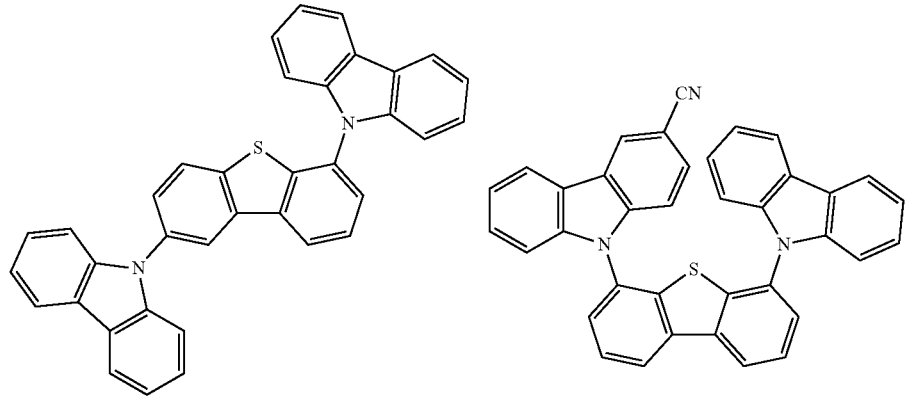
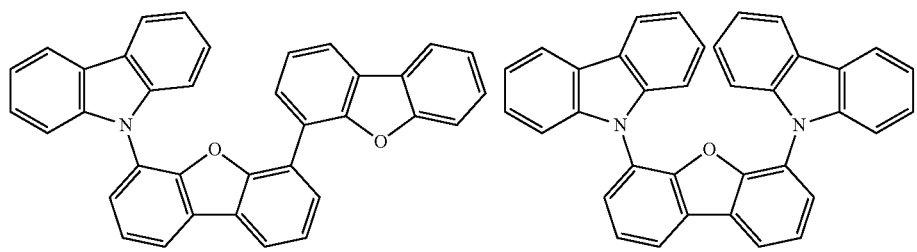

-continued
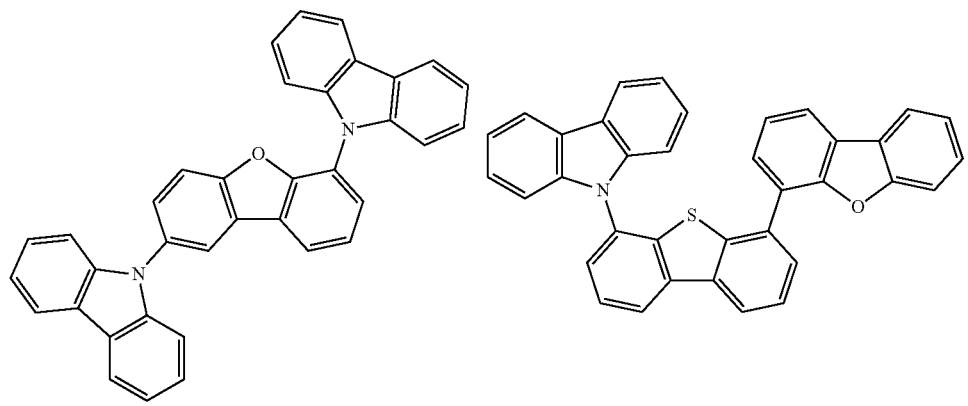
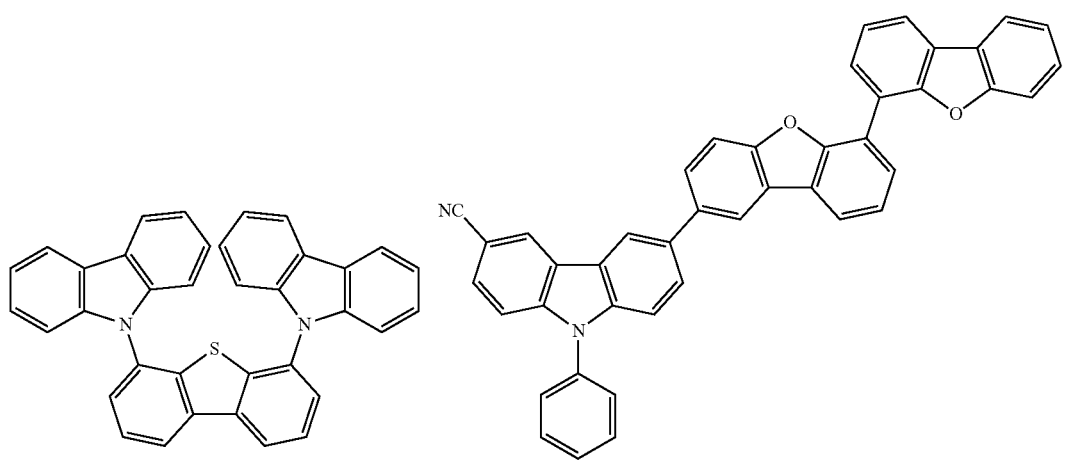
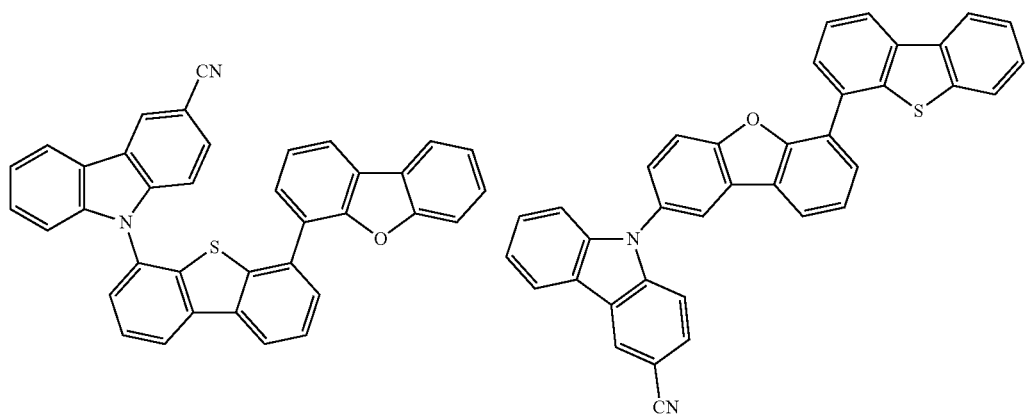
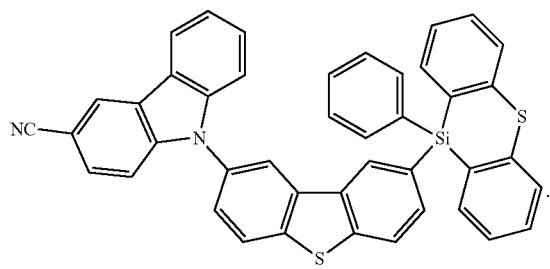

In one embodiment of the present disclosure, the organic material layer comprises a light emitting layer, and the light emitting layer comprises the compound of Chemical Formula 1; and a fluorescent emitter. In the embodiment, the fluorescent emitter is included in 0.1 parts by weight to 10 parts by weight with respect to 100 parts by weight of the compound of Chemical Formula 1.

In one embodiment of the present disclosure, the organic material layer comprises a light emitting layer, and the light emitting layer comprises the compound of Chemical Formula 1; a host; and a fluorescent emitter. In the embodiment, an amount of the compound of Chemical Formula 1 is from 1 parts by weight to 50 parts by weight with respect to 100 parts by weight of the host, and an amount of the fluorescent emitter can be from 0.5 parts by weight to 10 parts by weight with respect to 100 parts by weight of the host.

When the light emitting layer further comprises a fluorescent emitter, the compound of Chemical Formula 1 transfers exciton energy to the fluorescent emitter resulting in light emission in the fluorescent emitter, and therefore, a device capable of high luminance emission, having a low driving voltage, and capable of having long lifetime properties can be obtained.

As the fluorescent emitter, fluorescent materials such as anthracene-based compounds, pyrene-based compounds or boron-based compounds can be used, however, the fluorescent emitter is not limited thereto.

In one embodiment of the present specification, triplet energy of the fluorescent emitter is lower than triplet energy of the compound of Chemical Formula 1.

The compound of Chemical Formula 1 described above can be prepared using materials and reaction conditions known in the art.

The organic light emitting device of the present disclosure can be manufactured using common manufacturing methods and materials of an organic light emitting device except that one or more organic material layers are formed using the above-described compound.

The organic material layer of the organic light emitting device of the present specification can be formed in a single layer structure, but can also be formed in a multilayer structure in which two or more organic material layers are laminated. For example, the organic light emitting device of the present specification can have a structure further including, in addition to a light emitting layer, at least one of a hole injection layer, a hole buffer layer, a hole transfer layer, an electron blocking layer, a hole blocking layer, an electron transfer layer and an electron injection layer as the organic material layer. However, the structure of the organic light emitting device is not limited thereto, and can include less numbers of organic material layers.

According to one embodiment, the organic light emitting device can be an organic light emitting device having a structure in which an anode, one or more organic material layers and a cathode are consecutively laminated on a substrate (normal type). According to another embodiment, the organic light emitting device can be an organic light emitting device having a structure in a reverse direction in which a cathode, one or more organic material layers and an anode are consecutively laminated on a substrate (inverted type).

The organic light emitting device of the present specification can be manufactured using materials and methods known in the art, except that one or more layers of the organic material layers include the compound of Chemical Formula 1, that is, the compound of Chemical Formula 1.

For example, the organic light emitting device of the present specification can be manufactured by consecutively laminating a first electrode, an organic material layer and a second electrode on a substrate. Herein, the organic light emitting device can be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device can also be manufactured by consecutively depositing a cathode material, an organic material layer and an anode material on a substrate.

In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such a method, the organic light emitting device can also be manufactured by consecutively laminating a cathode material, an organic material layer and an anode material on a substrate (International Patent Application Publication No. WO2003/012890). However, the manufacturing method is not limited thereto.

In one embodiment of the present specification, the first electrode is an anode, and the second electrode is a cathode.

In another embodiment, the first electrode is a cathode, and the second electrode is an anode.

The organic light emitting device of the present specification can have a lamination structure as follows, however, the structure is not limited thereto.

(1) anode/hole transfer layer/light emitting layer/cathode (2) anode/hole injection layer/hole transfer layer/light emitting layer/cathode (3) anode/hole injection layer/hole buffer layer/hole transfer layer/light emitting layer/cathode (4) anode/hole transfer layer/light emitting layer/electron transfer layer/cathode (5) anode/hole transfer layer/light emitting layer/electron transfer layer/electron injection layer/cathode (6) anode/hole injection layer/hole transfer layer/light emitting layer/electron transfer layer/cathode (7) anode/hole injection layer/hole transfer layer/light emitting layer/electron transfer layer/electron injection layer/cathode (8) anode/hole injection layer/hole buffer layer/hole transfer layer/light emitting layer/electron transfer layer/cathode (9) anode/hole injection layer/hole buffer layer/hole transfer layer/light emitting layer/electron transfer layer/electron injection layer/cathode

(10) anode/hole transfer layer/electron blocking layer/light emitting layer/electron transfer layer/cathode

(11) anode/a hole transfer layer/electron blocking layer/light emitting layer/electron transfer layer/electron injection layer/cathode

(12) anode/hole injection layer/hole transfer layer/electron blocking layer/light emitting layer/electron transfer layer/cathode

(13) anode/hole injection layer/hole transfer layer/electron blocking layer/light emitting layer/electron transfer layer/electron injection layer/cathode

(14) anode/hole transfer layer/light emitting layer/hole blocking layer/electron transfer layer/cathode

(15) anode/hole transfer layer/light emitting layer/a hole blocking layer/electron transfer layer/electron injection layer/cathode

(16) anode/hole injection layer/hole transfer layer/light emitting layer/hole blocking layer/electron transfer layer/cathode

(17) anode/hole injection layer/hole transfer layer/light emitting layer/hole blocking layer/electron transfer layer/electron injection layer/cathode For example, structures of the organic light emitting device according to one embodiment of the present specification are illustrated in FIGS. 1 to 3.

FIG. 1 illustrates an example of the organic light emitting device formed with a substrate (1), an anode (2), a light emitting layer (3) and a cathode (4). In such a structure, the compound of Chemical Formula 1 can be included in the light emitting layer.

FIG. 2 illustrates an example of the organic light emitting device formed with a substrate (1), an anode (2), a hole injection layer (5), a hole transfer layer (6), a light emitting layer (3), an electron transfer layer (7) and a cathode (4). In such a structure, the compound of Chemical Formula 1 can be included in the light emitting layer.

FIG. 3 illustrates an example of the organic light emitting device formed with a substrate (1), an anode (2), a hole injection layer (5), a hole transfer layer (6), an electron blocking layer (8), a light emitting layer (3), a hole blocking layer (9), an electron injection and transfer layer (10) and a cathode (4). In such a structure, the compound of Chemical Formula 1 can be included in the light emitting layer.

The light emitting layer (3) can include a host material and a dopant material. In addition, the compound of Chemical Formula 1 can be used as the host material and the dopant material.

The anode (2) is an electrode injecting holes, and can be any one of indium tin oxide (ITO), indium zinc oxide (IZO) or zinc oxide (ZnO) having high work function. In addition, when the anode (2) is a reflective electrode, the anode (2) can further include a reflective layer formed with any one of aluminum (Al), silver (Ag) or nickel (Ni) below the layer formed with any one of the ITO, the IZO or the ZnO.

The hole injection layer (5) is a layer injecting holes from the anode (2) to the light emitting layer (3). In one embodiment, the hole injection layer can have a thickness of 1 nm to 150 nm. Herein, the hole injection layer having a thickness of 1 nm or greater has an advantage of preventing decline in the hole injection properties.

As materials of the hole transfer layer in addition thereto, hole transfer materials known in the art can be used. For example, the hole transfer layer (6) can be formed with any one or more selected from the group consisting of N,N-dinaphthyl-N,N'-diphenylbenzidine (NPD), N,N'-bis-(3-methyl-phenyl)-N,N'-bis-(phenyl)-benzidine (TPD), s-TAD and 4,4',4''-tris(N-3-methylphenyl-N-phenyl-amino)-triphenylamine (MTDATA), but is not limited thereto. For example, triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, polysilane-based, aniline-based copolymers, conductive polymer oligomers (particularly, thiophene oligomers) and the like can be included as the hole transfer layer material.

In one embodiment, a hole buffer layer can be further provided between the hole injection layer and the hole transfer layer. As the hole buffer layer, hole injection or transfer materials known in the art can be used.

The electron blocking layer is a layer preventing excess electrons passing through the light emitting layer from migrating toward the anode. As the electron blocking materials, materials having a lower lowest unoccupied molecular orbital (LUMO) level than the hole transfer layer are preferred, and proper materials can be selected considering energy levels of surrounding layers. In one embodiment, arylamine-based organic materials can be used as the electron blocking layer, however, the electron blocking layer is not limited thereto.

The hole blocking layer is layer preventing holes from passing through the light emitting layer and entering the cathode during driving of an organic light emitting device. As the hole blocking material, materials having a very low highest occupied molecular orbital (HOMO) level are preferably used. Specific examples of the hole blocking material can include TPBi, BCP, CBP, PBD, PTCBI, BPhen and the like, but are not limited thereto. In one embodiment, the hole blocking layer includes 2,9-dimethyl-4,7-diphenyl-1,10-phenanthroline.

The electron transfer layer is a layer facilitating electron transfer. As the electron transfer layer, materials known in the art such as tris(8-hydroxyquinolino)aluminum ($Alq_3$), PBD, TAZ, Spiro-PBD, BAlq or SAlq can be used. The electron transfer layer can have a thickness of 1 nm to 50 nm. Herein, the electron transfer layer having a thickness of 1 nm or greater has an advantage of preventing decline in the electron transfer properties, and the thickness being 50 nm or less has an advantage of preventing an increase in the driving voltage for enhancing electron migration caused from the electron transfer layer (7) becoming too thick.

The electron injection layer can perform a role of facilitating electron injection, and can be formed with organic materials or complexes such as tris(8-hydroxyquinolino) aluminum ($Alq_3$), PBD, TAZ, Spiro-PBD, BAlq or SAlq, or metal compounds. As the metal compound, metal halides can be used, and for example, LiQ, LiF, NaF, KF, RbF, CsF, FrF, $BeF_2$, $MgF_2$, $CaF_2$, $SrF_2$, $BaF_2$, $RaF_2$ and the like can be used. The electron injection layer can have a thickness of 1 nm to 50 nm. Herein, the electron injection layer having a thickness of 1 nm or greater has an advantage of preventing decline in the electron injection properties, and the thickness being 50 nm or less has an advantage of preventing an increase in the driving voltage for enhancing electron migration caused from the electron injection layer becoming too thick.

In one embodiment of the present specification, a layer performing a role of electron transfer and injection at the same time (electron transfer and injection layer) can be used as the organic material layer. As a material of the electron transfer and injection layer, materials of the electron injection layer and the electron transfer layer can be used. The electron transfer and injection layer can be formed with a single material, and can also be formed by doping another material to one material.

The cathode is an electrode injecting electrons, and can be formed with magnesium (Mg), calcium (Ca), aluminum (Al) or silver (Ag) having low work function, or an alloy thereof. Herein, when the organic light emitting device has a top- or dual-emission structure, the cathode can be formed to have a thickness thin enough to transmit light, and when the organic light emitting device has a bottom-emission structure, the cathode can be formed to have a thickness thick enough to reflect light.

According to another embodiment, the organic material layer includes two or more light emitting layers, and can include a charge generation layer including the compound of Chemical Formula 1 provided between the two light emitting layers. Herein, one of the light emitting layers can be employed to emit a different color to manufacture an organic light emitting device emitting white light. Between the light emitting layer and the anode or the cathode, and between the light emitting layer and the charge generation layer, one or more organic material layers such as the hole injection layer, the hole buffer layer, the hole transfer layer, the electron blocking layer, the hole blocking layer, the electron transfer layer or the electron injection layer described above can be further included.

The light emitting material is a material capable of emitting light in a visible light region by receiving holes and electrons from the hole transfer layer and the electron transfer layer, respectively, and binding the holes and the electrons, and is preferably a material having favorable quantum efficiency for fluorescence or phosphorescence. Specific examples thereof include 8-hydroxyquinoline aluminum complexes (Alq$_3$); carbazole-based compounds; dimerized styryl compounds; BAlq; 10-hydroxybenzoquinoline-metal compounds; benzoxazole-, benzthiazole- and benzimidazole-based compounds; poly(p-phenylenevinylene) (PPV)-based polymers; spiro compounds; polyfluorene, rubrene, and the like, but are not limited thereto.

The organic light emitting device according to the present disclosure can be a top-emission type, a bottom-emission type or a dual-emission type depending on the materials used.

EXAMPLES

Examples according to the present disclosure are for describing the present disclosure in more detail, and can be modified to various other forms in addition to the descriptions provided below, and the scope of a right of the present disclosure is not limited to the examples described below.

Preparation Example

The compound of Chemical Formula 1 can be formed by introducing various types of triazine groups to cyano group-substituted fluorophenylboronic acid as follows. After introducing the triazine group, indolocarbazole was finally introduced to synthesize the compounds.

Preparation Example 1-1: Synthesis of Compound 1-A

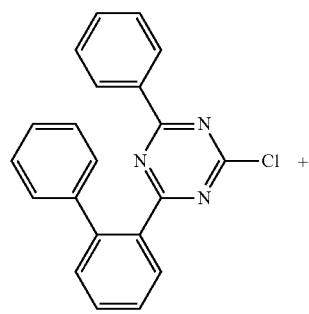

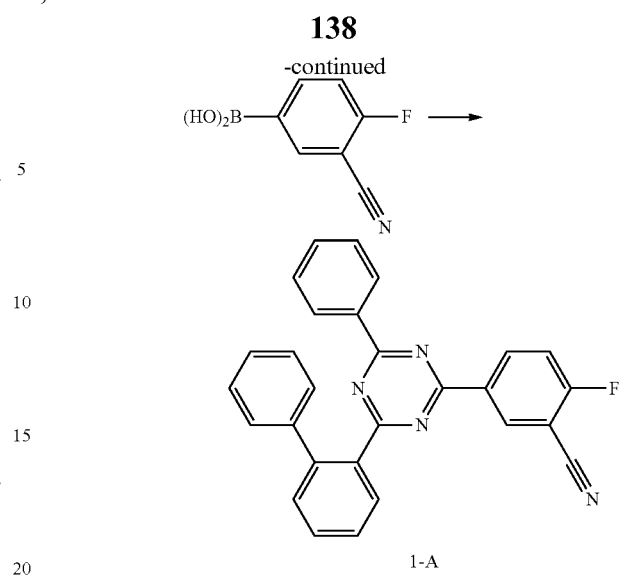

(3-Cyano-4-fluorophenyl)boronic acid (30 g, 181.9 mmol), 2-([1,1'-biphenyl]-2-yl)-4-chloro-6-phenyl-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-A (70.1 g, yield 90%).

MS[M+H]$^+$=428

Preparation Example 1-2: Synthesis of Compound 1-B

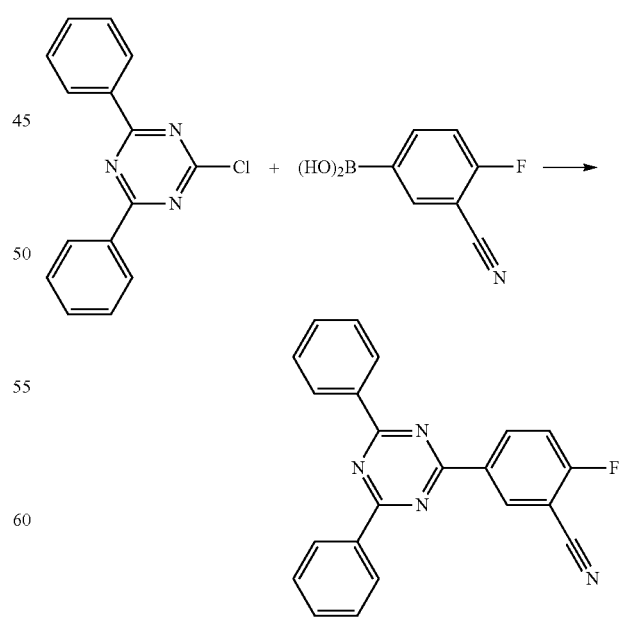

(3-Cyano-4-fluorophenyl)boronic acid (30 g, 181.9 mmol), 2-chloro-4,6-diphenyl-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-B (58.9 g, yield 92%).
MS[M+H]$^+$=352

Preparation Example 1-3: Synthesis of Compound 1-C

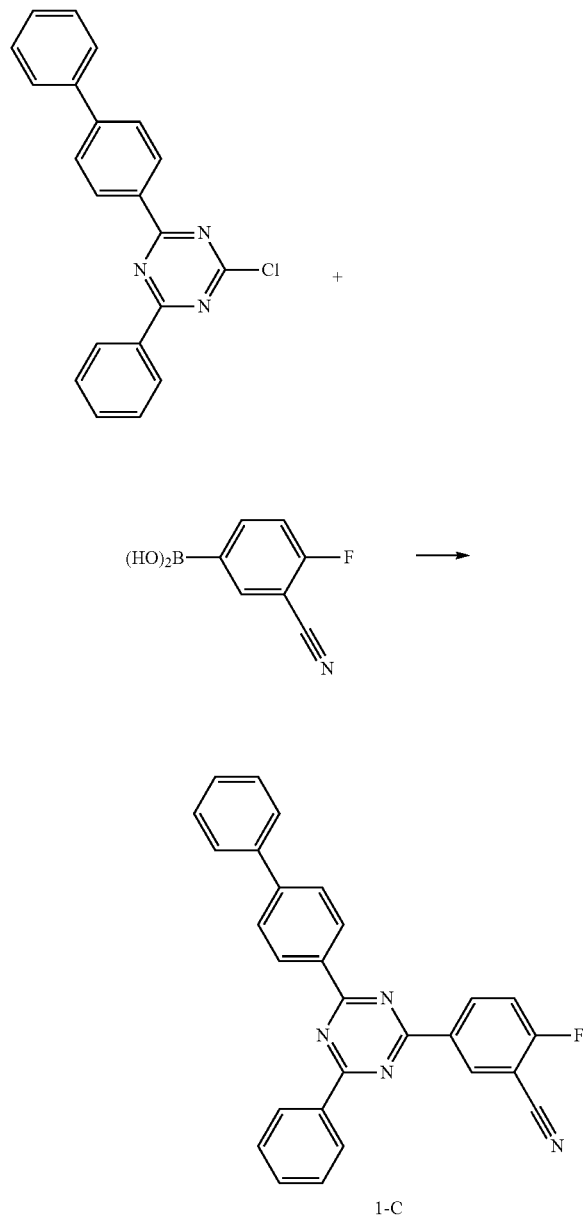

1-C (3-Cyano-4-fluorophenyl)boronic acid (30 g, 181.9 mmol), 2-([1,1'-biphenyl]-4-yl)-4-chloro-6-phenyl-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-C (68.6 g, yield 88%).
MS[M+H]$^+$=428

Preparation Example 1-4: Synthesis of Compound 1-D

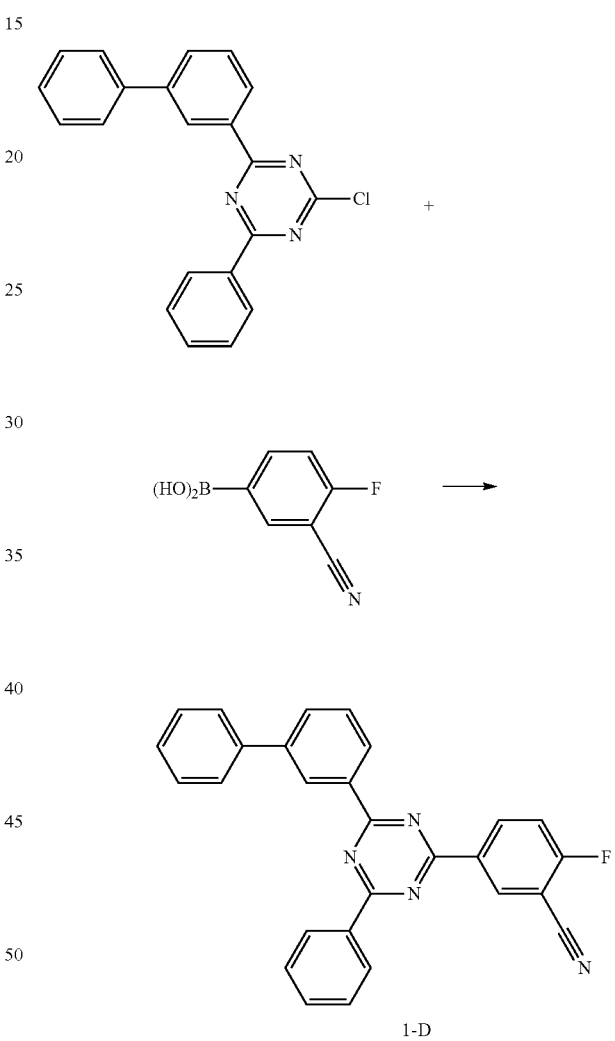

1-D (3-Cyano-4-fluorophenyl)boronic acid (30 g, 181.9 mmol), 2-([1,1'-biphenyl]-3-yl)-4-chloro-6-phenyl-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-D (67.8 g, yield 87%).
MS[M+H]$^+$=428

Preparation Example 1-5: Synthesis of Compound 1-E

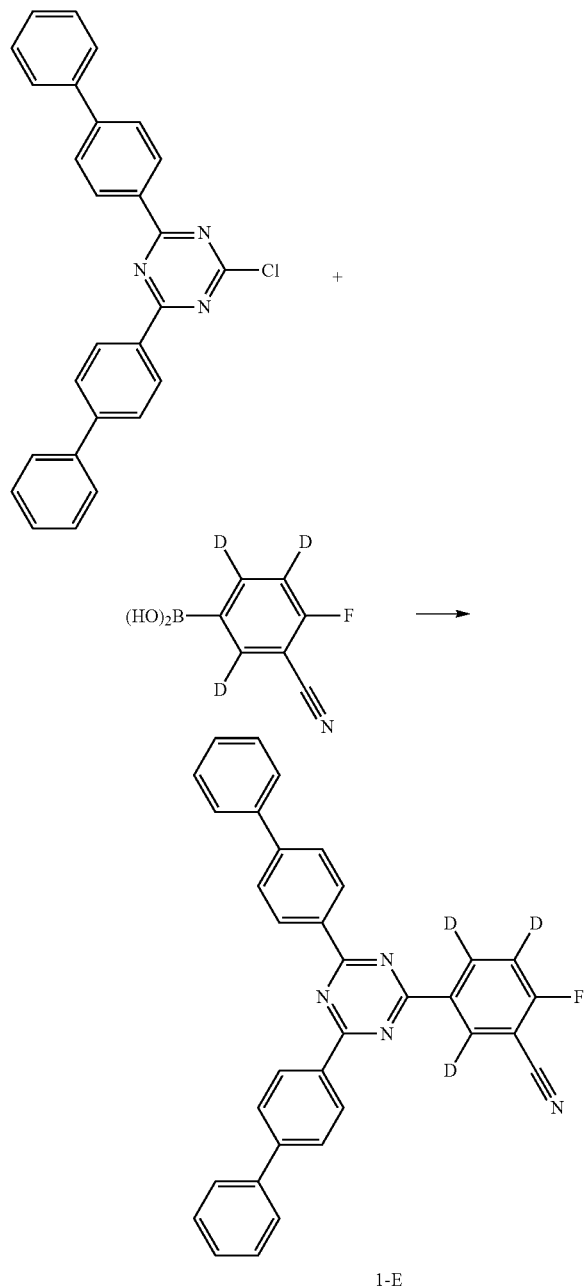

1-E (3-Cyano-4-fluorophenyl-2,5,6-D$_3$)boronic acid (30.5 g, 181.9 mmol), 2,4-di([1,1'-biphenyl]-4-yl)-6-chloro-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran/ethanol to obtain Compound 1-E (78.5 g, yield 85%).

MS[M+H]$^+$=507

Preparation Example 1-6: Synthesis of Compound 1-F

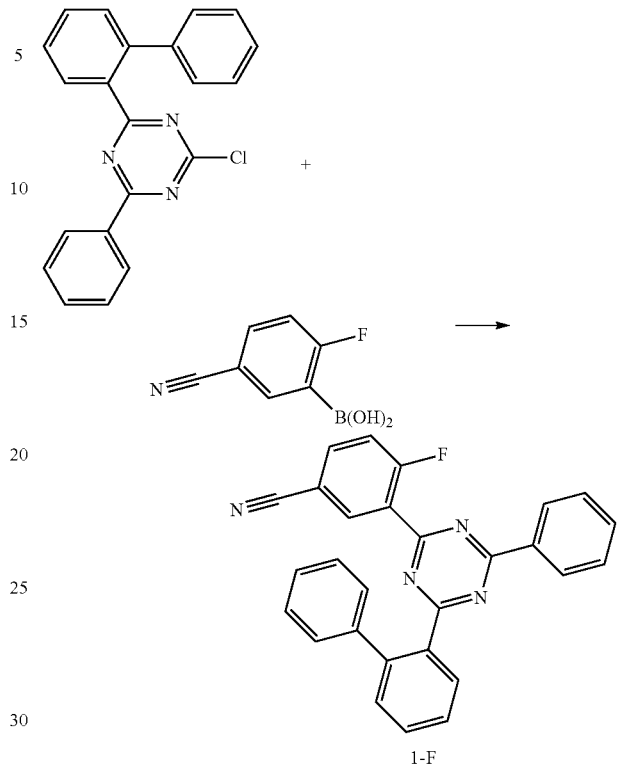

1-F (5-Cyano-2-fluorophenyl)boronic acid (30 g, 181.9 mmol), 2-([1,1'-biphenyl]-2-yl)-4-chloro-6-phenyl-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-F (47.8 g, yield 87%).

MS[M+H]$^+$=428

Preparation Example 1-7: Synthesis of Compound 1-G

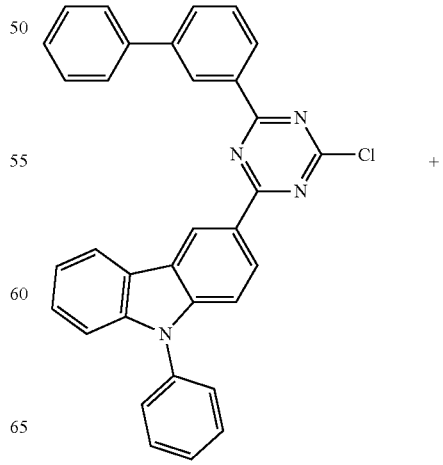

-continued

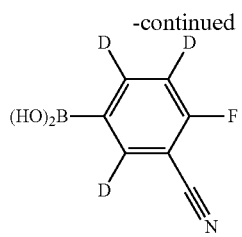

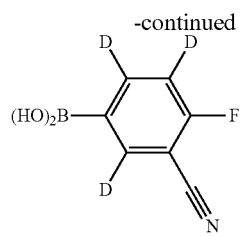

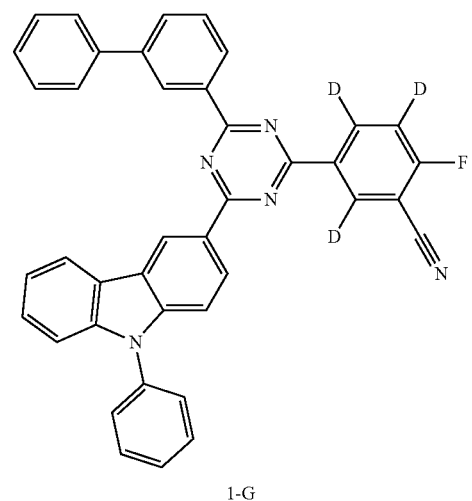

1-G

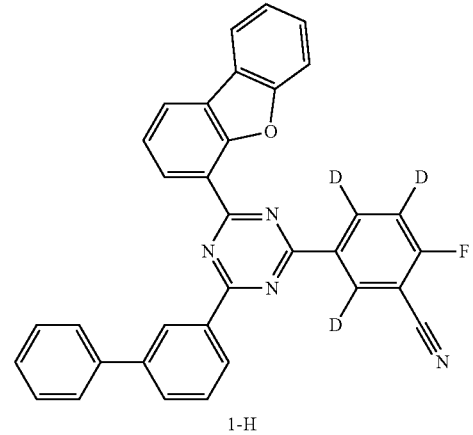

1-H (3-Cyano-4-fluorophenyl-2,5,6-$D_3$)boronic acid (30.5 g, 181.9 mmol), 3-(4-([1,1'-biphenyl]-3-yl)-6-chloro-1,3,5-triazin-2-yl)-9-phenyl-9H-carbazole (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-G (92.2 g, yield 85%).

MS[M+H]$^+$=596

Preparation Example 1-8: Synthesis of Compound 1-H

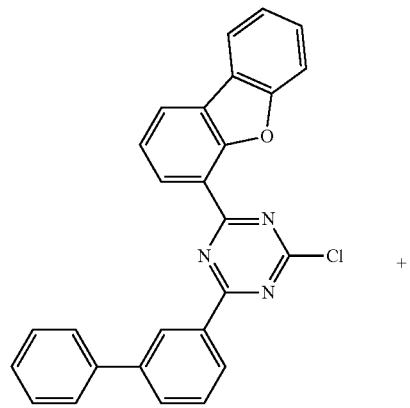

(3-Cyano-4-fluorophenyl-2,5,6-$D_3$)boronic acid (30.5 g, 181.9 mmol), 2-([1,1'-biphenyl]-3-yl)-4-chloro-6-(dibenzo-[b,d]furan-4-yl)-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-H (78.7 g, yield 83%).

MS[M+H]$^+$=521

Preparation Example 1-9: Synthesis of Compound 1-I

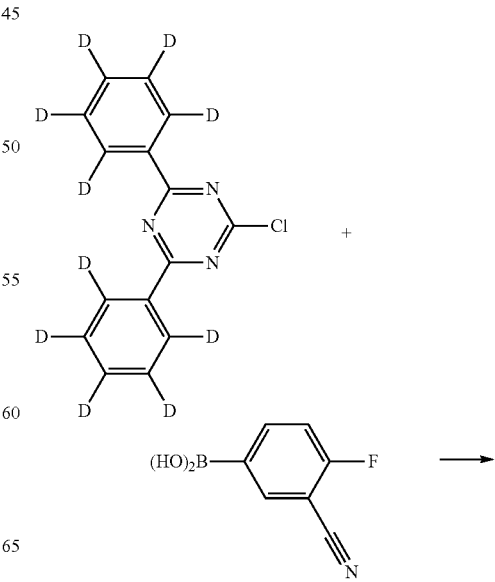

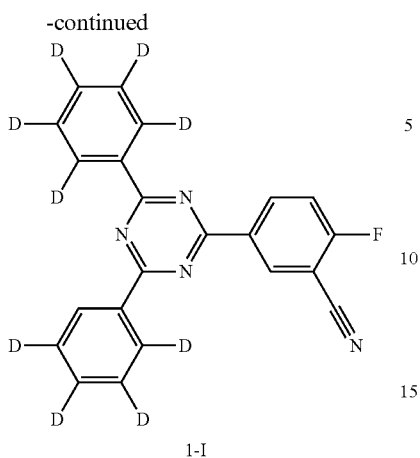

1-I (3-Cyano-4-fluorophenyl)boronic acid (30 g, 181.9 mmol), 2-chloro-4,6-bis(phenyl-D$_5$)-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-I (59.8 g, yield 91%).

MS[M+H]$^+$=361

Preparation Example 1-10: Synthesis of Compound 1-J

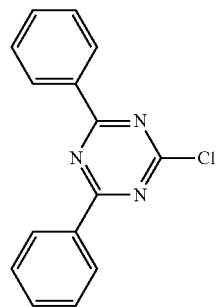

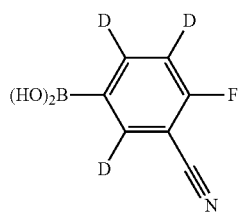

1-J (3-Cyano-4-fluorophenyl-2,5,6-D$_3$)boronic acid (30.5 g, 181.9 mmol), 2-chloro-4,6-diphenyl-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-J (58.8 g, yield 91%).

MS[M+H]$^+$=355

Preparation Example 1-11: Synthesis of Compound 1-K

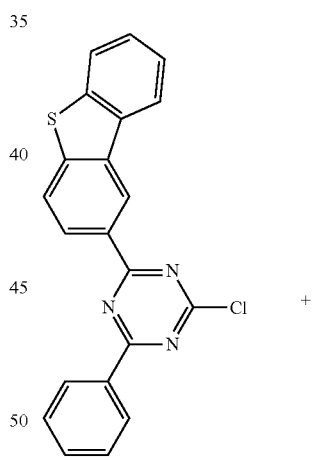

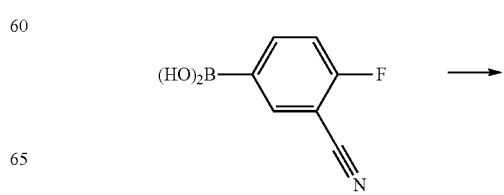

147

-continued

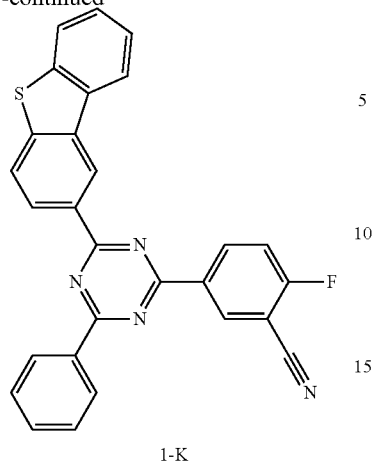

1-K (3-Cyano-4-fluorophenyl)boronic acid (30 g, 181.9 mmol), 2-chloro-4-(dibenzo[b,d]thiophen-2-yl)-6-phenyl-1,3,5-triazine (181.9 mmol), tetrahydrofuran (200 mL) and water (100 mL) were mixed, and heated to 60° C. Potassium carbonate (545.6 mmol) and tetrakistriphenylphosphine palladium (1 mmol) were added thereto, and the result was stirred for 3 hours under reflux. After the reaction, the reaction solution returned to room temperature was filtered to obtain a solid, and the solid was recrystallized twice with tetrahydrofuran and ethanol to obtain Compound 1-K (75.9 g, yield 91%).

MS[M+H]$^+$=458

Preparation Example 2-1: Synthesis of Compound 1

148

-continued

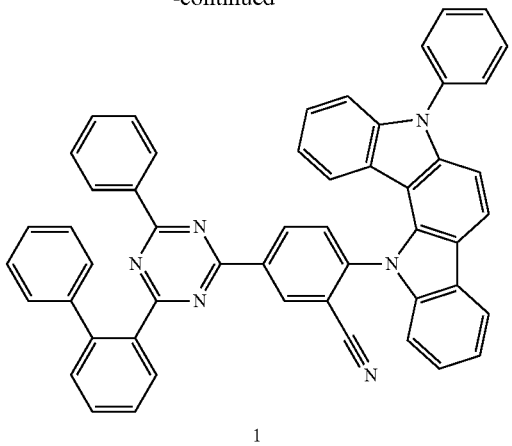

1

After completely dissolving Compound 1-A (18.3 g, 42.6 mmol) and 5-phenyl-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 1 (28.7 g, yield 91%).

MS[M+H]$^+$=740

Preparation Example 2-2: Synthesis of Compound 2

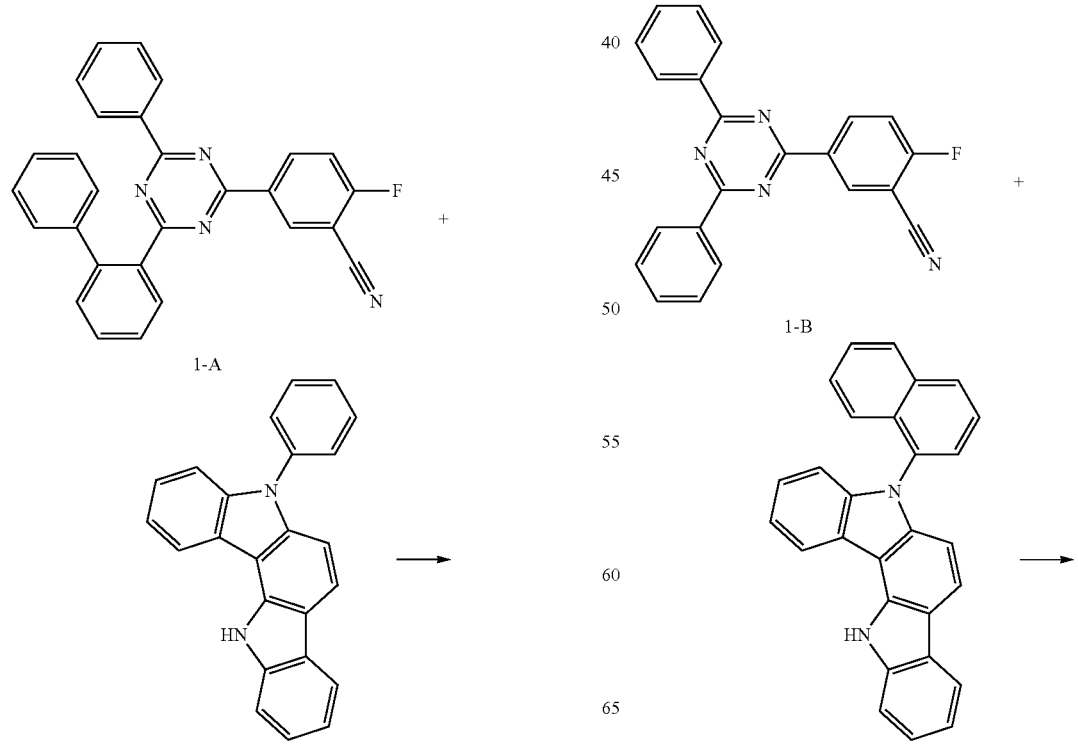

-continued

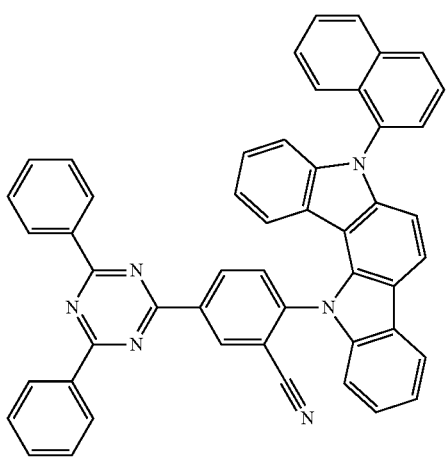

2

After completely dissolving Compound 1-B (15 g, 42.6 mmol) and 5-(naphthalen-1-yl)-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 2 (26.8 g, yield 88%).

MS[M+H]$^+$=714

Preparation Example 2-3: Synthesis of Compound 3

-continued

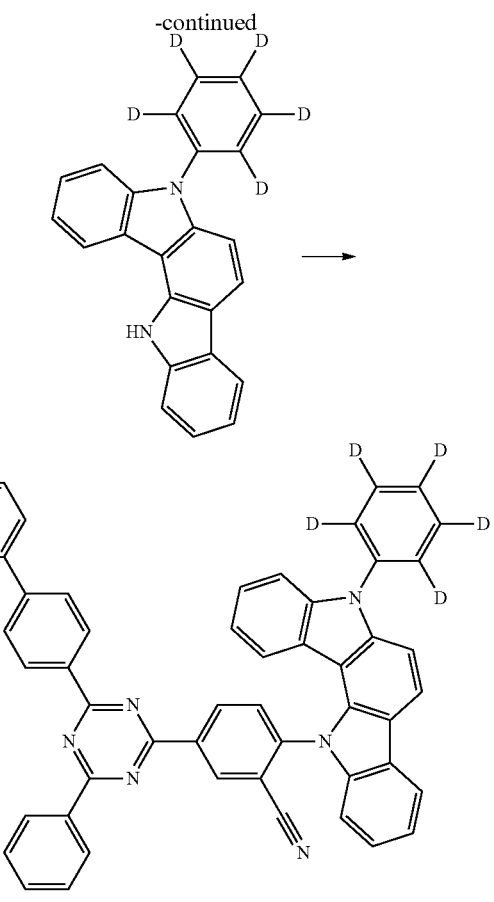

3

After completely dissolving Compound 1-C (18.3 g, 42.6 mmol) and 5-(phenyl-D$_5$)-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 3 (27 g, yield 85%).

MS[M+H]$^+$=745

Preparation Example 2-4: Synthesis of Compound 4

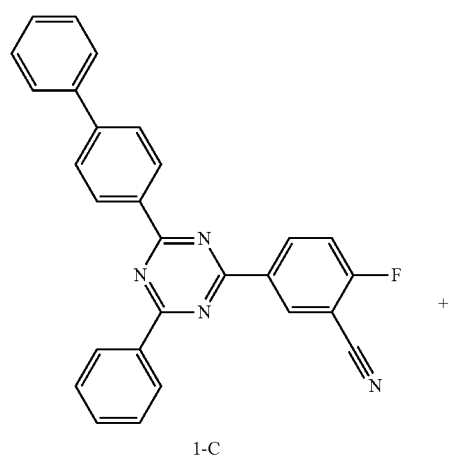

1-C

+

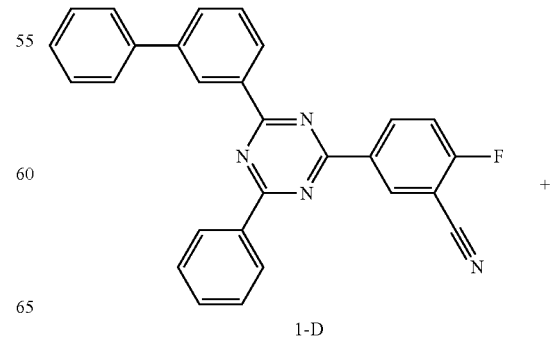

1-D

+

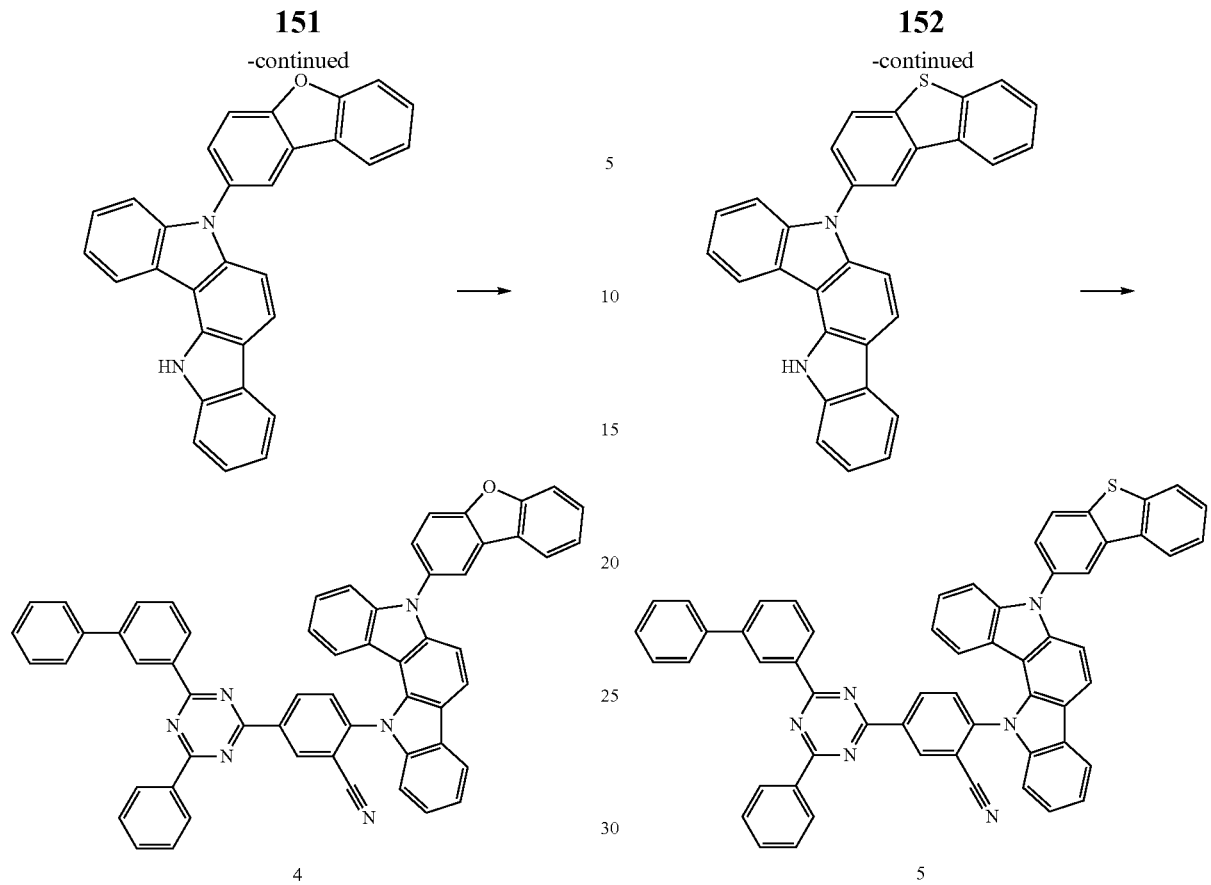

After completely dissolving Compound 1-D (18.3 g, 42.6 mmol) and 5-(dibenzo[b,d]furan-2-yl)-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 4 (30.1 g, yield 85%).

MS[M+H]$^+$=830

Preparation Example 2-5: Synthesis of Compound 5

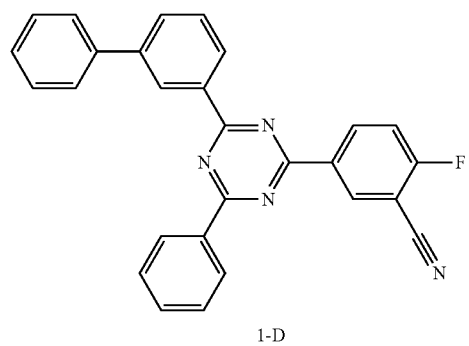

After completely dissolving Compound 1-D (18.3 g, 42.6 mmol) and 5-(dibenzo[b,d]thiophen-2-yl)-5,12-dihydroindolo-[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 5 (29.9 g, yield 83%).

MS[M+H]$^+$=847

Preparation Example 2-6: Synthesis of Compound 6

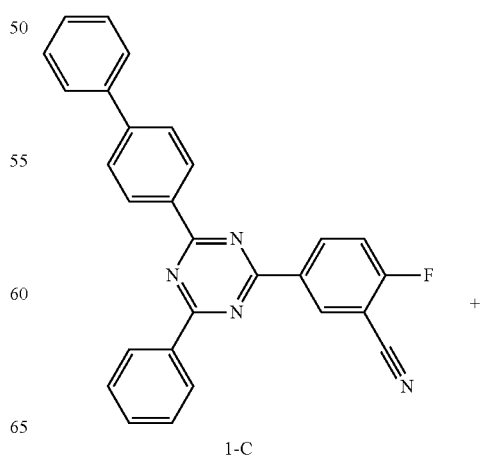

-continued

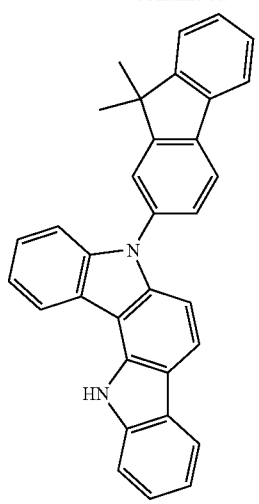

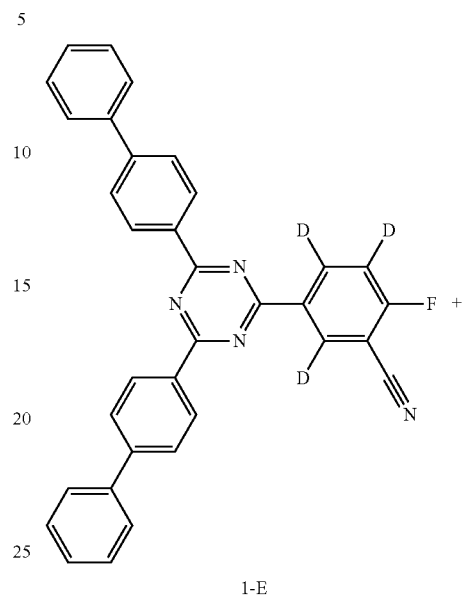

1-E

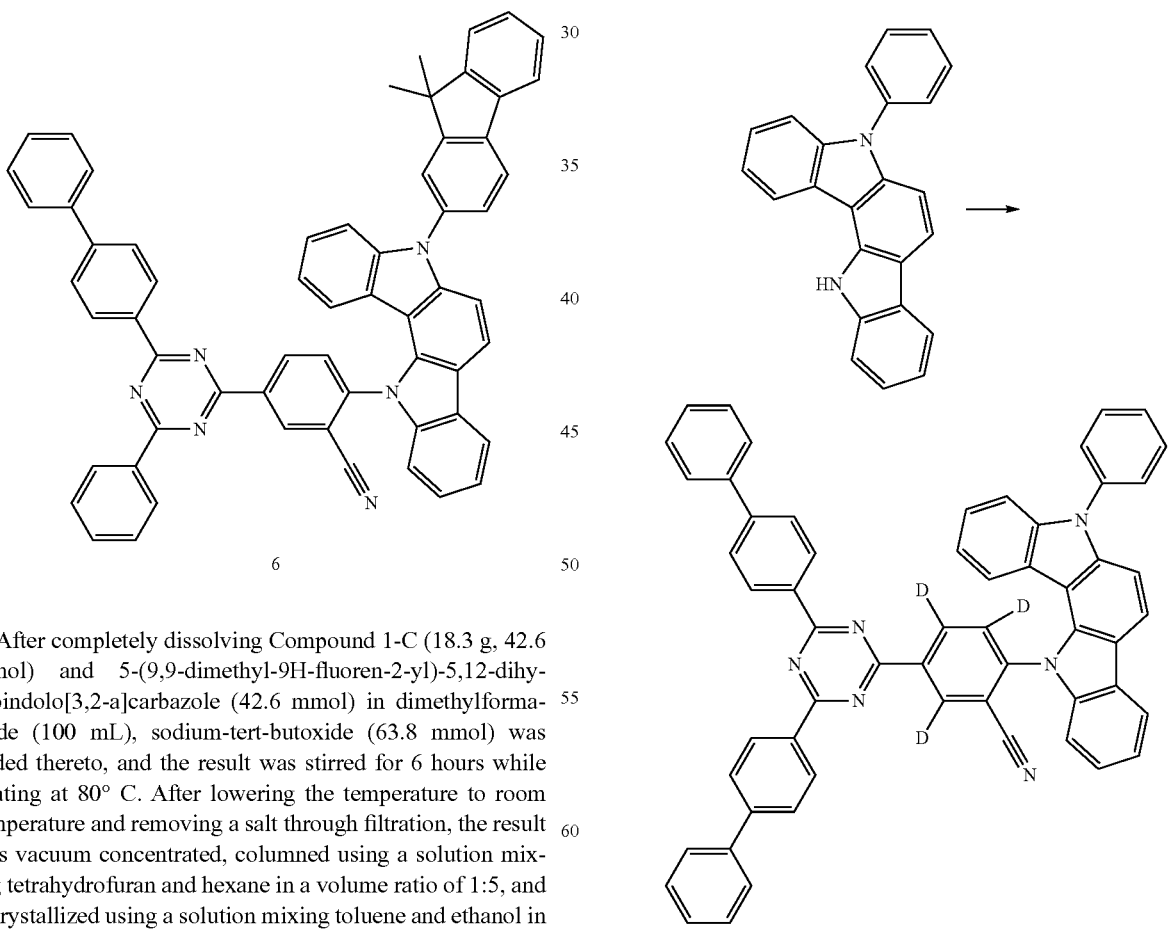

6

After completely dissolving Compound 1-C (18.3 g, 42.6 mmol) and 5-(9,9-dimethyl-9H-fluoren-2-yl)-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 6 (29.6 g, yield 81%).

MS[M+H]$^+$=857

Preparation Example 2-7: Synthesis of Compound 7

7

After completely dissolving Compound 1-E (21.6 g, 42.6 mmol) and 5-phenyl-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 7 (29.3 g, yield 84%).

MS[M+H]$^+$=819

Preparation Example 2-8: Synthesis of Compound 8

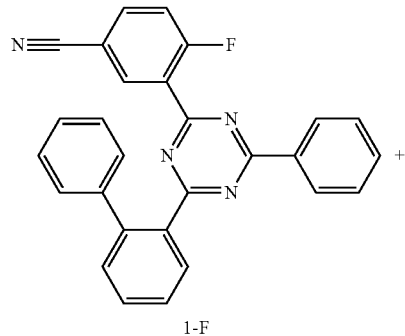

1-F

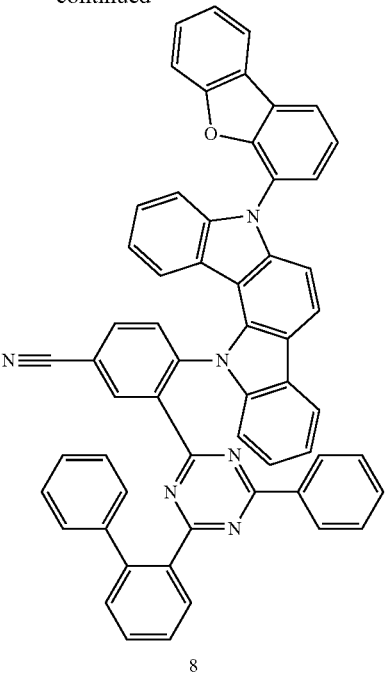

8

After completely dissolving Compound 1-F (18.3 g, 42 mmol) and 5-(dibenzo[b,d]furan-4-yl)-5,12-dihydroindolo[3,2-a]-carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 8 (28.3 g, yield 80%).

MS[M+H]$^+$=830

Preparation Example 2-9: Synthesis of Compound 9

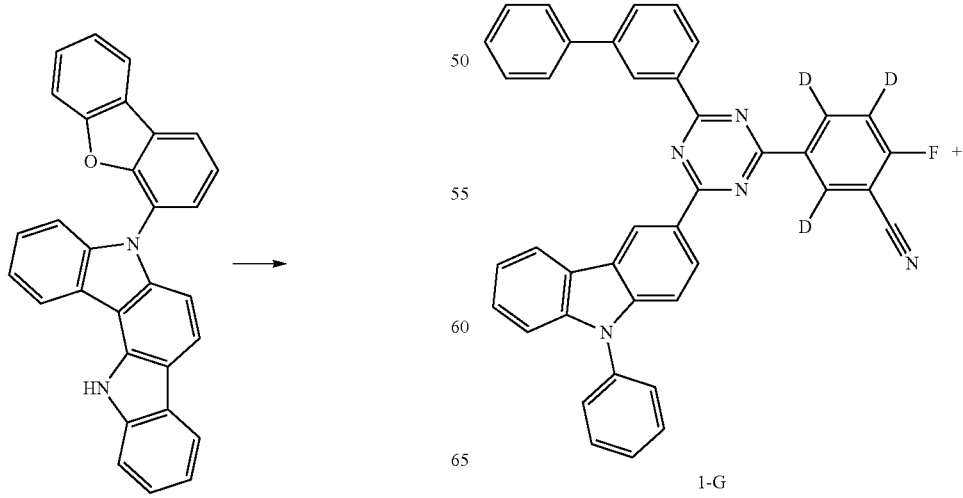

1-G

158

Preparation Example 2-10: Synthesis of Compound 10

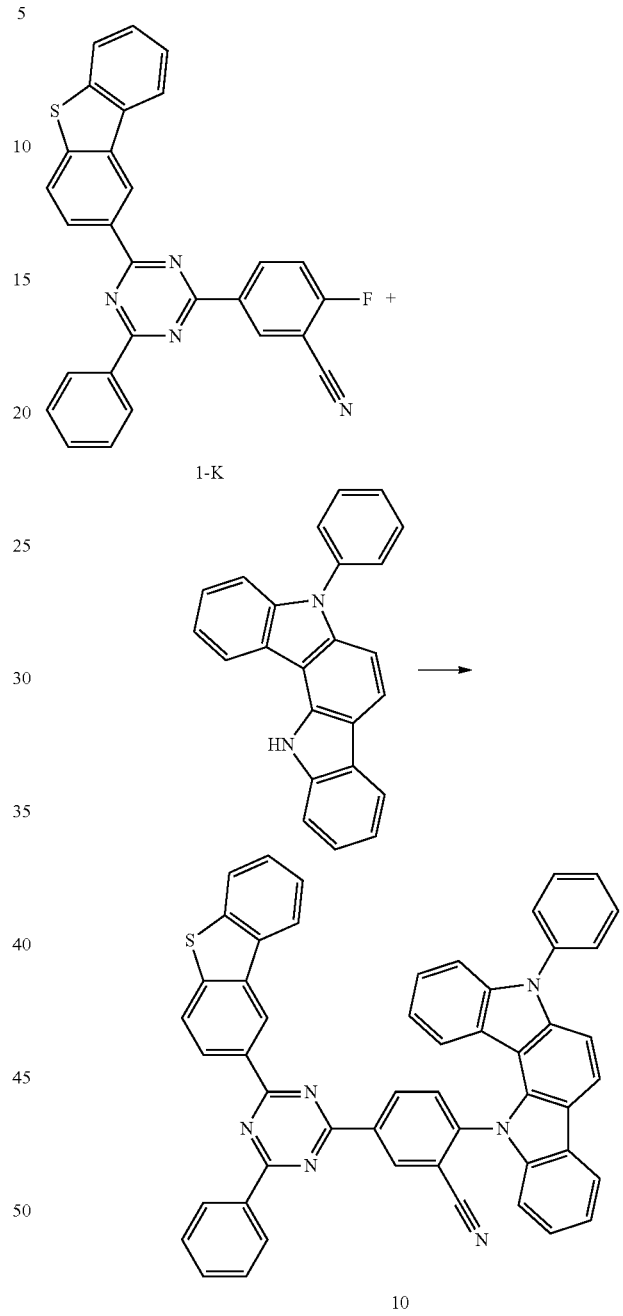

After completely dissolving Compound 1-G (25.4 g, 42.6 mmol) and 5-phenyl-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 9 (32 g, yield 83%).

MS[M+H]$^+$=906

After completely dissolving Compound 1-K (19.5 g, 42.6 mmol) and 5-phenyl-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 10 (26.6 g, yield 81%).

MS[M+H]$^+$=770

Preparation Example 2-11: Synthesis of Compound 11

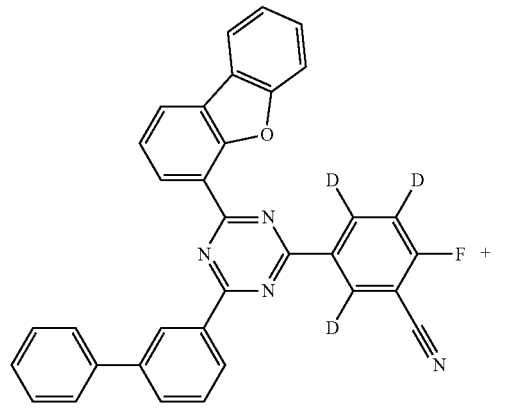

1-H

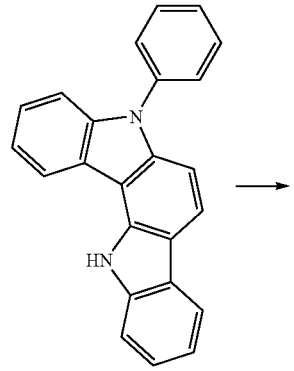

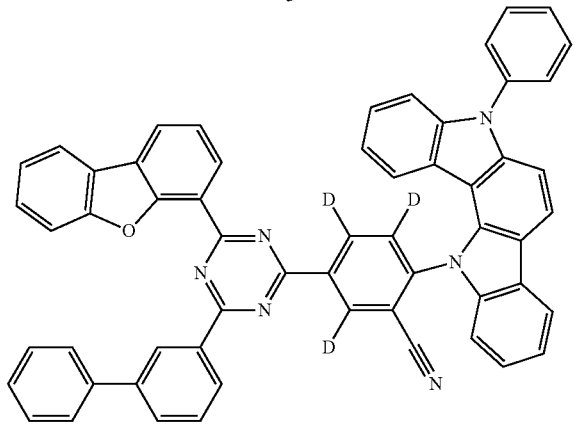

11

After completely dissolving Compound 1-H (22.2 g, 42.6 mmol) and 5-phenyl-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 11 (28.4 g, yield 80%).

MS[M+H]$^+$=833

Preparation Example 2-12: Synthesis of Compound 12

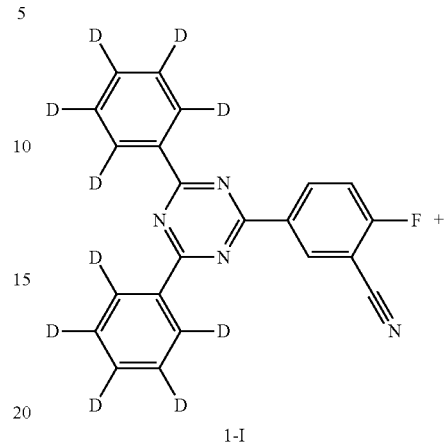

1-I

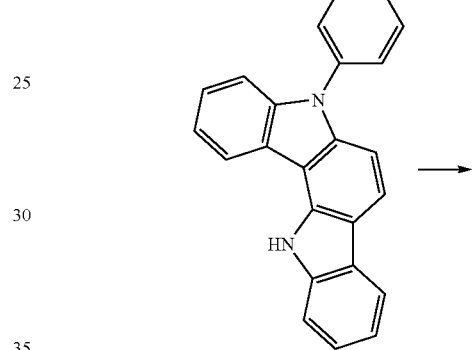

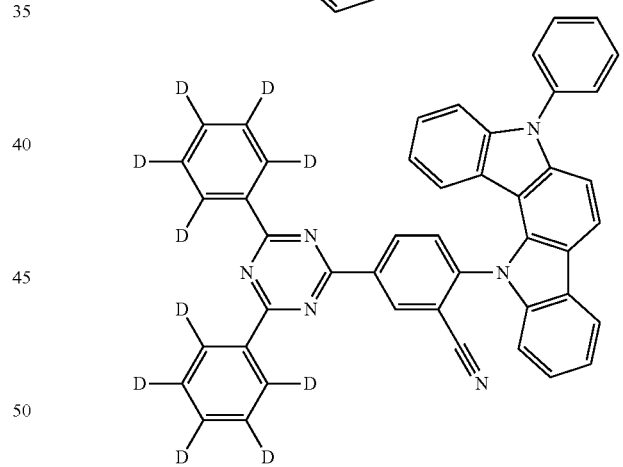

12

After completely dissolving Compound 1-I (15.4 g, 42.6 mmol) and 5-phenyl-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 12 (25 g, yield 87%).

MS[M+H]$^+$=674

Preparation Example 2-13: Synthesis of Compound 13

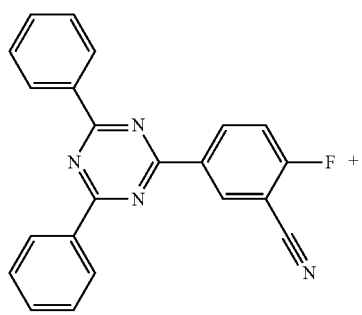

1-B

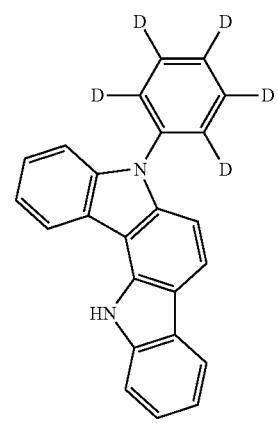

→

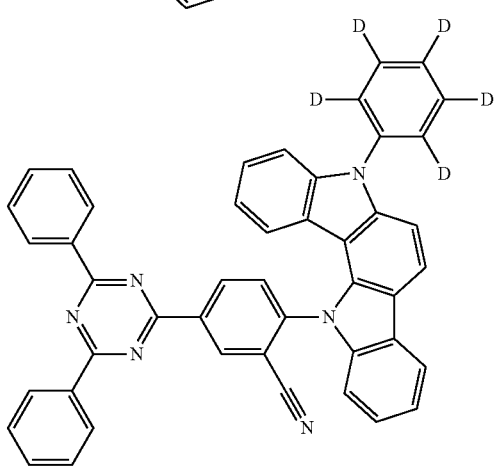

13

Preparation Example 2-14: Synthesis of Compound 14

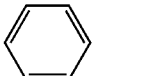

1-J

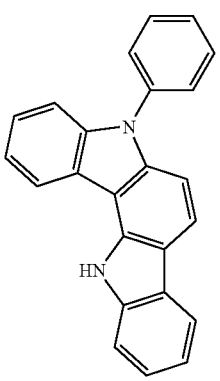

→

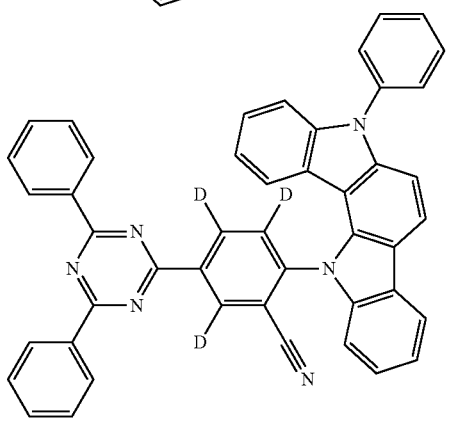

14

After completely dissolving Compound 1-B (15 g, 42.6 mmol) and 5-(phenyl-D$_5$)-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 13 (25.1 g, yield 88%).

MS[M+H]$^+$=669

After completely dissolving Compound 1-J (15.1 g, 42.6 mmol) and 5-phenyl-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 14 (24.2 g, yield 85%).

MS[M+H]$^+$=667

Preparation Example 2-15: Synthesis of Compound 15

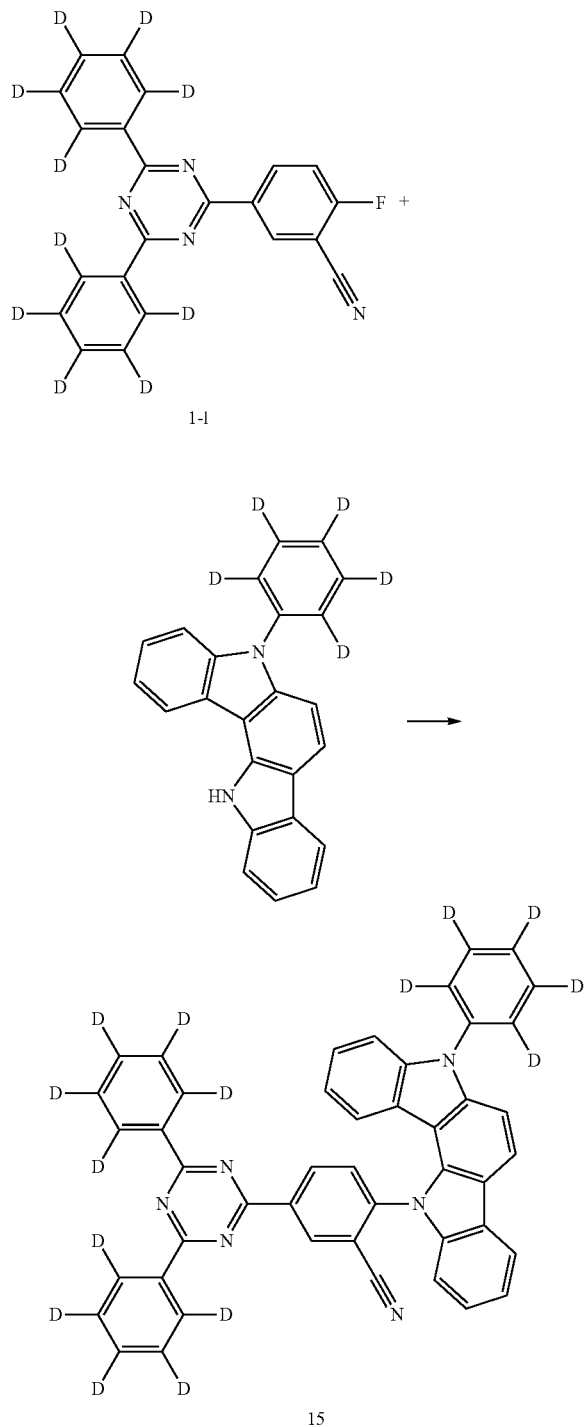

After completely dissolving Compound 1-I (15.4 g, 42.6 mmol) and 5-(phenyl-$D_5$)-5,12-dihydroindolo[3,2-a]carbazole (42.6 mmol) in dimethylformamide (100 mL), sodium-tert-butoxide (63.8 mmol) was added thereto, and the result was stirred for 6 hours while heating at 80° C. After lowering the temperature to room temperature and removing a salt through filtration, the result was vacuum concentrated, columned using a solution mixing tetrahydrofuran and hexane in a volume ratio of 1:5, and recrystallized using a solution mixing toluene and ethanol in a volume ratio of 1:1 to obtain Compound 15 (25.2 g, yield 87%).

MS[M+H]$^+$=679

Comparative Example 1-1

A green organic light emitting device was manufactured including a host material (m-CBP) having triplet energy of 2.4 eV or greater and Compound 4CzIPN having TADF (delayed fluorescence) properties with $\Delta E_{ST}$ (difference between singlet energy and triplet energy) of less than 0.2 eV in a light emitting layer, and the properties were evaluated.

A glass substrate on which indium tin oxide (ITO) was coated as a thin film to a thickness of 1,000 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus. On the transparent ITO electrode prepared as above, each thin film was laminated using a vacuum deposition method under a degree of vacuum of 5.0×10$^{-4}$ Pa. First, a hole injection layer was foamed on the ITO by thermal vacuum depositing hexaazatriphenylene-hexanitrile (HAT-CN) to a thickness of 500 Å.

On the hole injection layer, a hole transfer layer (300 Å) was formed by vacuum depositing the following Compound NPB.

On the hole transfer layer, an electron blocking layer (100 Å) was formed by vacuum depositing the following Compound EB1 to a film thickness of 100 Å.

Subsequently, a light emitting layer was formed on the electron blocking layer by vacuum depositing the following Compounds m-CBP and 4CzIPN in a weight ratio of 70:30 to a film thickness of 300 Å.

On the light emitting layer, a hole blocking layer was formed by vacuum depositing the following Compound HB1 to a film thickness of 100 Å.

On the hole blocking layer, an electron injection and transfer layer was formed to a thickness of 300 Å by vacuum depositing the following Compound ET1 and a lithium quinolate (LiQ) compound in a weight ratio of 1:1. On the electron injection and transfer layer, a cathode was formed by consecutively depositing lithium fluoride (LiF) to a thickness of 12 Å and aluminum to a thickness of 2,000 Å.

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at 2×10$^{-7}$ torr to 5×10$^{-6}$ torr to manufacture an organic light emitting device.

HAT-CN
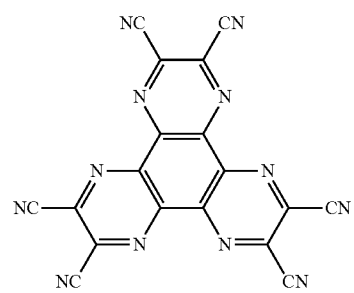
NPB
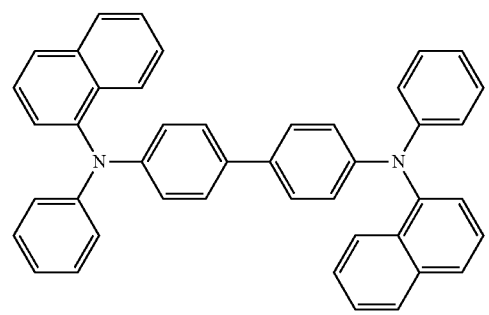
EB1
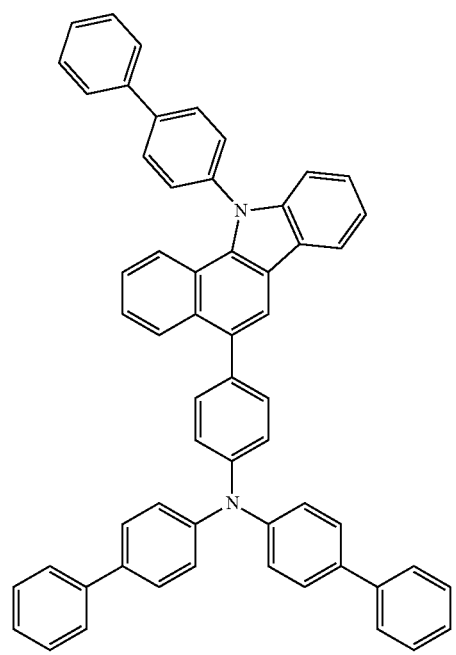
m-CBP
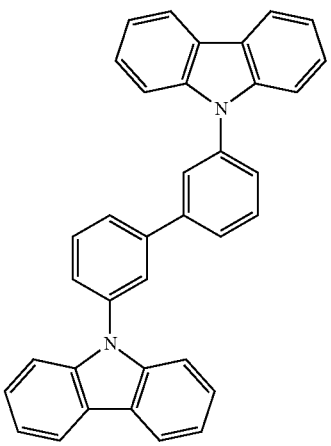
4CzIPN
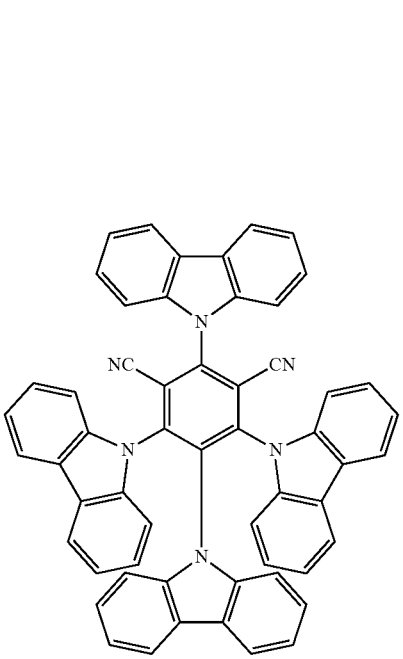
HB1
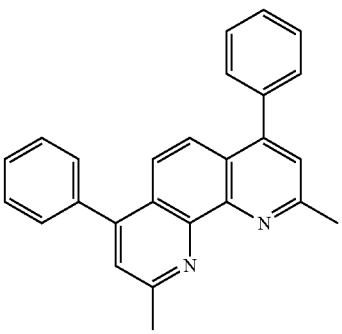

ET1
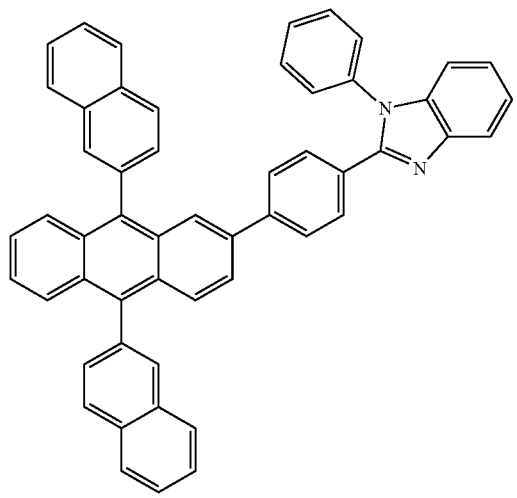
LiQ
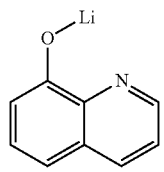
Examples 1-1 to 1-15
Organic light emitting devices were manufactured in the same manner as in Comparative Example 1-1 except that compounds of the following Table 1 were used instead of Compound 4CzIPN.
1
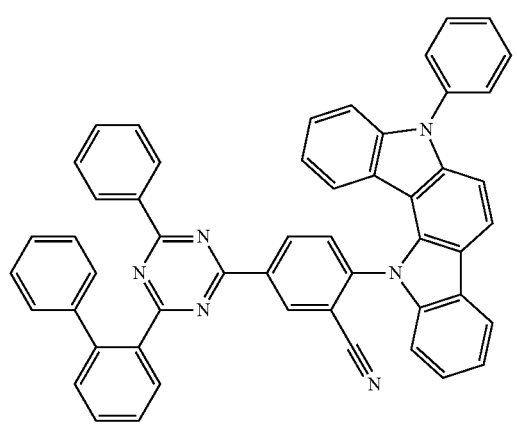
2
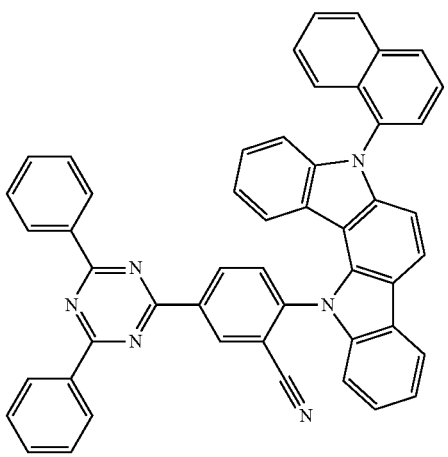
3
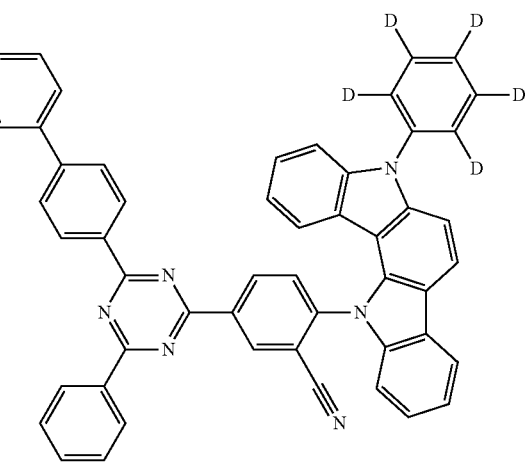
4
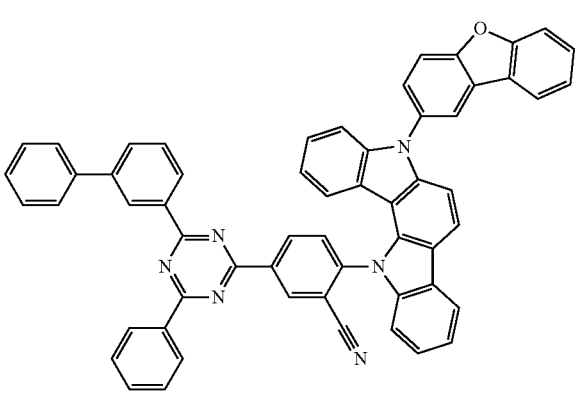

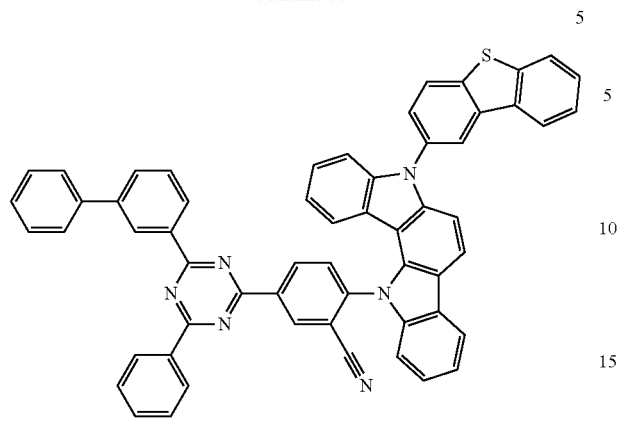
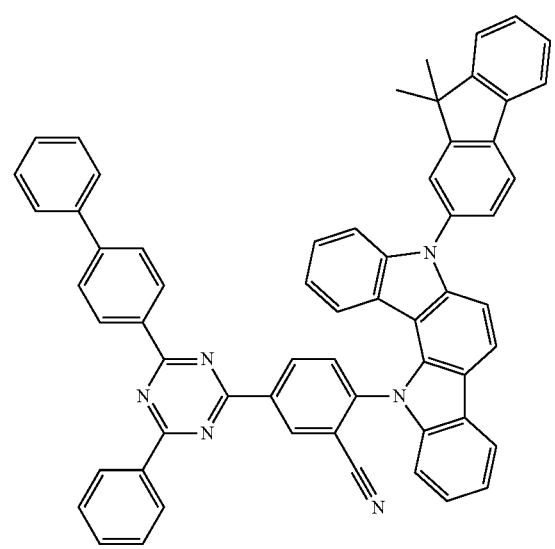
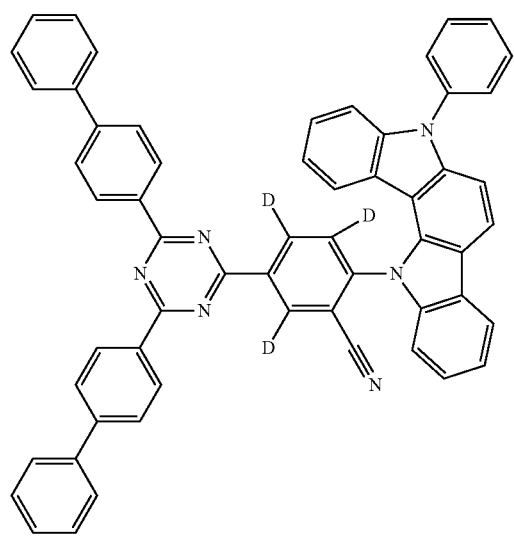
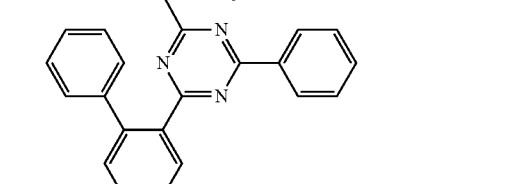
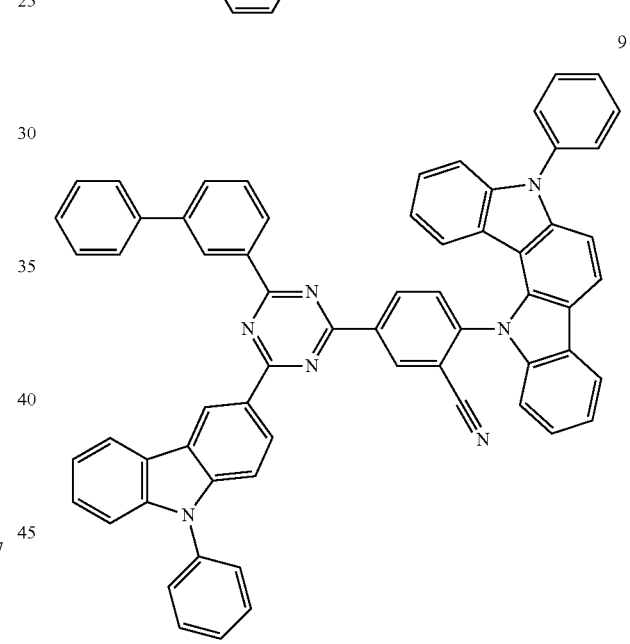
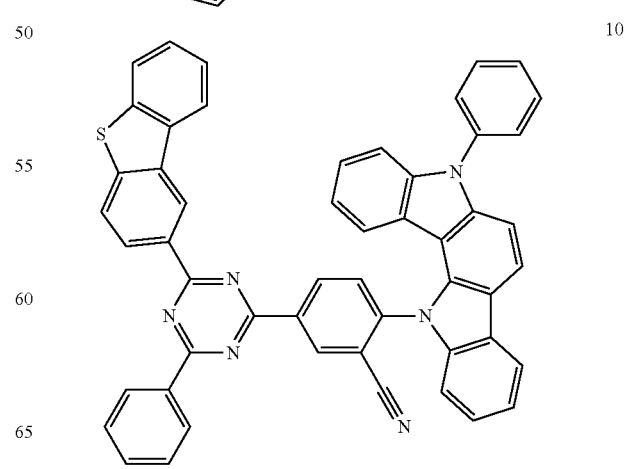

11
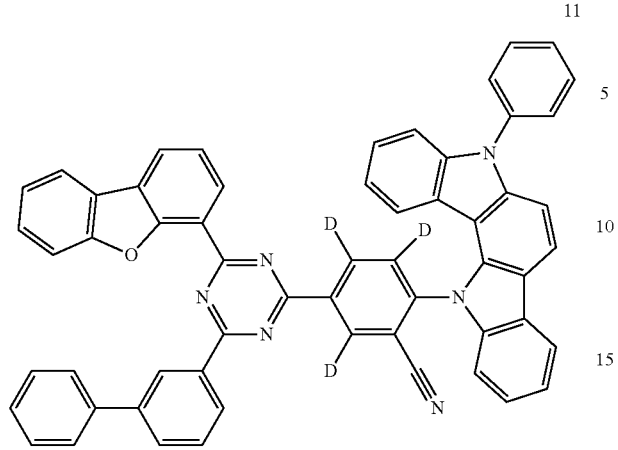
12
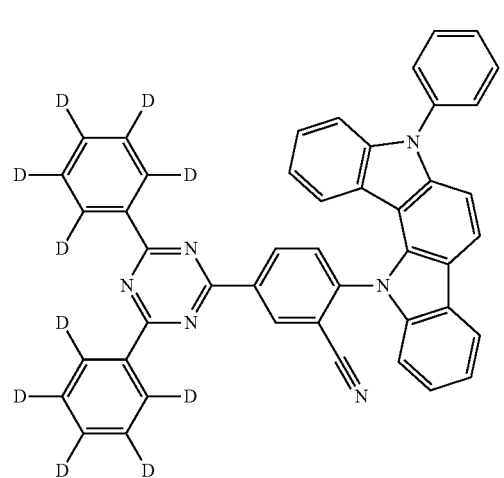
13
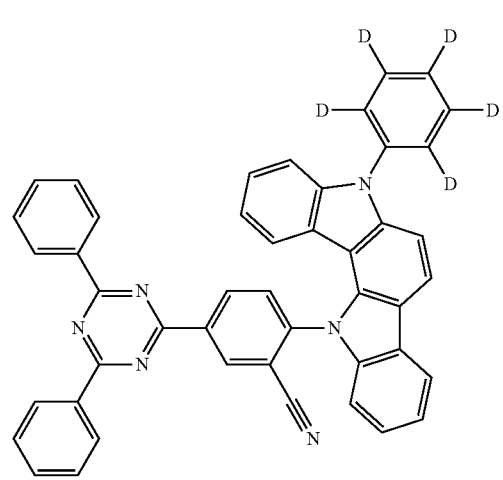
14
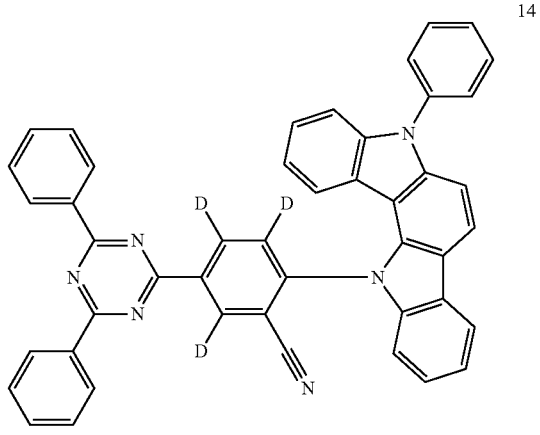
15
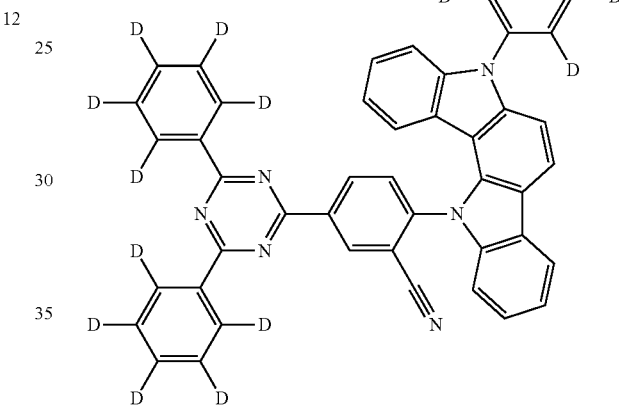
Comparative Examples 1-2 to 1-8
Organic light emitting devices were manufactured in the same manner as in Comparative Example 1-1 except that compounds of the following T1 to T7 were used instead of Compound 4CzIPN.
T1
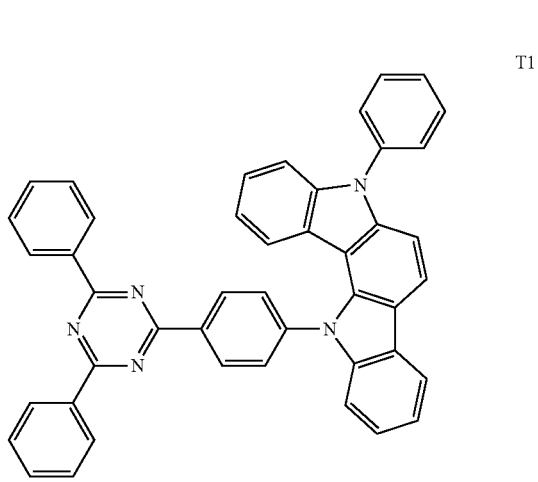

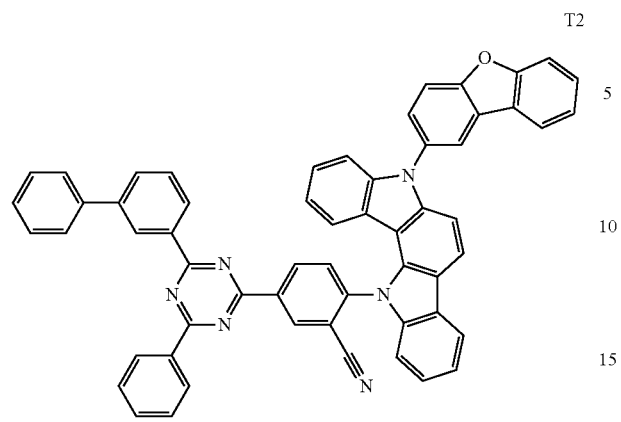
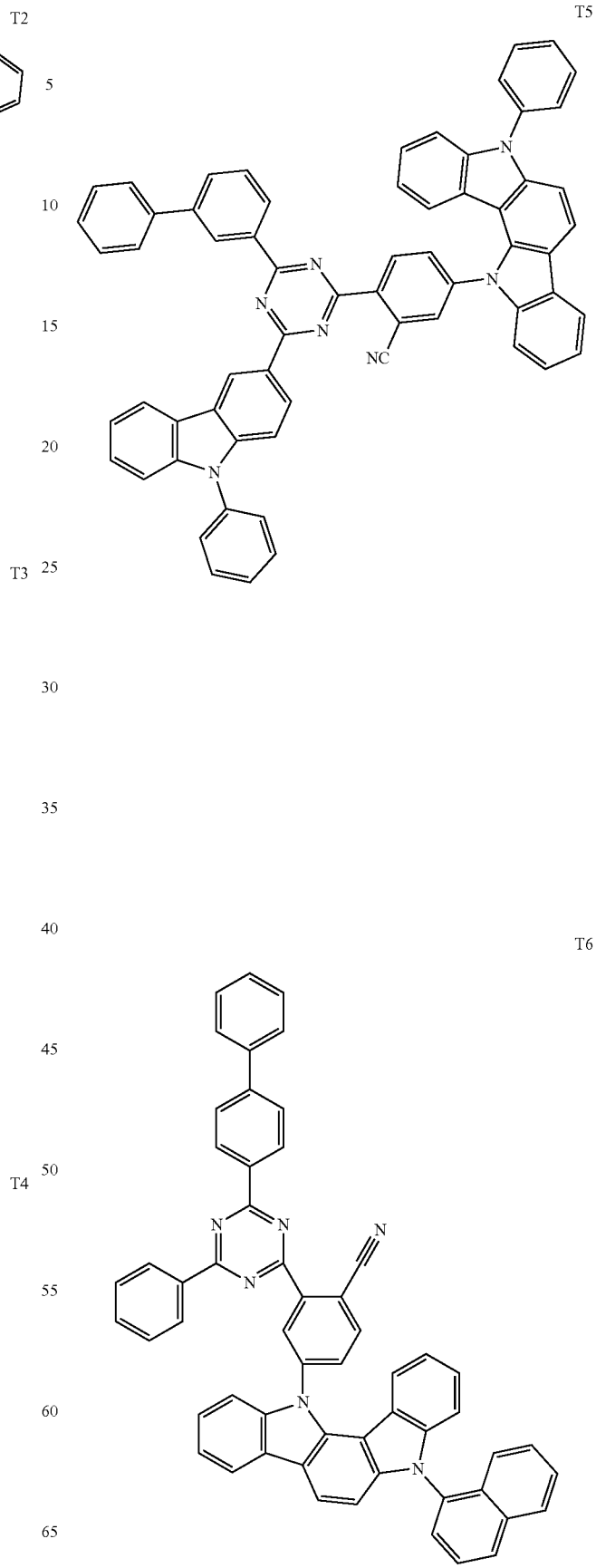

-continued

T7

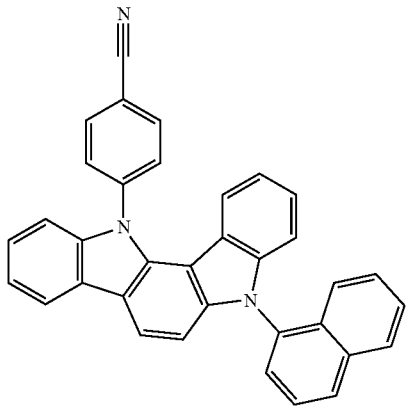

For the organic light emitting devices of Examples 1-1 to 1-15 and Comparative Examples 1-1 to 1-8, driving voltage (V) and current efficiency (cd/A) measured at current density of 10 mA/cm$^2$, a CIE color coordinate measured at luminance of 3000 cd/m$^2$, and time ($I_{95}$) taken for the luminance decreasing to 95% from 3000 cd/m$^2$ were measured, and the results are shown in the following Table 1.

TABLE 1

| Category | Compound (Light Emitting Layer) | Voltage (V) | Efficiency (cd/A) | CIE Color Coordinate (x, y) | $T_{95}$(hr) |
|---|---|---|---|---|---|
| Example 1-1 | 1 | 4.0 | 22 | (0.23, 0.63) | 105 |
| Example 1-2 | 2 | 4.1 | 23 | (0.24, 0.64) | 103 |
| Example 1-3 | 3 | 4.2 | 22 | (0.24, 0.64) | 125 |
| Example 1-4 | 4 | 4.1 | 21 | (0.23, 0.63) | 101 |
| Example 1-5 | 5 | 4.0 | 24 | (0.24, 0.64) | 100 |
| Example 1-6 | 6 | 4.1 | 23 | (0.23, 0.63) | 102 |
| Example 1-7 | 7 | 4.1 | 23 | (0.24, 0.63) | 127 |
| Example 1-8 | 8 | 4.0 | 22 | (0.22, 0.63) | 101 |
| Example 1-9 | 9 | 4.1 | 21 | (0.23, 0.64) | 102 |
| Example 1-10 | 10 | 4.0 | 22 | (0.23, 0.63) | 102 |
| Example 1-11 | 11 | 4.1 | 23 | (0.24, 0.64) | 124 |
| Example 1-12 | 12 | 4.2 | 24 | (0.22, 0.64) | 136 |
| Example 1-13 | 13 | 4.0 | 22 | (0.23, 0.63) | 125 |
| Example 1-14 | 14 | 4.0 | 21 | (0.22, 0.64) | 123 |
| Example 1-15 | 15 | 4.1 | 22 | (0.24, 0.63) | 138 |
| Comparative Example 1-1 | 4CzIPN | 4.7 | 16 | (0.21, 0.61) | 53 |
| Comparative Example 1-2 | T1 | 4.9 | 16 | (0.20, 0.60) | 51 |
| Comparative Example 1-3 | T2 | 4.8 | 15 | (0.22, 0.61) | 52 |
| Comparative Example 1-4 | T3 | 4.8 | 15 | (0.21, 0.61) | 49 |
| Comparative Example 1-5 | T4 | 4.7 | 14 | (0.22, 0.60) | 53 |
| Comparative Example 1-6 | T5 | 4.7 | 14 | (0.21, 0.60) | 52 |
| Comparative Example 1-7 | T6 | 4.9 | 15 | (0.21, 0.61) | 48 |
| Comparative Example 1-8 | T7 | 4.8 | 12 | (0.18, 0.26) | 11 |

As shown in Table 1, the devices of Examples 1-1 to 1-15 using the compound of Chemical Formula 1 all had decreased voltage and enhanced efficiency compared to the device using the material of Compound 4CzIPN in Comparative Example 1-1.

In addition, when comparing to the devices of Comparative Examples 1-2 to 1-7, it was seen that the devices using the compound of Chemical Formula 1 had enhanced properties in all aspects of voltage, efficiency and color purity compared to the structure in which the core is not substituted with triazine, the structure in which the cyano group or the triazinyl group is substituted at different positions, and the structure in which R1 to R3 of Chemical Formula 1 of the present application are all an unsubstituted phenyl group.

Particularly, it was identified that the devices of Comparative Examples 1-1 to 1-7 had a y value of less than 0.63 in the color coordinate resulting in lighter green compared to the devices using the compound of the present disclosure, and the device of Comparative Example 1-8 including Compound T7 that does not include triazine exhibited blue.

As shown from the results of Table 1, it was identified that the compound according to the present disclosure had excellent light emission capability and high color purity, and is usable in delayed fluorescent organic light emitting devices.

Comparative Example 2-1

A glass substrate on which indium tin oxide (ITO) was coated as a thin film to a thickness of 1,000 Å was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus. On the transparent ITO electrode prepared as above, each thin film was laminated using a vacuum deposition method under a degree of vacuum of 5.0×10$^{-4}$ Pa. First, a hole injection layer was famed on the ITO by thermal vacuum depositing hexaazatriphenylene-hexanitrile (HAT-CN) to a thickness of 500 Å.

On the hole injection layer, a hole transfer layer (300 Å) was formed by vacuum depositing the following Compound NPB.

On the hole transfer layer, an electron blocking layer (100 Å) was formed by vacuum depositing the following Compound EB1 to a film thickness of 100 Å.

Subsequently, a light emitting layer was formed on the electron blocking layer by vacuum depositing the following Compounds m-CBP, 4CzIPN and GD1 in a weight ratio of 68:30:2 to a film thickness of 300 Å.

On the light emitting layer, a hole blocking layer was formed by vacuum depositing the following Compound HB1 to a film thickness of 100 Å.

On the hole blocking layer, an electron injection and transfer layer was formed to a thickness of 300 Å by vacuum depositing the following Compound ET1 and a lithium quinolate (LiQ) compound in a weight ratio of 1:1. On the electron injection and transfer layer, a cathode was formed by consecutively depositing lithium fluoride (LiF) to a thickness of 12 Å and aluminum to a thickness of 2,000 Å.

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at 2×10$^{-7}$ torr to 5×10$^{-6}$ torr to manufacture an organic light emitting device.

HAT-CN
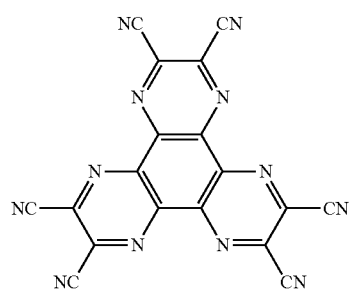
NPB
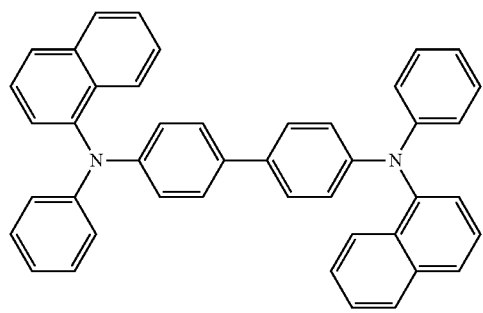
EB1
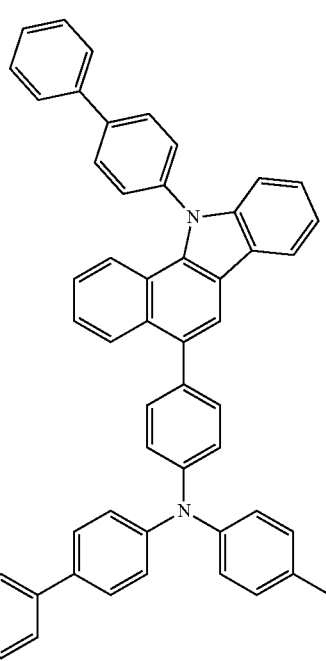
m-CBP
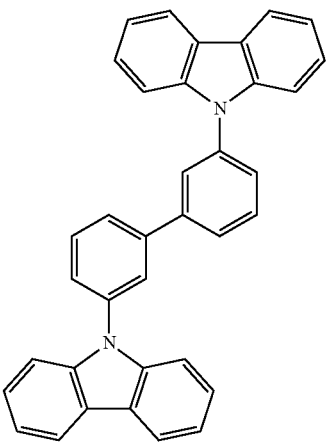
4CzIPN
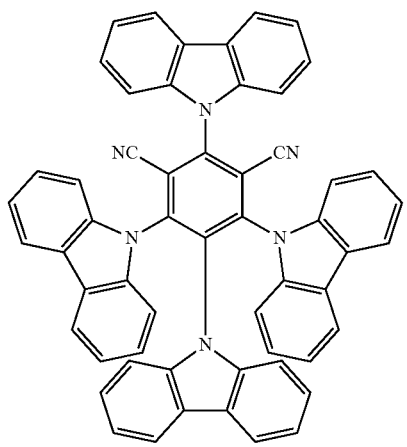
GD1
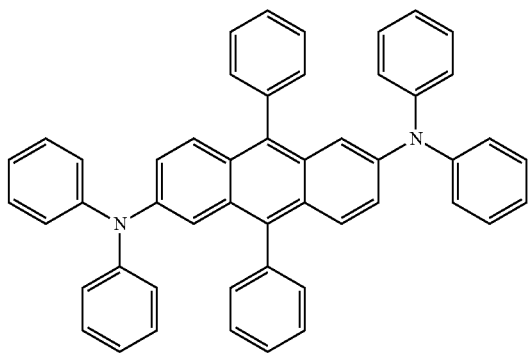

ET1
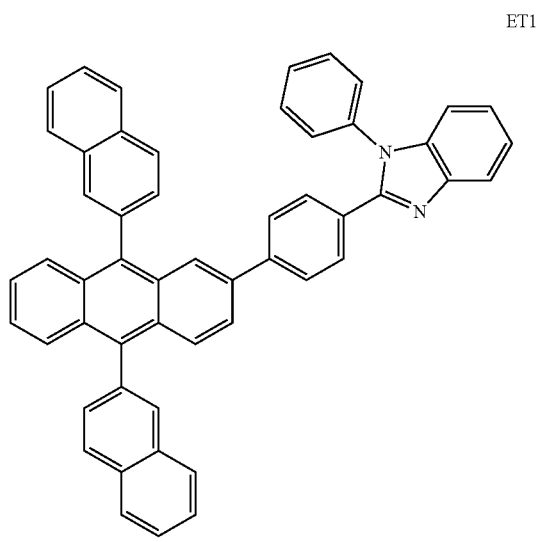
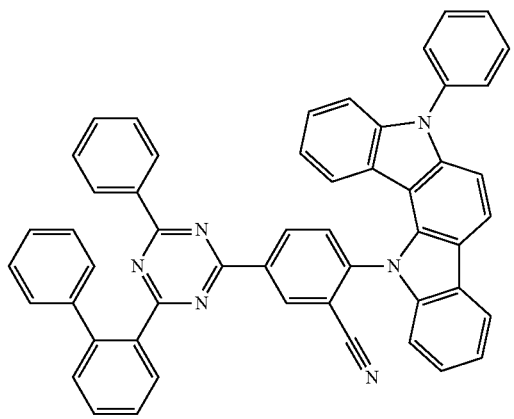
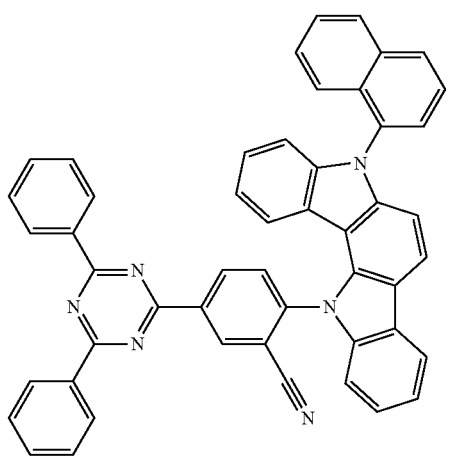
LiQ
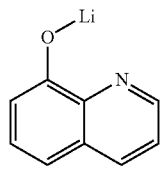
HB1
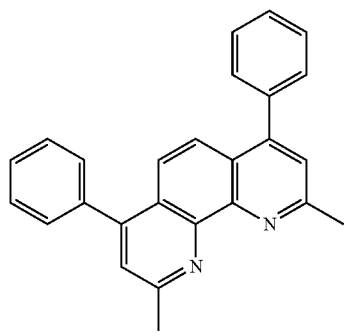
Examples 2-1 to 2-15
Organic light emitting devices were manufactured in the same manner as in Comparative Example 2-1 except that compounds of the following Table 2 were used instead of Compound 4CzIPN.
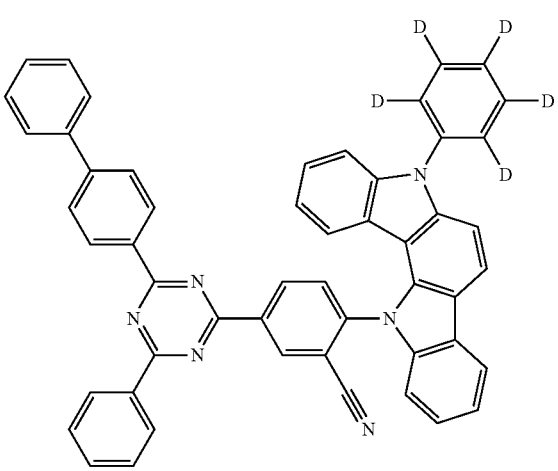

181
-continued
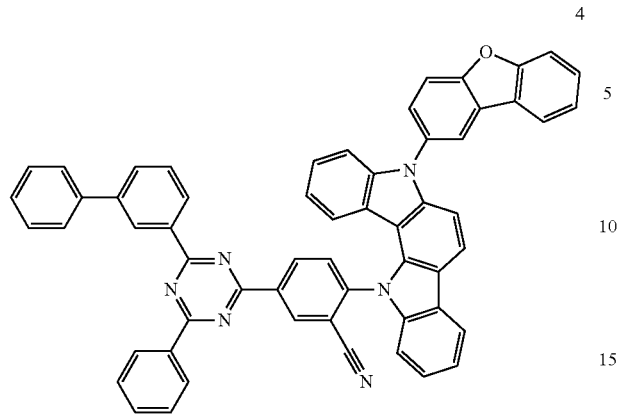
4
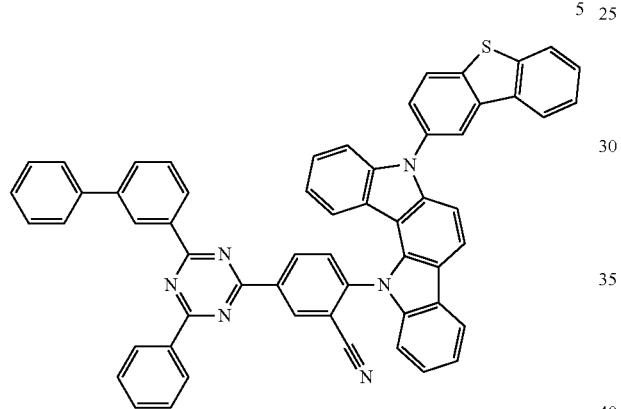
5
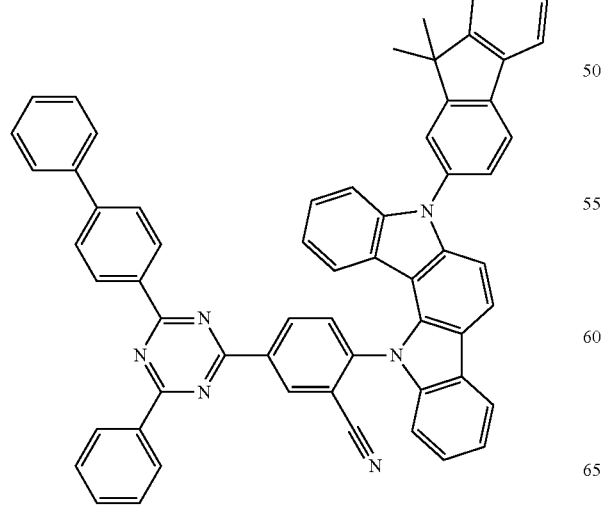
6
182
-continued
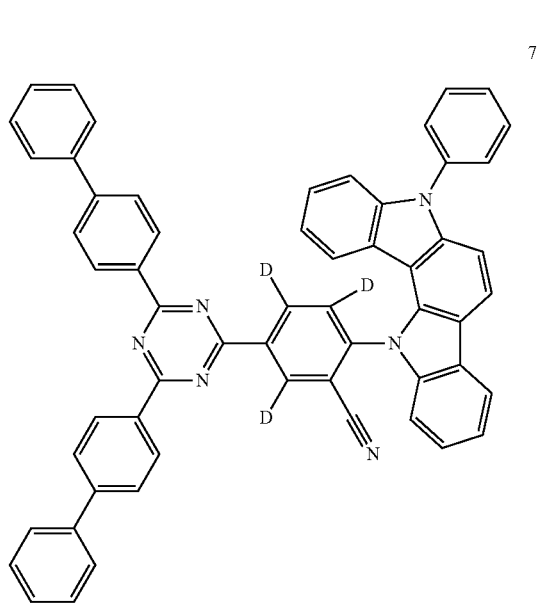
7
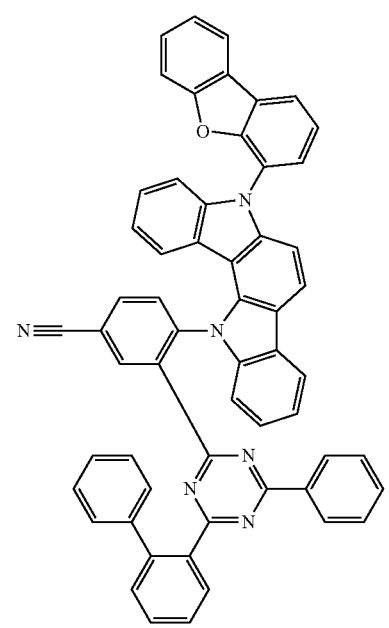
8

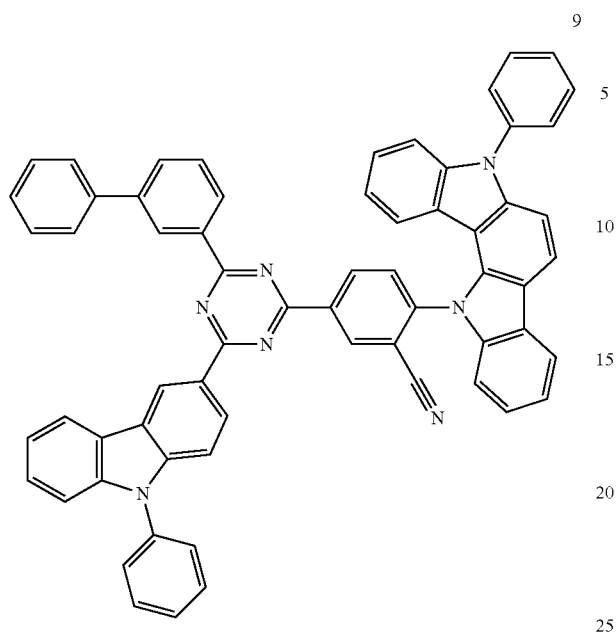
9
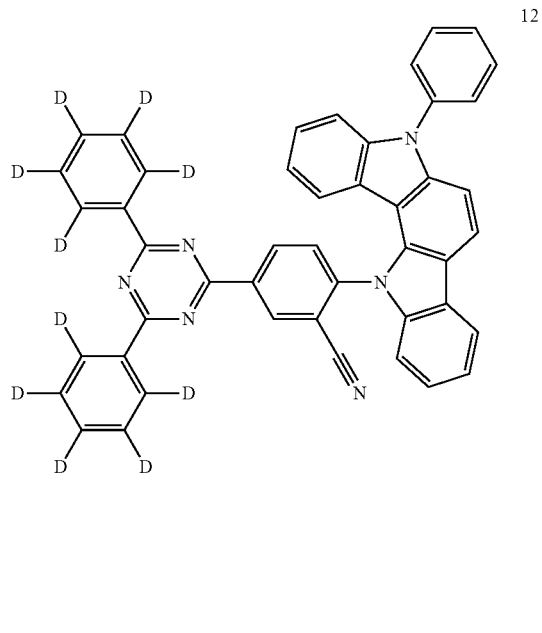
12
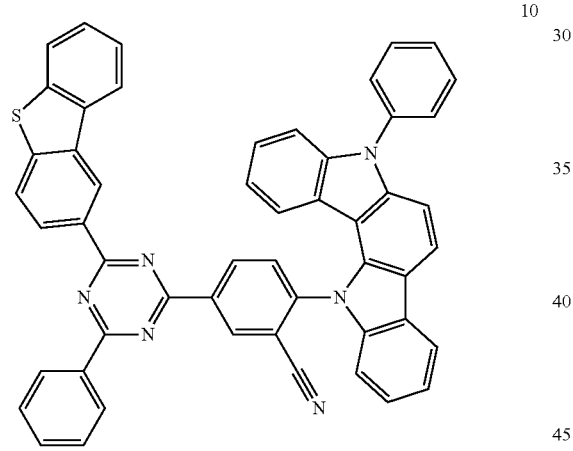
10
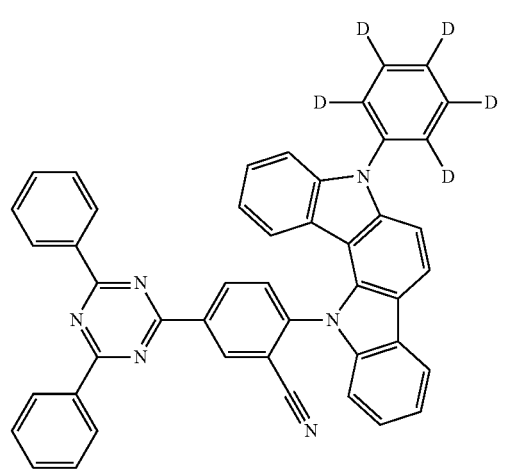
13
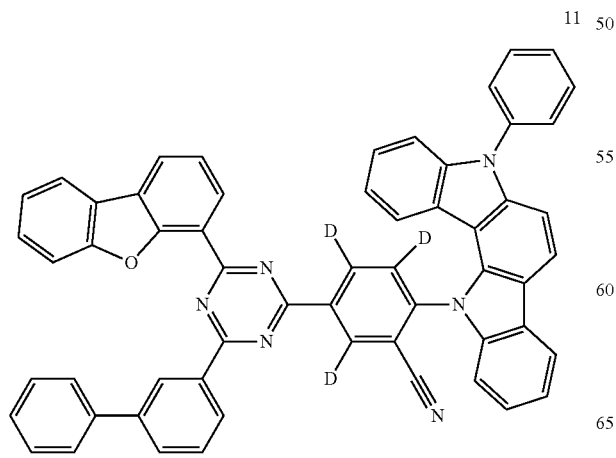
11
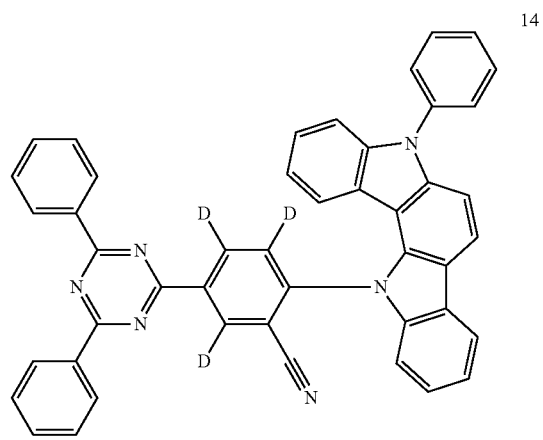
14

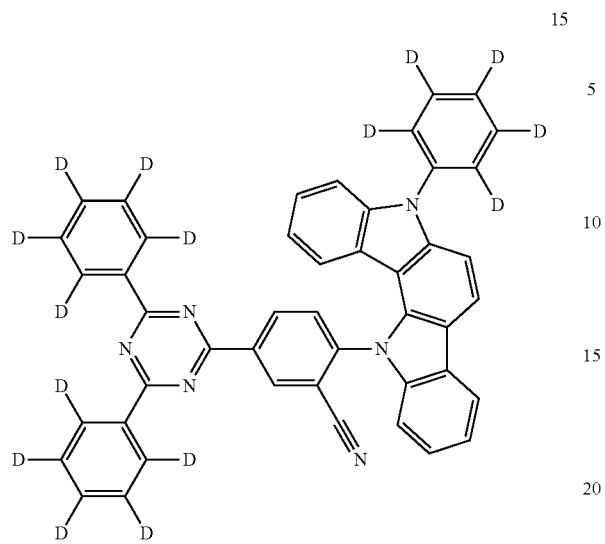
Comparative Examples 2-2 to 2-7
Organic light emitting devices were manufactured in the same manner as in Comparative Example 2-1 except that compounds of the following Table 2 were used instead of Compound 4CzIPN.
T1
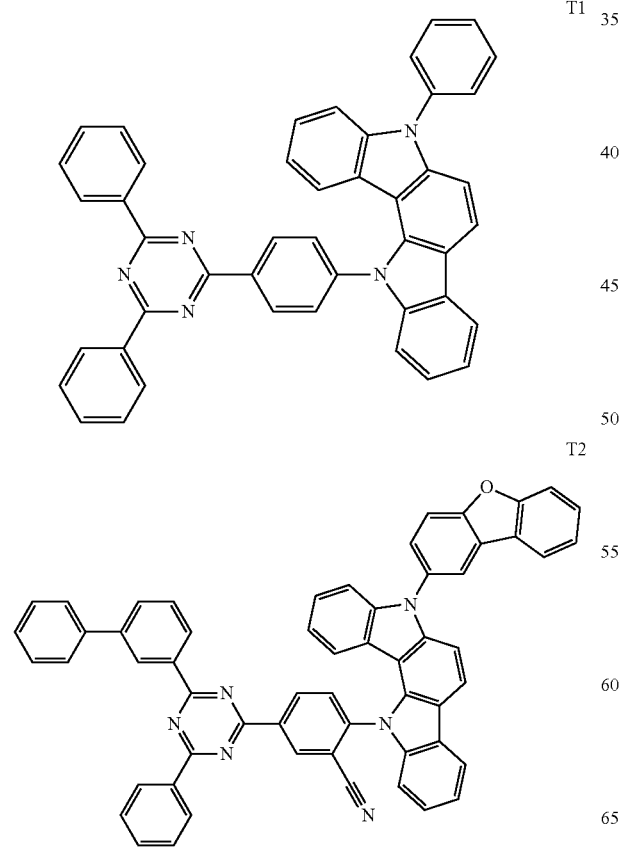
T2
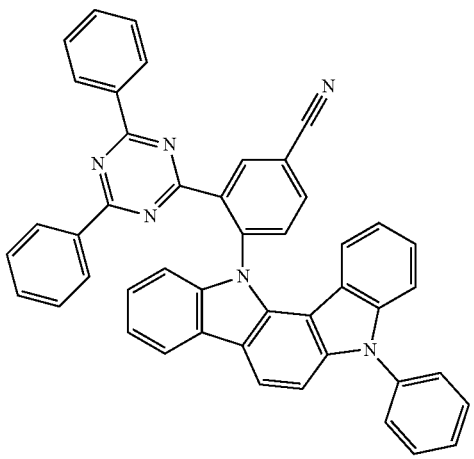
T3
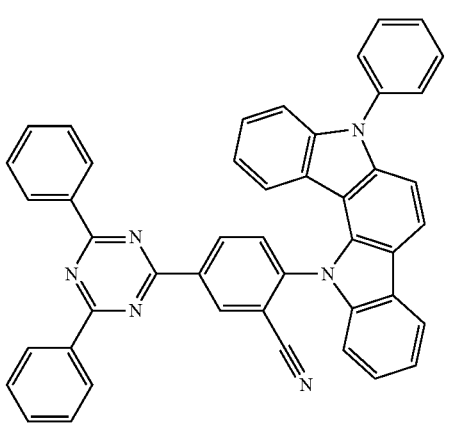
T4
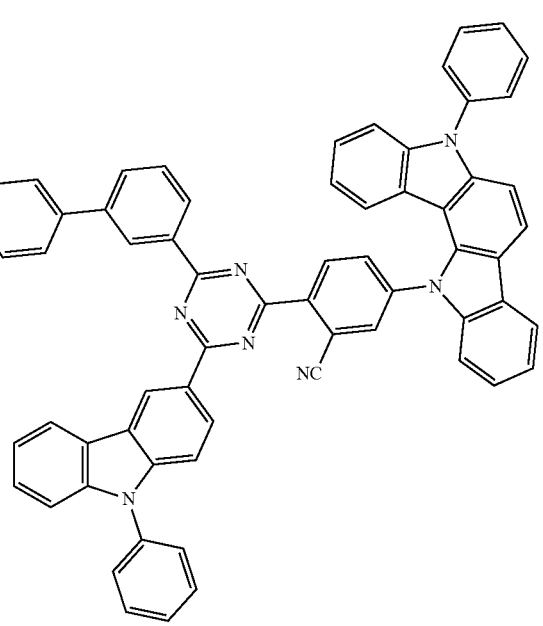
T5

-continued

T6

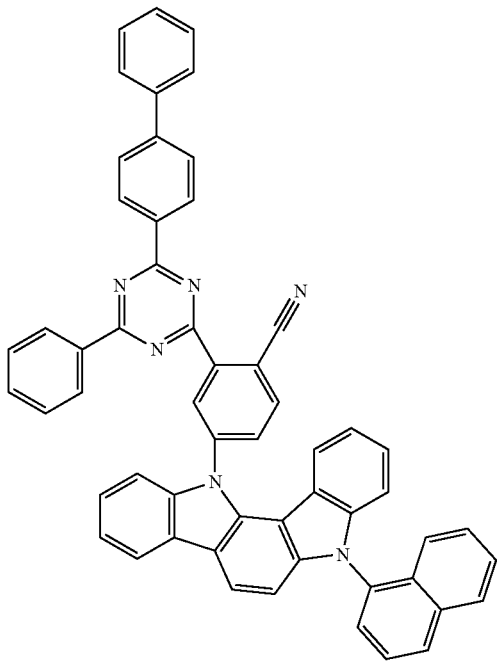

T7

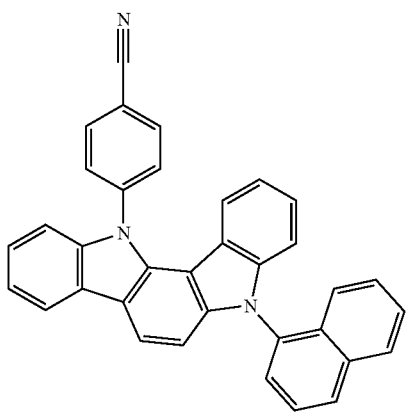

For the organic light emitting devices of Examples 2-1 to 2-15 and Comparative Examples 2-1 to 2-7, driving voltage (V) and current efficiency (cd/A) measured at current density of 10 mA/cm$^2$, and a CIE color coordinate measured at luminance of 3000 cd/m$^2$ were measured, and the results are shown in the following Table 2.

TABLE 2

| Category | Compound (Light Emitting Layer) | Voltage (V) | Efficiency (cd/A) | CIE Color Coordinate (x, y) |
|---|---|---|---|---|
| Example 2-1 | 1 | 3.9 | 23 | (0.19, 0.70) |
| Example 2-2 | 2 | 4.0 | 24 | (0.19, 0.70) |
| Example 2-3 | 3 | 4.1 | 23 | (0.19, 0.69) |
| Example 2-4 | 4 | 4.0 | 22 | (0.20, 0.70) |
| Example 2-5 | 5 | 3.9 | 25 | (0.20, 0.69) |
| Example 2-6 | 6 | 4.0 | 24 | (0.20, 0.70) |
| Example 2-7 | 7 | 4.0 | 24 | (0.19, 0.70) |
| Example 2-8 | 8 | 3.9 | 23 | (0.20, 0.70) |
| Example 2-9 | 9 | 4.0 | 22 | (0.20, 0.69) |
| Example 2-10 | 10 | 3.9 | 23 | (0.19, 0.70) |
| Example 2-11 | 11 | 4.0 | 24 | (0.20, 0.70) |
| Example 2-12 | 12 | 4.1 | 24 | (0.19, 0.70) |
| Example 2-13 | 13 | 3.9 | 23 | (0.19, 0.69) |
| Example 2-14 | 14 | 3.9 | 22 | (0.19, 0.70) |
| Example 2-15 | 15 | 4.0 | 23 | (0.19, 0.69) |
| Comparative Example 2-1 | 4CzIPN | 4.6 | 15 | (0.15, 0.67) |
| Comparative Example 2-2 | T1 | 4.8 | 13 | (0.17, 0.52) |
| Comparative Example 2-3 | T2 | 4.7 | 14 | (0.15, 0.66) |
| Comparative Example 2-4 | T3 | 4.7 | 14 | (0.15, 0.67) |
| Comparative Example 2-5 | T4 | 4.6 | 13 | (0.16, 0.66) |
| Comparative Example 2-6 | T5 | 4.6 | 14 | (0.15, 0.66) |
| Comparative Example 2-7 | T6 | 4.8 | 14 | (0.16, 0.67) |

As shown in Table 2, the devices of Examples 2-1 to 2-15 using the compound employing the structure of Chemical Formula 1 as a core all had decreased voltage and enhanced efficiency compared to the device using the material of Compound 4CzIPN of Comparative Example 2-1.

In addition, when comparing to the devices of Comparative Examples 2-1 to 2-7, it was seen that the devices using the compound of Chemical Formula 1 had enhanced properties in all aspects of voltage and efficiency.

As shown from the results of Table 2, it was identified that the compound according to the present disclosure had excellent light emission capability and was capable of light emission wavelength tuning, and organic light emitting devices with high color purity was able to be obtained.

Example 3

HOMO and LUMO energy levels were identified by dissolving the compound to be measured in a concentration of 5 mM and an electrolyte in a concentration of 0.1 M in dimethylformamide (DMF), identifying oxidation and reduction potential through measurement using a CV instrument, and comparing the result based on a ferrocene compound.

Measurement of HOMO Energy Level

The HOMO energy level and the LUMO energy level of the compound were measured using a cyclic voltammetry (CV) method comparing oxidation and reduction potential of a dimethylformamide (DMF) solution dissolving the compound to measure in a concentration of 5 mM and an electrolyte in a concentration of 0.1 M based on a ferrocene compound. A specific measurement condition is as follows.

CV Instrument: Iviumstat of Ivium Technologies

Measuring solution: dimethylformamide (DMF) solution dissolving compound to measure in concentration of 5 mM and electrolyte (KNO$_3$, Aldrich) in concentration of 0.1 M Working electrode: carbon electrode Reference electrode: Al/AgCl electrode Counter electrode: platinum electrode Measuring temperature: 25° C.

Scan rate: 50 mV/S

The HOMO energy level (E(HOMO)) and the LUMO energy level (E(LUMO)) were calculated through the following equations.

$E(\text{HOMO}) = [V_{solvent} - (E_{onset\,ox} - E_{1/2}(\text{solvent}))]\text{eV}$ $E(\text{LUMO}) = [V_{solvent} - (E_{onset\,red} - E_{1/2}(\text{solvent}))]\text{eV}$ In the equations, $V_{solvent}$ is an energy level of the solvent, $E_{1/2}$ (solvent) is a half wave level of the solvent, $E_{onset\,ex}$ is a point where oxidation starts, and $E_{onset\,red}$ is a point where reduction starts.

Measurement of Triplet Energy

Triplet energy (T1) was measured at a cryogenic temperature using properties of a triplet exciton having a long lifetime. Specifically, the compound was dissolved in a toluene solvent to preparing a sample having a concentration of $10^{-5}$ M, and the sample was placed in a quartz kit and cooled to 77K. A phosphorescence spectrum was measured by irradiating a 300 nm light source on the sample for phosphorescent measurement while changing a wavelength. The spectrum was measured using a spectrophotometer (FP-8600 spectrophotometer, JASCO).

The vertical axis of the phosphorescence spectrum was employed as phosphorescence intensity, and the horizontal axis was employed as a wavelength. A tangential line was drawn with respect to a rise in the short wavelength side of the phosphorescence spectrum, and after obtaining a wavelength value ($\lambda_{edge1}$ (nm)) of the intersection between the tangential line and the horizontal axis, this wavelength value was substituted into the following Conversion Formula 1 to calculate triplet energy.

$T1(\text{eV}) = 1239.85/\lambda_{edge1}$  Conversion Formula 1:

The tangential line with respect to a rise in the short wavelength side of the phosphorescence spectrum is drawn as follows. First, a maximum value of the shortest wavelength side among maximum values of the spectrum is determined. Herein, a maximum point having peak intensity of 15% or less of the maximum peak intensity of the spectrum is not included in the maximum value of the shortest wavelength side described above. A tangential line at each point on the spectrum curve from the short wavelength side of the phosphorescence spectrum to the maximum value is considered. Among these tangential lines, a tangential line having a largest slope value (that is, a tangential line at an inflection point) is employed as the tangential line with respect to a rise in the short wavelength side of the corresponding phosphorescence spectrum.

Measurement of Singlet Energy

Singlet energy (S1) was measured as follows.

A $10^{-5}$ M toluene solution of the compound to measure was prepared and placed in a quartz kit, and a light emission spectrum (vertical axis: light emission intensity, horizontal axis: wavelength) of the sample with a 300 nm light source was measured at room temperature (300 K). A tangential line was drawn with respect to a rise in the short wavelength side of this light emission spectrum, and a wavelength value ($\lambda_{edge2}$ (nm)) of the intersection between the tangential line and the horizontal axis was substituted into the following Conversion Formula 2 to calculate singlet energy. The light emission spectrum was measured using a spectrophotometer of JASCO (FP-8600 spectrophotometer).

$S1(\text{eV}) = 1239.85/\lambda_{edge2}$  Conversion Formula 2:

The tangential line with respect to a rise in the short wavelength side of the light emission spectrum is drawn as follows. First, a maximum value of the shortest wavelength side among maximum values of the spectrum is determined. A tangential line at each point on the spectrum curve from the short wavelength side of the light emission spectrum to the maximum value is considered. Among these tangential lines, a tangential line having a largest slope value (that is, a tangential line at an inflection point) is employed as the tangential line with respect to a rise in the short wavelength side of the corresponding light emission spectrum. A maximum point having peak intensity of 15% or less of the maximum peak intensity of the spectrum is not included in the maximum value of the shortest wavelength side described above.

TABLE 3

| Compound | S1 (eV) | T1 (eV) | HOMO (eV) | LUMO (eV) | $\Delta E_{ST}$ (eV) |
|---|---|---|---|---|---|
| 1 | 2.41 | 2.39 | 5.71 | 3.02 | 0.02 |
| 2 | 2.42 | 2.39 | 5.78 | 3.10 | 0.03 |
| 3 | 2.42 | 2.39 | 5.79 | 3.06 | 0.03 |
| 4 | 2.43 | 2.40 | 5.70 | 3.10 | 0.03 |
| 5 | 2.41 | 2.38 | 5.78 | 3.08 | 0.03 |
| 6 | 2.40 | 2.38 | 5.71 | 3.01 | 0.02 |
| 7 | 2.42 | 2.41 | 5.70 | 3.06 | 0.01 |
| 8 | 2.41 | 2.39 | 5.77 | 3.09 | 0.02 |
| 9 | 2.42 | 2.41 | 5.75 | 3.10 | 0.01 |
| 10 | 2.40 | 2.39 | 5.78 | 3.05 | 0.01 |
| 11 | 2.42 | 2.39 | 5.77 | 3.04 | 0.03 |
| 12 | 2.43 | 2.39 | 5.76 | 3.07 | 0.04 |
| 13 | 2.42 | 2.38 | 5.76 | 3.09 | 0.04 |
| 14 | 2.41 | 2.40 | 5.78 | 3.08 | 0.01 |
| 15 | 2.42 | 2.39 | 5.77 | 3.11 | 0.03 |
| T1 | 2.73 | 2.58 | 6.01 | 2.65 | 0.15 |
| T2 | 2.52 | 2.38 | 5.98 | 2.63 | 0.14 |
| T3 | 2.49 | 2.40 | 5.81 | 2.99 | 0.09 |
| T4 | 2.50 | 2.36 | 5.80 | 2.97 | 0.14 |
| T5 | 2.51 | 23.36 | 5.82 | 2.99 | 0.15 |
| T6 | 2.48 | 2.37 | 5.88 | 3.00 | 0.11 |
| T7 | 2.82 | 2.59 | 6.03 | 2.61 | 0.23 |
| 4CzIPN | 2.44 | 2.39 | 5.55 | 3.15 | 0.05 |

It was seen that Compounds 1 to 15 used in the examples of the present application all had $\Delta E_{ST}$ of 0.3 eV or less and were suited as a delayed fluorescent material.

Although Compounds T1, T2, T3, T4. T5, T6, T7 and 4CzIPN used in the comparative examples correspond to a delayed fluorescent material with $\Delta E_{ST}$ of 0.3 eV or less, it was seen that, as examined in Table 1 and Table 2, the devices using Compounds 1 to 15 had enhanced properties in all aspects of voltage and efficiency.

Hereinbefore, preferred embodiments of the present disclosure have been described, however, the present disclosure is not limited thereto, and various modifications can be made within the scope of the claims and the detailed descriptions of the disclosure, and these also fall within the category of the disclosure.

REFERENCE NUMERALS

1: Substrate

2: Anode

3: Light Emitting Layer

4: Cathode

5: Hole Injection Layer

6: Hole Transfer Layer

7: Electron Transfer Layer

8: Electron Blocking Layer

9: Hole Blocking Layer

10: Electron Injection and Transfer Layer

The invention claimed is:
1. A compound of Chemical Formula 1:

[Chemical Formula 1]

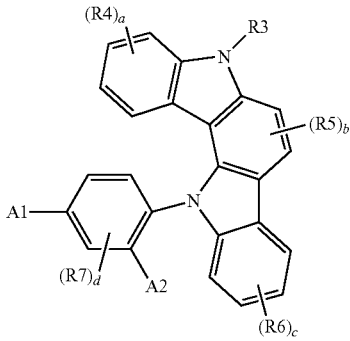

wherein, in Chemical Formula 1:
one of A1 and A2 is substituent of the following Chemical Formula 2, and the other one is a cyano group;
R3 is a substituted or unsubstituted aryl group or a substituted or unsubstituted heteroaryl group;
R4 to R7 are each independently hydrogen, deuterium, a halogen group, a substituted or unsubstituted silyl group, a substituted or unsubstituted alkyl group, a substituted or unsubstituted amine group, a substituted or unsubstituted arylamine group, a substituted or unsubstituted alkylamine group, a substituted or unsubstituted aryl group, or a substituted or unsubstituted heteroaryl group;
a is an integer of 0 to 4, and when a is 2 or greater, the R4s are the same as or different from each other;
b is an integer of 0 to 2, and when b is 2, the R5s are the same as or different from each other;
c is an integer of 0 to 4, and when c is 2 or greater, the R6s are the same as or different from each other; and
d is an integer of 0 to 3, and when d is 2 or greater, the R7s are the same as or different from each other;

[Chemical Formula 2]

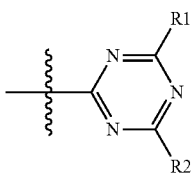

wherein in Chemical Formula 2:
R1 and R2 are each independently a substituted or unsubstituted aryl group or a substituted or unsubstituted heteroaryl group; and
wherein at least one of R1 and R2 is:
a phenyl group substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or substituted with a substituent in which two or more substituents selected from the group consisting of a $C_1$ to $C_{10}$ alkyl group, a $C_6$ to $C_{20}$ aryl group and a $C_2$ to $C_{20}$ heteroaryl group are linked to each other; or
a $C_{10}$ to $C_{20}$ aryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of a $C_1$ to $C_{10}$ alkyl group, a $C_6$ to $C_{20}$ aryl group and a $C_2$ to $C_{20}$ heteroaryl group are linked to each other; or
a $C_2$ to $C_{20}$ heteroaryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of a $C_1$ to $C_{10}$ alkyl group, a $C_6$ to $C_{20}$ aryl group and a $C_2$ to $C_{20}$ heteroaryl group are linked to each other.

2. A compound of Chemical Formula 1:

[Chemical Formula 1]

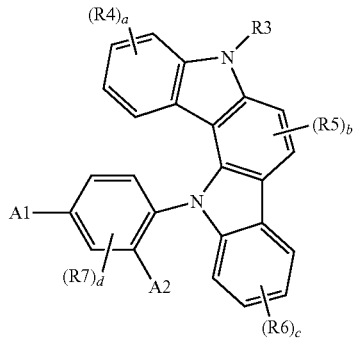

wherein, in Chemical Formula 1:
one of A1 and A2 is substituent of the following Chemical Formula 2, and the other one is a cyano group;
R3 is:
a phenyl group substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or substituted with a substituent in which two or more substituents selected from the group consisting of a $C_1$ to $C_{10}$ alkyl group, a $C_6$ to $C_{20}$ aryl group and a $C_2$ to $C_{20}$ heteroaryl group are linked to each other; or
a $C_{10}$ to $C_{20}$ aryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of a $C_1$ to $C_{10}$ alkyl group, a $C_6$ to $C_{20}$ aryl group and a $C_2$ to $C_{20}$ heteroaryl group are linked to each other; or
a $C_2$ to $C_{20}$ heteroaryl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group, or unsubstituted or substituted with a substituent in which two or more substituents selected from the group consisting of a $C_1$ to $C_{10}$ alkyl group, a $C_6$ to $C_{20}$ aryl group and a $C_2$ to $C_{20}$ heteroaryl group are linked to each other;
R4 to R7 are each independently hydrogen, deuterium, a halogen group, a substituted or unsubstituted silyl group, a substituted or unsubstituted alkyl group, a substituted or unsubstituted amine group, a substituted or unsubstituted arylamine group, a substituted or unsubstituted alkylamine group, a substituted or unsubstituted aryl group, or a substituted or unsubstituted heteroaryl group;

a is an integer of 0 to 4, and when a is 2 or greater, the R4s are the same as or different from each other;

b is an integer of 0 to 2, and when b is 2, the R5s are the same as or different from each other;

c is an integer of 0 to 4, and when c is 2 or greater, the R6s are the same as or different from each other; and d is an integer of 0 to 3, and when d is 2 or greater, the R7s are the same as or different from each other;

[Chemical Formula 2]

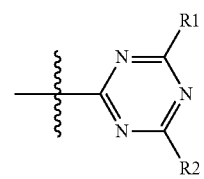

wherein:
R1 and R2 are each independently a substituted or unsubstituted aryl group or a substituted or unsubstituted heteroaryl group; and
(1) at least one of R1 and R2 is a substituted phenyl group, a substituted or unsubstituted $C_{10}$ or higher aryl group, or a substituted or unsubstituted heteroaryl group; or
(2) R7 is deuterium and d is 1 or greater.

3. The compound of claim 1, wherein R3 is a substituted or unsubstituted phenyl group, a substituted or unsubstituted biphenyl group, a substituted or unsubstituted fluorenyl group, a substituted or unsubstituted naphthyl group, a substituted or unsubstituted dibenzofuranyl group, or a substituted or unsubstituted dibenzothiophenyl group.

4. The compound of claim 1, wherein the substituted or unsubstituted aryl group of R1 and R2 is independently selected from the group consisting of
an unsubstituted phenyl group,
a phenyl group substituted with deuterium, and
a biphenyl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group; and the substituted or unsubstituted heteroaryl group of R1 and R2 is independently selected from the group consisting of
a carbazolyl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group;
a dibenzofuranyl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group; and
a dibenzothiophenyl group that is unsubstituted or substituted with one or more substituents selected from the group consisting of deuterium, a $C_1$ to $C_{10}$ alkyl group, a $C_6$ to $C_{20}$ aryl group and a $C_2$ to $C_{20}$ heteroaryl group.

5. The compound of claim 1, wherein the compound of Chemical Formula 1 comprises at least one deuterium.

6. A compound selected from among the following compounds:

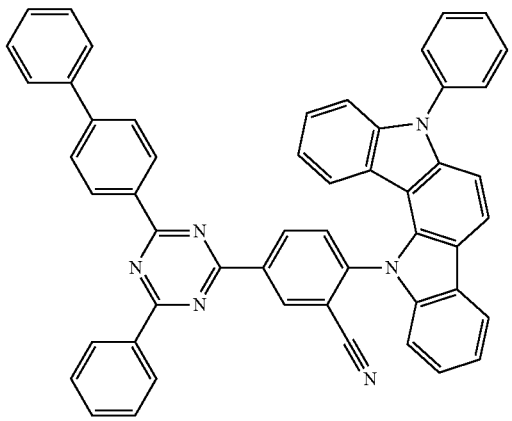

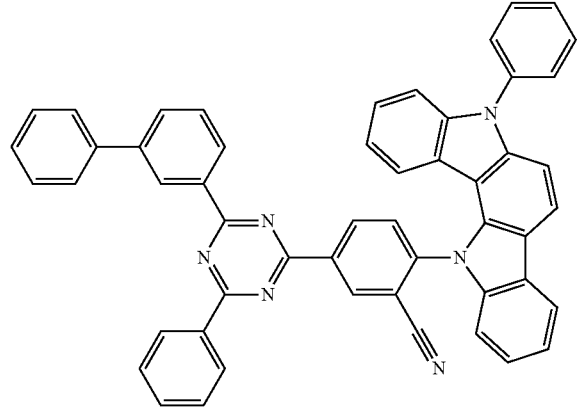

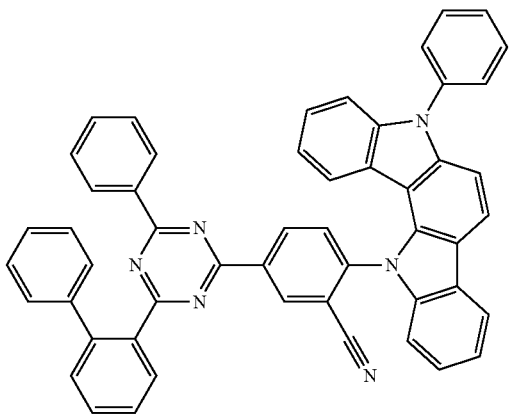

195
-continued
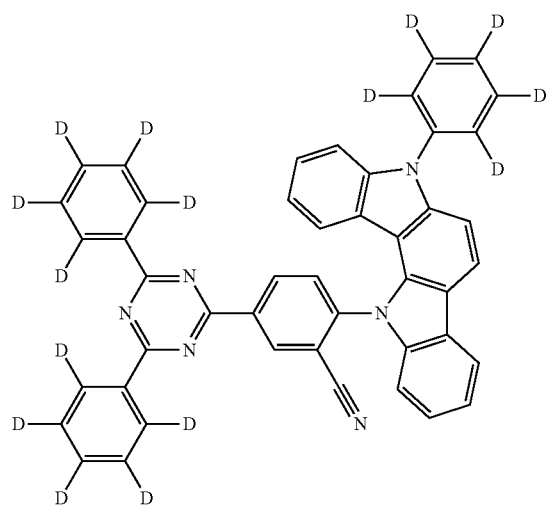
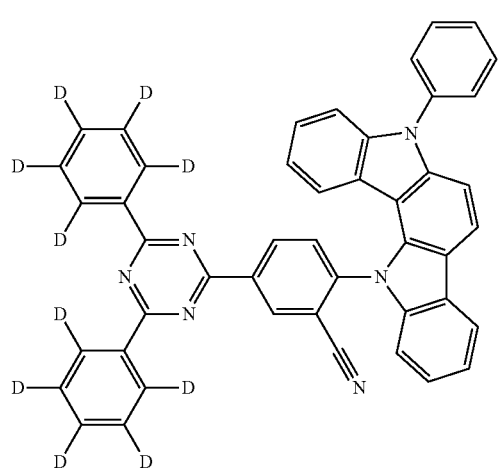
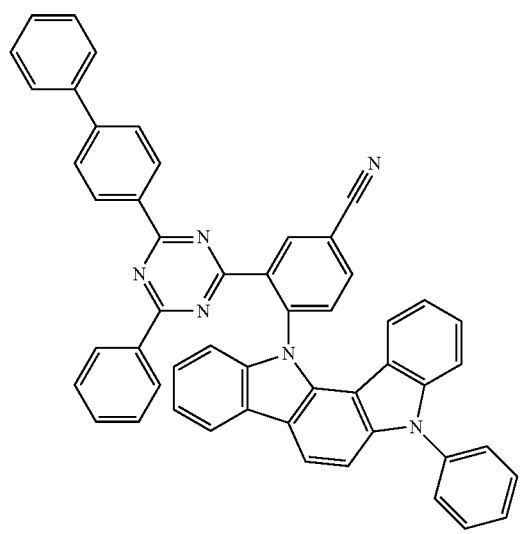
196
-continued
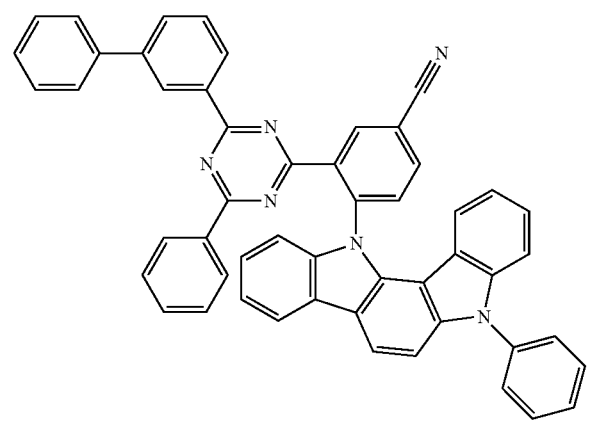
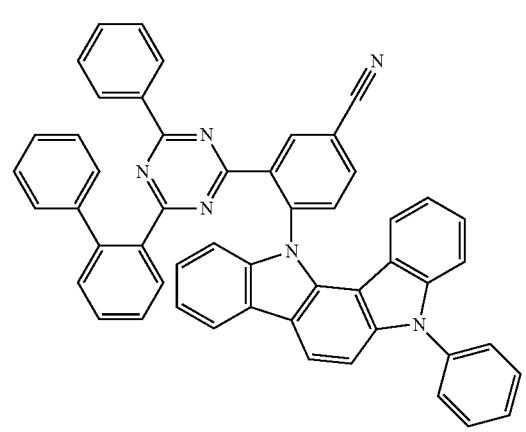
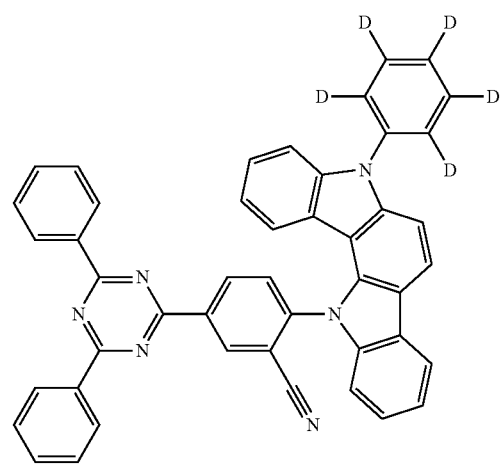

197
-continued
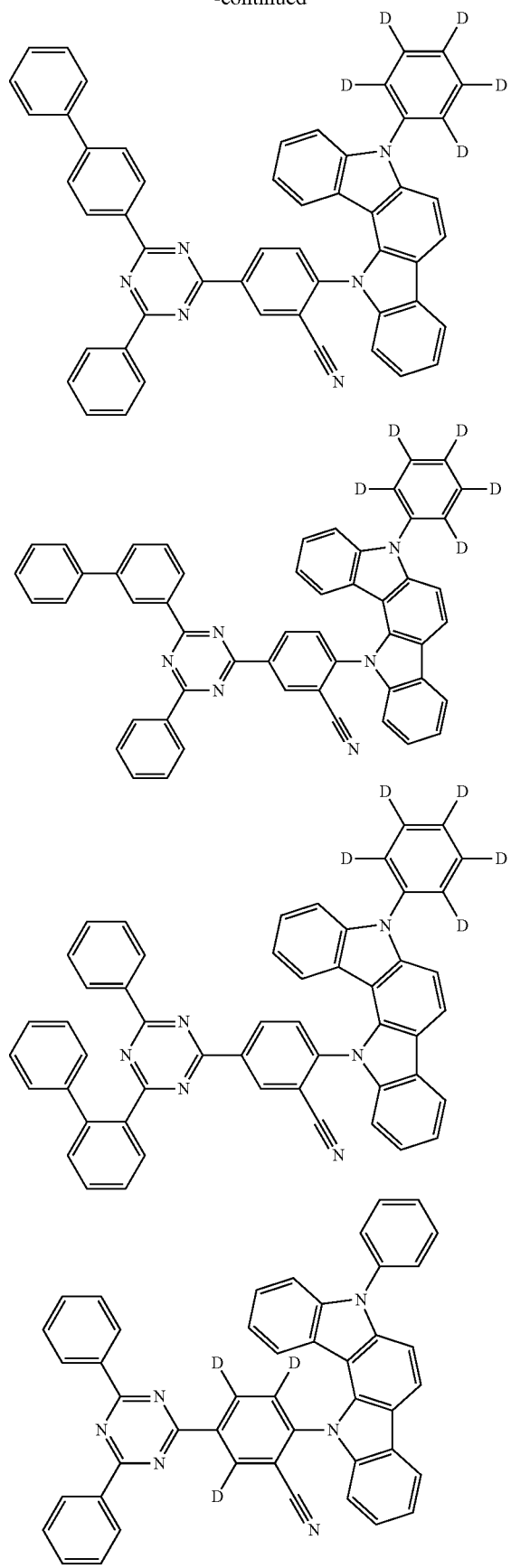
198
-continued
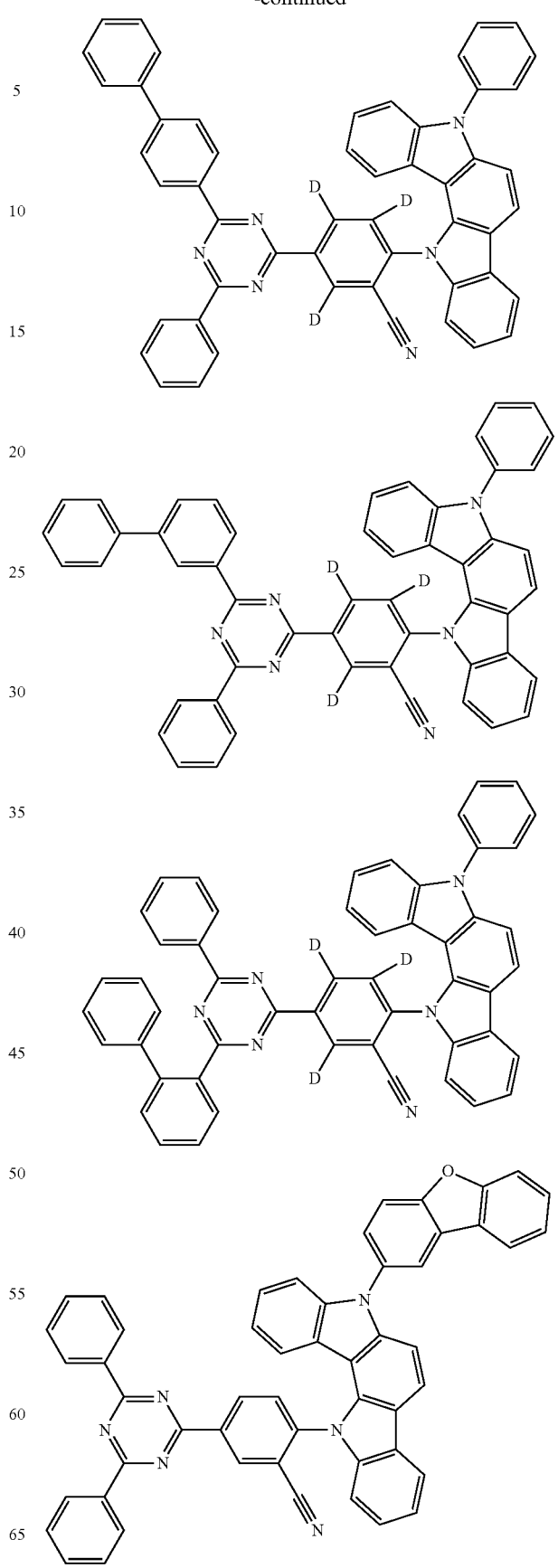

199
-continued
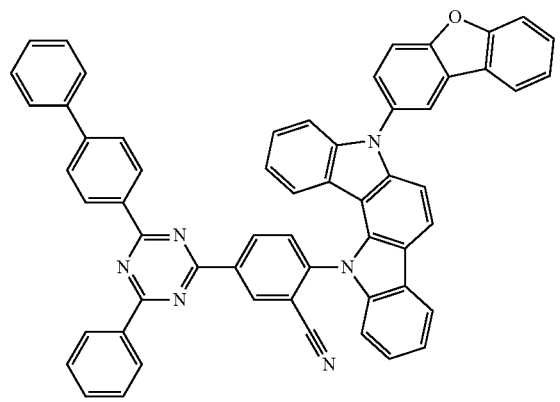
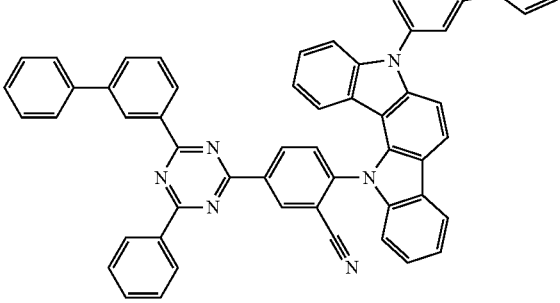
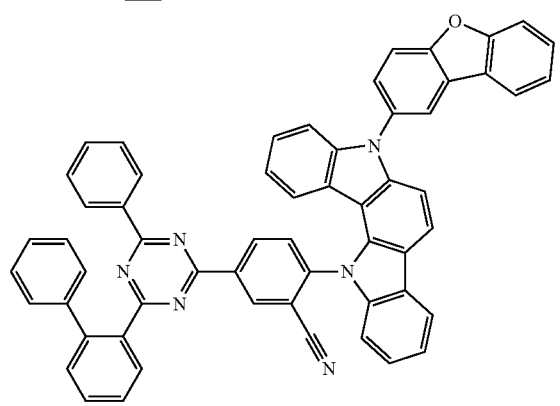
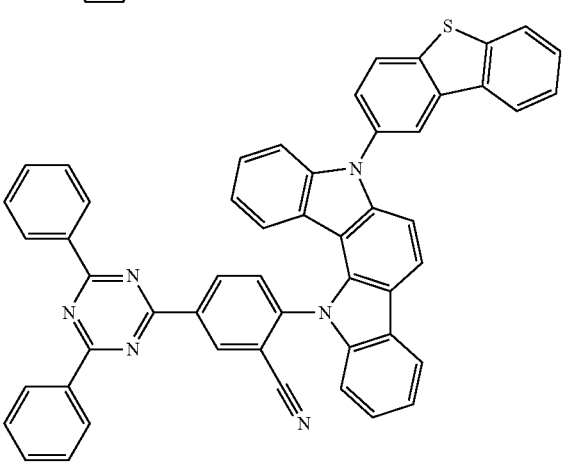
200
-continued
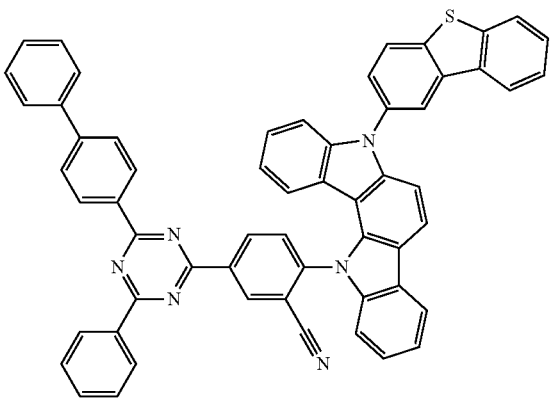
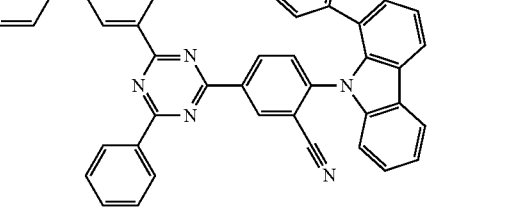
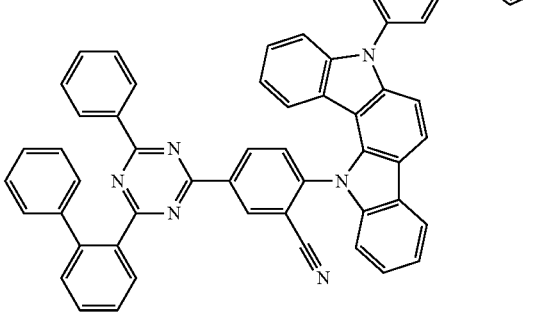
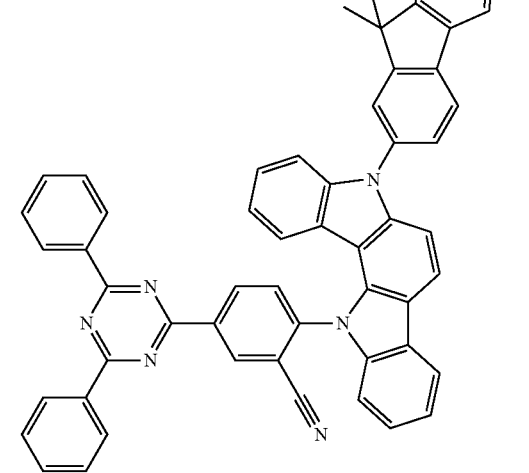

201
-continued
202
-continued
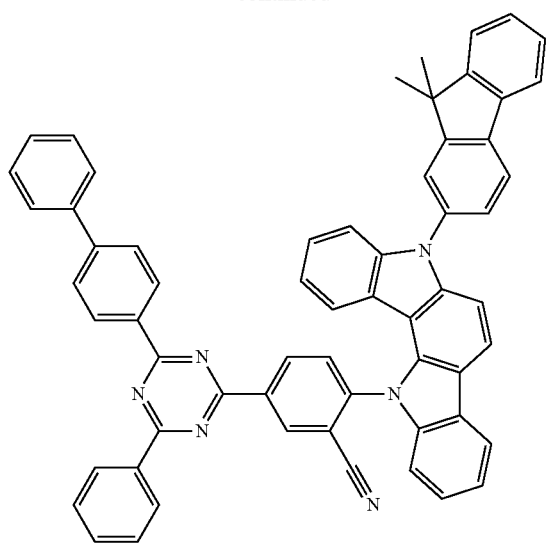
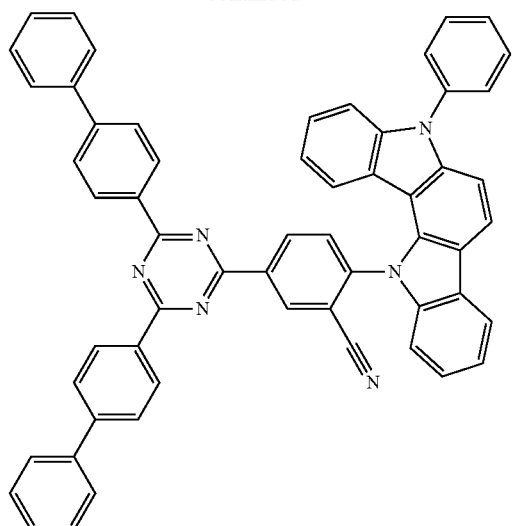
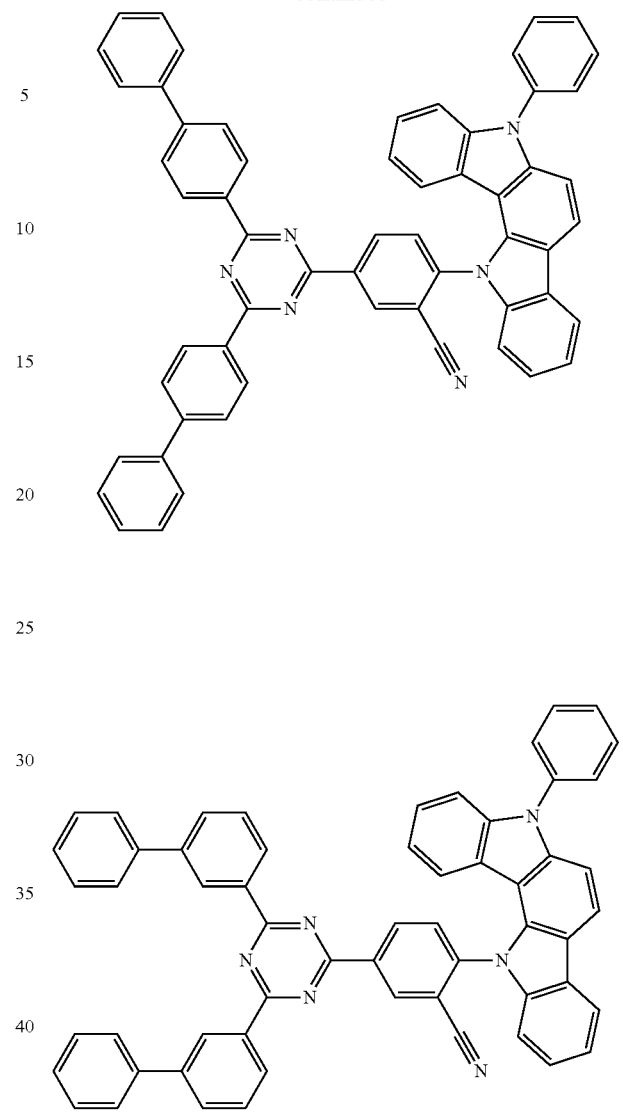
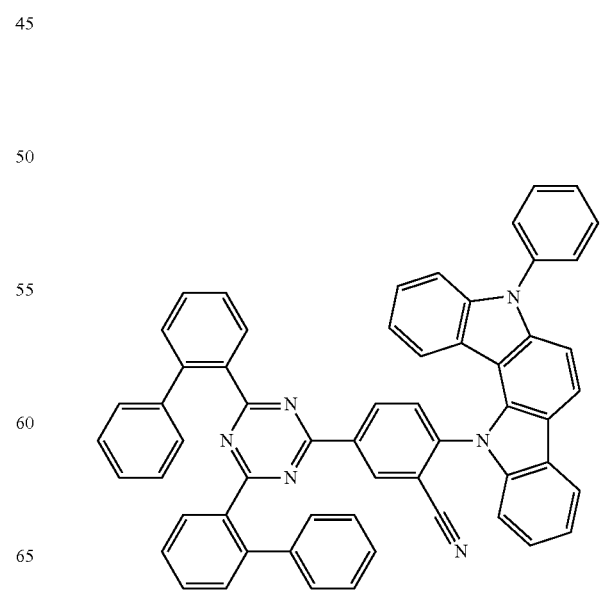

203
-continued
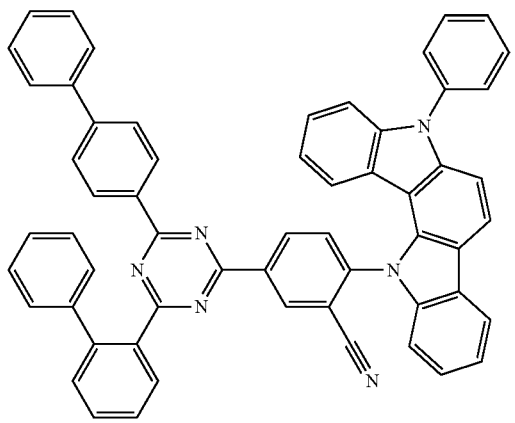
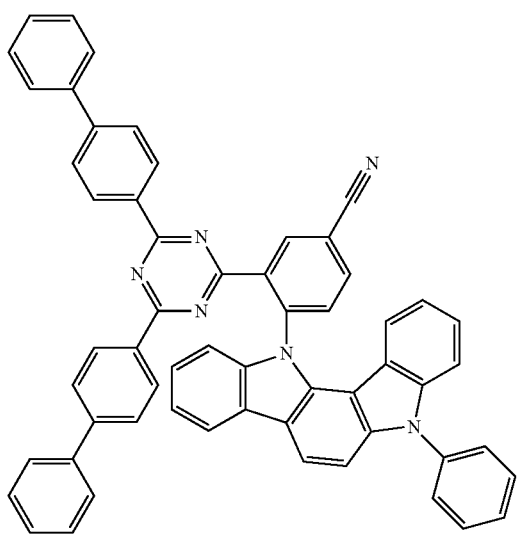
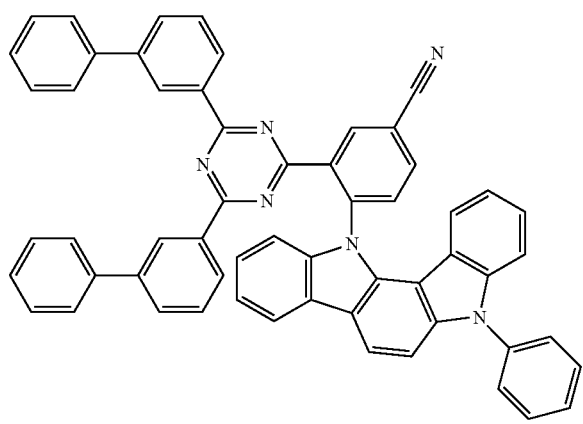
204
-continued
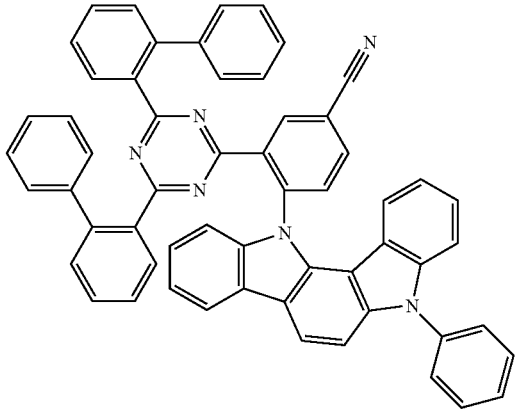
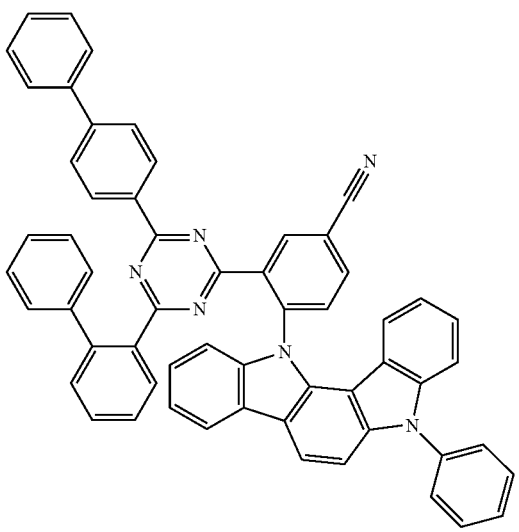
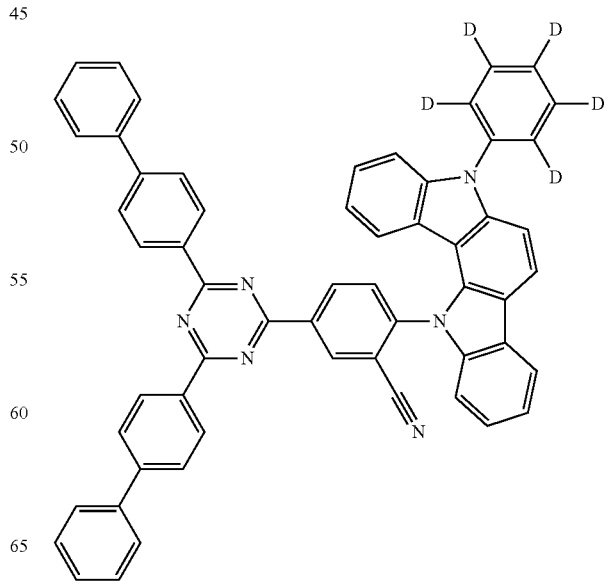

205
-continued
206
-continued
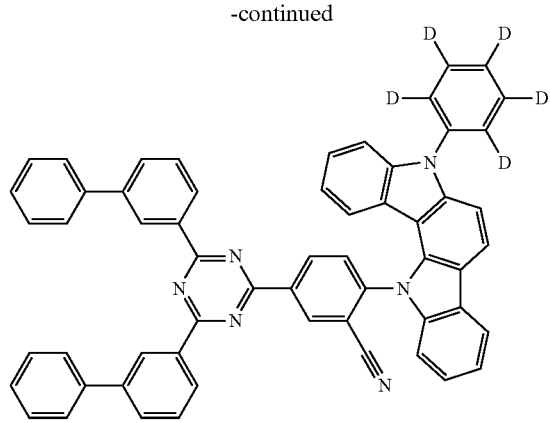
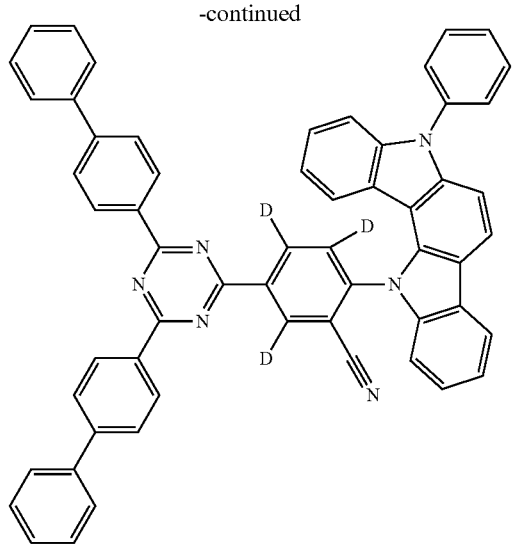
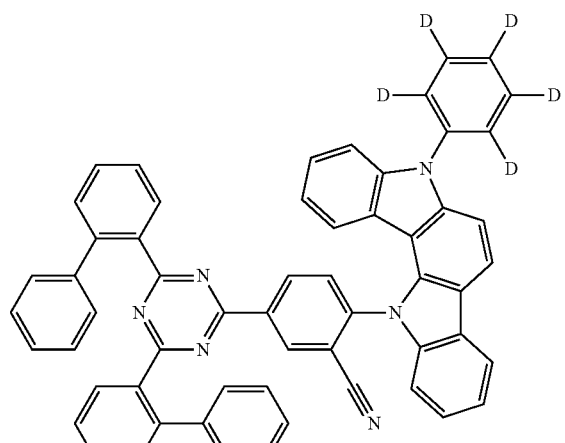
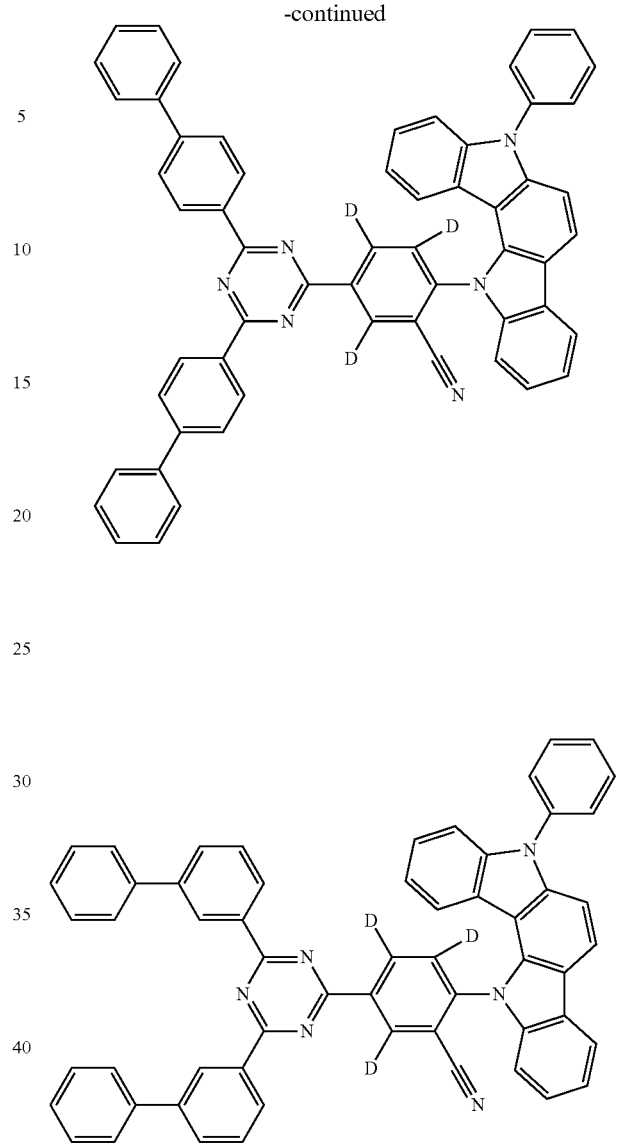
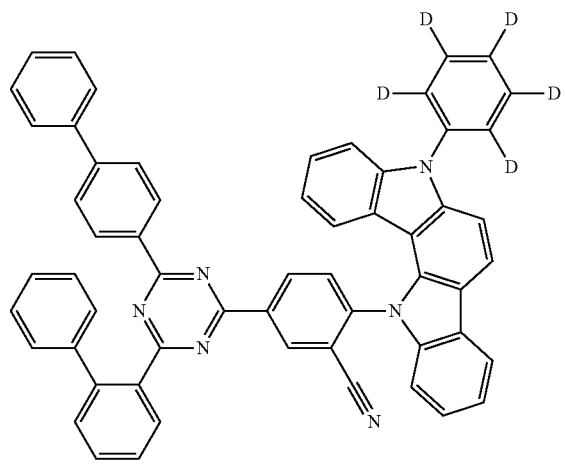

207
-continued
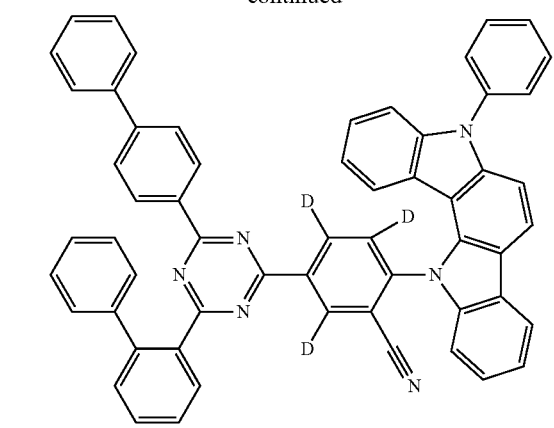
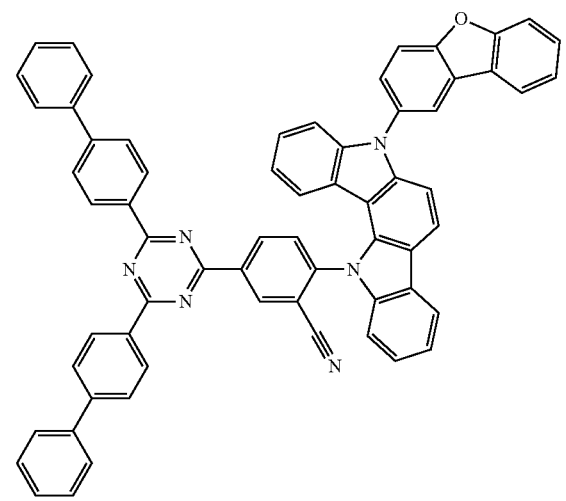
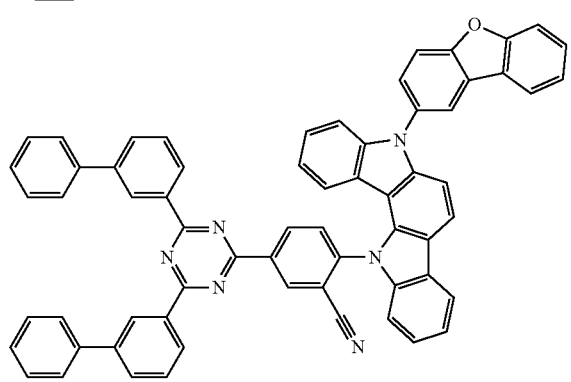
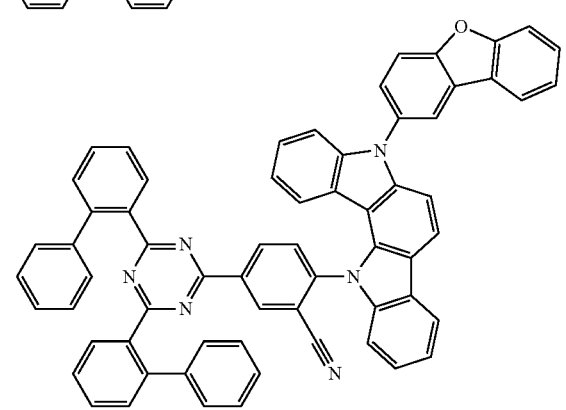
208
-continued
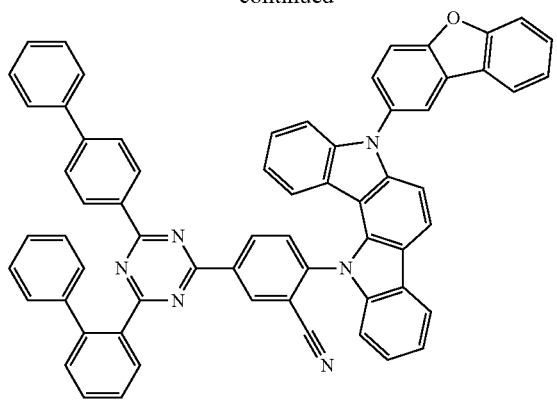
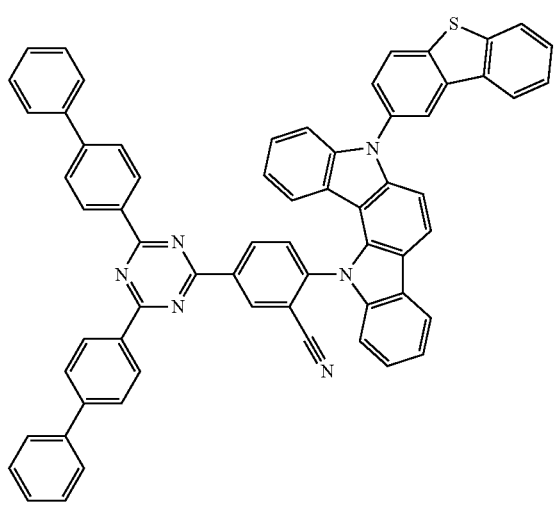
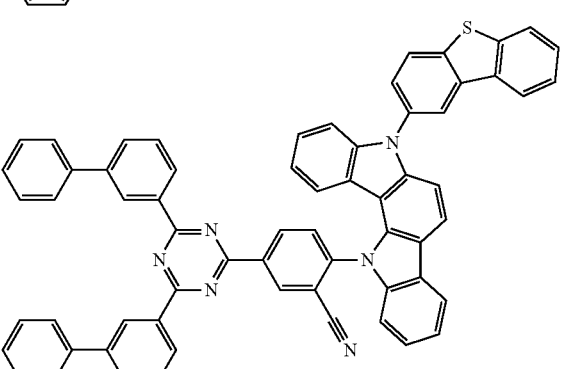
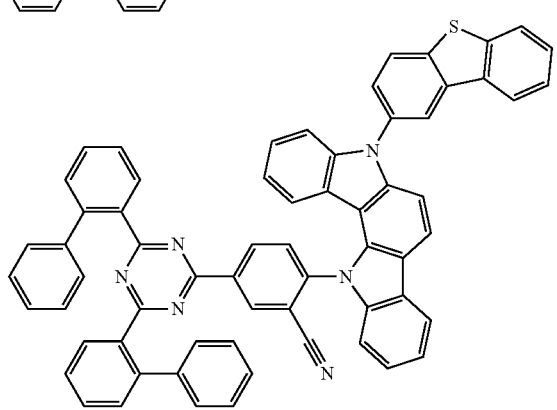

209
-continued
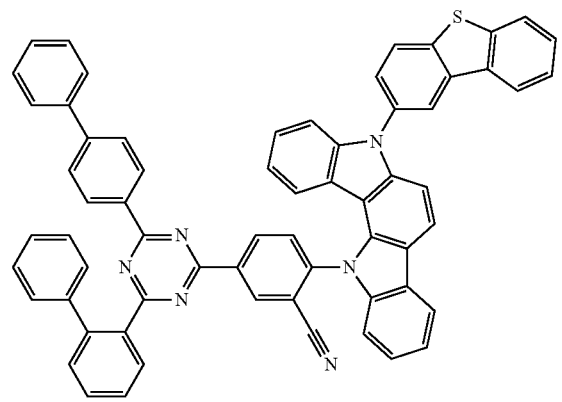
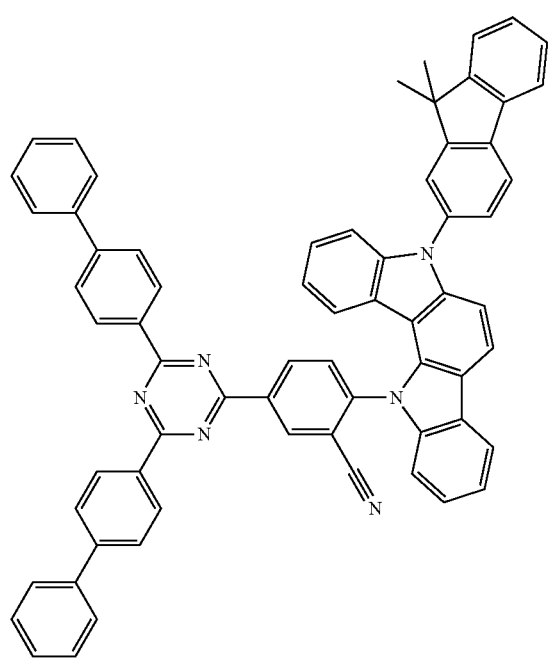
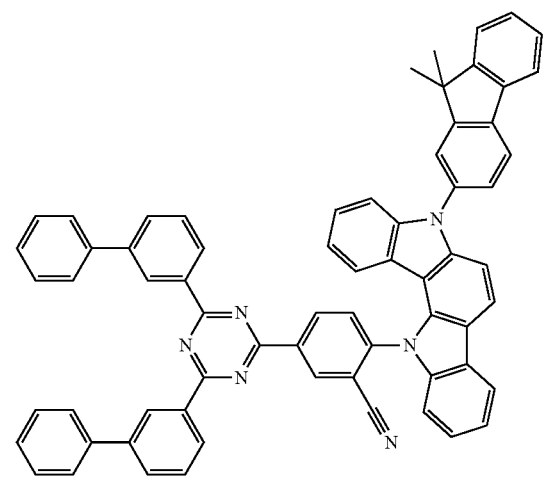
210
-continued
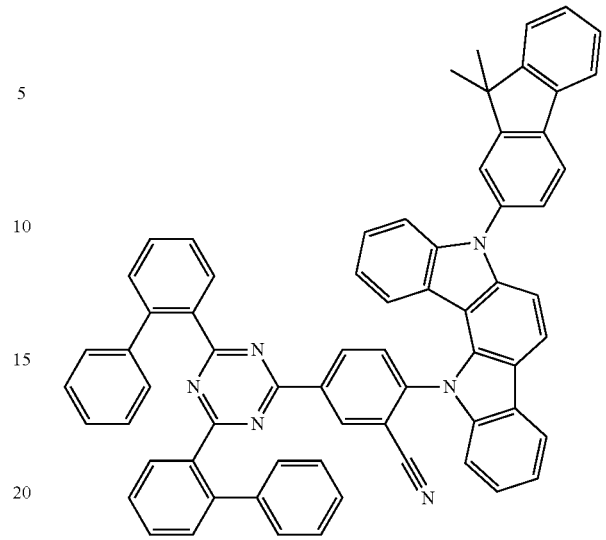
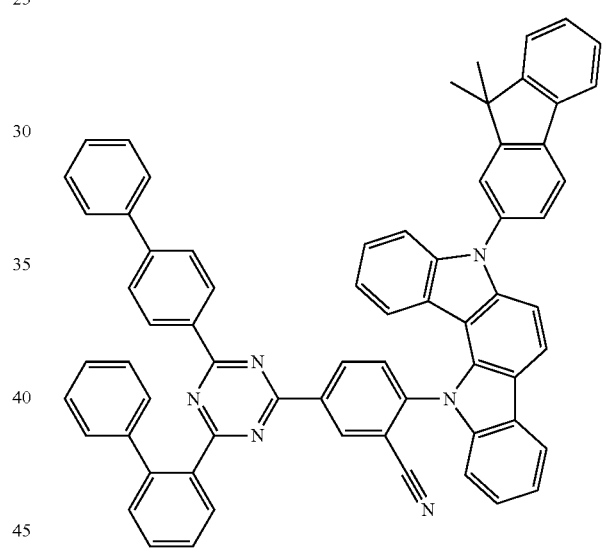
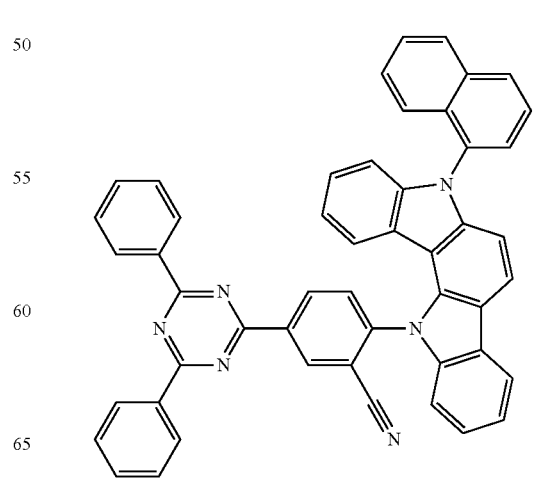

211
-continued
212
-continued
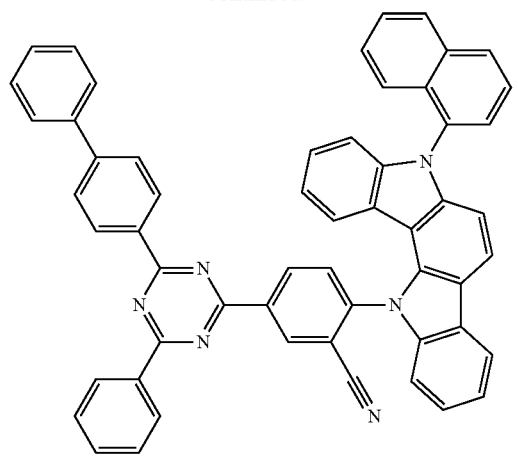
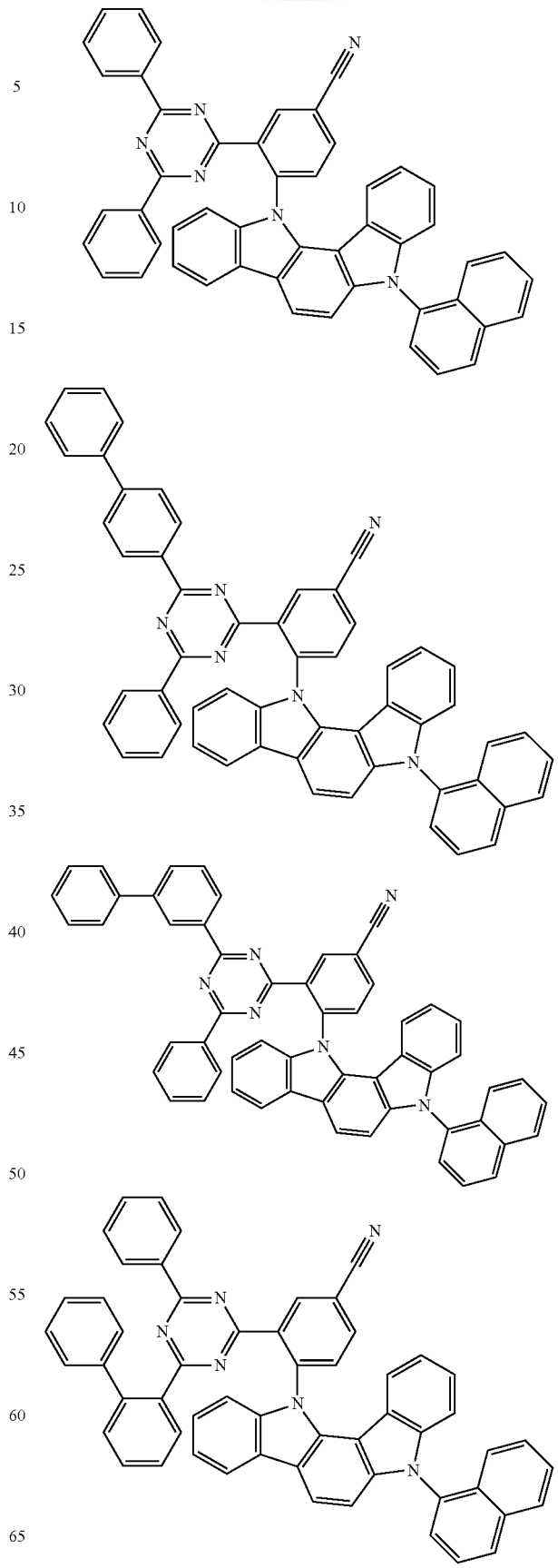

213
-continued
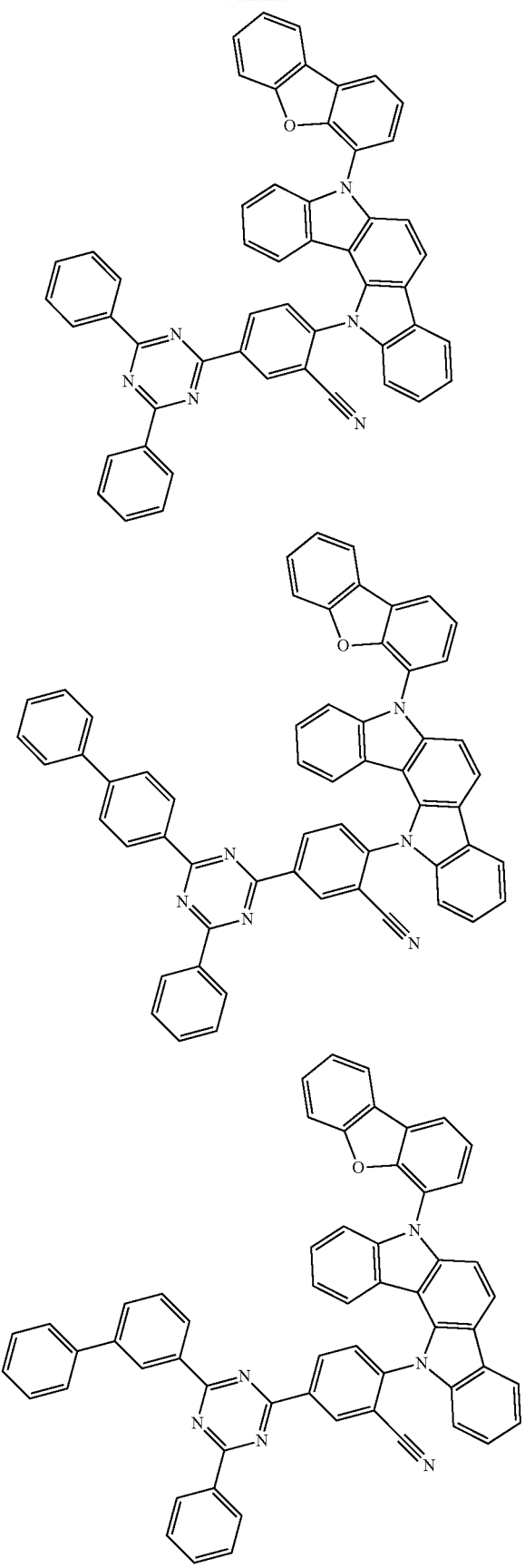
214
-continued
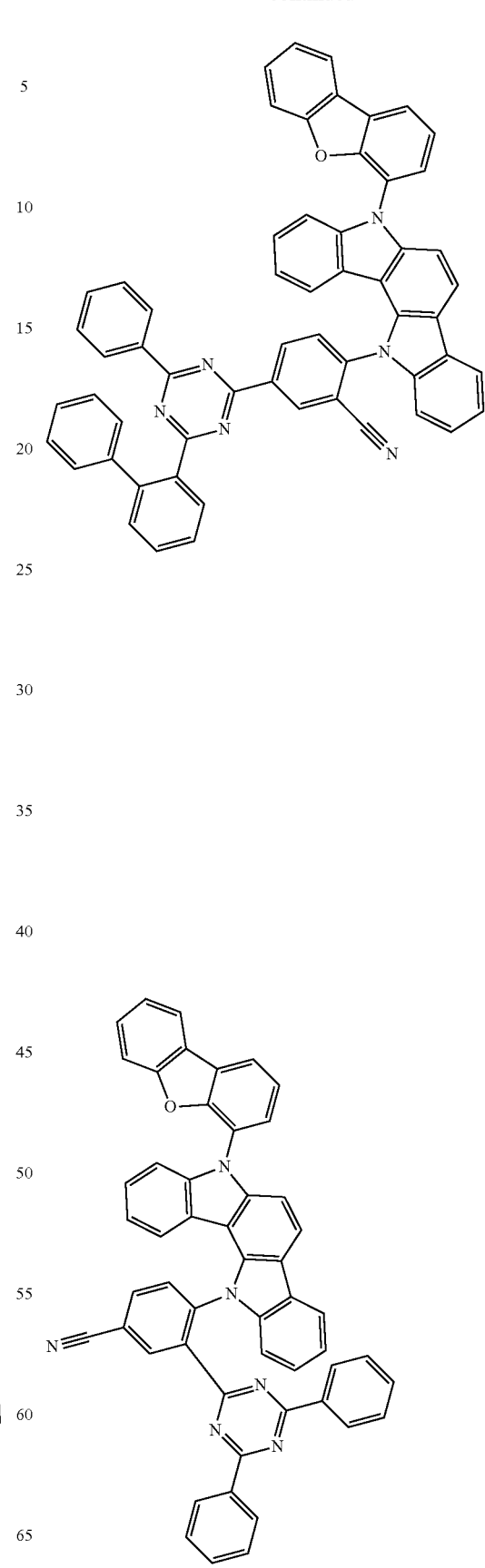

215
-continued
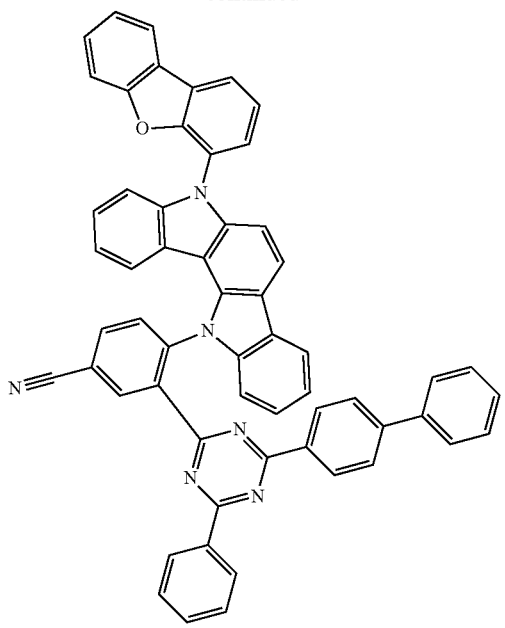
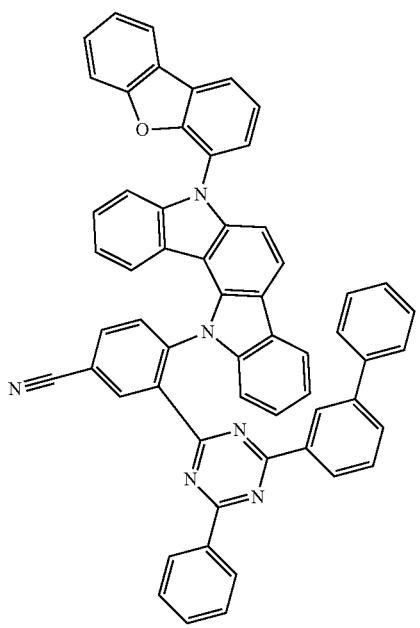
216
-continued
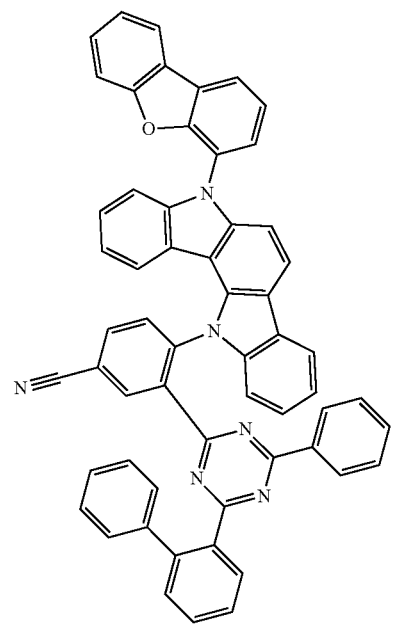
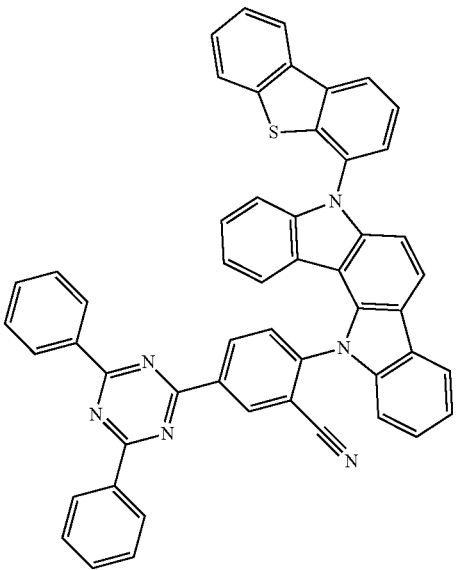

217
-continued
218
-continued
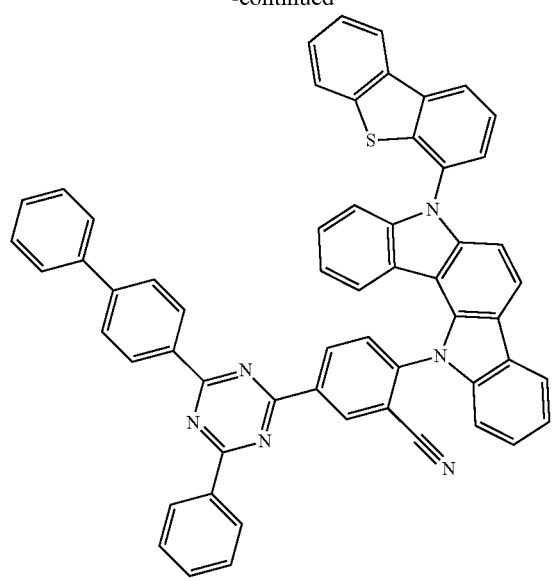

219
-continued
220
-continued
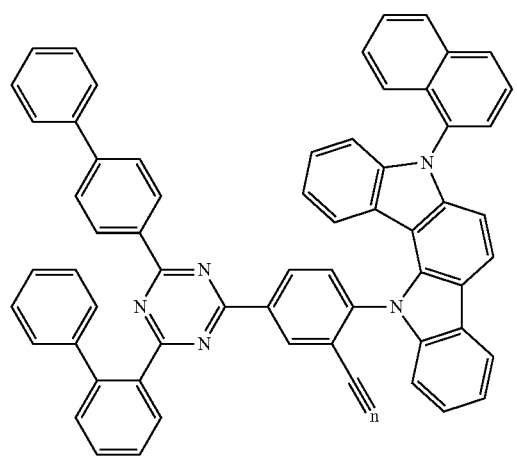
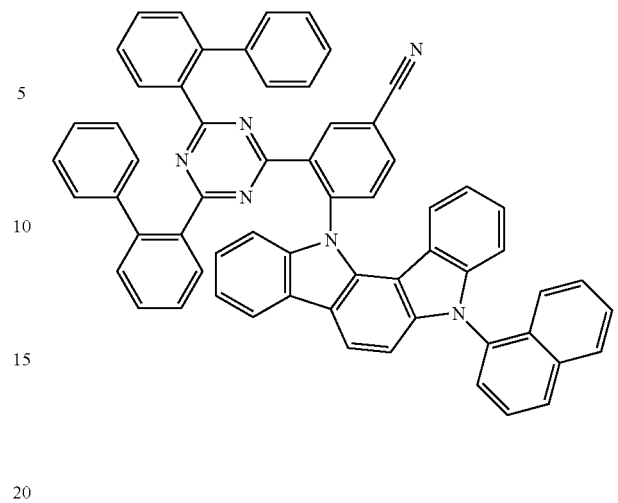
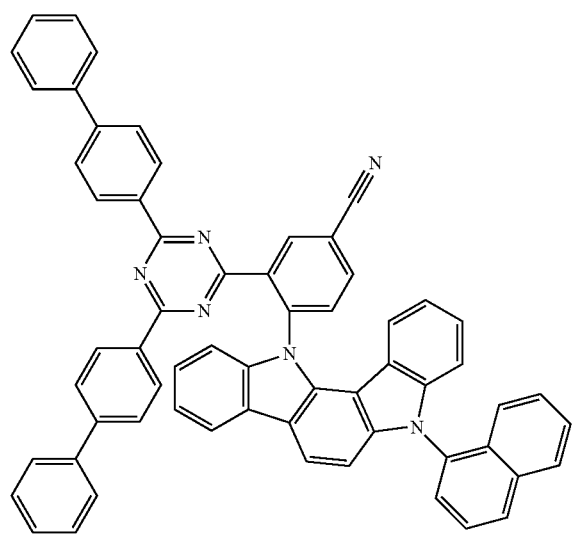
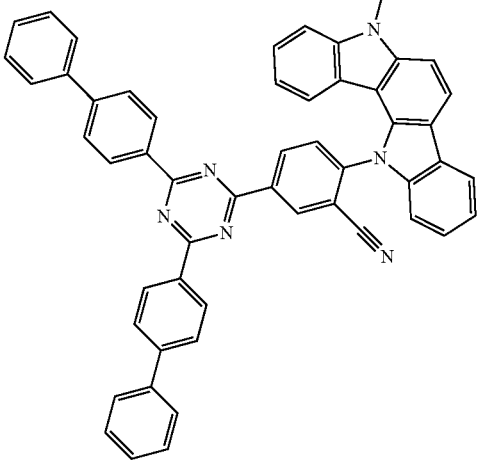
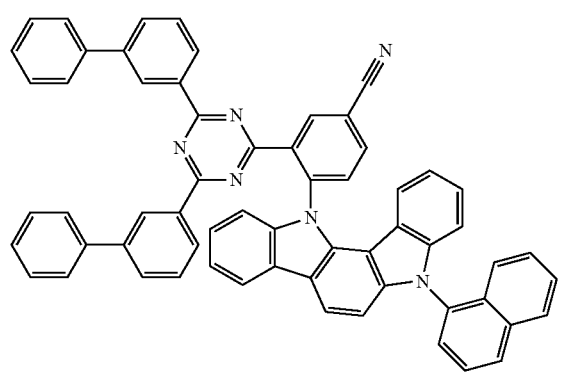

221
-continued
222
-continued
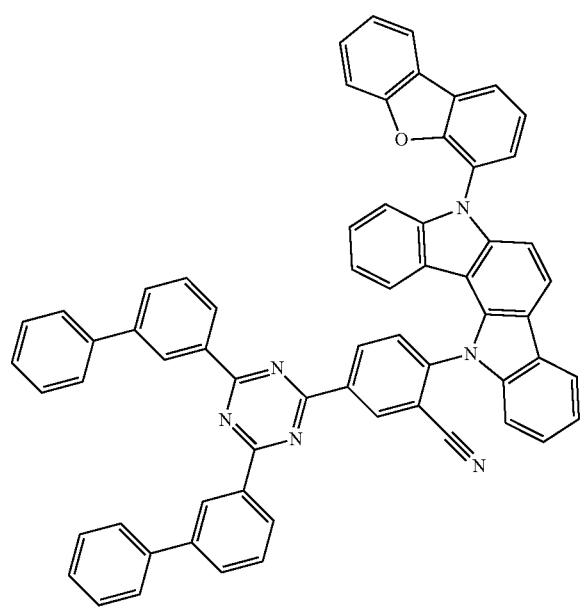
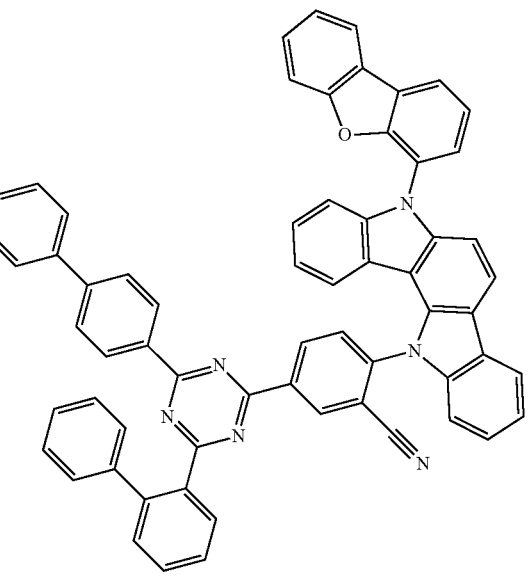

223
-continued
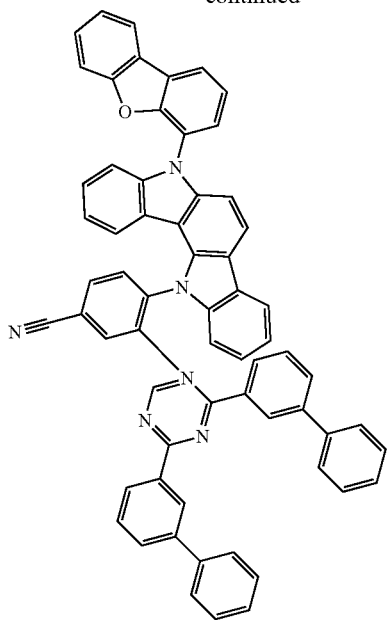
224
-continued
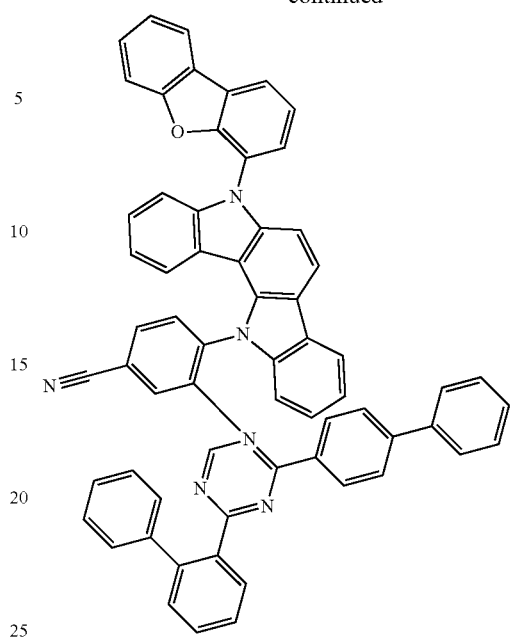
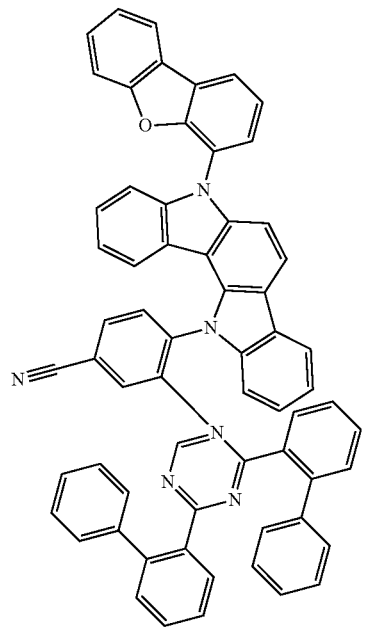
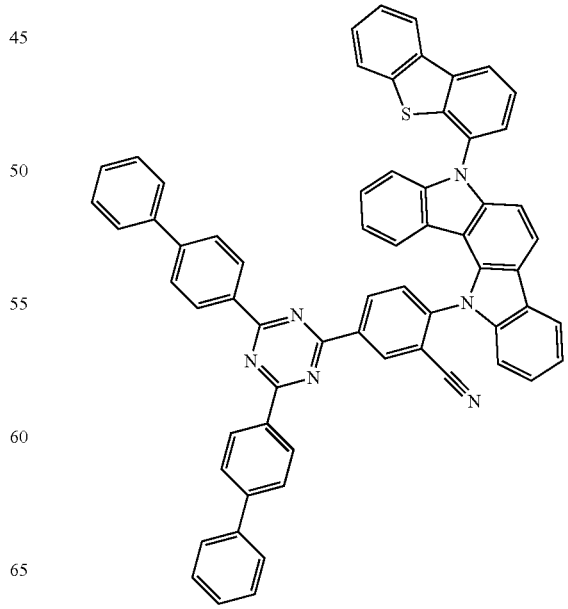

225
-continued
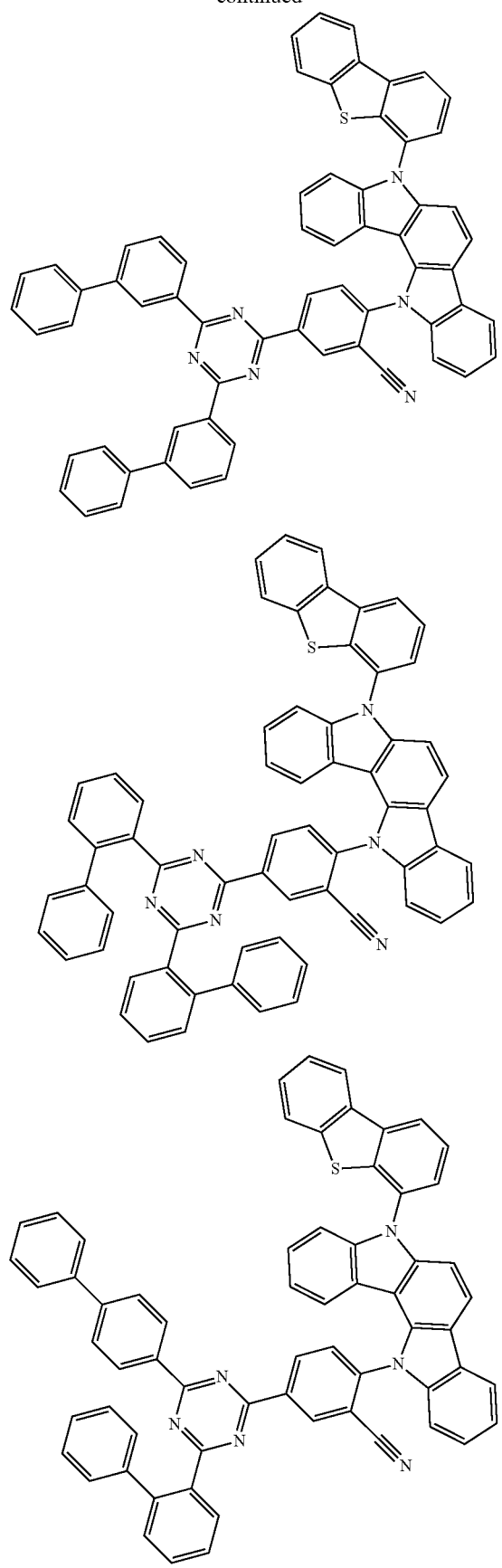
226
-continued
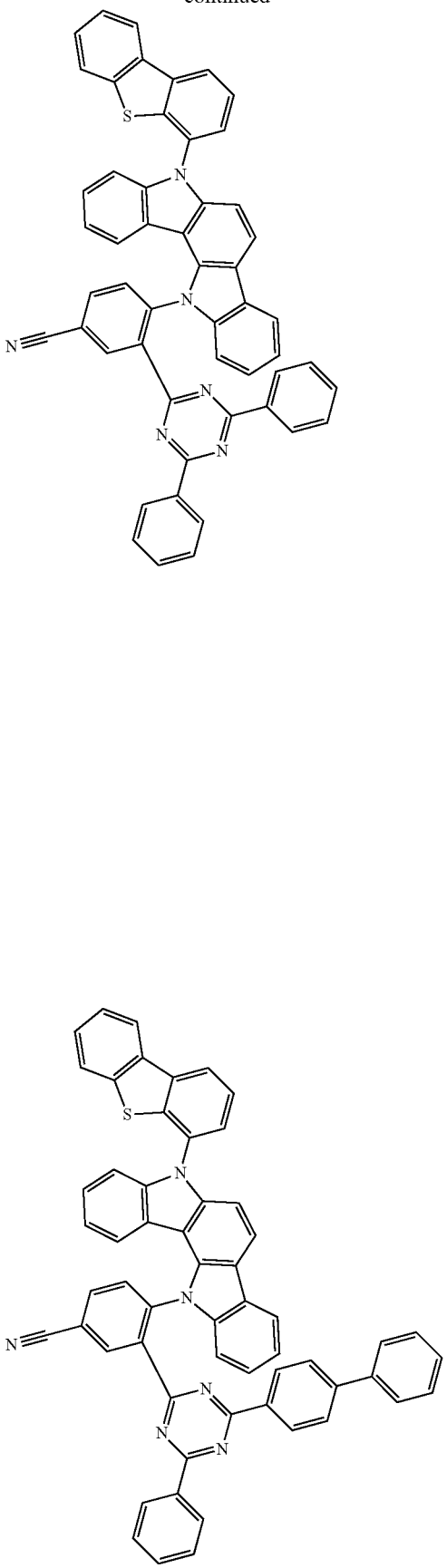

227
-continued
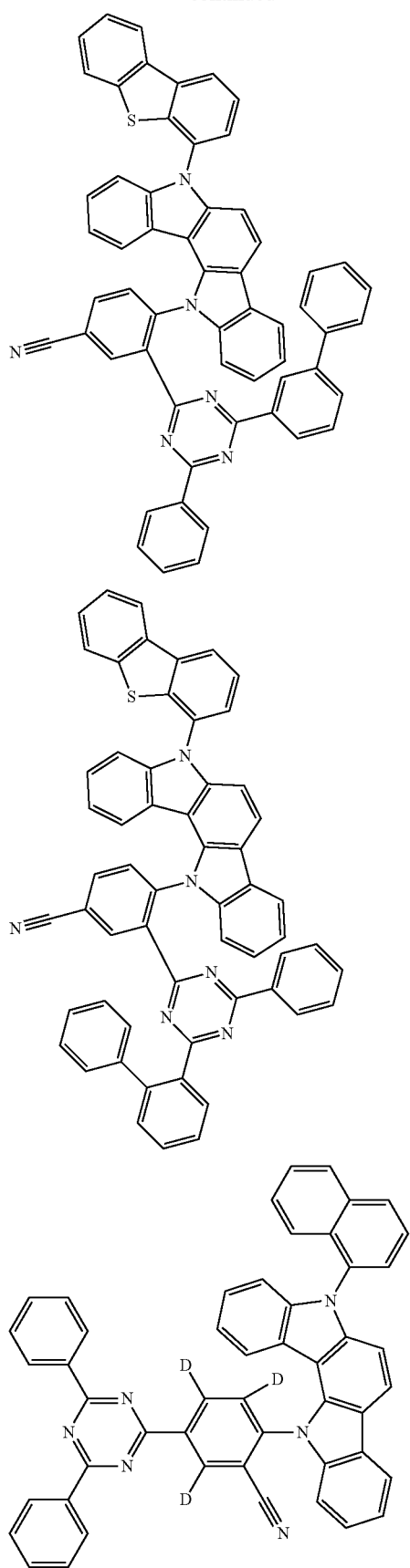
228
-continued
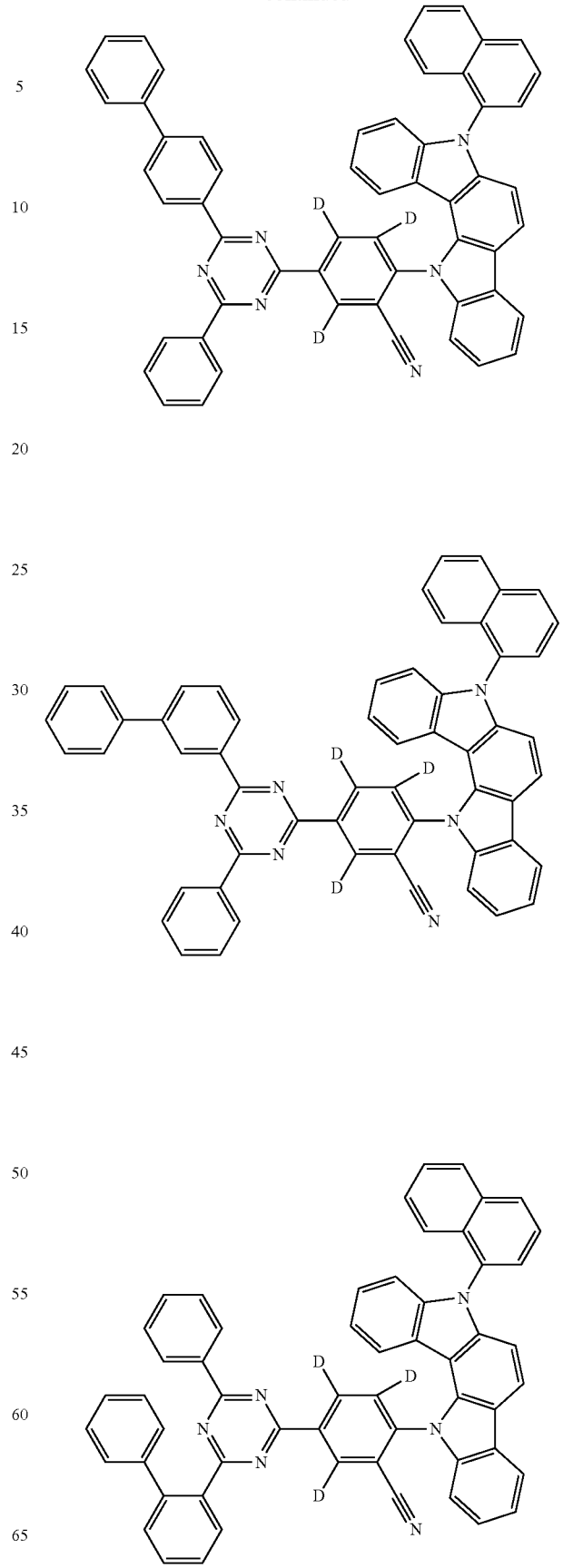

229
-continued
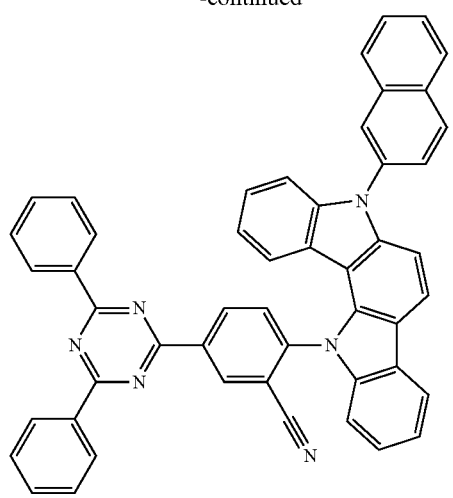
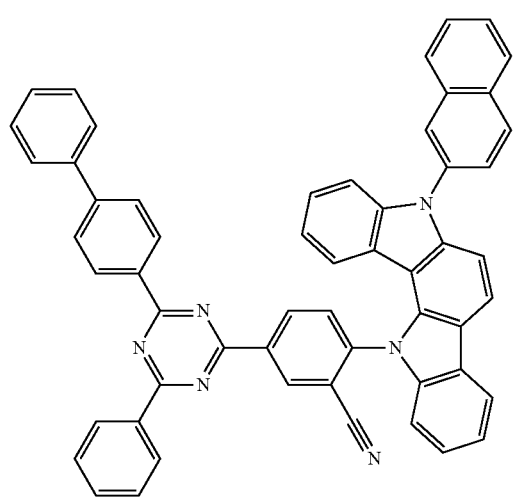
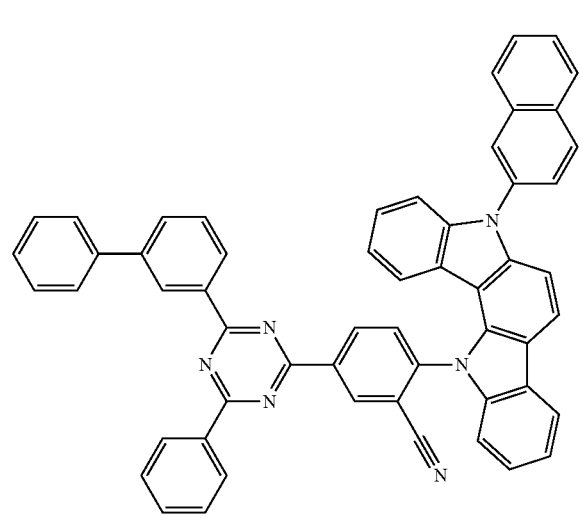
230
-continued
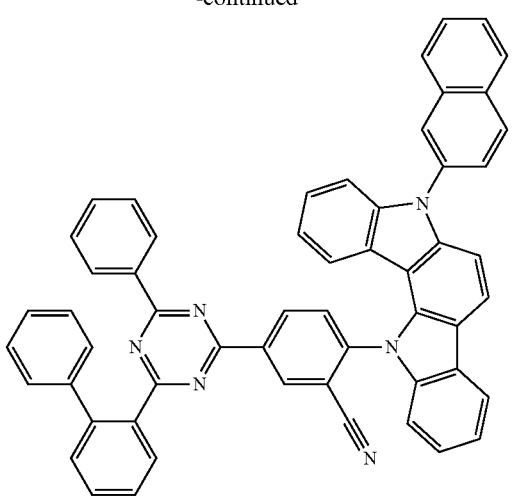
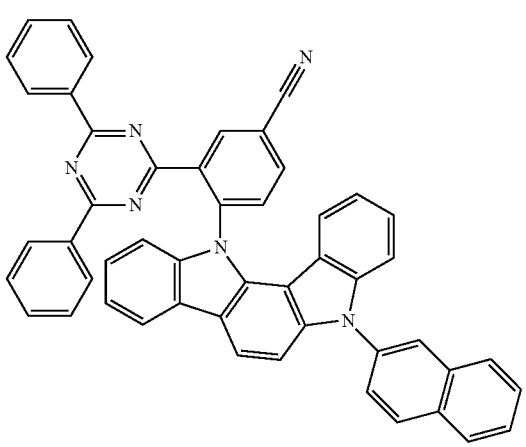
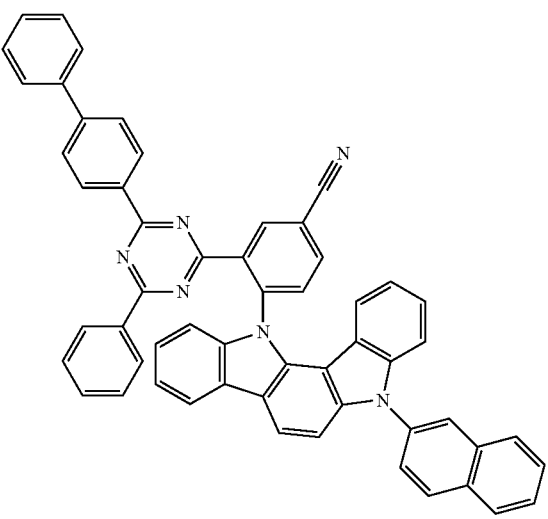

231
-continued
232
-continued
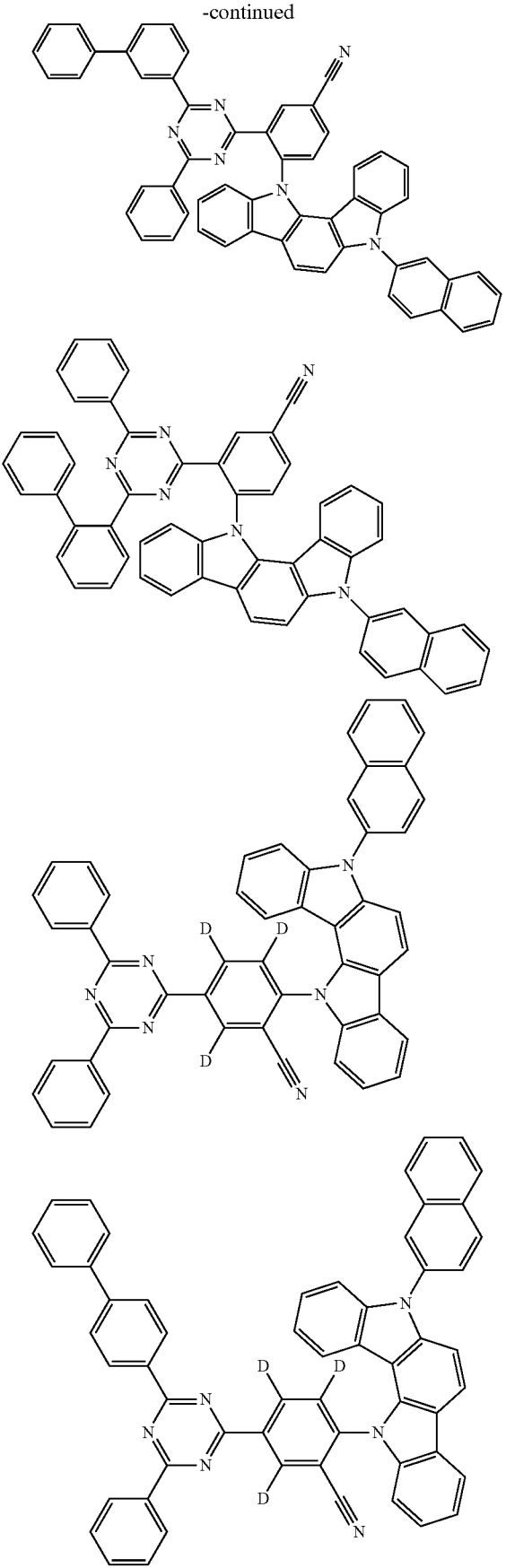
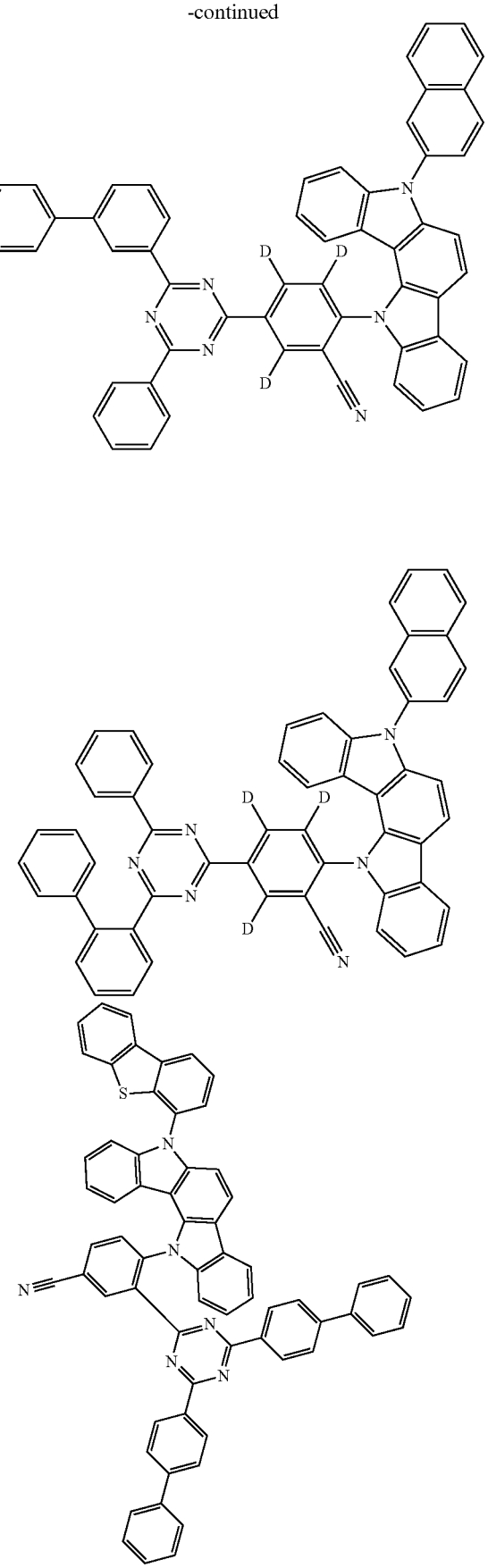

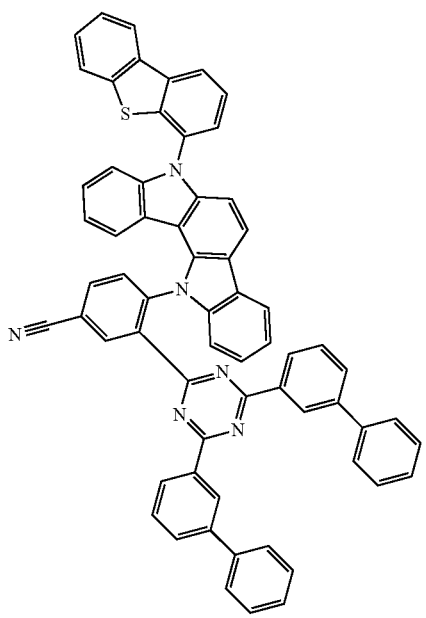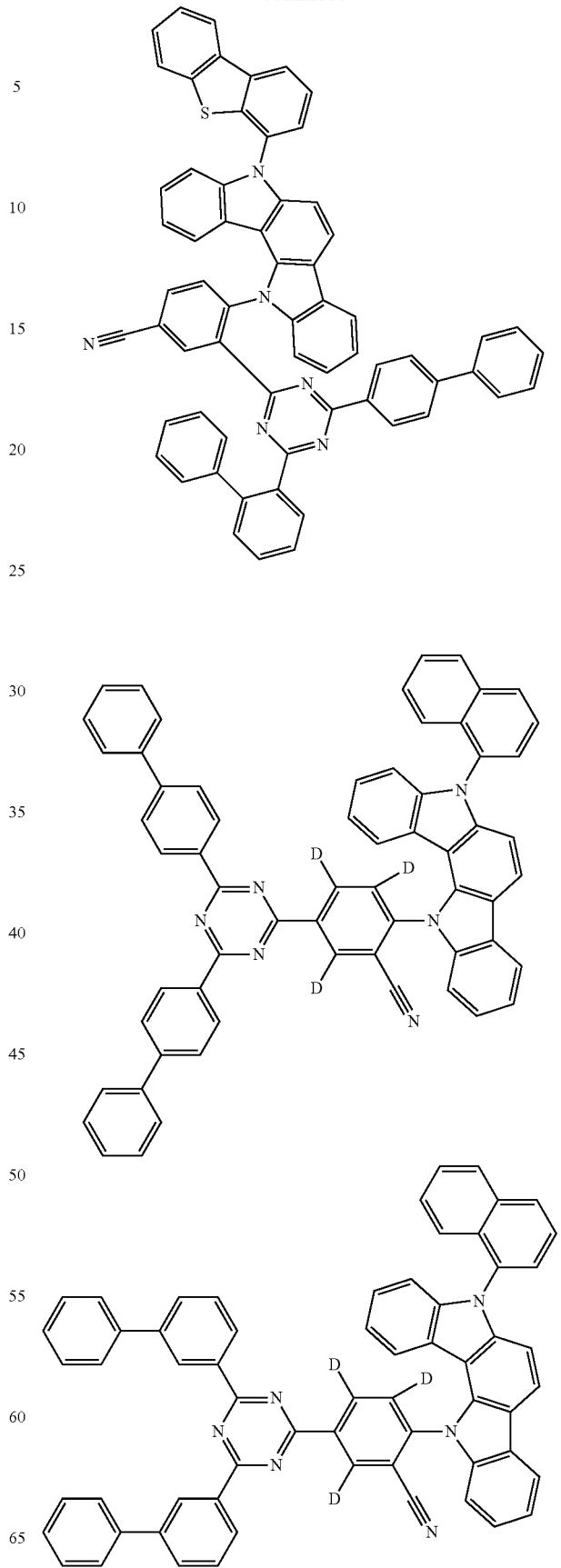

235
-continued
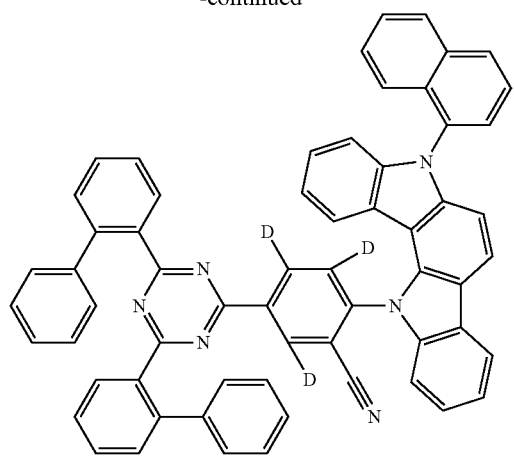
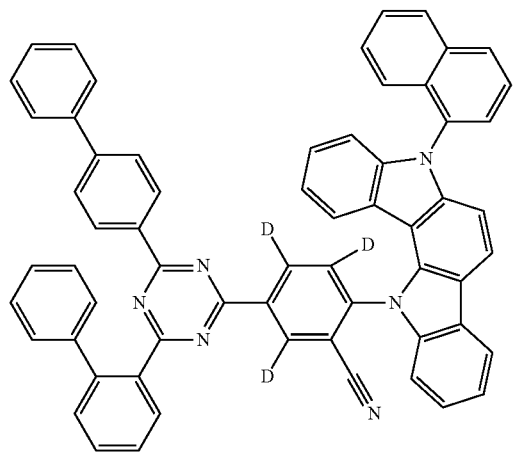
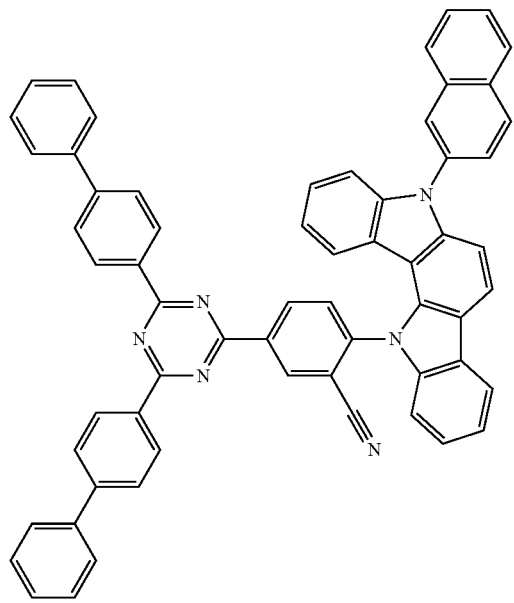
236
-continued
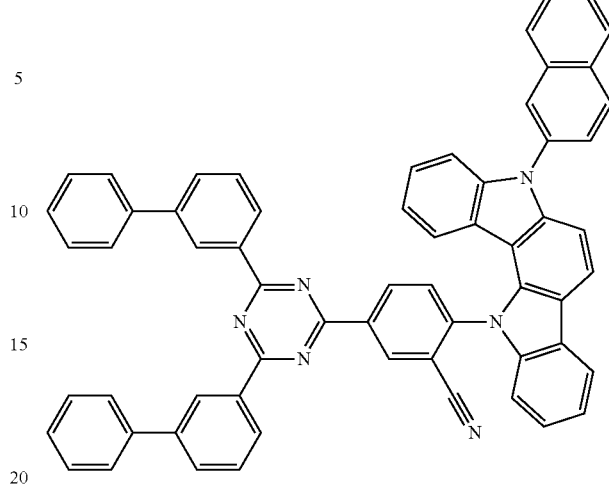
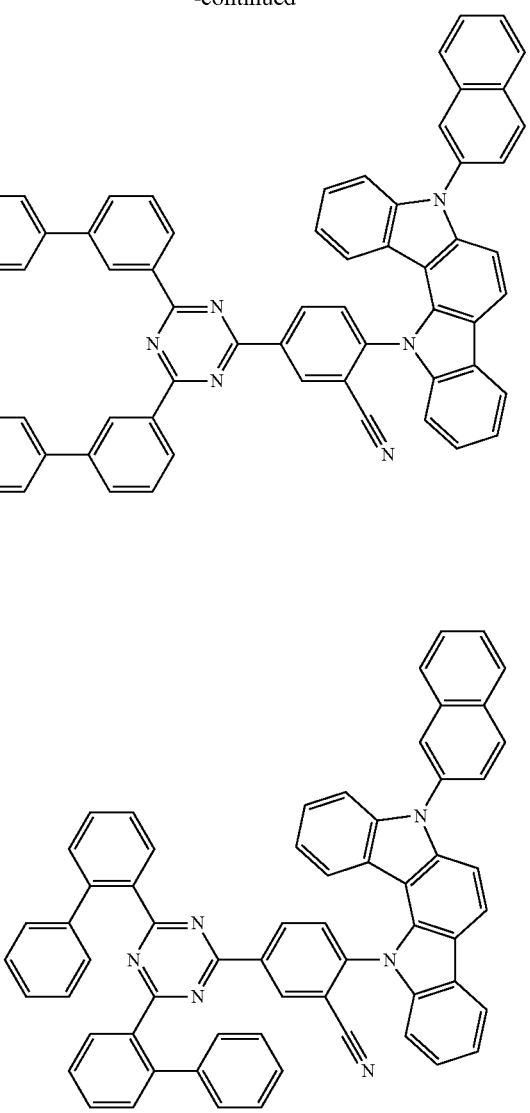
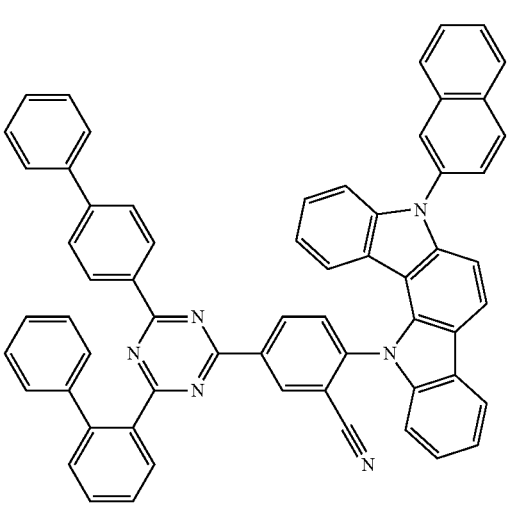

237
-continued
238
-continued
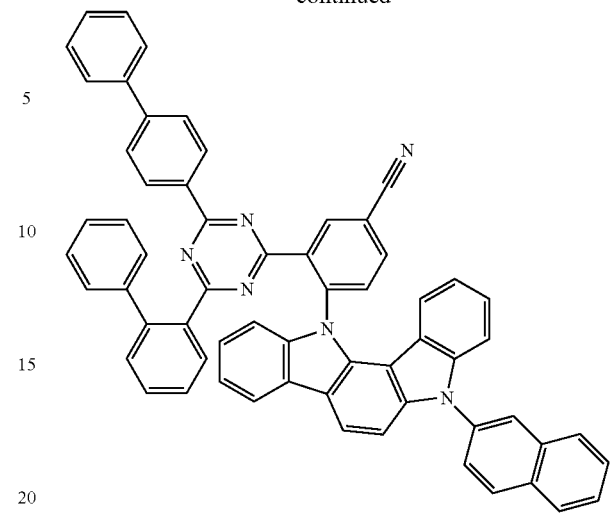
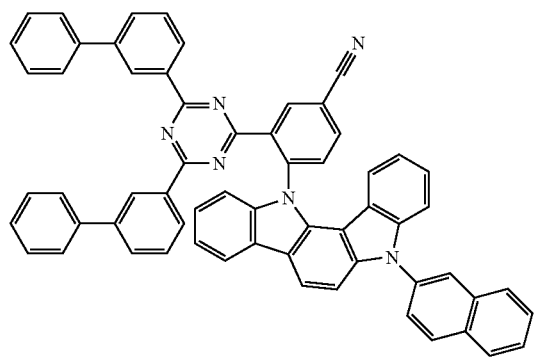
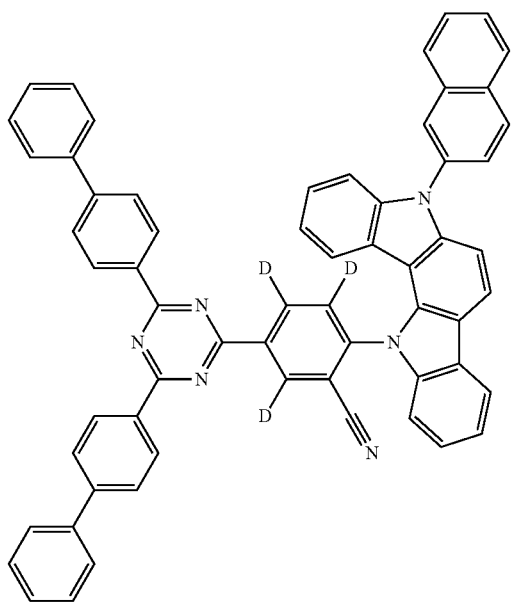
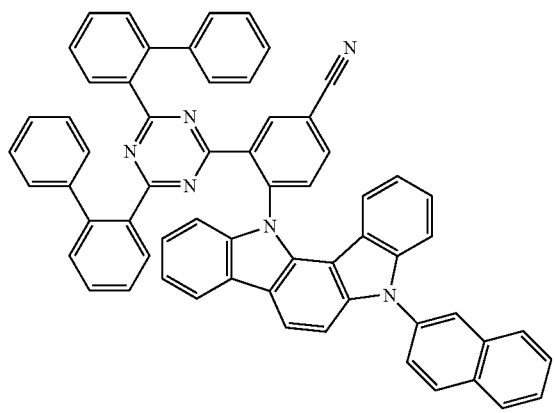
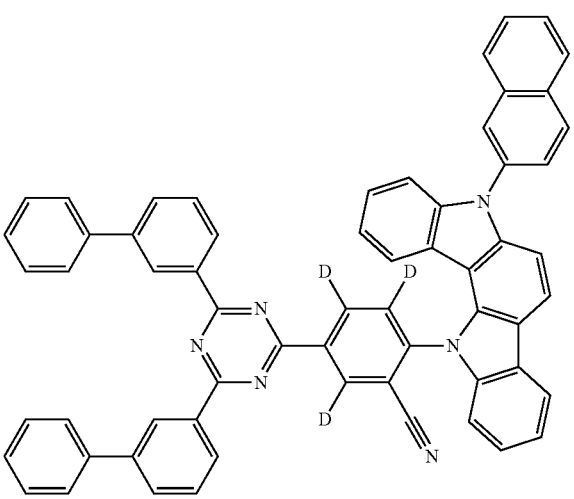

239
-continued
240
-continued
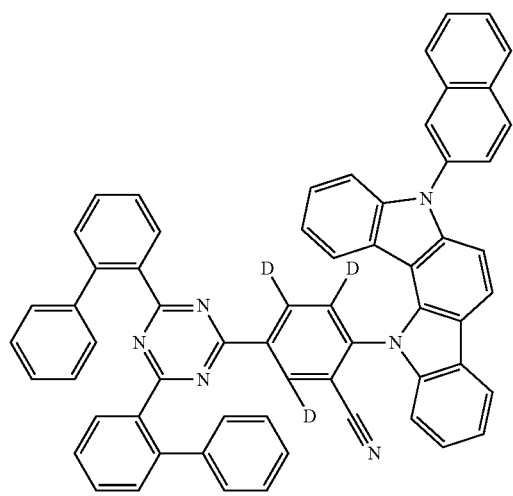
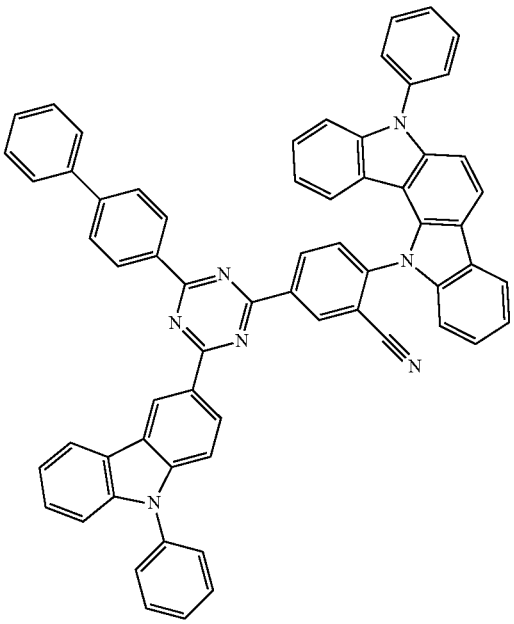
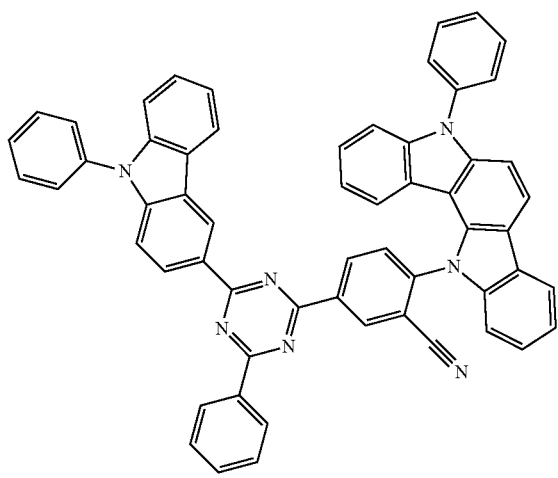

241
-continued
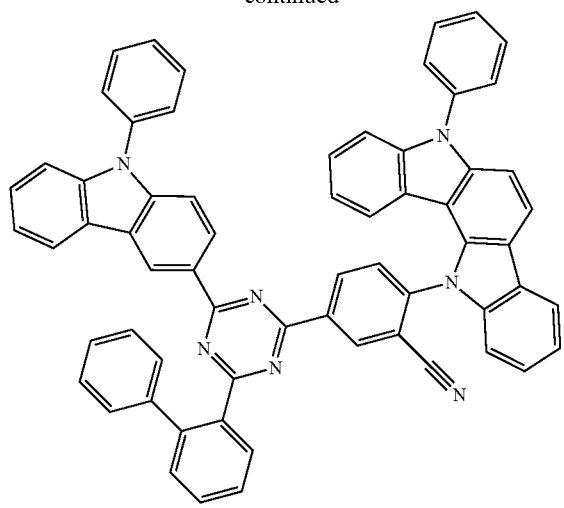
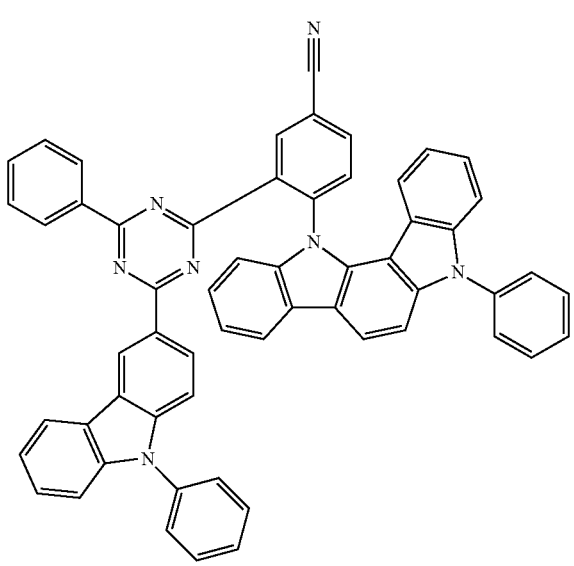
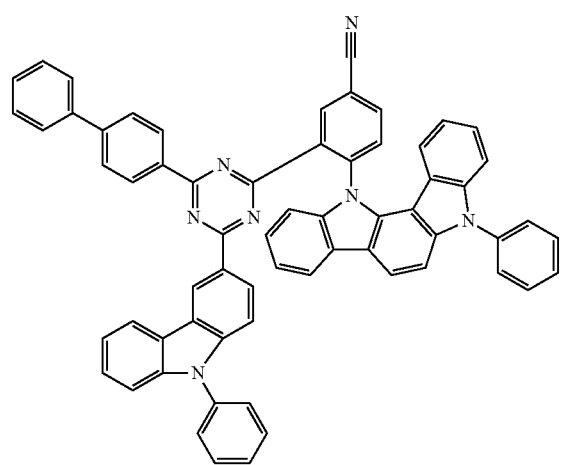
242
-continued
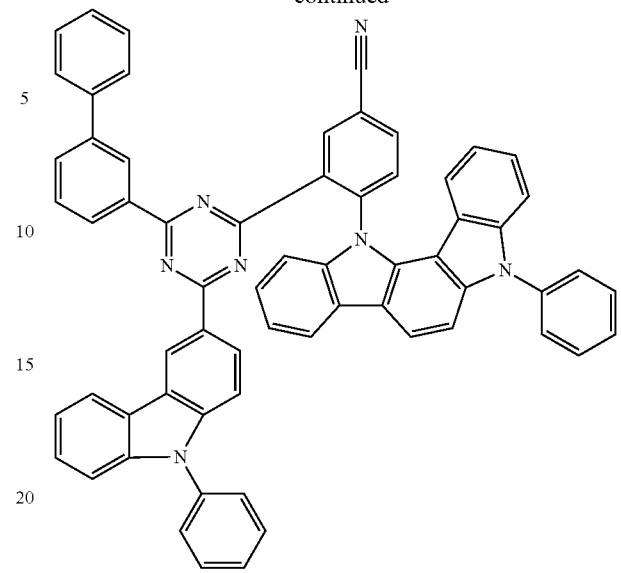
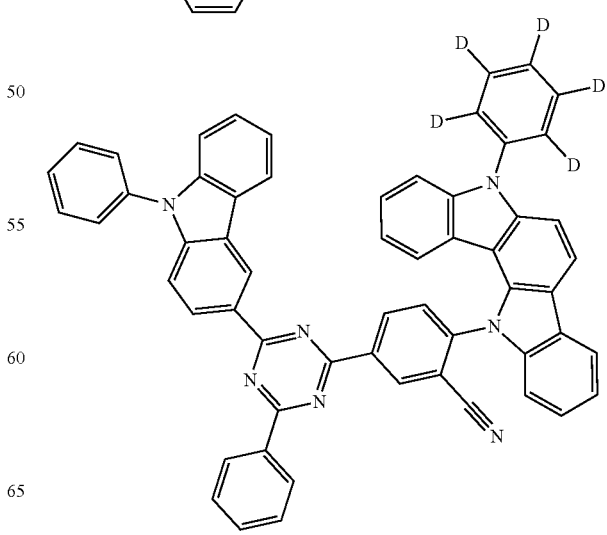

243
-continued
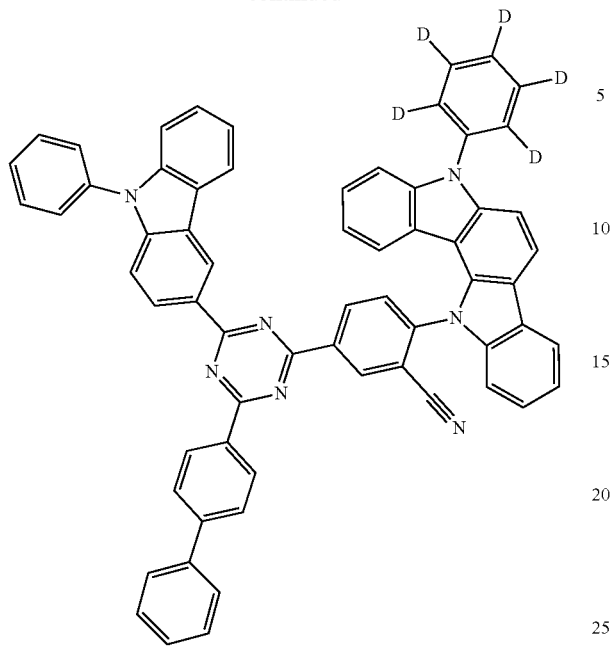
244
-continued
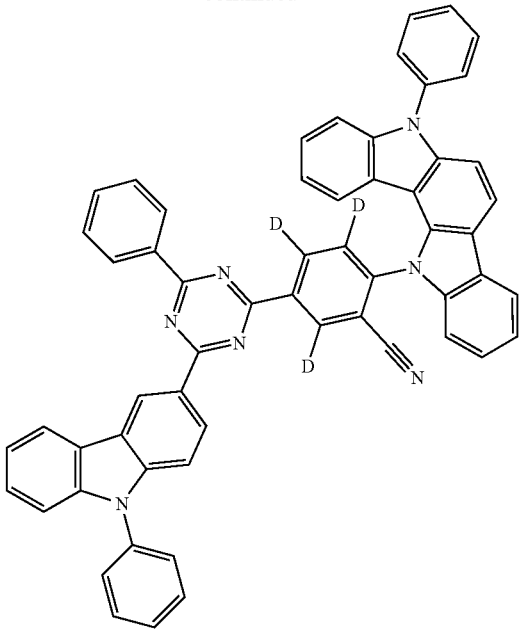
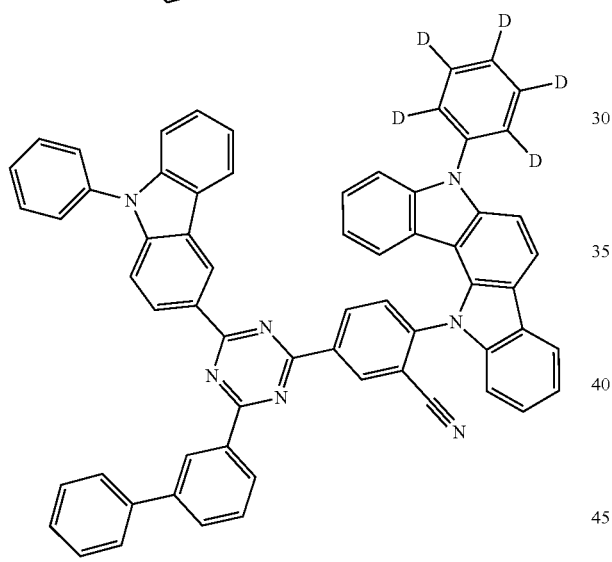
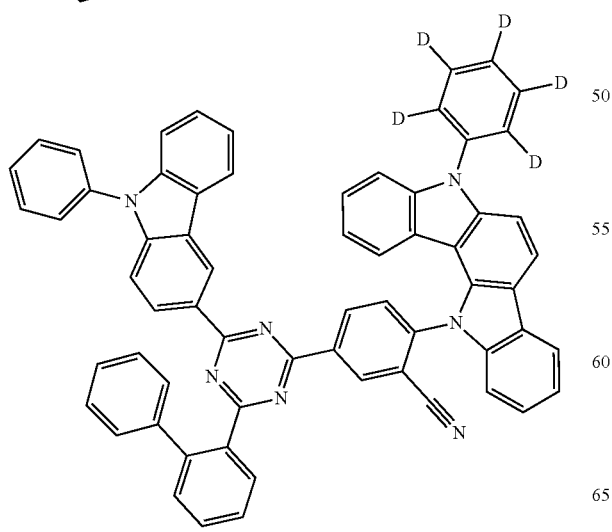
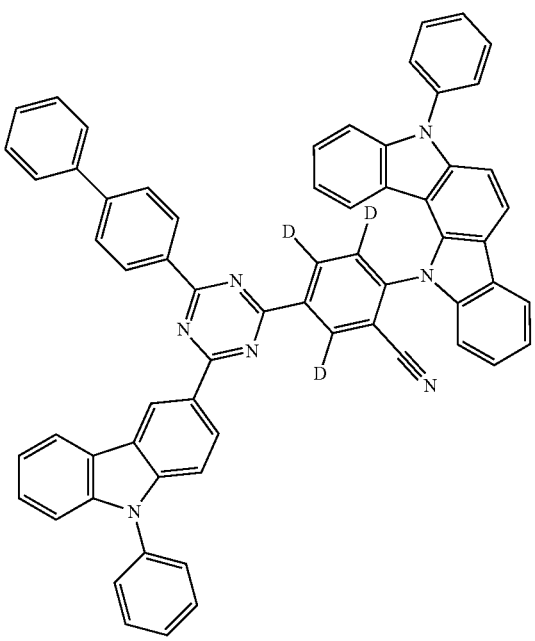

245
-continued
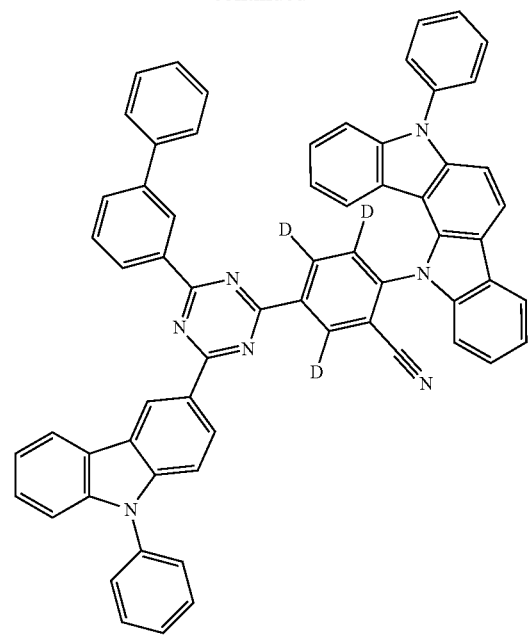
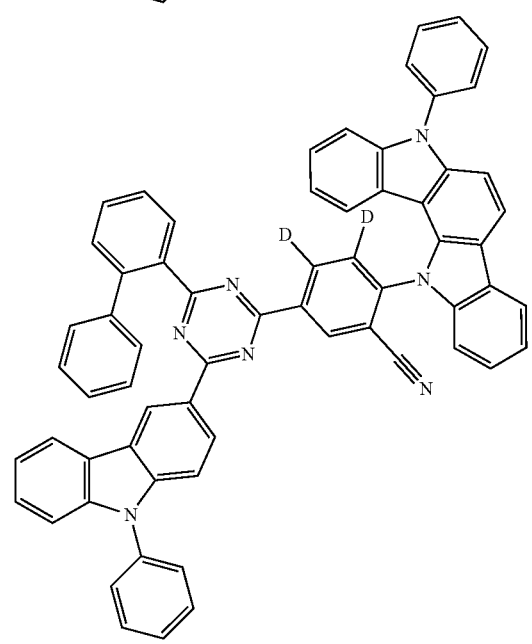
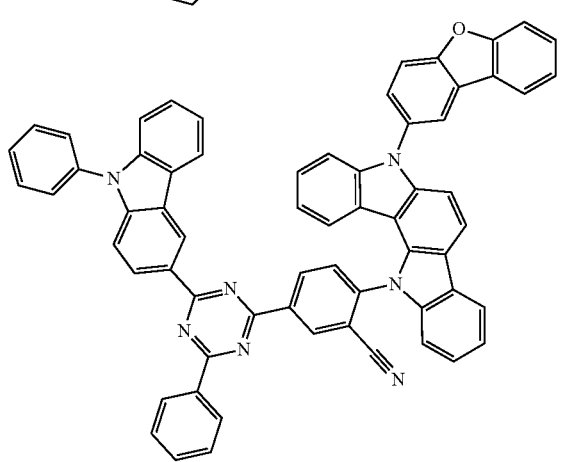
246
-continued
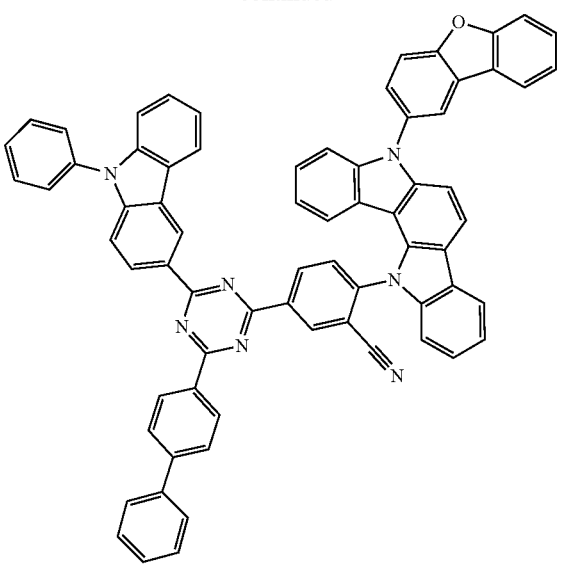
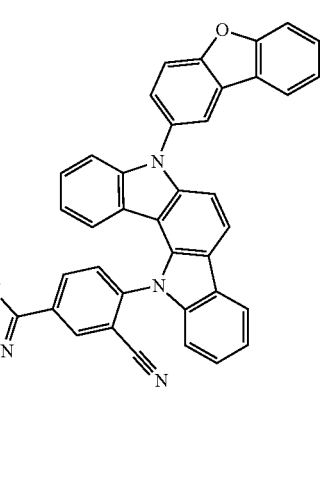
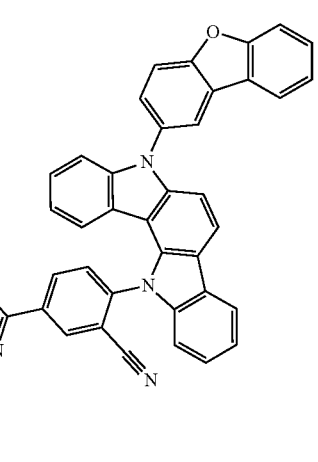

247
-continued
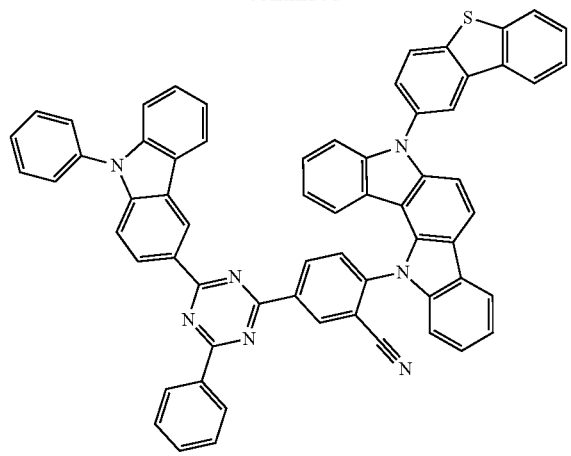
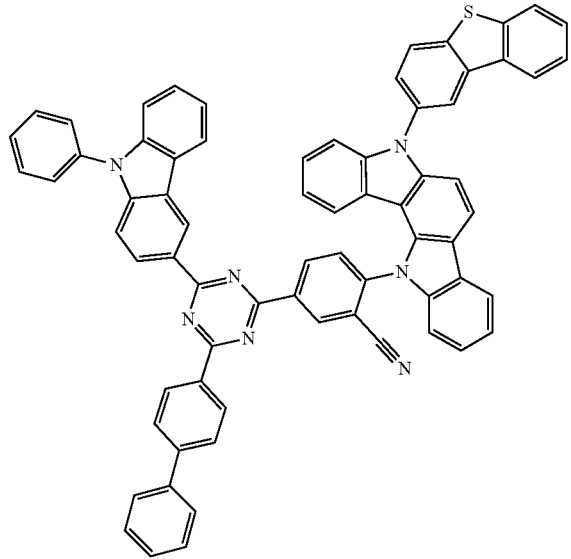
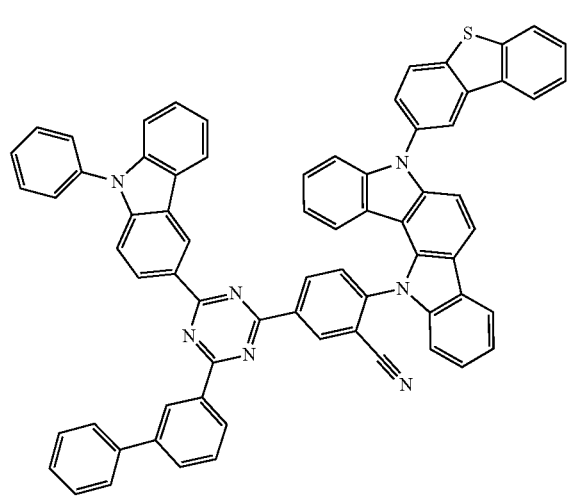
248
-continued
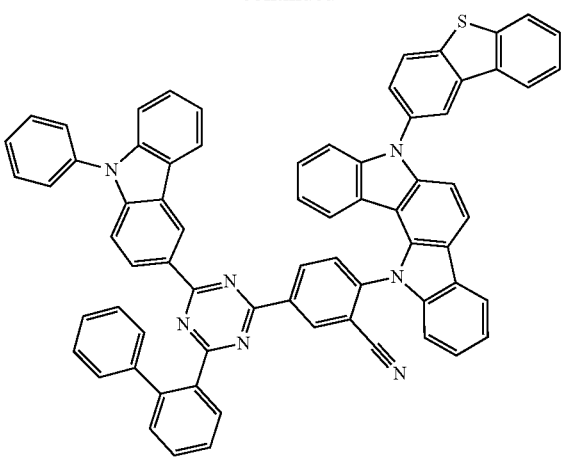
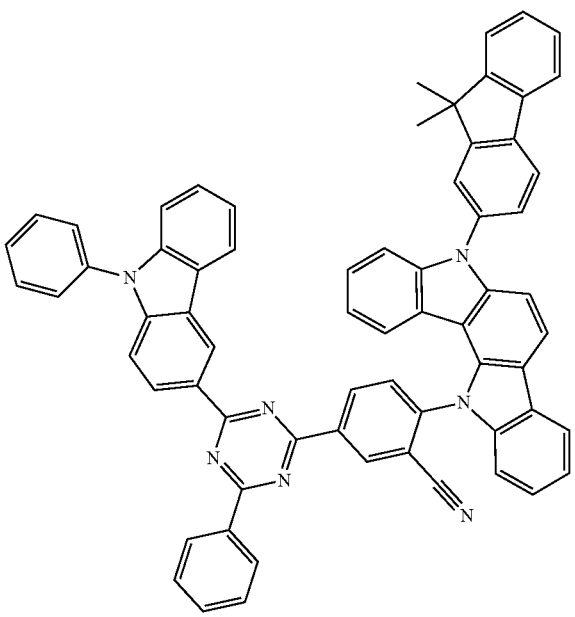
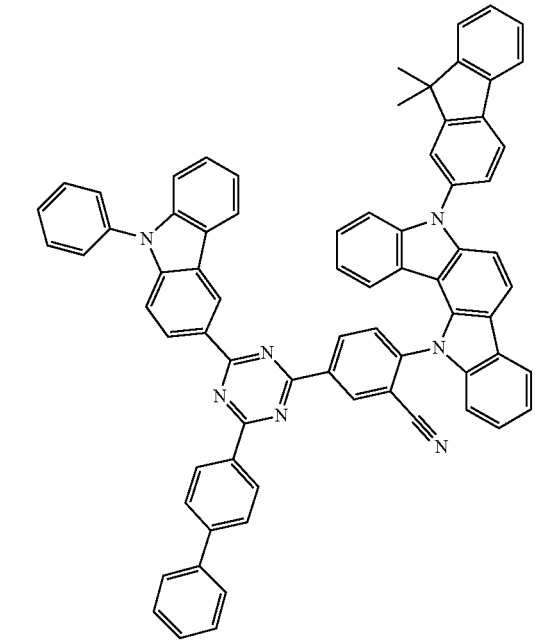

249
-continued
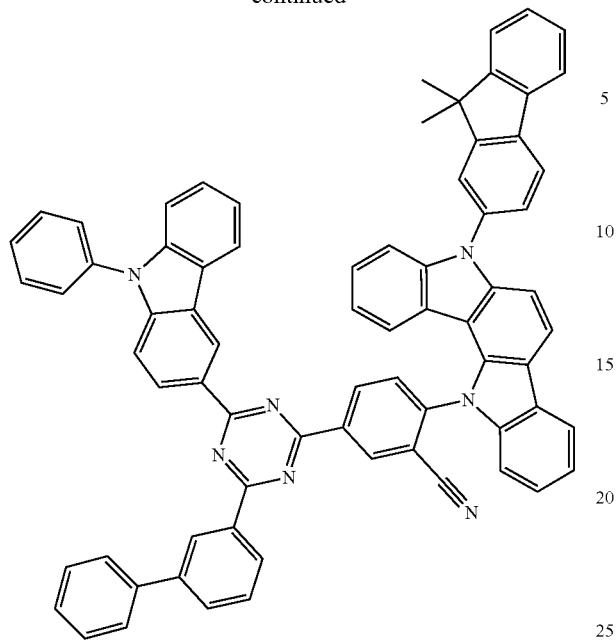
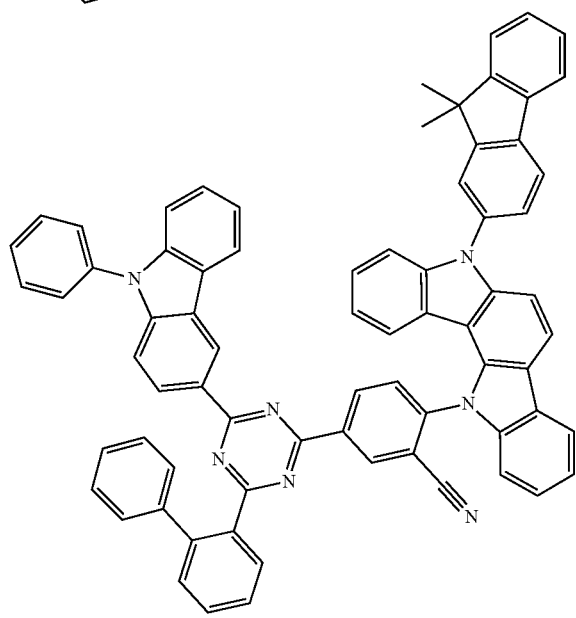
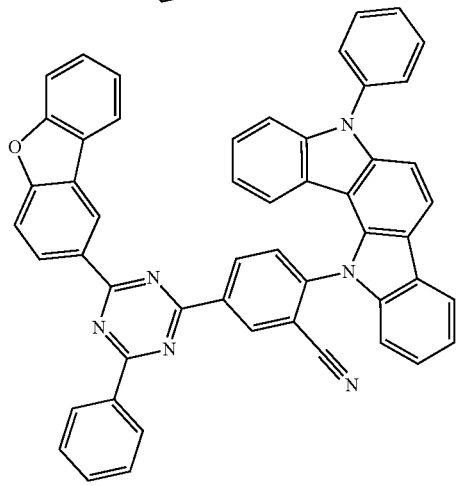
250
-continued
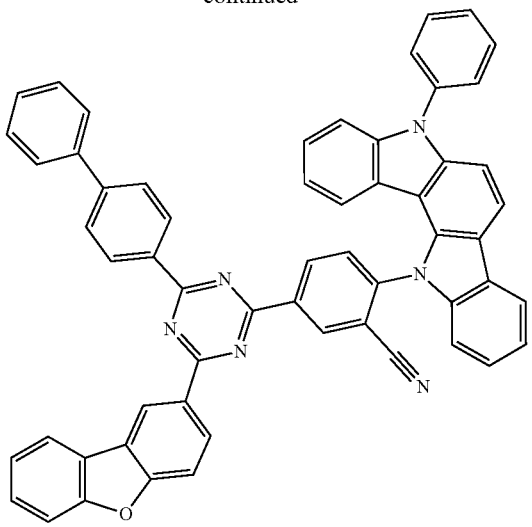
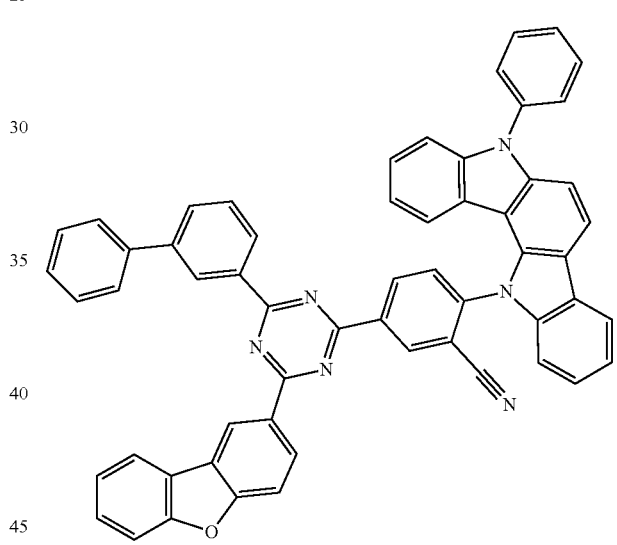
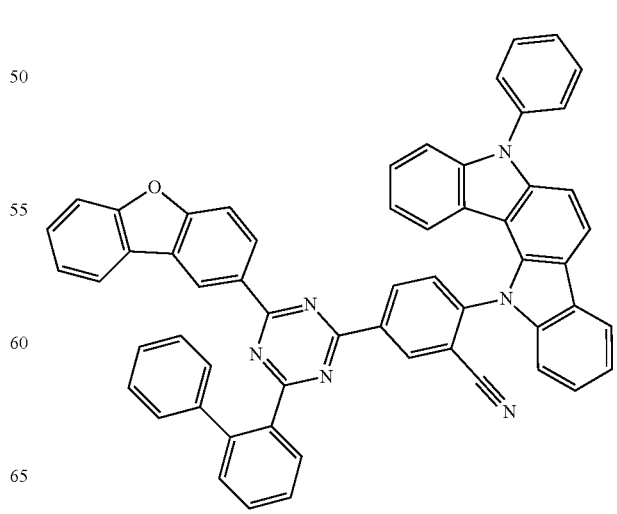

251
-continued
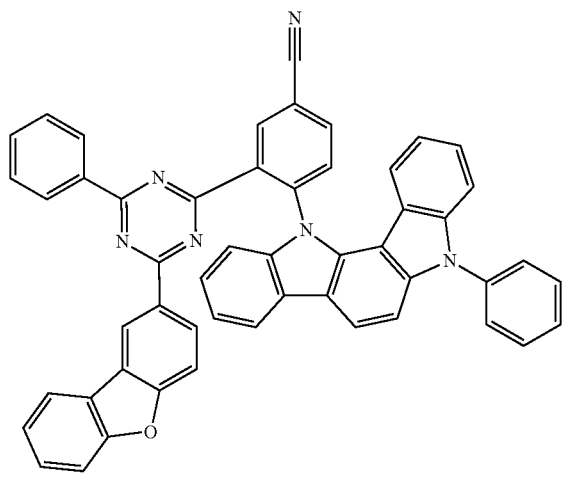
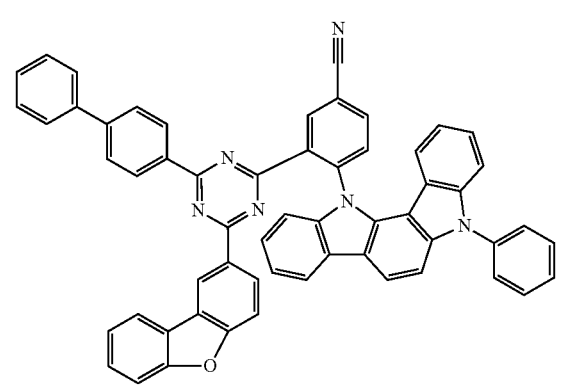
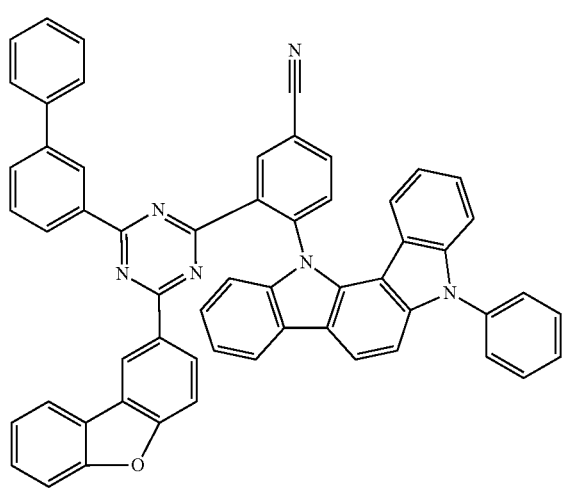
252
-continued
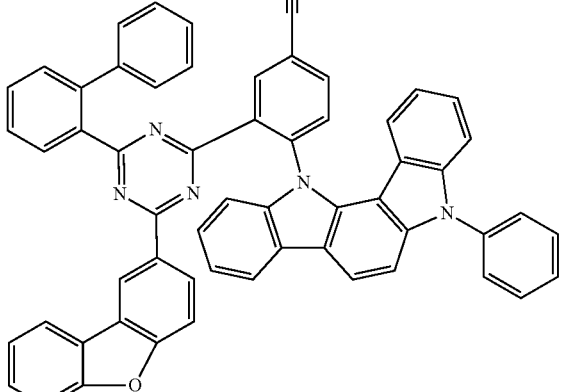
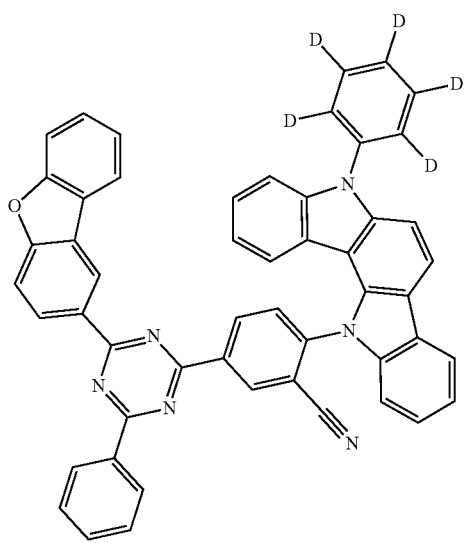
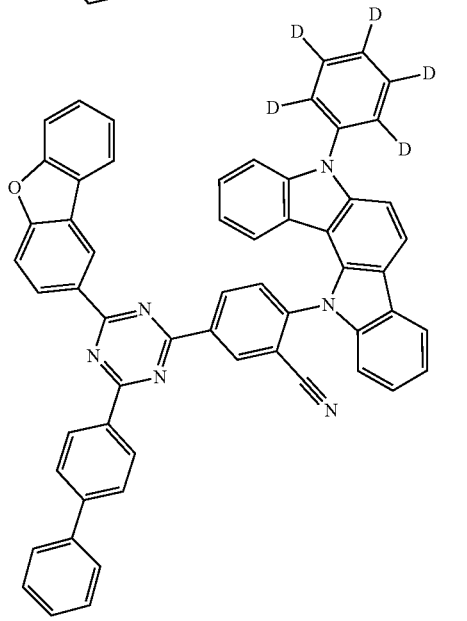

253
-continued
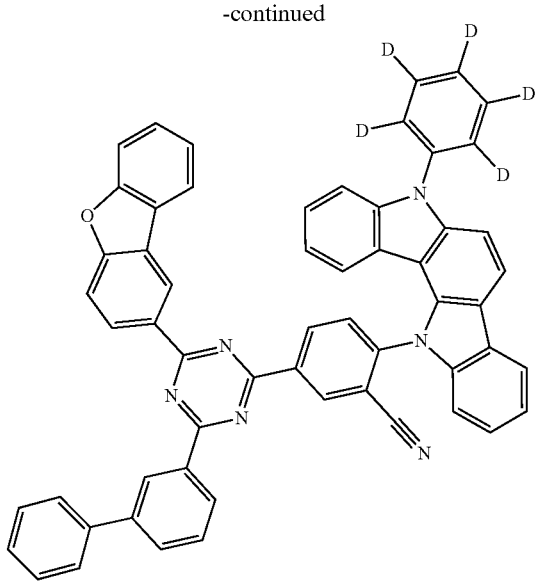
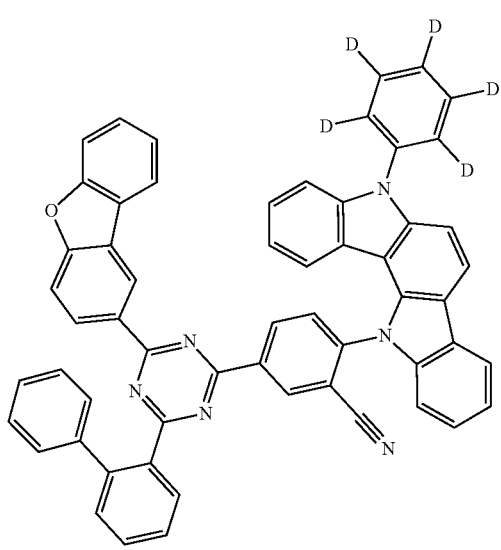
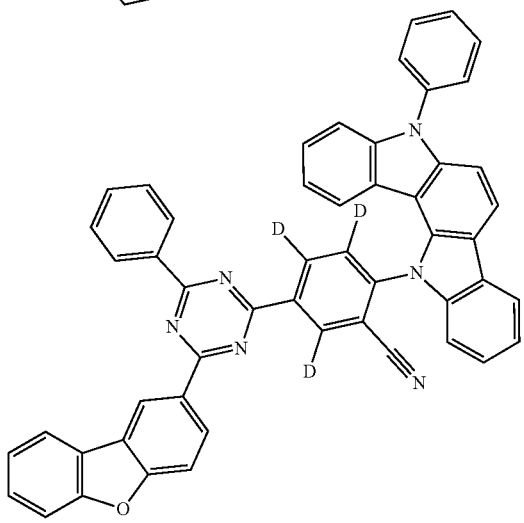
254
-continued
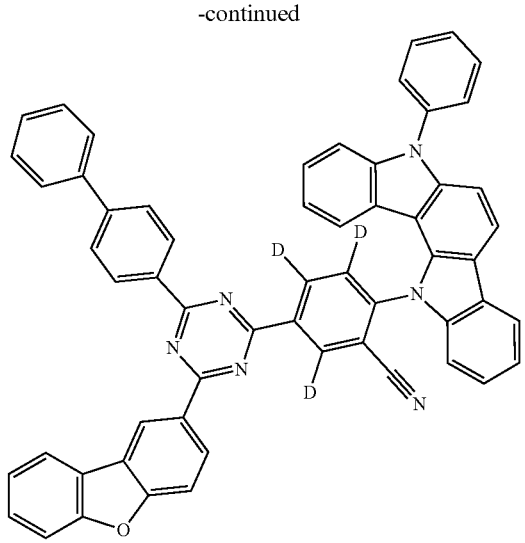
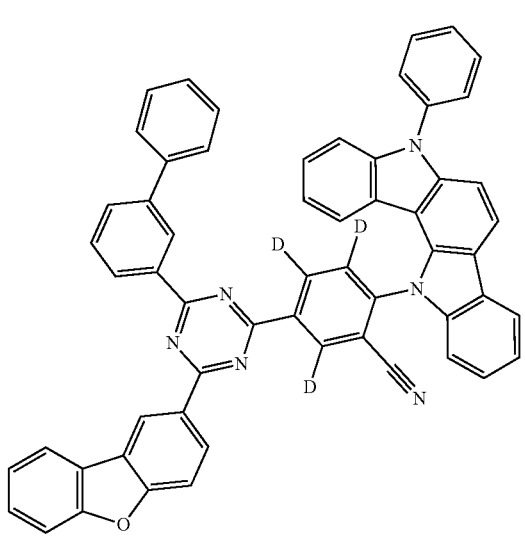
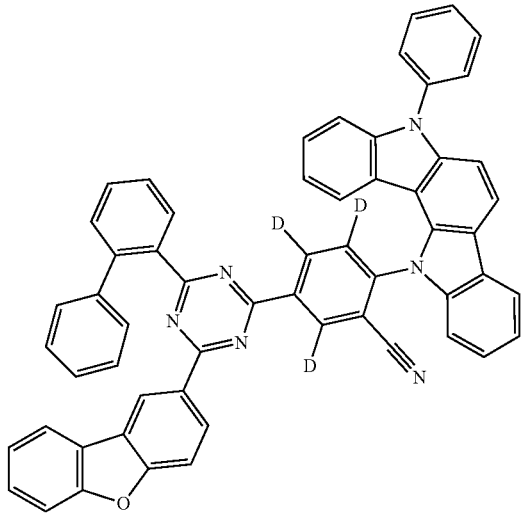

255
-continued
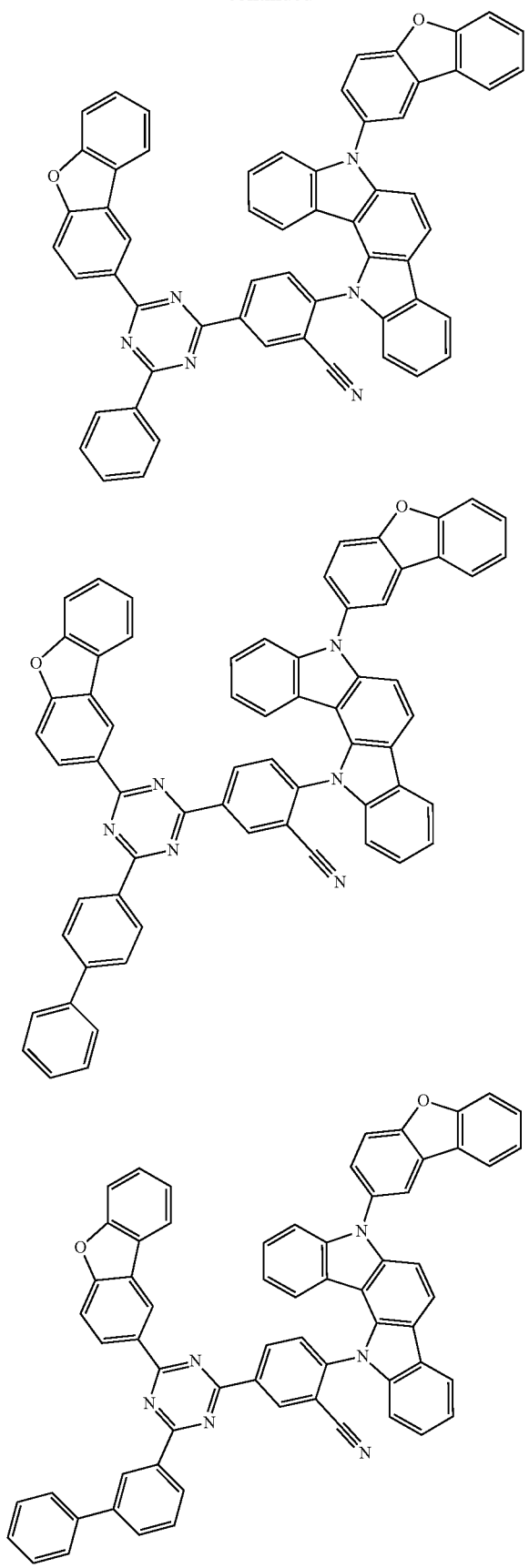
256
-continued
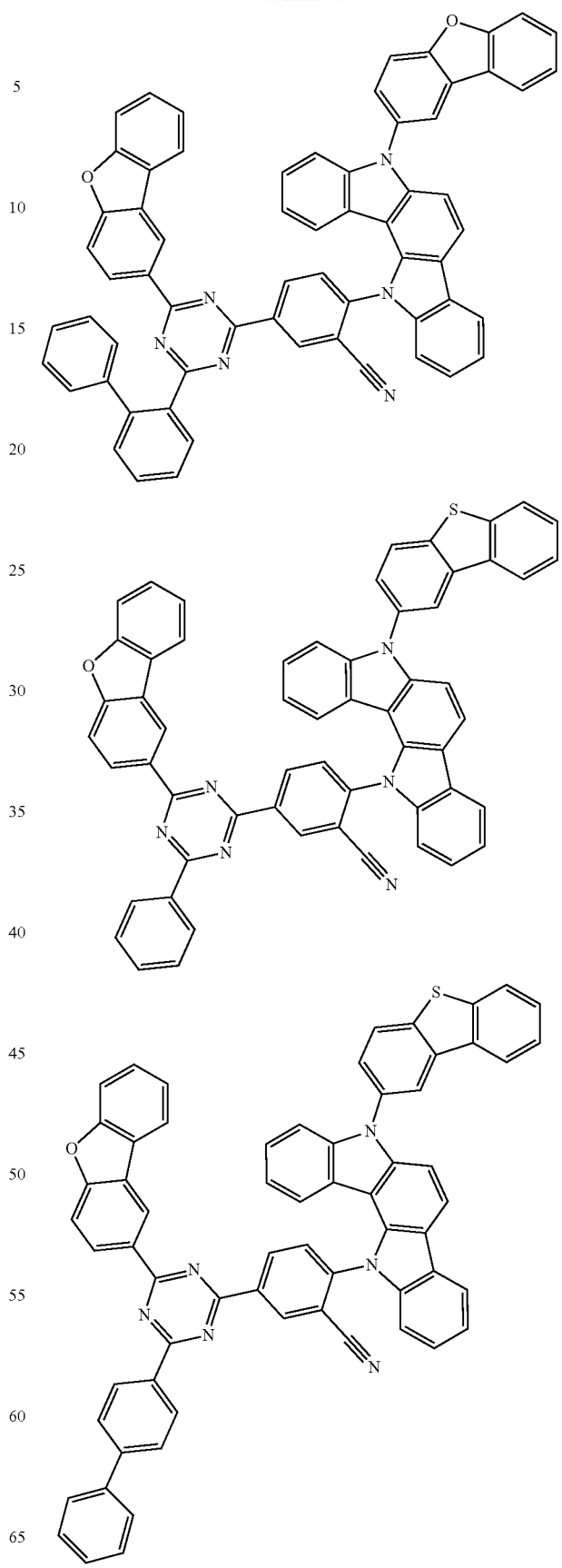

257
-continued
258
-continued
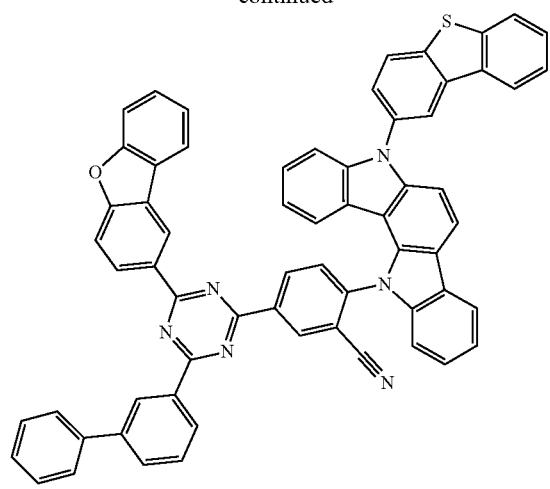
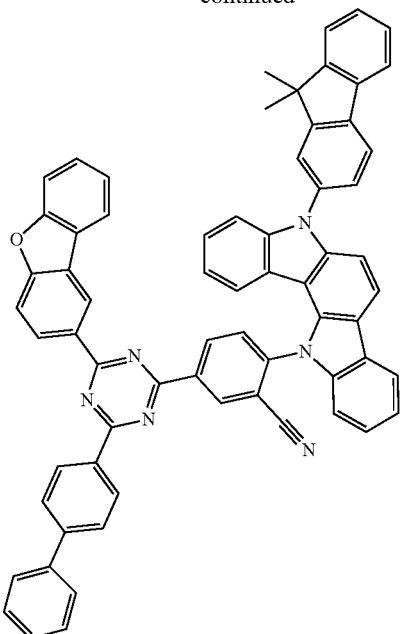
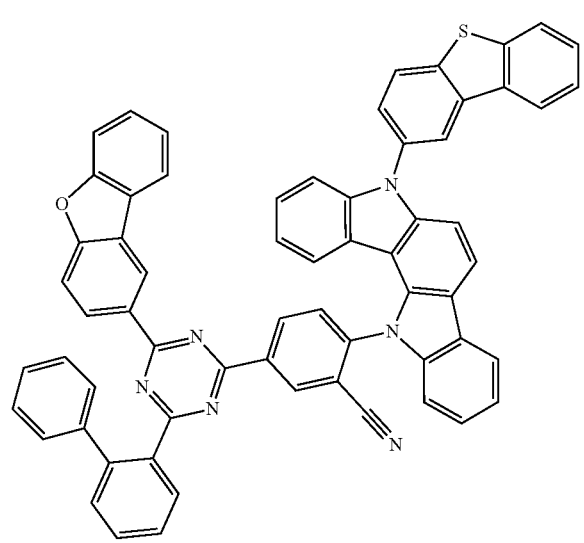
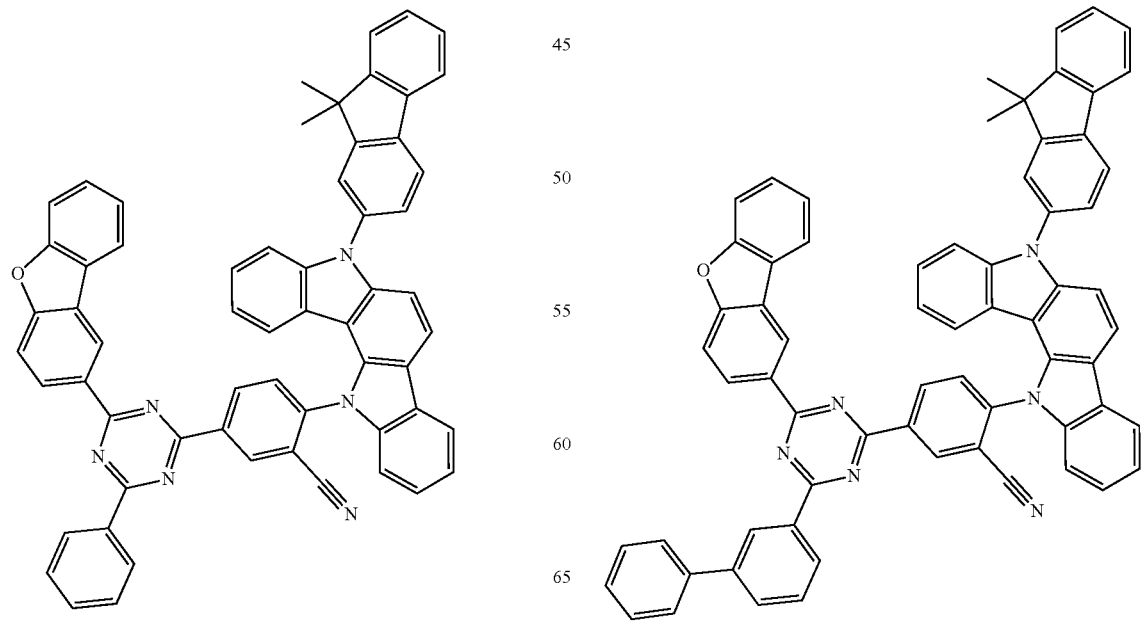

259
-continued
260
-continued
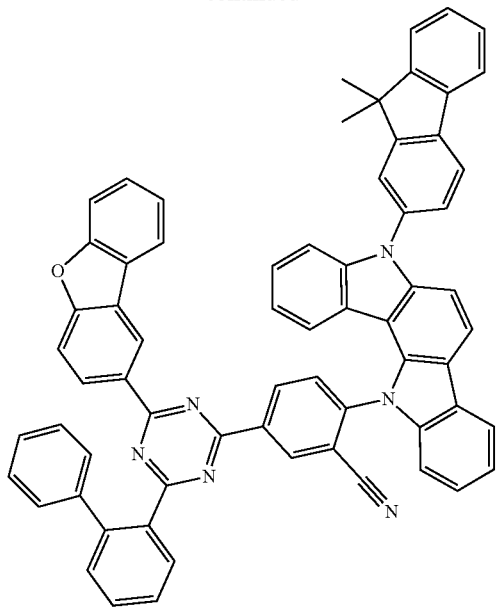
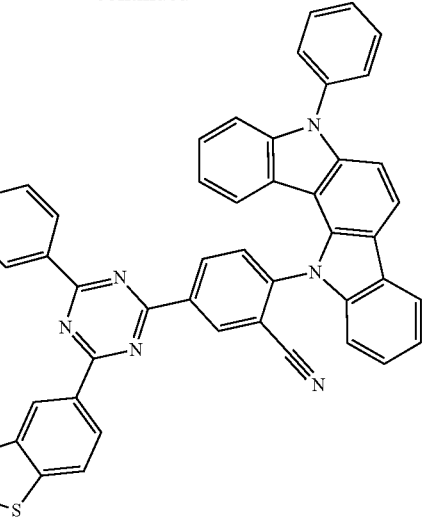
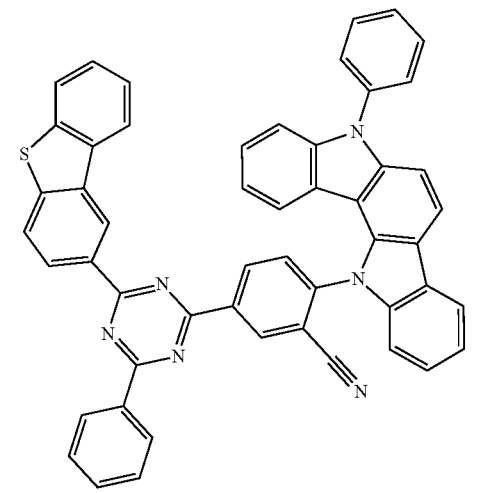
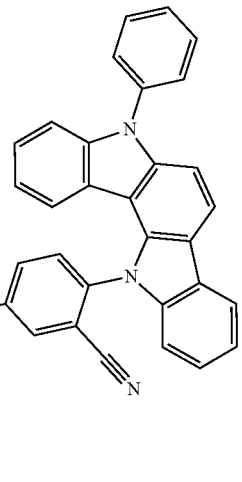
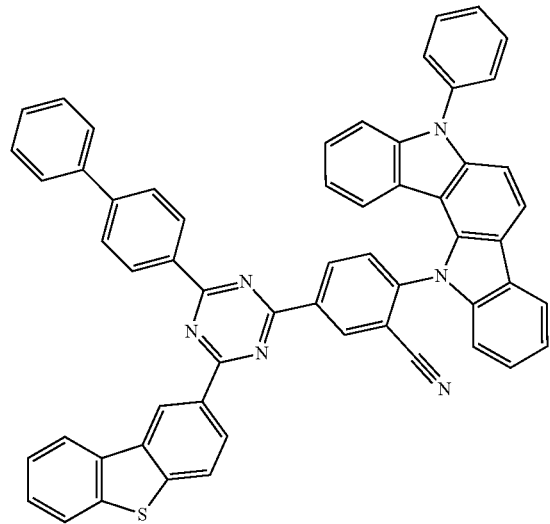

261
-continued
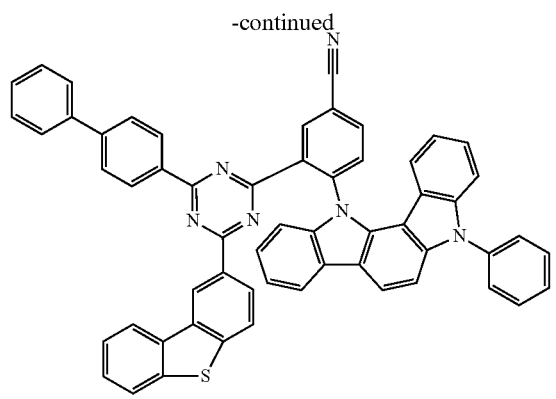
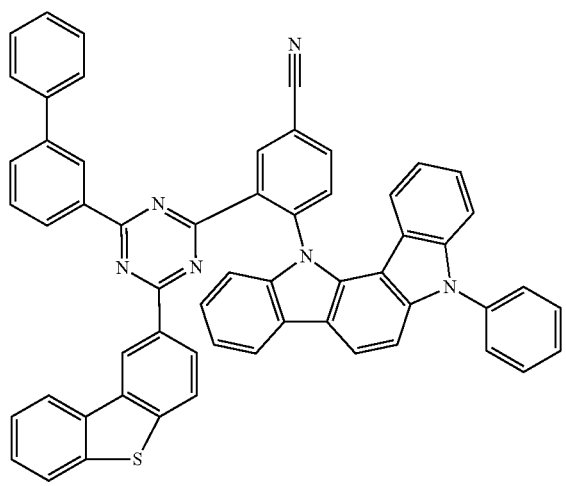
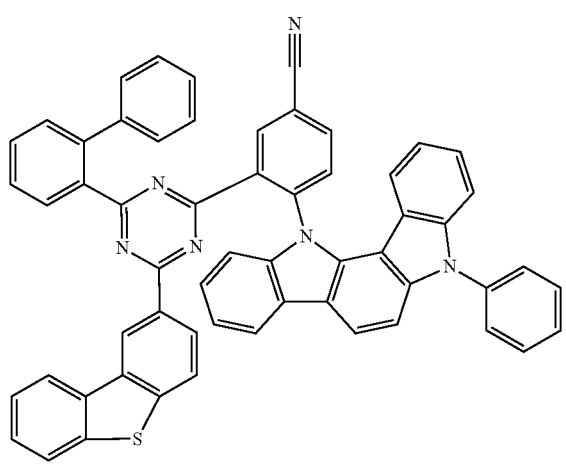
262
-continued
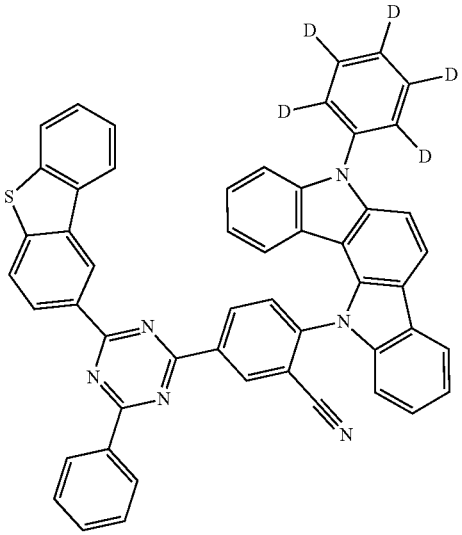
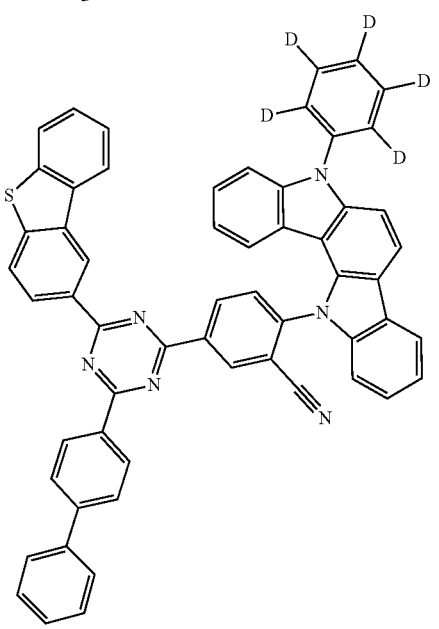
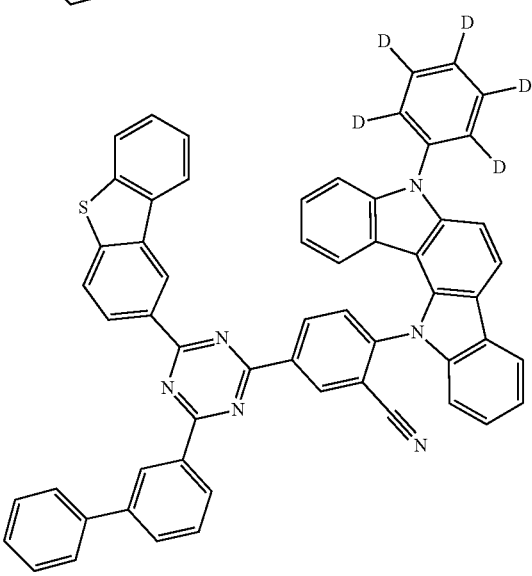

263
-continued
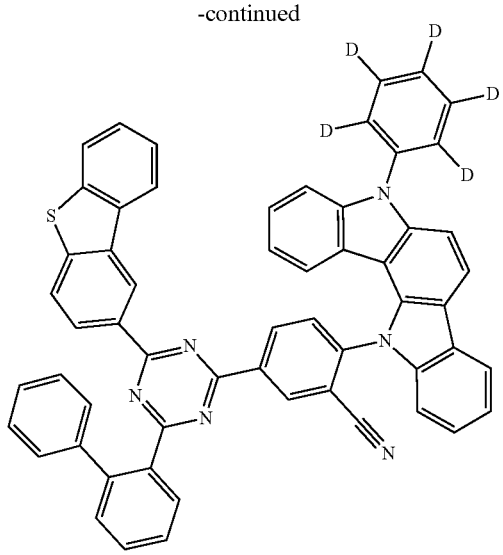
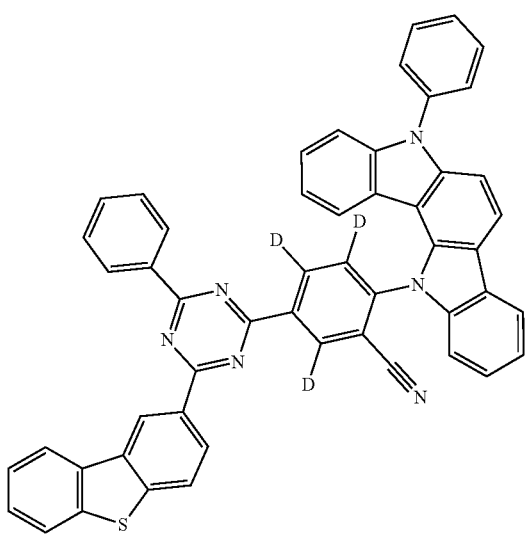
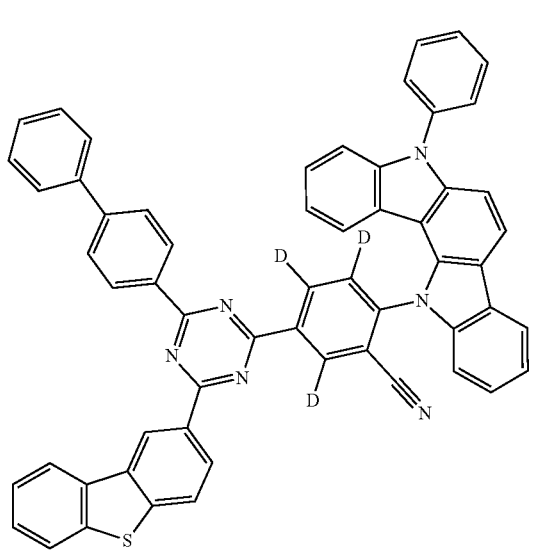
264
-continued
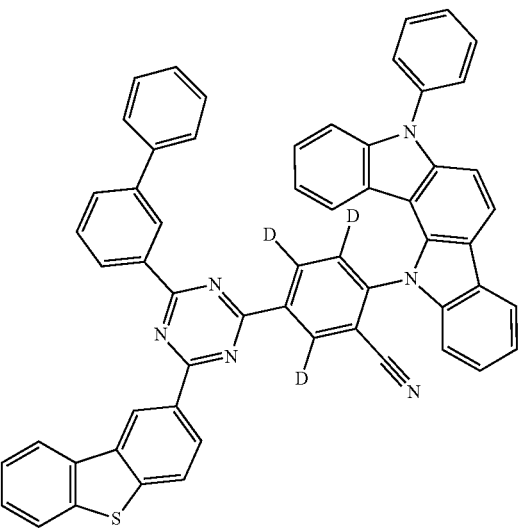
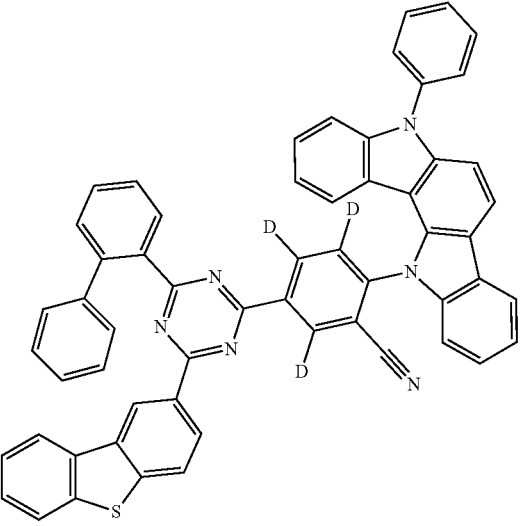
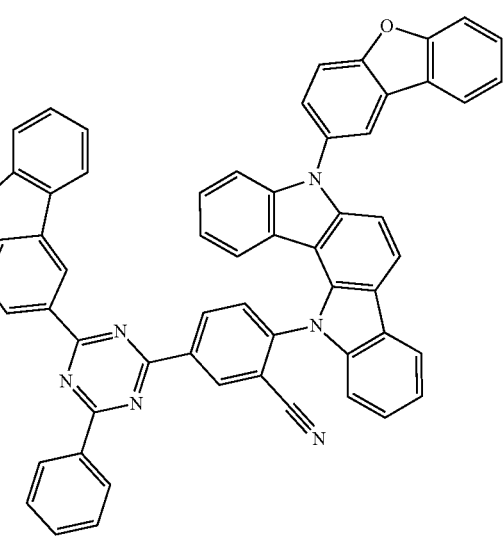

265
-continued
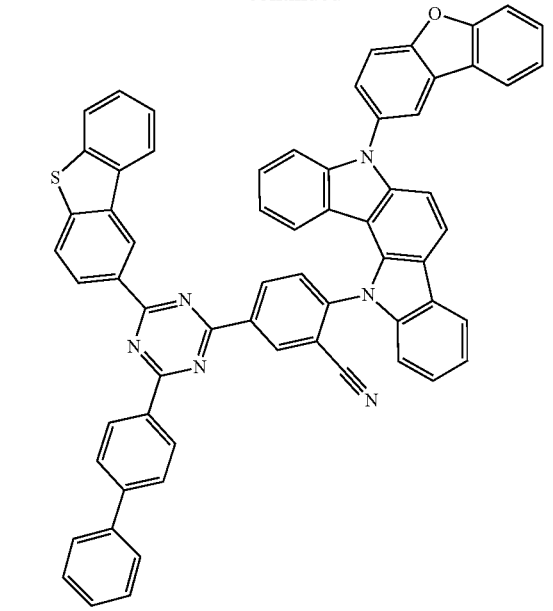
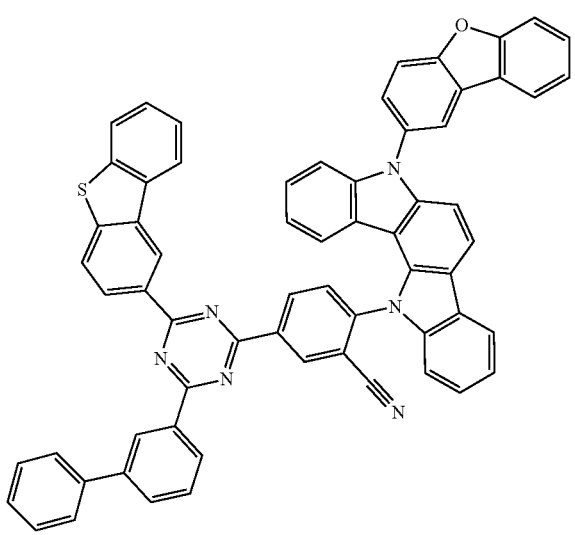
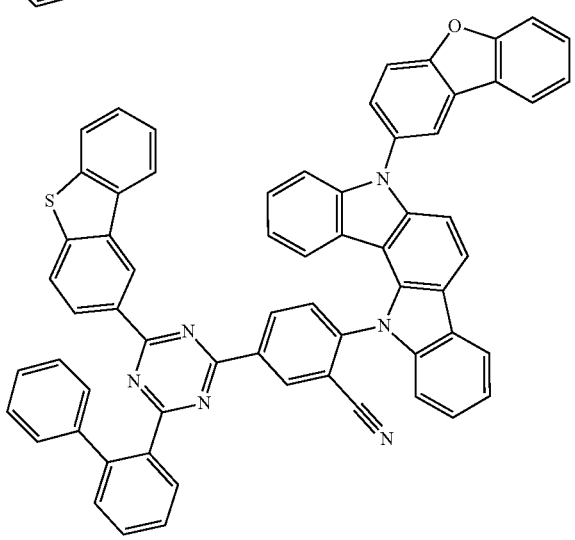
266
-continued
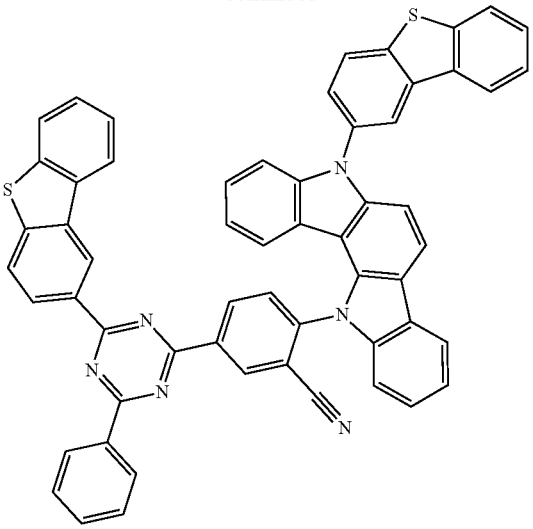
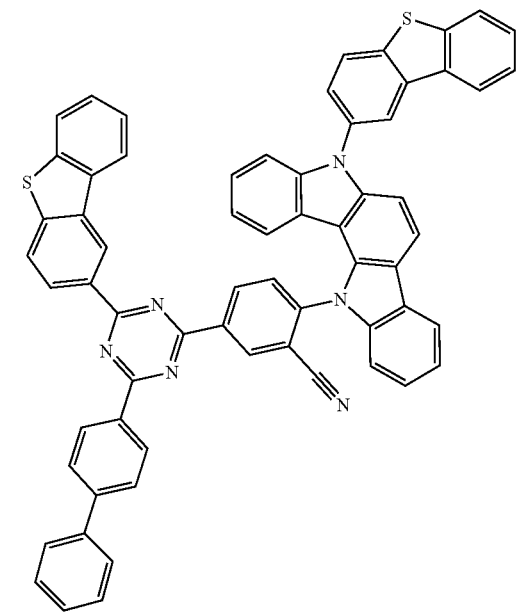
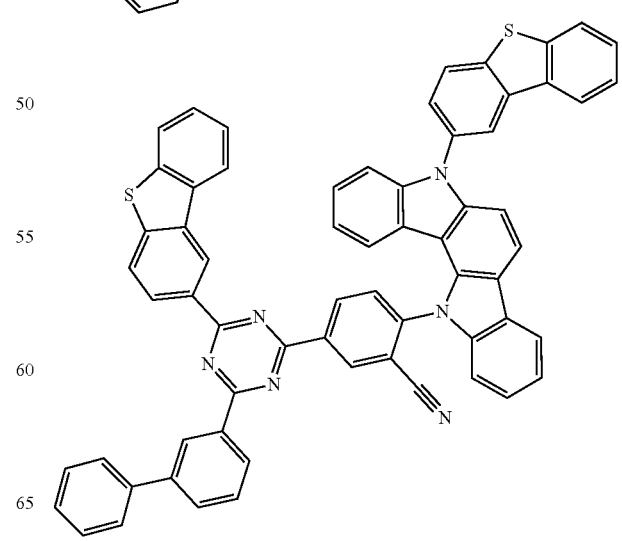

267
-continued
268
-continued
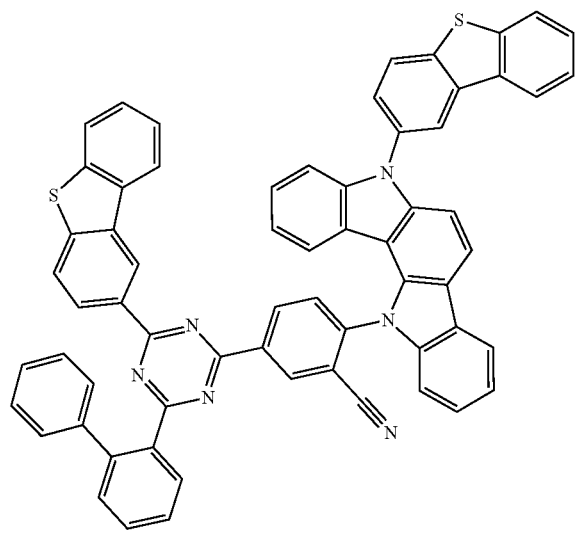
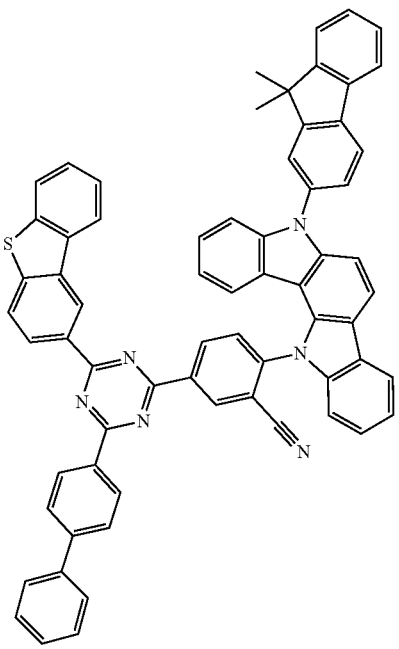
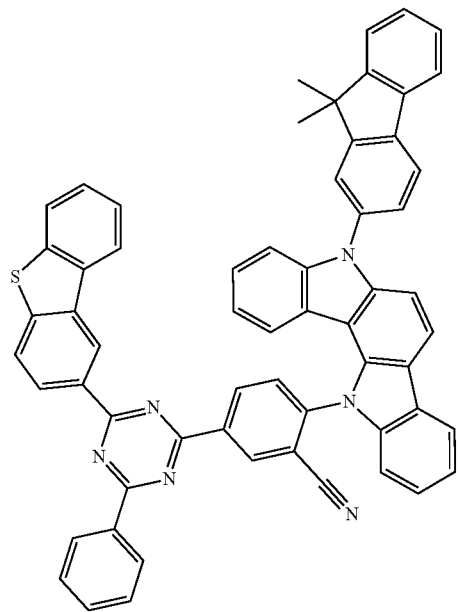

269
-continued
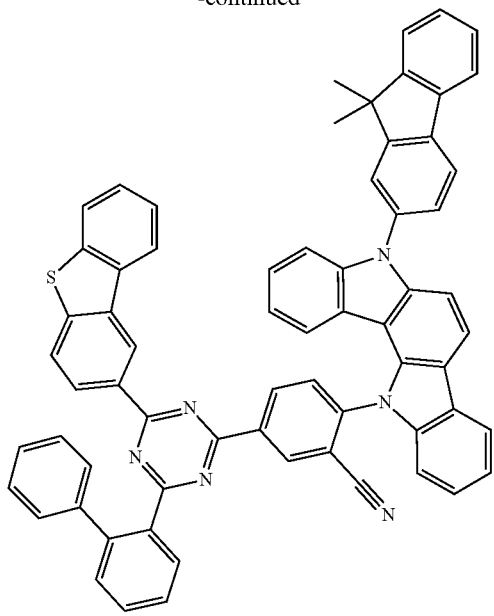
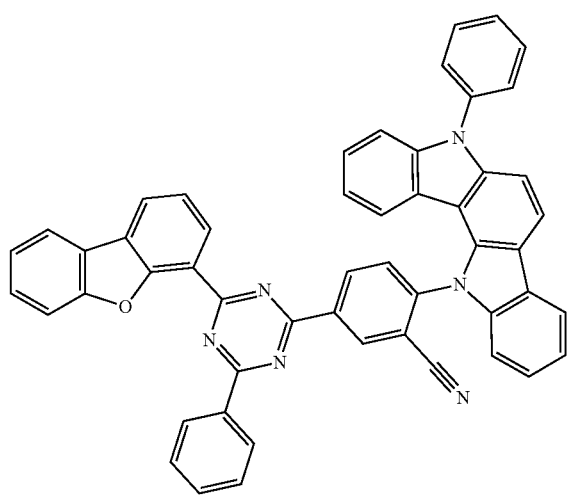
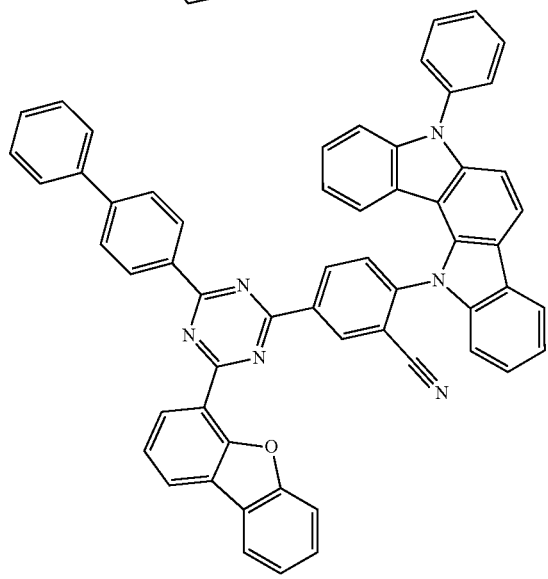
270
-continued
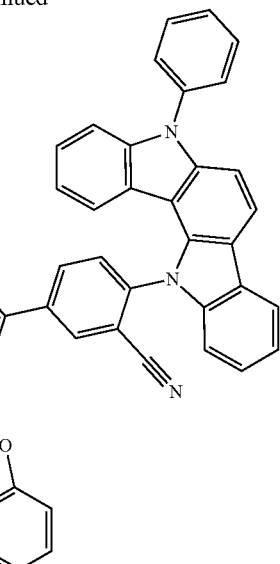
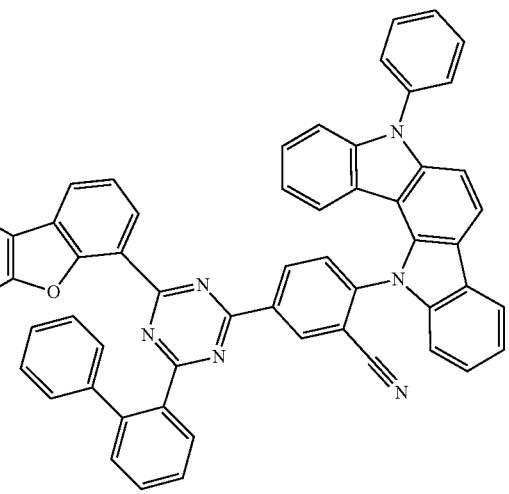
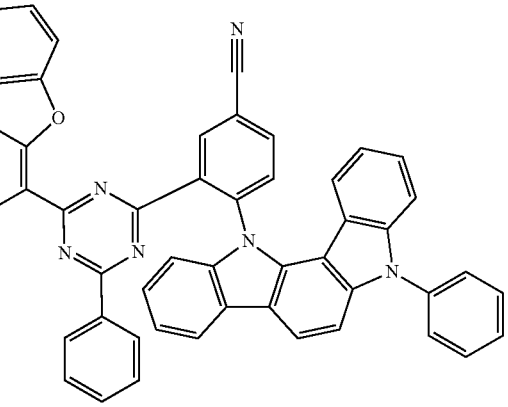

271
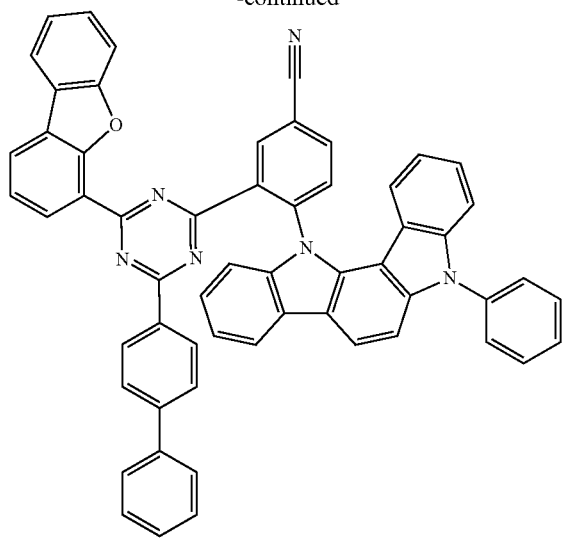
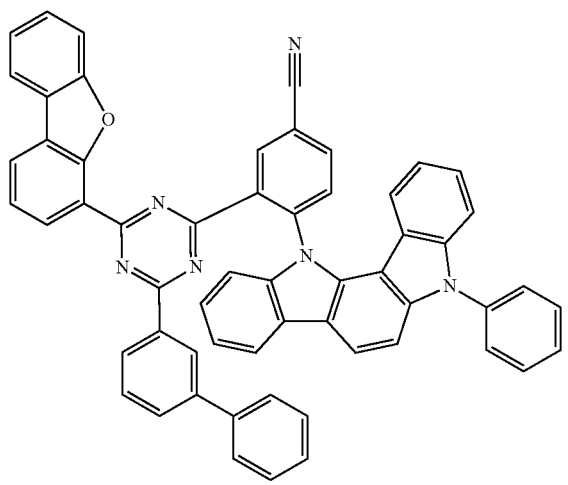
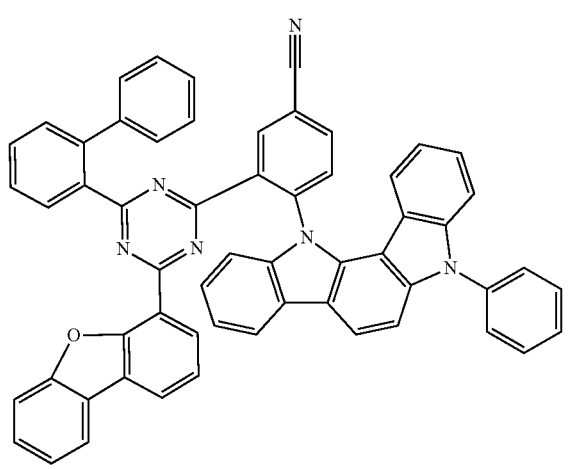
272
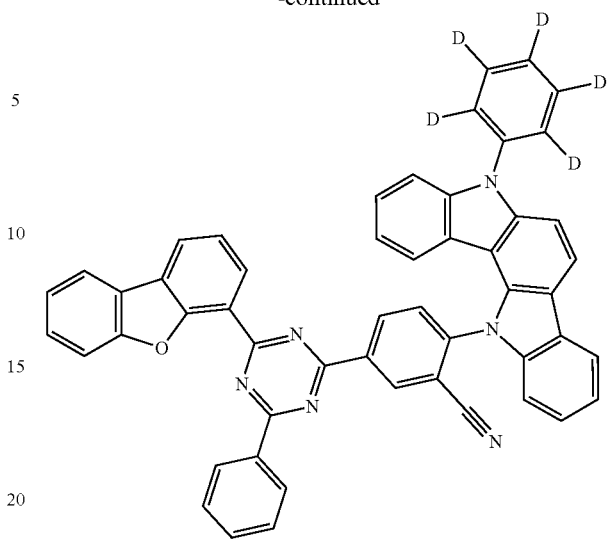
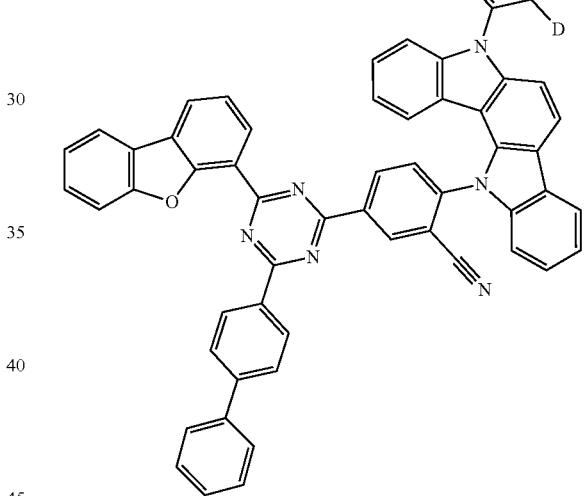
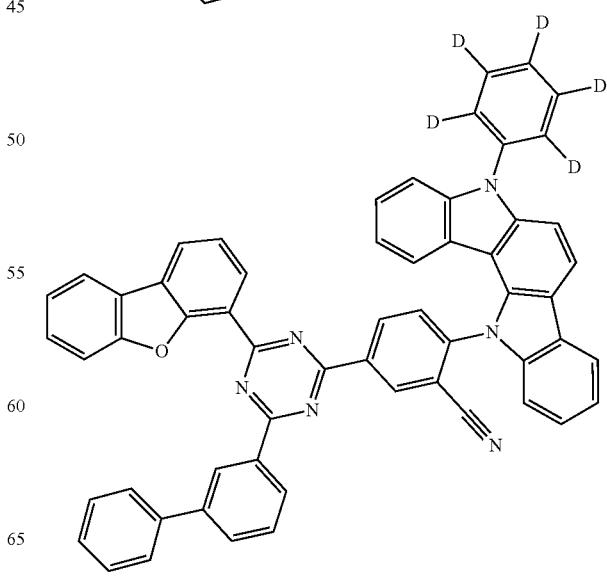

273
-continued
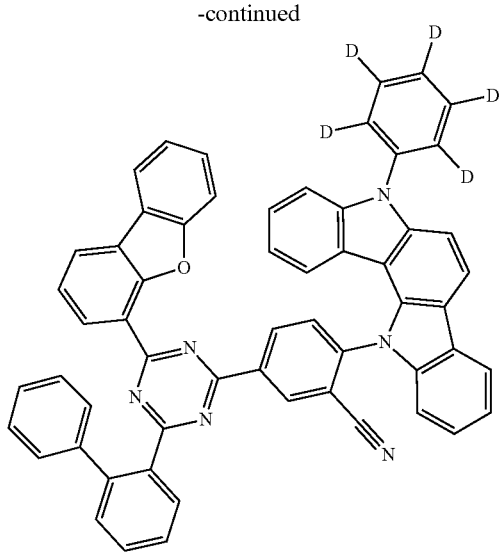
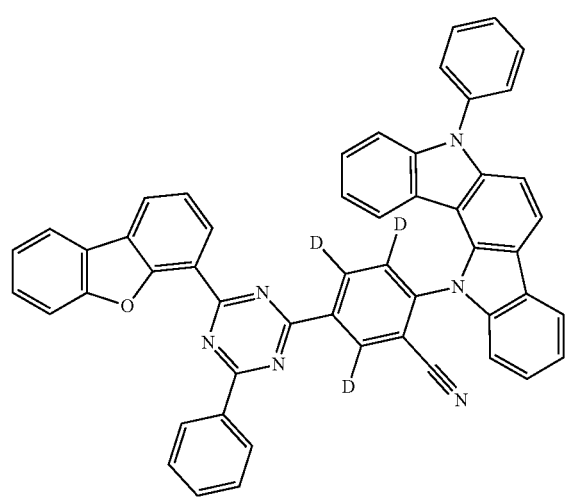
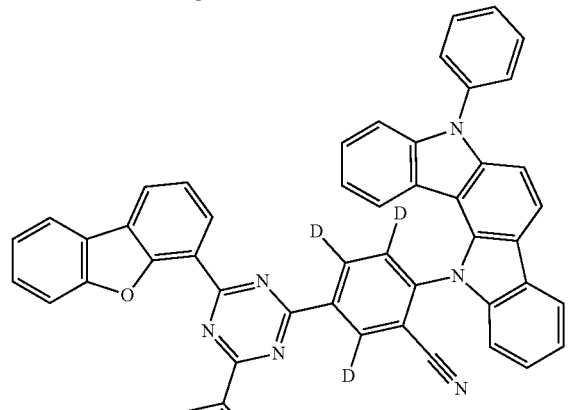
274
-continued
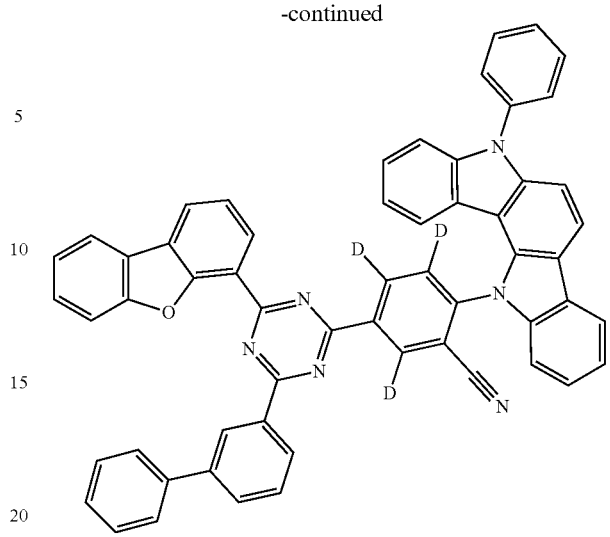
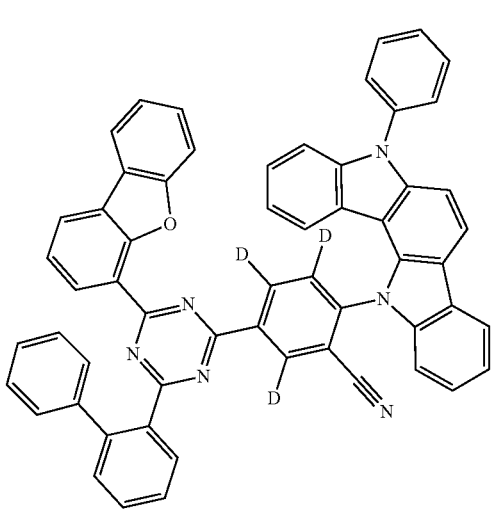
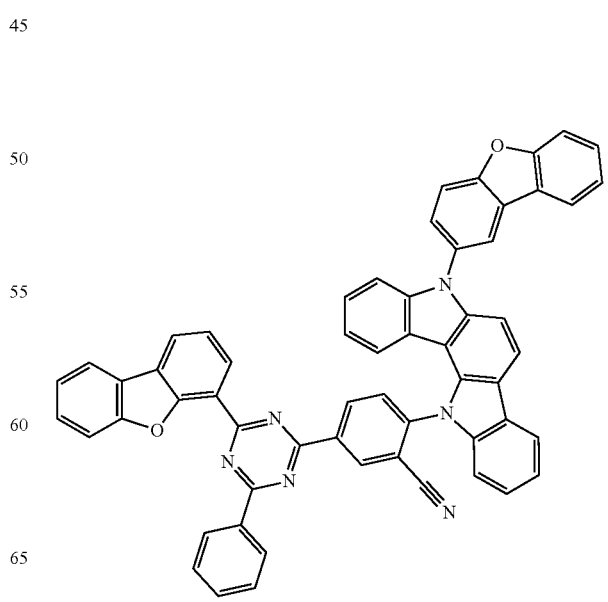

275
-continued
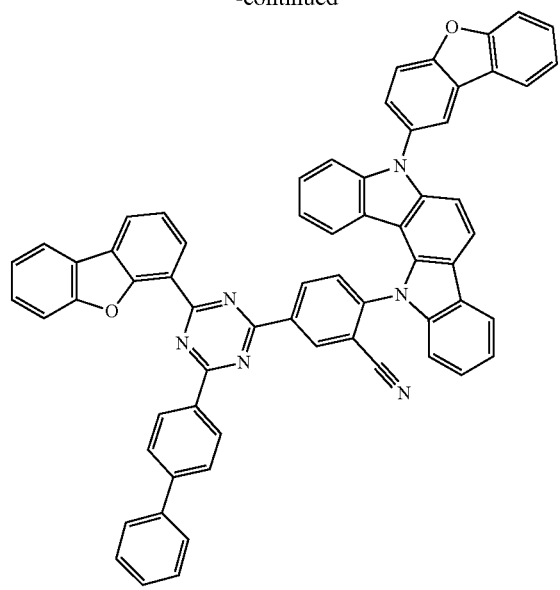
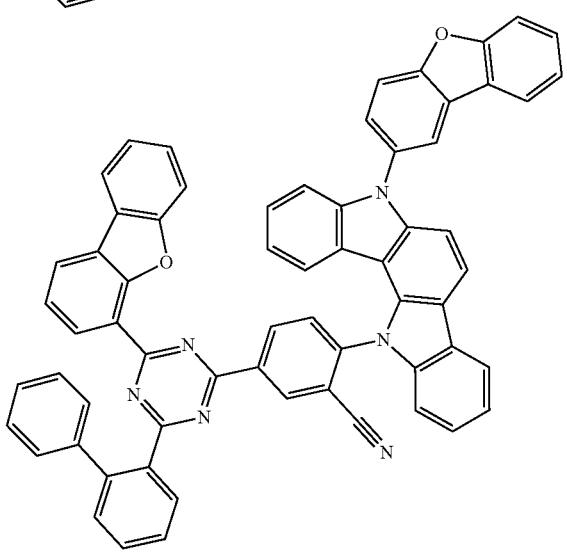
276
-continued
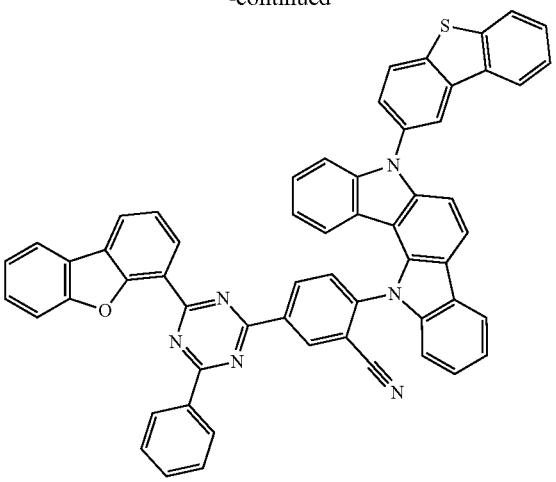
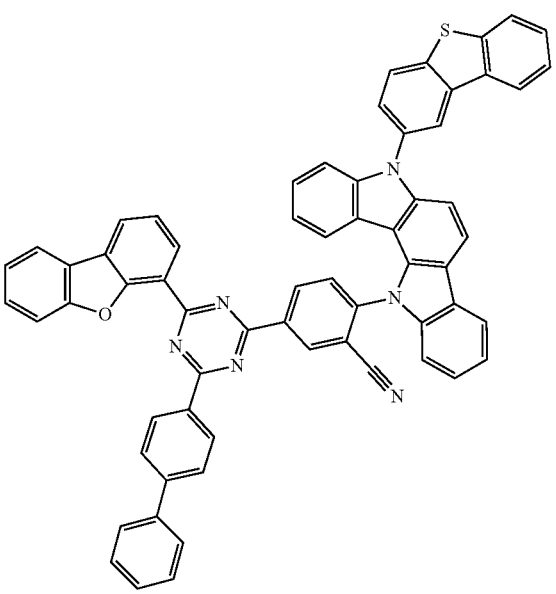
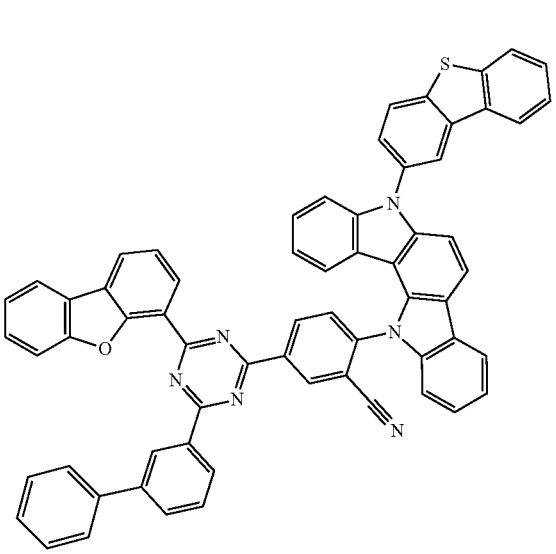

277
-continued
278
-continued
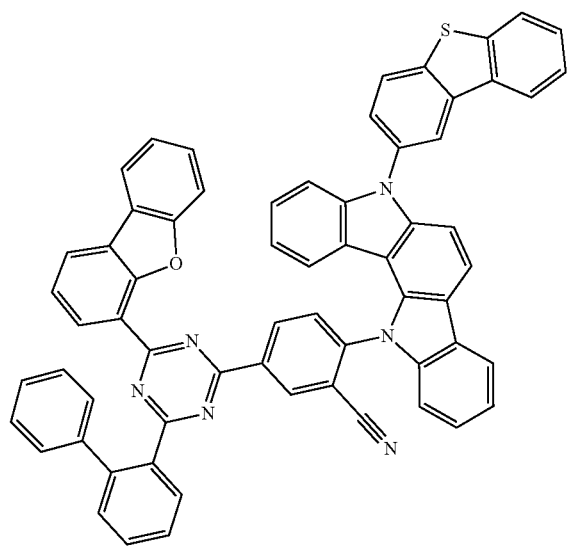
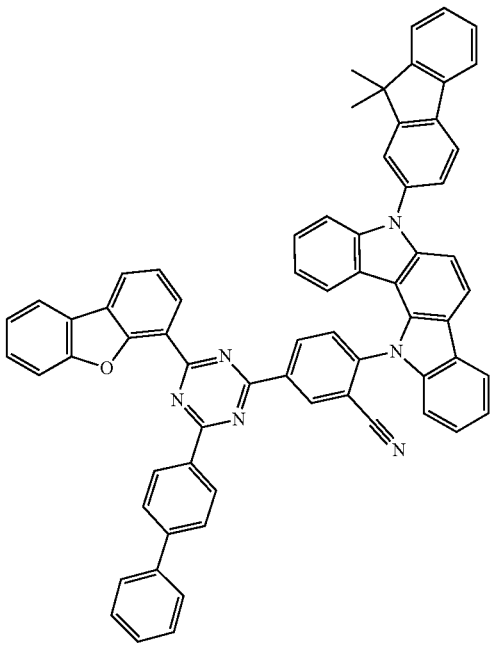
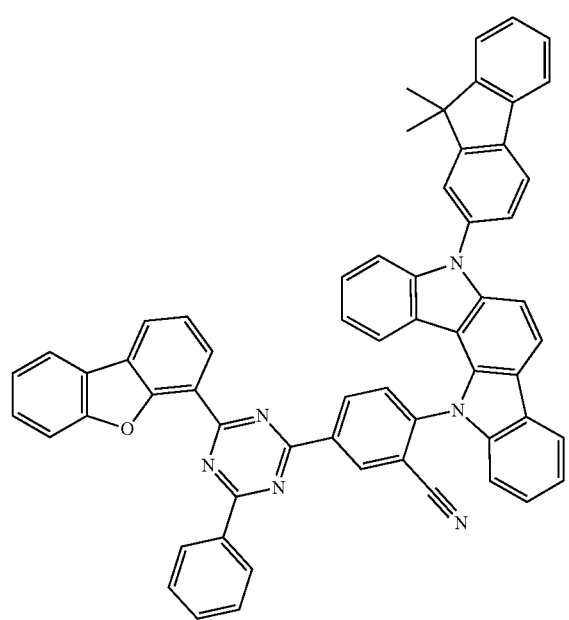
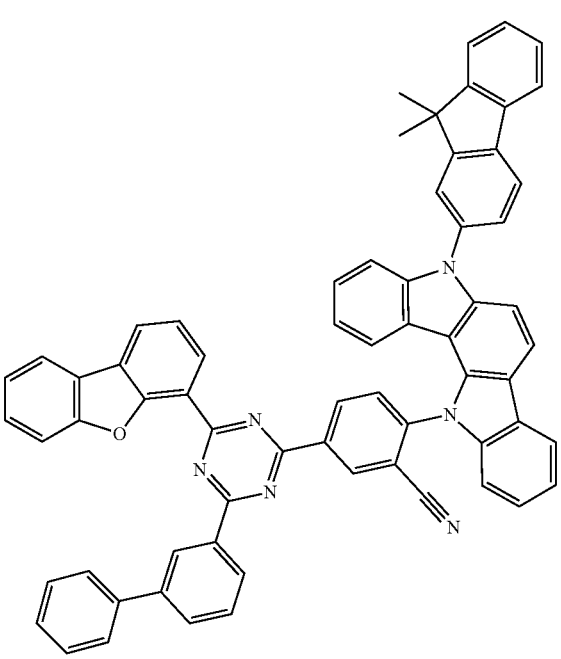

279
-continued
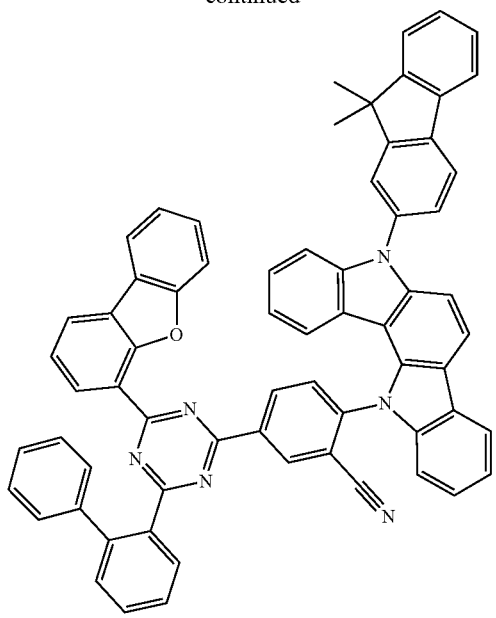
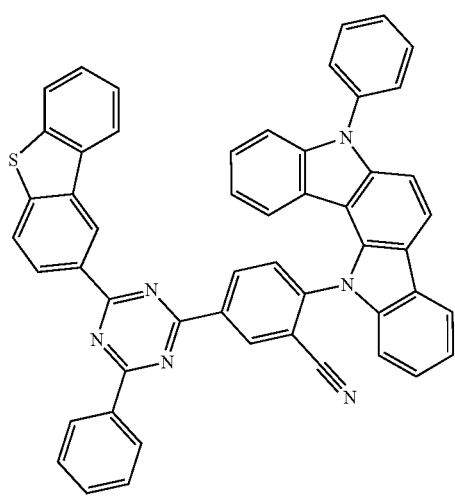
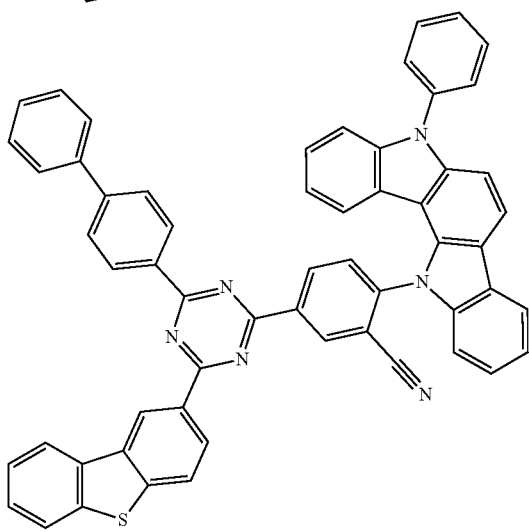
280
-continued
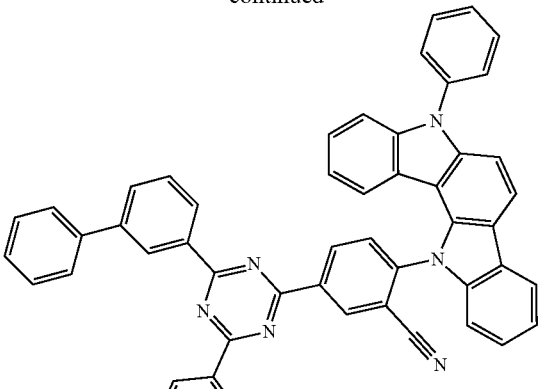
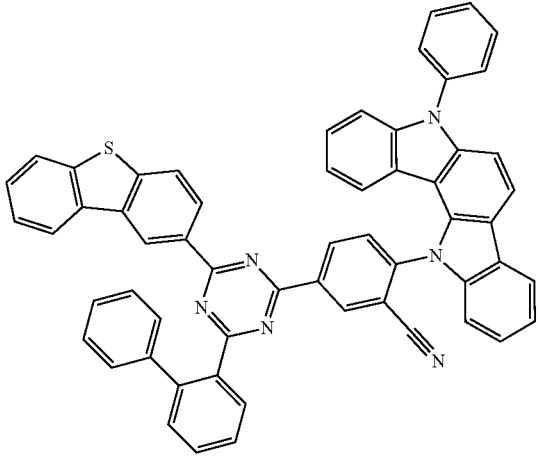
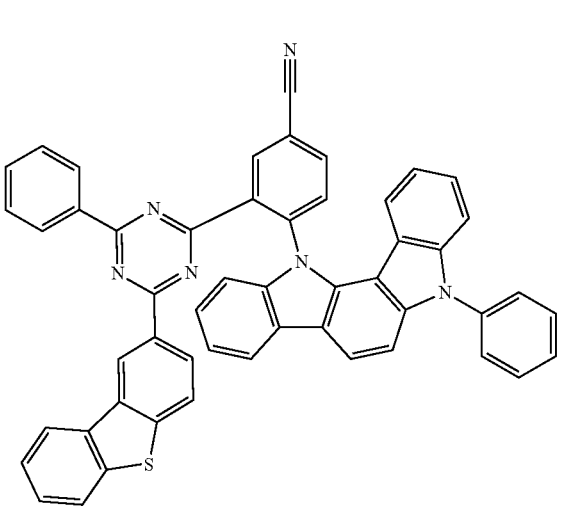

281
-continued
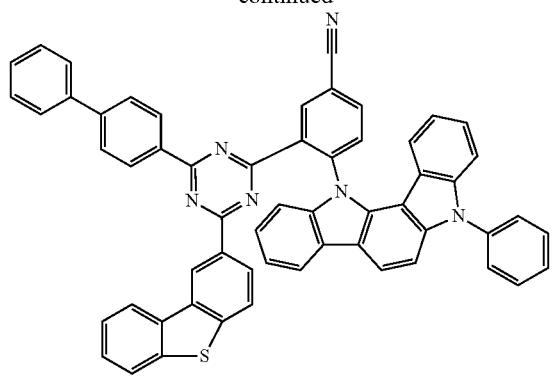
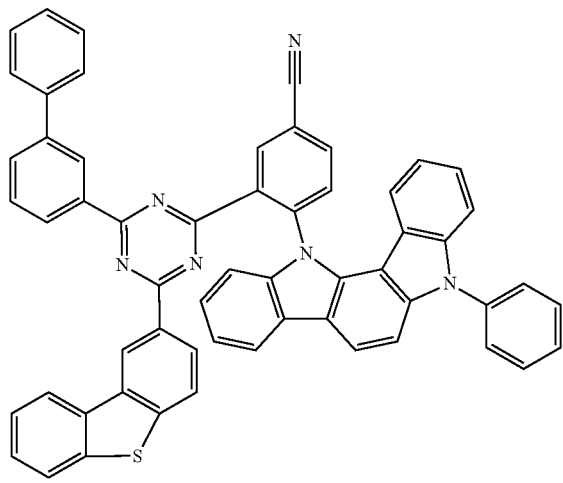
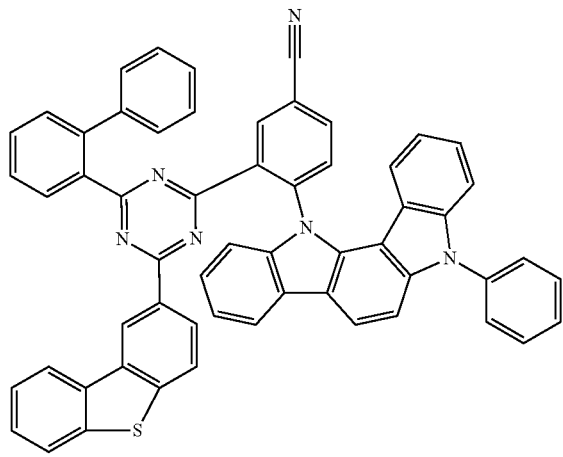
282
-continued
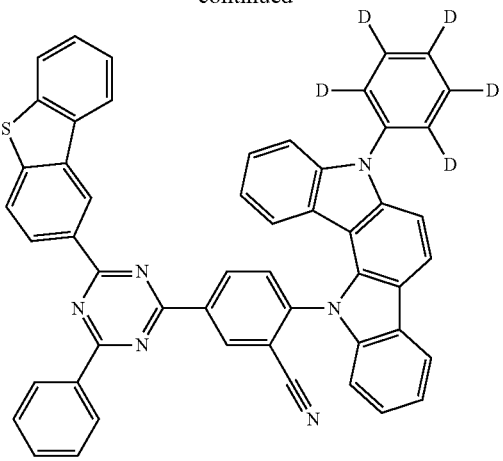
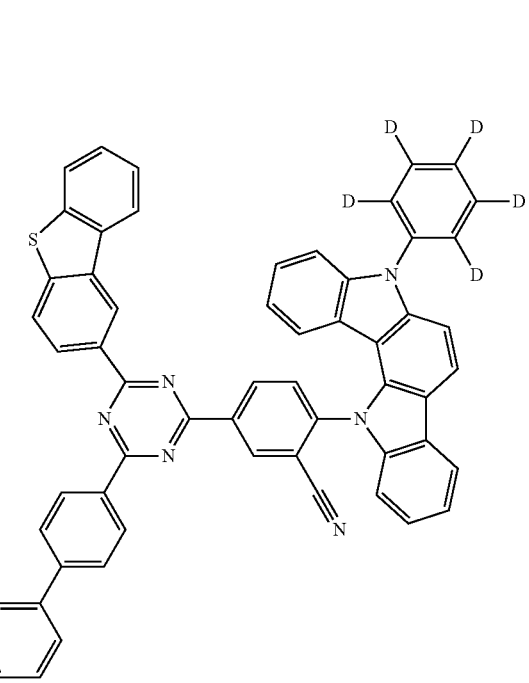

283
-continued
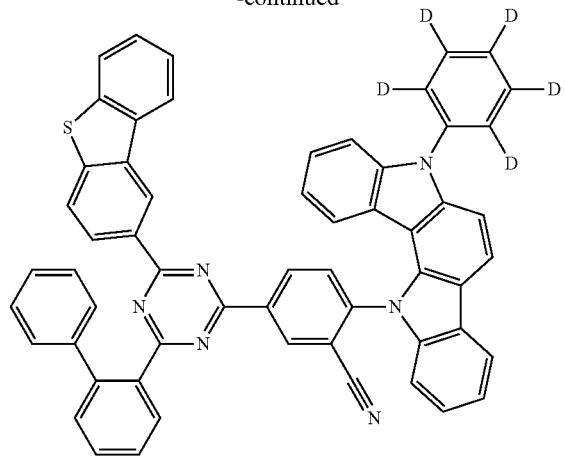
284
-continued
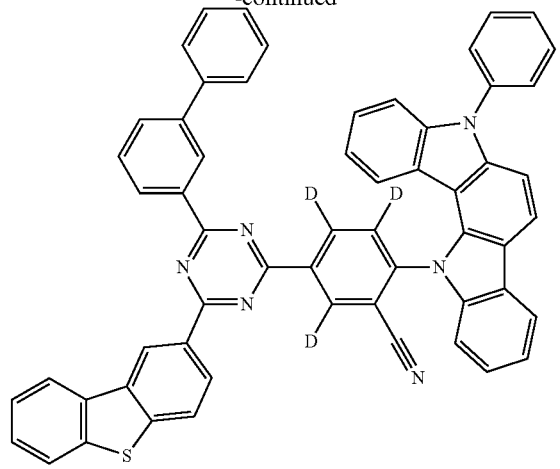
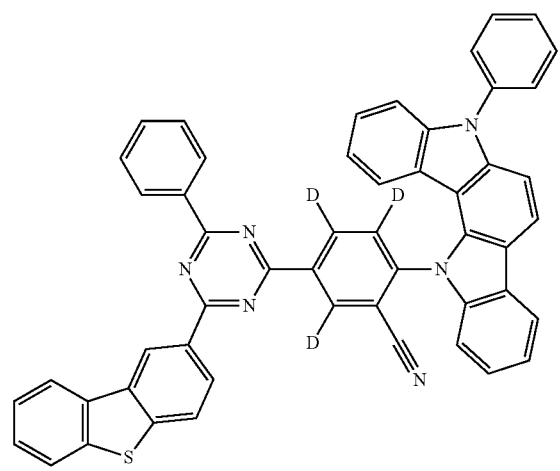
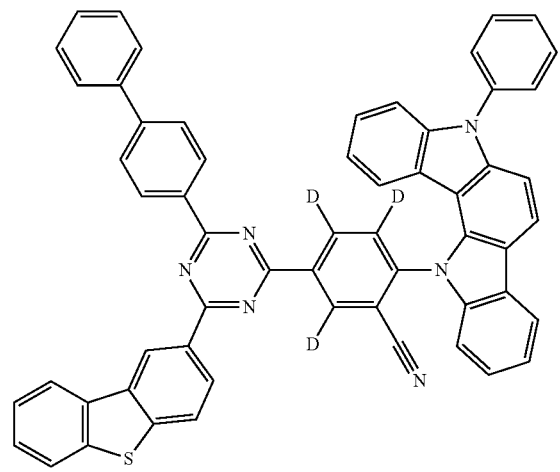
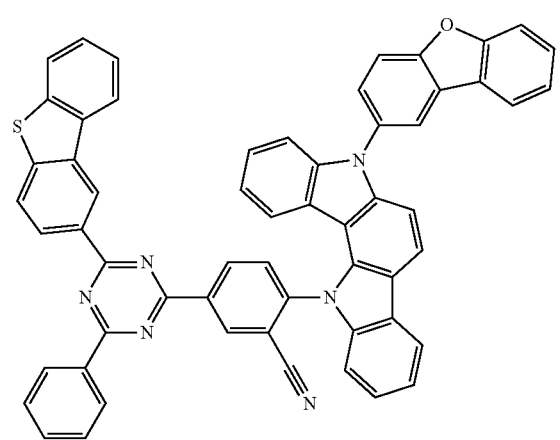

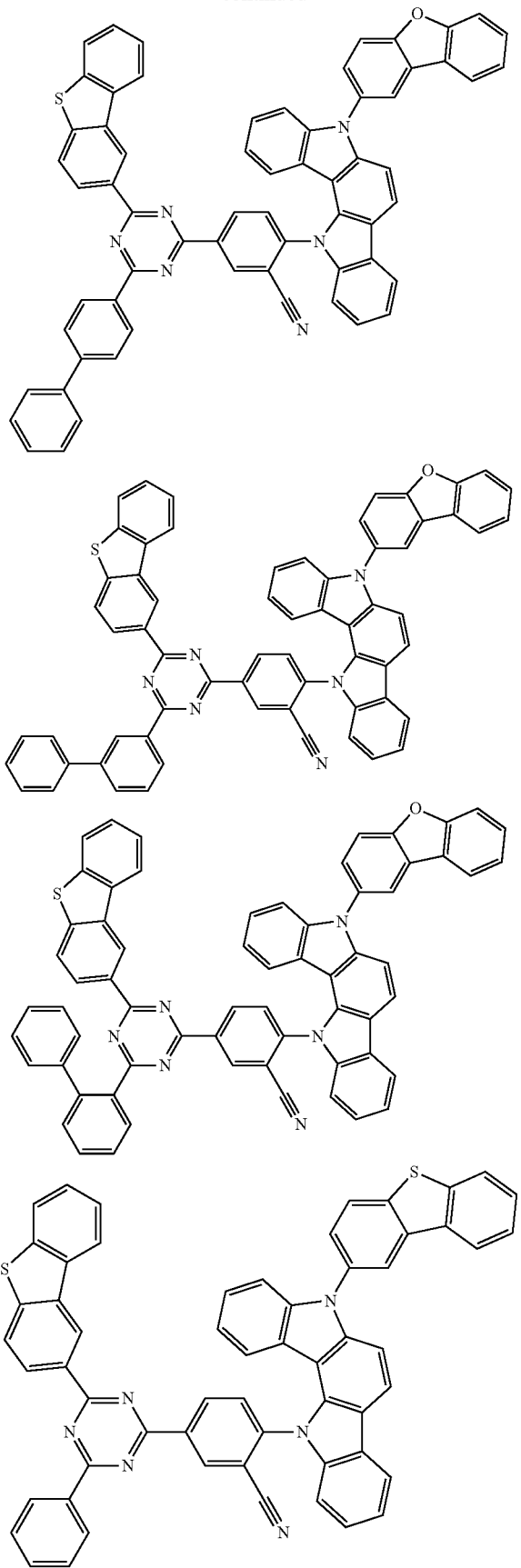
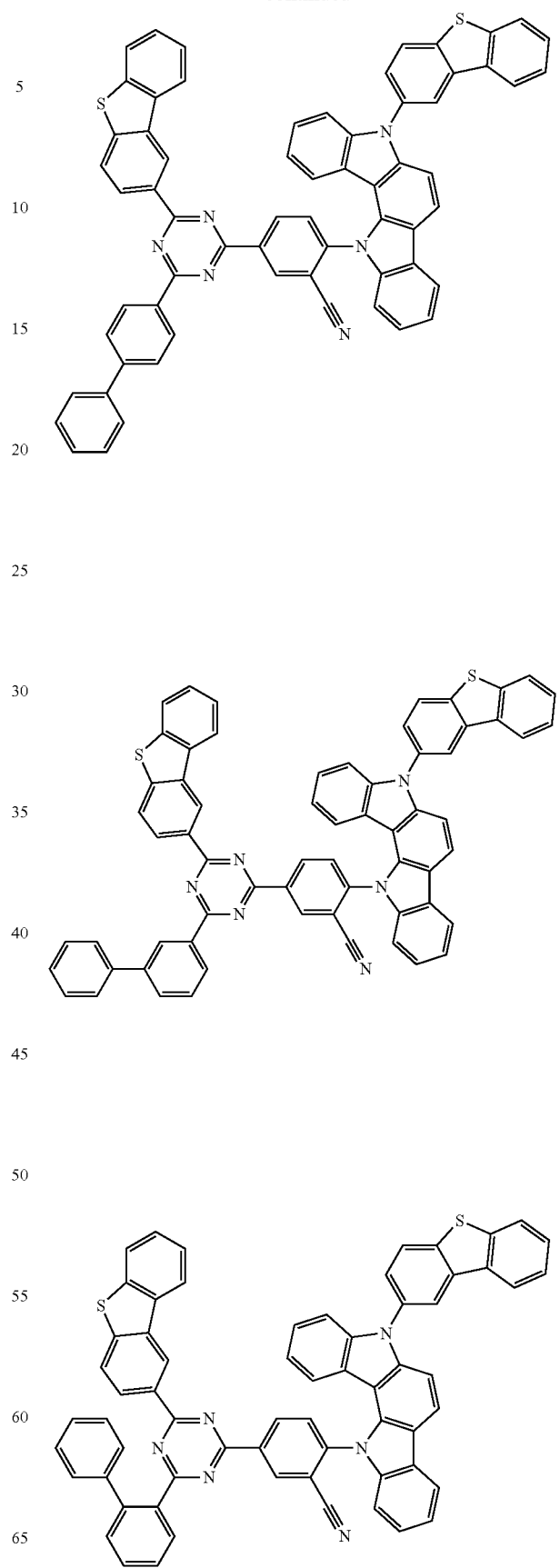

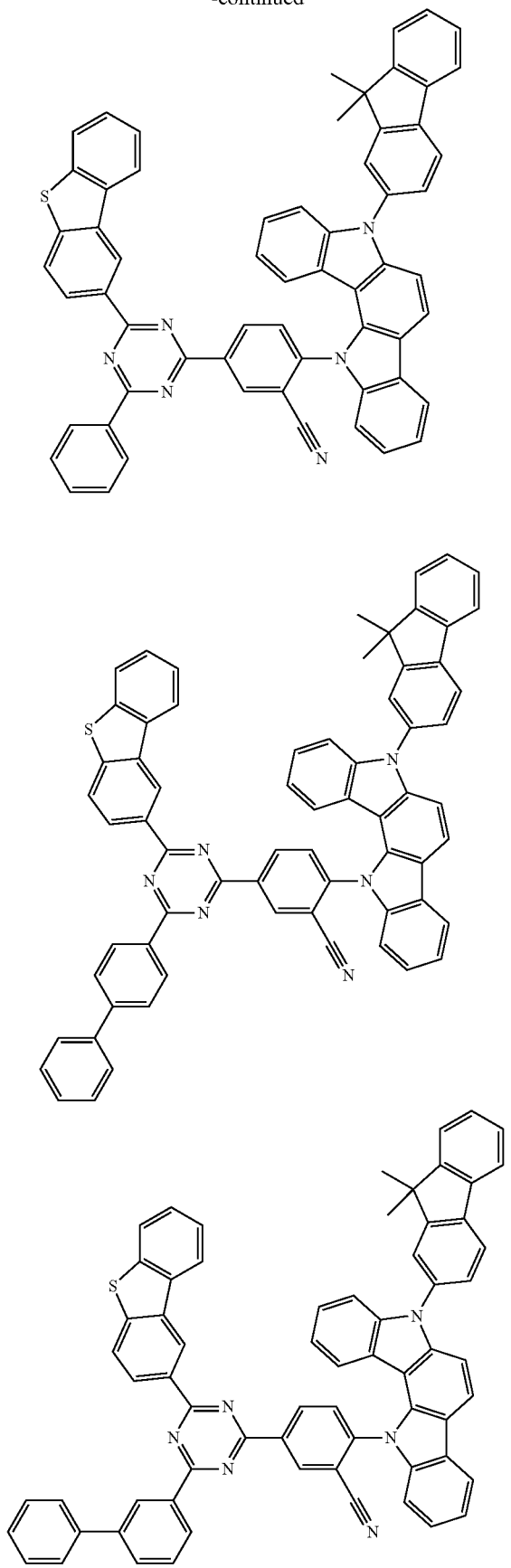

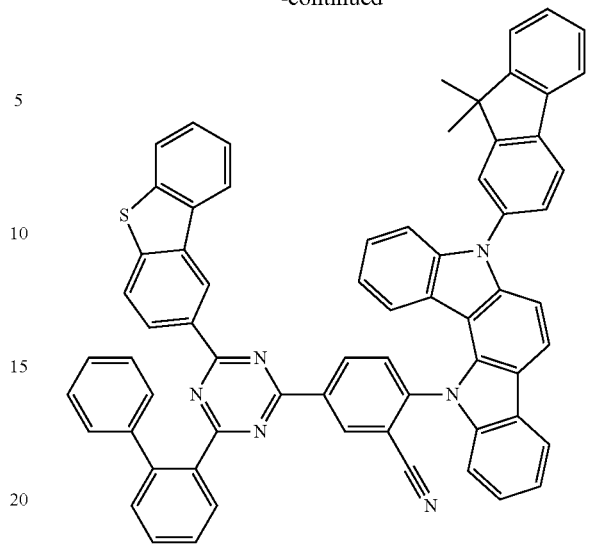

7. The compound of claim 1, wherein a difference between singlet energy ($S1_D$) and triplet energy ($T1_D$) of the compound of Chemical Formula 1 ($\Delta E_{ST\_D}$) is greater than or equal to 0 eV and less than or equal to 0.3 eV.

8. An organic light emitting device comprising:
   a first electrode;
   a second electrode; and
   one or more organic material layers disposed between the first electrode and the second electrode,
   wherein the organic material layer comprises the compound of Chemical Formula 1 of claim 1.

9. The organic light emitting device of claim 8, wherein the organic material layer comprises a light emitting layer, the light emitting layer comprises a dopant, and the dopant is the compound of Chemical Formula 1.

10. The compound of claim 2, wherein a difference between singlet energy ($S1_D$) and triplet energy ($T1_D$) of the compound of Chemical Formula 1 ($\Delta E_{ST\_D}$) is greater than or equal to 0 eV and less than or equal to 0.3 eV.

11. An organic light emitting device, comprising:
   a first electrode;
   a second electrode; and
   one or more organic material layers disposed between the first electrode and the second electrode,
   wherein the organic material layer comprises the compound of Chemical Formula 1 of claim 2.

12. The organic light emitting device of claim 11, wherein the organic material layer comprises a light emitting layer, the light emitting layer comprises a dopant, and the dopant is the compound of Chemical Formula 1.

13. The compound of claim 6, wherein a difference between singlet energy ($S1_D$) and triplet energy ($T1_D$) of the compound of Chemical Formula 1 ($\Delta E_{ST\_D}$) is greater than or equal to 0 eV and less than or equal to 0.3 eV.

14. An organic light emitting device, comprising:
   a first electrode;
   a second electrode; and
   one or more organic material layers disposed between the first electrode and the second electrode,
   wherein the organic material layer comprises a compound of claim 6.

15. The organic light emitting device of claim 14, wherein the organic material layer comprises a light emitting layer, the light emitting layer comprises a dopant, and the dopant is the compound of Chemical Formula 1.

\* \* \* \* \*

UNITED STATES PATENT AND TRADEMARK OFFICE
CERTIFICATE OF CORRECTION

| | |
|---|---|
| PATENT NO. | : 11,767,324 B2 |
| APPLICATION NO. | : 16/761348 |
| DATED | : September 26, 2023 |
| INVENTOR(S) | : Hongsik Yoon et al. |

It is certified that error appears in the above-identified patent and that said Letters Patent is hereby corrected as shown below:

In the Claims

In Claim 2, at Column 193, Line 34, the text that reads:
"(2) R7 is deuterium and dis 1 or greater."
Should read:
—(2) R7 is deuterium and d is 1 or greater.—

Signed and Sealed this
Twenty-third Day of January, 2024

Katherine Kelly Vidal
*Director of the United States Patent and Trademark Office*